(12) United States Patent
Nguyen et al.

(10) Patent No.: US 7,541,193 B2
(45) Date of Patent: Jun. 2, 2009

(54) CAGED SENSORS, REGULATORS AND COMPOUNDS AND USES THEREOF

(75) Inventors: Quan Nguyen, San Ramon, CA (US); Gary McMaster, Ann Arbor, MI (US)

(73) Assignee: Panomics, Inc., Fremont, CA (US)

( * ) Notice: Subject to any disclaimer, the term of this patent is extended or adjusted under 35 U.S.C. 154(b) by 599 days.

(21) Appl. No.: 10/716,174

(22) Filed: Nov. 17, 2003

(65) Prior Publication Data

US 2004/0166553 A1     Aug. 26, 2004

Related U.S. Application Data

(60) Provisional application No. 60/427,664, filed on Nov. 18, 2002, provisional application No. 60/436,855, filed on Dec. 26, 2002, provisional application No. 60/439,917, filed on Jan. 13, 2003, provisional application No. 60/451,177, filed on Feb. 27, 2003, provisional application No. 60/456,870, filed on Mar. 21, 2003, provisional application No. 60/484,785, filed on Jul. 3, 2003, provisional application No. 60/501,599, filed on Sep. 9, 2003.

(51) Int. Cl.
*G01N 21/76* (2006.01)

(52) U.S. Cl. ............... 436/172; 436/164; 435/183; 435/193

(58) Field of Classification Search ............... 435/4, 435/7.1, 7.2, 6, 7.6, 21, 15, 183, 287.1, 7.71, 435/7.72, 7.9, 174, 176, 177; 436/501, 518, 436/519, 86

See application file for complete search history.

(56) References Cited

U.S. PATENT DOCUMENTS 5,252,743 A * 10/1993 Barrett et al. ............ 548/303.7
5,412,087 A * 5/1995 McGall et al. ............ 536/24.3
5,430,175 A    7/1995 Hess et al.
5,563,050 A   10/1996 Peyman et al.
5,635,608 A    6/1997 Haugland et al.

(Continued)

FOREIGN PATENT DOCUMENTS

| WO | 97/28261 | * 8/1997 |
|---|---|---|
| WO | WO 00/73437 A1 | 12/2000 |
| WO | WO 2003/000933 A1 | 1/2003 |
| WO | WO 2004/037983 | 5/2004 |
| WO | WO 2004/045547 | 6/2004 |

OTHER PUBLICATIONS

Truong et al., The use of FRET imaging microscopy to detect protein-protein interactions and protein conformational changes in vivo, 2001, Current Opinion in Structural Biology, vol. 11, pp. 573-578.*

(Continued)

*Primary Examiner*—Bao-Thuy L Nguyen
*Assistant Examiner*—Melanie Yu
(74) *Attorney, Agent, or Firm*—Quine Intellectual Property Law Group, P.C.; Monicia Elrod-Erickson

(57) ABSTRACT

A number of caged (e.g., photoactivatable) compositions are provided, for example, caged enzyme sensors, caged binding sensors, caged nucleic acid probes, caged interfering RNAs, caged antisense nucleic acids, caged ribozymes, caged biomolecular analogs, caged transcription factors, caged antibodies, caged molecular decoys, and caged aptamers. Compositions comprising a plurality of caged components are also provided, as are labeled and optionally caged modulators. Also provided are kits for making the caged compositions and methods for making and for using the caged compositions. Related systems and devices are also provided (e.g., an uncaging device that can trigger photoactivatable assays and optionally detect signals from the assays).

23 Claims, 63 Drawing Sheets

U.S. PATENT DOCUMENTS

| | | | |
|---|---|---|---|
| 5,837,832 A * | 11/1998 | Chee et al. | 536/22.1 |
| 5,872,243 A | 2/1999 | Gee et al. | |
| 5,888,829 A | 3/1999 | Gee et al. | |
| 5,925,517 A | 7/1999 | Tyagi et al. | |
| 5,981,207 A | 11/1999 | Burbaum et al. | |
| 5,998,580 A * | 12/1999 | Fay et al. | 530/333 |
| 6,037,130 A | 3/2000 | Tyagi et al. | |
| 6,043,065 A | 3/2000 | Kao et al. | |
| 6,143,495 A | 11/2000 | Lizardi et al. | |
| 6,150,097 A | 11/2000 | Tyagi et al. | |
| 6,197,599 B1 | 3/2001 | Chin et al. | |
| 6,242,258 B1 | 6/2001 | Haselton et al. | |
| 6,395,544 B1 | 5/2002 | Cowsert et al. | |
| 6,410,255 B1 | 6/2002 | Pollok et al. | |
| 6,472,541 B2 | 10/2002 | Tsien et al. | |
| 6,498,035 B1 | 12/2002 | Wyatt | |
| 6,500,615 B1 | 12/2002 | Schmidt et al. | |
| 6,632,655 B1 * | 10/2003 | Mehta et al. | 435/288.5 |
| 6,670,144 B1 * | 12/2003 | Craig et al. | 435/21 |
| 6,770,261 B2 | 8/2004 | Meade et al. | |
| 6,806,056 B2 * | 10/2004 | Glickman et al. | 435/7.21 |
| 6,900,304 B2 * | 5/2005 | Tsien et al. | 536/23.4 |
| 2002/0177157 A1 | 11/2002 | Luo et al. | |
| 2002/0182223 A1 | 12/2002 | LaCount et al. | |
| 2003/0082827 A1 * | 5/2003 | Craig et al. | 436/518 |
| 2003/0219722 A1 * | 11/2003 | Ladner et al. | 435/5 |
| 2005/0054024 A1 | 3/2005 | Lawrence | |
| 2005/0148031 A1 * | 7/2005 | Allbritton et al. | 435/7.2 |
| 2006/0147378 A1 | 7/2006 | Tung et al. | |

OTHER PUBLICATIONS

Endo et al. A new protein containing an SH2 domain that inhibits JAK kinases, 1997, Nature, vol. 387, pp. 921-924.*

Walker et al., Signaling pathways underlying eosinophil cell motility revealed by using caged peptides, 1998, PNAS, vol. 95, pp. 1568-1573.*

Ting et al., Genetically encoded fluorescent reporters of protein tyrosine kinase activities in linving cells, 2001, PNAS, vol. 98, pp. 15003-15008.*

Curley & Lawrence (1999) "Caged Regulators of Signaling Pathways" *Pharmacol. Ther.* 82(2-3): 347-354.

Muralidharan & Nerbonne (1995) "Photolabile "caged" adrenergic receptor agonists and related model compounds" *J. of Photochemistry and Photobiology B: Biology* 27:123-137.

Adams, S.R. (1993) "Controlling Cell Chemistry With Caged Compounds" *Annu. Rev. Physiol.* 1993.55.755-784.

Ando et al. (2001) "Photo-mediated gene activation using caged RNA/DNA in zebrafish embryos" *Nature Genetics*, vol. 28:2001:317-325.

Barak et al (1999) "Real-time visualization of the cellular redistribution of G protein-coupled receptor kinase 2 and beta-arrestin 2 during homologous desensitization of the substance P receptor" *J Biol Chem* 274(11): 7565-9.

Beaucage, S.L. & Iyer, R.P (1993) "The Synthesis of Modified Oligonucleotides by the Phosphoramidite Approach and Their Applications" *Tetrahedron* 49(28): 6123-6194.

Bishop et al. (2000) "40-Aminomethyl-2,20-bipyridyl-4-carboxylic Acid (Abc) and Related Derivatives: Novel Bipyridine Amino Acids for the Solid-Phase Incorporation of a Metal Coordination Site Within a Peptide Backbone" *Tetrahedron* 56:4629-4638.

Bonetta (2002) "Getting Proteins Into Cells: The Discovery and commercialization of protein transduction domains frees researchers from transfection troubles" *The Scientist* 16:38.

Caplen (2002) "A new approach to the inhibition of gene expression" *Trends in Biotech* 20(2): 49-51.

Chaulk et al. (1998) "Caged RNA: photo-control of a ribozyme reaction" *Nucleic Acids Res.* (1998) 26(13): 3173-3178.

Chen et al. (2002) "Design and Synthesis of a fluorescent Reporter of Protein Kinase Activity" *J. Am. Chem. Soc.* 124:3840-3841.

Ching et al. (1996) "Polymers As Surface-Based Tethers with Photolytic triggers Enabling Laser-Induced Release/Desorption of Covalently Bound Molecules" *Bioconjugate Chemistry* 7(5):525-528.

Conrad II et al. (2000) "*p*-Hydroxyphenacyl Phototriggers: The reactive Excited State of Phosphate Photorelease" *J. Am. Chem. Soc.* 122:9346-9347.

Conrad II et al. (2000) "New Phototriggers: [1] Extending the *p*-Hydroxyphenacyl π-π* Absorption Range" *Org. Lett.* 2:1545-1547.

Cook, P. D. (1991) "Medicinal chemistry of antisense oligonucleotides—future opportunities" *Anti-Cancer Drug Design* 6: 585-607.

Ding et al. (2001) "Size-dependent control of the binding of biotinylated proteins to streptavidin using a polymer shield" *Nature* 411:59-62.

Falsey et al. (2001) "Peptide and Small Molecule Microarray for High Throughput Cell Adhesion and Functional Assays" *Bioconjug. Chem.* 12:346-53.

Fang et al. (1999) "Designing a novel molecular beacon for surface-immobilized DNA hybridization studies" *J. Am. Chem. Soc.* 121:2921-2922.

Fischer et al. (2001) "Cellular Delivery of Impermeable Effector Molecules in the Form of Conjugates with Peptides capable of Mediating Membrane Translocation" *Bioconju Chem.*, 12:825-841.

Furuta et al. (1999) "Brominated 7-hydroxycoumarin-4-ylmethyls: novel photolabile protecting groups with biologically useful cross-sections for two photon photolysis" *Proc. Natl. Acad. Sci.* 96(4):1193-1200.

Galaev and Mattisasson (1999) "Smart' polymers and what they could do in biotechnology and medicine" *Trends Biotech.* 17:335-340.

Gallouzi and Steitz (2001) "Delineation of mRNA export pathways by the use of cell-permeable peptides" *Science* 294:1895.

Giuliano et al. (2003) "Fluorescent protein biosensors: A new screening tool moves drug targets out of the test tube and into the cell" *Modern Drug Discovery* 6:33-37.

Givens et al. (2000) "A New Phototriggers 9: *p*-Hydroxyphenacyl as a C-Terminal Photoremovable Protecting Group for Oligopeptides" *J. Am. Chem. Soc.* 122:2687-2697.

Glickman et al. (2002) "A Comparison of ALPHAScreen, TR-FRET, and TRF as Assay Methods for FXR Nuclear Receptors" *J Mol Screening*, vol. 7,1:3-10.

Goodchild, J. (1990) "Conjugates of oligonucleotides and modified oligonucleotides: a review of their synthesis and properties" *Bioconjugate Chem.* 1(3):165-187.

Gossen and Bujard (1992) "Tight control of gene expression in mammalian cells by tetracycline-responsive promoters" *Proc. Natl. Acad. Sci. USA* 89:5547-5551.

Guo et al (2002) "Probing the molecular basis for potent and selective protein-tyrosine phosphatase 1B inhibition" *J Biol Chem* 277:41014-22.

Gupta et al (2004) "Inducible, reversible, and stable RNA interference in mammalian cells" *Proc. Natl. Acad. Sci. USA* 101:1927-1932.

Jianbing et al. (2003) "High-density fiber optic array technology and its applications in functional genomic studies" *Chinese Science Bulletin* 48(18):1903-1905.

Kaplan et al, (1988) "Photolabile chelators for the rapid photorelease of divalent cations" *Proc Natl Acad Sci USA* 85(17):6571-5.

Kardinal et al. (2000) "Cell-penetrating SH3 domain blocker peptides inhibit proliferation of primary blast cells from CML patients" *FASEB* 14:1529-1538.

Kossel et al. (2001) "A caged Ab reveals an immediate/instructive effect of BDNF during hippocampal synaptic potentiation" *Proc. Natl. Acad. Sci. USA* 98:14702-14707.

Kusunoki et al. (2002) "Solution structure of the DNA-binding domain of the MafG" *Nature Structural Biol* 9:252-56.

Lackey et al (2002) "A biomimetic pH-responsive polymer directs endosomal release and intracellular delivery of an endocytosed antibody complex" *Bioconjugate Chem* 13:996-1001.

Lee et al. (1997) "Caged Nicotinic Acid Adenine Dinucleotide Phosphate: Synthesis And Use" *J Biol Chem* 272(7):4172-8.

Lehel (1997) "A Chemiluminescent Microtiter Plate Assay for Sensitive Detection of Protein Kinase Activity" *Anal Bioch.*, 244, 2: 340-6.

Li et al. (1998) "Cell-permeant caged InsP$_3$ ester shows that Ca$^{2+}$ spike frequency can optimize gene expression" *Nature* 392:936-541.

Lipp & Niggli (1998) "Fundamental calcium release events revealed by two-photon excitation photolysis of caged calcium in Guinea-pig cardiac myocytes" *J Physiol* 508.3, 801.

Lin et al. (2002) "Spatially discrete, light-driven protein expression" *Chem. Biol.* 9:1347-1353.

Llopis et al. (2000) "Ligand-dependent interactions of coactivators steroid receptor coactivator-1 and peroxisome proliferator-activated receptor binding protein with nuclear hormone receptors can be imaged in live ceills and are required for transcription" *Proc. Natl. Acad. Sci. USA* 97:4363-4368.

Lundblad et al. (1998) "The human T-cell leukemia virus-1 transcriptional activator Tax enhances cAMP-responsive element-binding protein (CREB) binding activity through interactions with the DNA minor groove" *J Biol Chem* 273(30):19251-58.

Marriot et al. (1999) "Caged peptides and proteins: new probes to study polypeptides function in complex biological systems" *Trends Plant Sci* 4(8):330-334.

Mastrobattista et al (2002) "Functional Characterization Of An Endosome-Disruptive Peptide And Its Application In Cytosolic Delivery Of Immunoliposome-Entrapped Proteins" *J Biol Chem* 277:27135-43.

McCray and Trentham (1989) "Properties and Uses of Photoreactive Caged Compounds" *Annu Rev Biophys Biophys Chem* 18:239-270.

McCray et al. (1980) "A new approach to time-resolved studies of ATP-requiring biological systems; laser flash photolysis of caged ATP" *Proc. Natl. Acad. Sci. USA* 77:7237-41.

Miller et al (1998) "Flash decaging of tyrosine sidechains in an ion channel" *Neuron* 20, 619-624.

Mitchell et al. (2000) "Polyarginine enters cells more efficiently than other polycationic homopolymers" *J. Pept. Res.* 56:318-25.

Miyata et al. (1999) "A reversibly antigen-responsive hydrogel" *Nature* 399:766-769.

Monroe et al. (1999) "Targeting expression with light using caged DNA" *J Biol Chem.* 274(30):20895-20900.

Murthy et al. (1999) "The design and synthesis of polymers for eukaryotic membrane disruption" *Journal of Controlled Release*(1999) 61:137-143.

Murthy et al. (2003) "Bioinspired pH-responsive polymers for the intracellular delivery of biomolecular drugs" *Bioconjugate Chem.* 14:412-419.

Nagal et al. (2000) "A fluorescent indicator for visualizing cAMP-induced phosphorylation in vivo" *Nature Bio.*, vol. 18:313-16.

Ohuchi et al. (2001) "Fluorescence-based Sensing of Protein Kinase A Activity Using the Dual Fluorescent-labeled Peptide" *Analytical Sciences.*, vol. 17:i1456-67.

Okamato et al (2003) "Phototriggered Drug Release from Functionalized Oligonucleotides by a Molecular Beacon Strategy" *Angew Chem Int Ed* 42:2502-2504.

Pan & Bayley (1997) "Caged cysteine and thiophosphoryl peptides" *FEBS Letters* 405:81-85.

Park et al (1999) "Homogeneous proximity tyrosine kinase assays: scintillation proximity assay versus homogeneous time-resolved fluorescence" *Anal Bioch*, 269: 94-104.

Paul et al. (2002) "Effective expression of small interfering RNA in human cells" *Nature Biotech* 29:505-507.

Pettit et al. (1997) "Chemical two-photon uncaging: a novel approach to mapping glutamate receptors" *Neuron* 19:465-471.

Perlette et al. (2001) "Real-time monitoring of intracellular mRNA hybridization inside single living cells" *Anal Chem* 73:5544-50.

Pinna and Ruzzene (1996) "How doe protein kinases recognize their substrates?" *Biochimica et Biophysica Acta* 1314:191-225.

Pooga et al. (1998) "Cell penetrating PNA constructs regulate galanin receptor levels and modify pain transmission in vivo" *Nat. Biotech.*, 16:857-861.

Rehman et al. (2003) "Protection of islets by in Situ peptide-mediated transduction of the Ikappa B kinase inhibitor Nemo-binding domain peptide" *J Biol Chem* 278:9862-9868.

Robbins et al. (2002) "Peptide delivery to tissues via reversibly linked protein transduction sequences" *Biotechniques* 33:190-192.

Ross et al. (2002) "A non-radioactive method for the assay of many serine/threonine-specific protein kinases" *Biochem. J.* 366, 977-981.

Saez et al. (1997) "Inducible gene expression in mammalian cells and transgenic mice" *Curr. Opin. Biotechnol.* 8:608-616.

Schutze-Redelmeiner et al. (1996) "Introduction of Exogenous Antigens into the MHC Class I Processing and Presentation Pathway by *Drosophila* Antennapedia Homeodomain Primes Cytotoxic T Cells In Vivo" *J. Immunol.* 157:650-655.

Schwartz et al. (2000) "Peptide-mediated cellular delivery" *Curr Opin Mol Ther* 2:162-7.

Shigeri et al. (2001) "Synthesis and application of caged peptides and proteins" *Pharmacology & Therapeutics* 91:85-92.

Shimoboji et al. (2002) "Photoresponsive polymer-enzyme switches" *Proc. Natl. Acad. Sci. USA* 99:16592-16596.

Shults MD, Imperiali B. (2003) "Versatile fluorescence probes of protein kinase activity" *J Am Chem Soc.*125(47):14248-9.

Simeoni et al. (2003) "Insight into the mechanism of the peptide-based gene delivery system MPG: Implications for delivery of siRNA into mammalian cells" *Nucl Acids Res* 31:2717-2724.

Smits et al. (1999) "Development and Evaluation of a Rapid Dipstick Assay for Serodiagnosis of Acute Human Brucellosis" *J Clin Microbiol*37:4179-4182.

Sokol et al. (1998) "Real time detection of DNA:RNA hybridization in living cells" *Proc. Natl. Acad. Sci. U.S.A.* 95:11538-11543.

Stuckey et al. (Jul. 2002) "Physiomics and drug discovery: Using automated fluorescence microscopy, researchers are performing high-content cell-based screening assays" *Modern Drug Discovery*, 37-42.

Sueda et al. (2000) "Homogeneous DNA Hybridization Assay by Using Europium Luminescence Energy Transfer" *Bioconj. Chem.* 11:827-831.

Sueda et al. (2002) "A homogeneous DNA hybridization system by using a new luminescence terbium chelate" *Bioconj. Chem.* 13:200-205.

Tawa et al, (2001) "Quantitative analysis of fluorescent caspase substrate cleavage in intact cells and identification of novel inhibitors of apoptosis" *Cell Death Differ* (2001) 8:30-37.

Ting et al. (2001) "Genetically encoded fluorescent reportes of protein tyrosine kinase activities in living cells" *Proc. Natl. Acad. Sci. USA* vol. 98:15003-08.

Tsourkas & Bao (2001) "Detecting mRNA transcripts using FRET-enhanced molecular beacons." In Proceedings of the 2001 Bioengineering Conference. ASME BED, New York, NY, vol. 50, pp. 169-170.

Tyagi et al. "Molecular beacons: probes that fluoresce upon hybridization" *Nature Biotech.* 14:303-8 (1996).

Tyagi et al., (1998) "Multicolor molecular beacons for allele discrimination" *Nature Biotech.* 16:49-53.

Tyas et al (2002) "Rapid caspase-3 activation during apoptosis revealed using fluorescence-resonance energy transfer" *EMBO Reports*, 1(3):266-270.

Uhlmann, E. & Pepan, A. (1990) *Chem. Rev.* "Antisense oligonucleotides: a new therapeutic principle" 90(4): 543-584.

Velduyzen et al. (2003) "A light-activated probe of intracellular protein kinase activity" *J. Am. Chem. Soc.* 125:13358-13359.

Wagner et al (1992) "Influenza virus hemagglutinin HA-2 N-terminal fusogenic peptides augment gene transfer by transferrin-polylysine-DNA complexes: toward a synthetic virus-like gene-transfer vehicle" *Proc Natl Acad Sci* 89:7934-38.

Walker et al. "Signaling pathways underlying eosinophil cell motility revealed by using caged peptides" *Proc. Natl. Acad. Sci. USA* (1998) 95:1568-1573.

Watanabe (Jan. 13, 2003) "Knocking Down Genes for Fun and Function" *Scientist* 17(1):36.

Wu et al (2002) "Identification of a High-Affinity Anti-Phosphoserine Antibody for the Development of Homogeneous Fluorescence Polarization Assay of Protein Kinase C"*J. Mol. Screening*, vol. 5,1:23-30.

Yeh et al. (2002) "Real time visualization of protein kinase activity in living cells" *J Biol Chem* 277: 11527-11532.

Zhang et al. (2001) "Design of a Molecular Beacon DNA Probe with Two Fluorophores" *Angw. Chem. Int. Ed.* 40(2):402-405.

Zhang et al. (2002) "Creating New Fluorescent Probes For Cell Biology" *Nat. Rev. Mol. Cell. Biol.*, 3:906-18.

Ziauddin and Sabatini (2001) "Microarrays of cells expressing defined cDNAs" *Nature* 411(6833):107-10.

Zou et al. (2002) "Catalytic subunit of protein kinase A caged at the activating phosphothreonine" *J. Amer. Chem. Soc.* 124:8220-8229.

Zou et al. (2001) "Caged Thiophosphotyrosine Peptides" *Angew. Chem. Int. Ed.* 40:3049-3051.

Funovics et al. (2003) "Protease sensors for bioimaging." Anal. Bioanal. Chem. 377:956-963.

Pham et al. (2002) "An Azulene Dimer as a Near-Infrared Quericher." Angew. Chem. Int. Ed. 41(10):3659-3662.

* cited by examiner

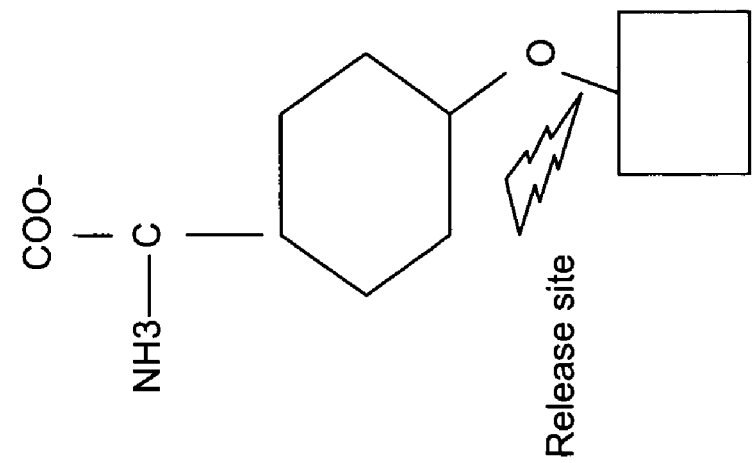
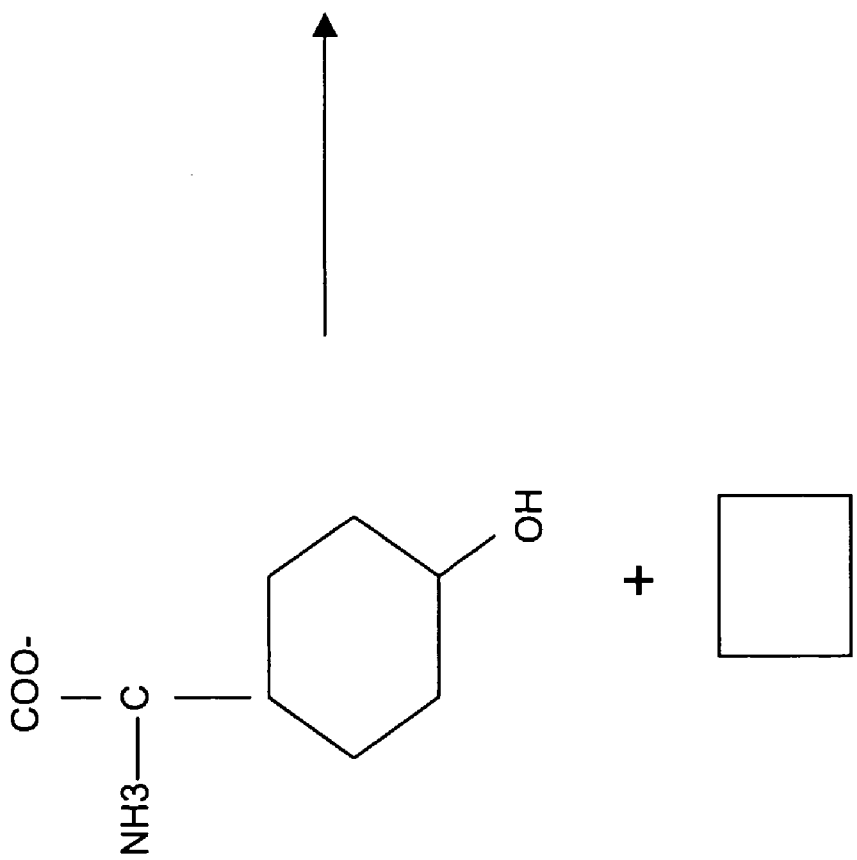
Fig. 19

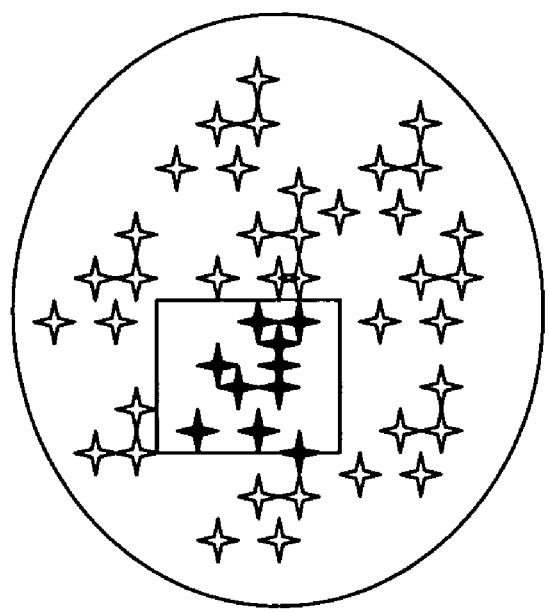
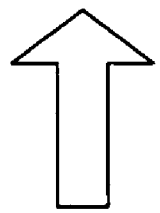
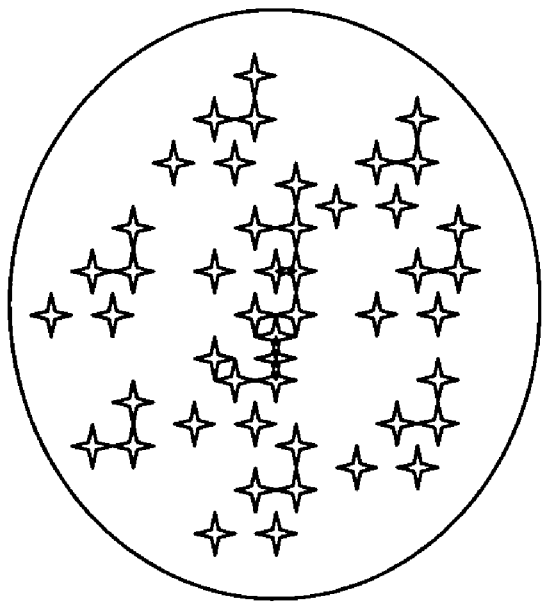
Fig. 36

CAGED SENSORS, REGULATORS AND COMPOUNDS AND USES THEREOF

CROSS REFERENCE TO RELATED APPLICATIONS

This application is a non-provisional utility patent application claiming priority to, and benefit of, the following prior provisional patent applications: U.S. Ser. No. 60/427,664, filed Nov. 18, 2002, entitled "Photo Activated Sensors, Regulators and Compounds" by Nguyen and McMaster; U.S. Ser. No. 60/436,855, filed Dec. 26, 2002, entitled "Caged Sensors, Regulators and Compounds and Uses Thereof" by Nguyen and McMaster; U.S. Ser. No. 60/439,917, filed Jan. 13, 2003, entitled "Caged Sensors, Regulators and Compounds and Uses Thereof" by Nguyen and McMaster; U.S. Ser. No. 60/451,177, filed Feb. 27, 2003, entitled "Caged Sensors, Regulators and Compounds and Uses Thereof" by Nguyen et al.; U.S. Ser. No. 60/456,870, filed Mar. 21, 2003, entitled "Caged Sensors, Regulators and Compounds and Uses Thereof" by Nguyen et al.; U.S. Ser. No. 60/484,785, filed Jul. 3, 2003, entitled "RNAi-based Sensors and Methods of Use Thereof, by Nguyen et al., and U.S. Ser. No. 60/501,599, filed Sep. 9, 2003, entitled "Caged Sensors, Regulators and Compounds and Uses Thereof" by Nguyen et al., each of which is incorporated herein by reference in its entirety for all purposes.

FIELD OF THE INVENTION

The invention is in the field of caged sensors, regulators and compounds. For example, this invention relates to the use of photoactivatable caged compounds to precisely control the timing and location of biochemical, cell-lysate and cell-based reactions, including photo activated (photoactivatable, PA) sensors, regulators and compounds suitable for monitoring signal transduction pathways in cells. The sensors are designed for simple operation and are suitable for use in a wide array of instrument platforms. Systems and apparatus (e.g., containing caged compounds of the invention or for using caged compounds) are also described.

BACKGROUND OF THE INVENTION

Cellular assays are critical tools in the drug discovery process and in basic research. In the future, these assays will play a major role in systems biology, permitting the examination of cell structure and function and the determination of a drug compound's ability to enter a cell, the compound's toxicity and its overall efficacy. Advances in imaging technologies, florescent probes, and assay automation are predicted to drive the worldwide cellular assays market from an estimated $300 million in 2002 to $500 million in 2007. The most common application for cellular assay technology in drug discovery is target validation and lead identification and optimization. However, the complexity and richness in cellular assay data sets, compared to genomics and proteomics studies, will provide scientists with unparalleled tools to aid discovery efforts throughout the drug discovery process as well as for basic research applications.

To achieve the goal of measuring the spectrum of molecular events in cells, there is definite need for "in cell sensor probes" that quantitatively measure protein (or other) activities directly in cells in a regulated fashion to give real time functional data, without using expression vectors. These "in cell sensor probes" will define pathways in a Parallel Quantitative Biology (PQB) format for systems biology and enable novel regulated cell-based functional screening in a high throughput mode. This invention provides these and other probes, termed PAC probes (PhotoActivated Cell probes) herein.

Just as RNA abundance does not always correlate to protein synthesis, protein abundance does not always correlate to a protein's activity and function within the cell. For example, depending on the protein's subcellular location (e.g. cytoplasm, nucleus, etc.), if it is membrane bound, or if it is bound to another molecule (e.g. aptamer, peptide, protein, RNA, DNA), its activity may or may not correlate to its abundance within the cell. In addition, how a drug binds to a protein in vitro and in vivo can differ significantly, not to mention that the drug may not enter the cell and, thus, may not be functionally active. The PAC probes of the invention measure activities in a regulated real-time fashion in the cell while co-locating, interrogating the function of proteins, pathways and networks and detecting the mode of action of drugs within the cells in a high throughput fashion. Thus, PAC probes enable functional proteomics and genomics.

SUMMARY OF THE INVENTION

The invention relates to using caging groups to keep reaction components separate and/or inactive, in vitro and/or in vivo. The reaction components are uncaged by application of appropriate uncaging energy (light, sonication, heat, etc.) and/or exposure to an uncaging chemical or condition. This caging/uncaging approach provides for dramatically simplified assays, as well as greater assay uniformity between correlated biochemical, in cell and in organism assays.

In a first aspect, the invention provides caged enzyme sensors. A first general class of embodiments provides a composition comprising a cell that comprises a caged sensor for detecting an activity of an enzyme. The caged sensor includes one or more molecules, which collectively comprise a substrate for the enzyme and a first label, and one or more first caging groups associated with the one or more molecules. The substrate is in a first state on which the enzyme can act, thereby converting the substrate to a second state. A first signal exhibited by the first label when the substrate is in its first state is distinguishable from a second signal exhibited by the first label when the substrate is in its second state. The first caging groups inhibit (e.g., prevent) the enzyme from acting upon the substrate.

Depending on the application, the enzyme can be any of a variety of enzymes, e.g., an oxidoreductase, a transferase, a hydrolase, a lyase, a ligase, and/or an isomerase. The enzyme can be, e.g., a kinase, a phosphatase, a GTPase, an ATPase, a phosphodiesterase, a luciferase, an acetylase, a glycosylase, a ubiquitin-conjugating enzyme, a hydrogenase, a polymerase, a peroxidase, a protease and/or a caspase.

A second general class of embodiments provides a composition comprising a caged sensor for detecting an activity of an enzyme. The caged sensor includes one or more molecules, which collectively comprise a substrate for the enzyme and a first label, and one or more first caging groups associated with the one or more molecules. The substrate is in a first state on which the enzyme can act, thereby converting the substrate to a second state. The first state is not converted to the second state by cleavage by the enzyme. A first signal exhibited by the first label when the substrate is in its first state is distinguishable from a second signal exhibited by the first label when the substrate is in its second state. The first caging groups inhibit (e.g., prevent) the enzyme from acting upon the substrate. The composition optionally comprises the enzyme, a cell (e.g., a cell comprising the caged sensor and/or the enzyme) and/or a cell lysate.

In this general class of embodiments, the enzyme can be any of a variety of enzymes, providing that the first state of the substrate is not cleaved by the enzyme to form the second state. Thus, the enzyme is typically an oxidoreductase, a transferase, a ligase, and/or an isomerase. The enzyme can be a hydrolase or a lyase, for example, if the activity being assayed is one that does not involve cleavage of the substrate. The enzyme can be, e.g., a kinase, an acetylase, a ubiquitin-conjugating enzyme, a hydrogenase, or a polymerase.

For either of these related general classes of embodiments, the first label can be an optically (or spectroscopically) detectable label such as a fluorophore. However, non-optical labels can also be used. Thus, the first signal and/or the second signal can be, e.g., an optical signal, a fluorescent signal, a luminescent signal, a nonoptical signal, a magnetic signal, or the like, as appropriate to the assay.

The one or more first caging groups associated with the one or more molecules can be covalently or non-covalently attached to the one or more molecules. In a preferred aspect, the one or more first caging groups are photoactivatable (e.g., photolabile). For example, in one embodiment, the first caging groups can be removed by exposure to light with a wavelength between about 60 nm and about 400 nm, between about 400 nm and about 700 nm, and/or between about 700 nm and about 1000 nm (i.e., the light can be UV, near-UV, visible, near-infrared, and/or infrared). Other first caging groups are removable via input of different uncaging energies, e.g., the one or more first caging groups can be removable by sonication or application of heat, or via environmental changes (e.g., change in pH or ionic strength).

In the caged sensors herein, the first label and the substrate are optionally physically connected. The substrate can include, e.g., an amino acid, a polypeptide, a nitrogenous base, a nucleoside, a nucleotide, a nucleic acid, a carbohydrate, and/or a lipid.

In embodiments in which the sensor is located inside a cell, the cell can be, e.g., a prokaryotic cell (e.g., a eubacterial or an archaebacterial cell) such as an *Escherichia coli* cell, or a eukaryotic cell, e.g., a mammalian cell or a yeast cell.

In one embodiment, the enzyme of the caged sensor is a kinase, e.g., a protein kinase that phosphorylates tyrosine, serine and/or threonine. For example, one polypeptide can comprise the first label and the substrate for the kinase, where the substrate includes a serine, -threonine, or tyrosine residue capable of being phosphorylated by the kinase. The first label can be located at the serine, threonine, or tyrosine residue and exhibits the first signal when the residue is not phosphorylated and the second signal when the residue is phosphorylated. The one or more first caging groups are optionally located on one or more amino acid residues involved in binding the kinase.

In one embodiment, one polypeptide comprises the substrate for the kinase and the first label and further comprises a second label or a quencher. The first label and the second label or the quencher interact to produce the first signal when the substrate is not phosphorylated. Phosphorylation of the substrate prevents the interaction of the first label and the second label or the quencher, resulting in production of the second signal. Optionally, the one or more first caging groups are located on one or more amino acid residues involved in binding the kinase and/or on a residue that can be phosphorylated by the kinase. One of the first label and the second label or the quencher can be located at the N-terminus of the polypeptide and the other of the first label and the second label or the quencher at the C-terminus of the polypeptide. Here again, one label can be a fluorophore and the other a quencher. For example, the first and second labels are optionally hydrophobic fluorophores, e.g., the first label can be FITC and the second label rhodamine or coumarin (listed by way of example only; a large number of other suitable fluorophores and quenchers are known in the art).

In one kinase-based sensor, phosphorylation of the substrate triggers a conformational change in the polypeptide, where the conformational change prevents interaction of the first label and the second label or the quencher.

In one embodiment, phosphorylation of the substrate results in binding of a phosphobinder to the phosphorylated substrate, the binding of the phosphobinder preventing the interaction of the first and the second label or the quencher. Optionally, the phosphobinder is associated with one or more second caging groups, the presence of which prevents the phosphobinder from binding the phosphorylated substrate. Indeed, one aspect of the invention is simply a caged phosphobinder. The second caging groups are optionally removable under different conditions than the first caging groups preventing phosphorylation of the substrate. In one embodiment, the phosphobinder is an antibody. In other embodiments, the phosphobinder comprises an SH-2 domain, a PTB domain, a 14-3-3 domain, an FHA domain, a WD40 domain and/or a WW domain.

In another embodiment, one polypeptide comprises the substrate for the kinase and the first label. Optionally in this embodiment, the polypeptide further comprises a second label or a quencher and a phosphobinder; where the first label and the second label or the quencher do not interact when the substrate is not phosphorylated, thereby producing the first signal. Phosphorylation of the substrate results in intramolecular binding of the phosphobinder to the phosphorylated substrate, resulting in the interaction of the first label and the second label or the quencher, producing the second signal. Optionally, the one or more first caging groups are located on one or more amino acid residues involved in binding the kinase and/or on a residue that can be phosphorylated by the kinase. As with other embodiments, one of the first label and the second label or the quencher is optionally located at the N-terminus of the polypeptide and the other of the first label and the second label or the quencher at the C-terminus of the polypeptide. In this embodiment as well, one label can be a fluorophore and the other a quencher. The first and second labels can exhibit FRET.

Here as well, the phosphobinder is optionally associated with one or more second caging groups, the presence of which prevents the phosphobinder from binding the phosphorylated substrate. Optionally, the second caging groups are removable under different conditions than the first caging groups inhibiting phosphorylation of the substrate. The phosphobinder can be any of those noted above.

In one aspect, a first polypeptide comprises the substrate for the kinase and the first label while a second polypeptide comprises a second label or a quencher and a phosphobinder. The first label and the second label or the quencher do not interact when the substrate is not phosphorylated, thereby producing the first signal. Phosphorylation of the substrate results in intermolecular binding of the phosphobinder to the phosphorylated substrate, resulting in the interaction of the first label and the second label or the quencher, thereby producing the second signal. All of the features noted above, e.g., with respect to location of caging groups, labels, optional use of fluorophores and quenchers, FRET pairs, types of phosphobinders, differential removal of different caging groups, and the like, apply to this embodiment as well.

In an additional embodiment, one polypeptide comprises the substrate for the kinase, a second substrate, the first label, a third label, a fourth label or a quencher, and a phosphobinder. The substrate includes a serine, threonine, or tyrosine residue capable of being phosphorylated by the kinase. The second substrate is associated with one or more third caging groups, the presence of which prevents phosphorylation of the second substrate. The first label is located at the serine, threonine, or tyrosine residue and exhibits the first signal when the residue is not phosphorylated and the second signal when the residue is phosphorylated. The third label and the fourth label or the quencher do not interact when the second substrate is not phosphorylated, thereby producing a third signal. Phosphorylation of the second substrate results in intramolecular binding of the phosphobinder to the phosphorylated second substrate, resulting in the interaction of the third label and the fourth label or the quencher, thereby producing a fourth signal, the fourth signal being distinguishable from the first, second and third signals. Optionally, the one or more first caging groups are located on one or more amino acid residues involved in binding the kinase that phosphorylates the first substrate. The second substrate is optionally a target for the same kinase, but can be a target for a different kinase. The one or more first caging groups are optionally located on one or more amino acid residues involved in binding the kinase and/or on a residue that can be phosphorylated by the kinase. Optionally, the third caging groups preventing phosphorylation of the second substrate are removable under different conditions than the first caging groups inhibiting phosphorylation of the substrate. All of the features noted above, e.g., with respect to location of caging groups, labels, optional use of fluorophores and quenchers, FRET pairs, types of phosphobinders differential removal of different caging groups, and/or the like apply to this embodiment as well. For example, one of the third label and the fourth label or the quencher is optionally located at the C-terminus of the polypeptide and the other of the third label and the fourth label or the quencher within the polypeptide. The third and fourth labels are optionally fluorophores capable of exhibiting FRET.

The above kinase sensor example embodiments illustrate principles that can be applied to the design of other enzyme sensors, including sensors for other types of enzymes (for example, by substituting appropriate substrates, binding moieties, and the like in the above example sensors).

For any of the above embodiments, the one or more molecules can further comprise a fifth label, the fifth label exhibiting a unique fifth signal, the fifth signal being independent of the state of the substrate. For example, the fifth label can be a fluorophore, a quantum dot or the like.

Optionally, for any of the above embodiments, the one or more molecules are associated with a cellular delivery module that can mediate introduction of the sensor into a cell. For example, the cellular delivery module optionally comprises a polypeptide, e.g., a PEP-1 peptide, an amphipathic peptide (e.g., an MPG or MPG$^{\Delta NLS}$ peptide), or a cationic peptide (e.g., a homopolymer of histidine, lysine, or D-arginine) that is covalently or non-covalently associated with the one or more molecules. In one embodiment, the cellular delivery module comprises a protein transduction domain, e.g., derived from an HIV-1 Tat protein, from a herpes simplex virus VP22 protein, and/or from a Drosophila antennapedia protein. In one aspect, the protein transduction domain is a model protein transduction domain (e.g., a homopolymer of D-arginine, e.g., 8-D-Arg). As another example, the cellular delivery module associated with the one or more molecules can comprise a lipid, e.g., a fatty acid. For example, the one or more molecules can be covalently attached to one or more myristoyl groups, e.g., via a photolabile linker. Optionally, the cellular delivery module is covalently attached to the one or more molecules. For example, the covalent attachment is optionally reversible by exposure to light of a preselected wavelength. As another example, the covalent attachment is optionally a disulfide or ester linkage that is reduced or cleaved once the sensor is inside a cell.

In one aspect, the cellular delivery module is associated with one or more additional fourth caging groups, the presence of which prevents the cellular delivery module from mediating introduction of the sensor into a cell.

Optionally, the one or more molecules are associated with at least one subcellular delivery module, e.g., comprising a polypeptide, a nucleic acid, and/or a carbohydrate. For example, the subcellular delivery module can mediate localization of the sensor to a membrane, a mitochondrion, a peroxisome, a nucleus, an endoplasmic reticulum, a Golgi, a vesicle, a lysosome, an endosome, and/or a chloroplast. Thus, the subcellular delivery module optionally comprises a mitochondrial matrix-targeting sequence, a nuclear localization signal, a signal peptide, an ER retention signal, a peroxisomal targeting motif, a chloroplast stromal targeting sequence, a transmembrane domain, and/or a lipid attachment site. Optionally, the subcellular delivery module comprises a binding domain that mediates localization of the sensor by binding to a target protein. The subcellular delivery module can be covalently or non-covalently attached to the one or more molecules, e.g., a covalent attachment reversible by exposure to light of a preselected wavelength or by reduction or enzymatic cleavage within the cell. In one aspect, the subcellular delivery module is associated with one or more fifth caging groups, the presence of which prevents the subcellular delivery module from mediating subcellular localization of the sensor.

Optionally, in the embodiments herein, the caged sensor is bound to a matrix (e.g., electrostatically, covalently, directly or via linker). In one aspect, the matrix is a surface and the sensor is bound to the surface at a predetermined location within an array comprising other sensors. In one embodiment, the matrix comprises a bead (e.g., color color-coded or otherwise addressable).

For example, in one matrix embodiment, the caged sensor comprises a first oligonucleotide, the first oligonucleotide being complementary to a second oligonucleotide, the second oligonucleotide being bound to a matrix. The matrix can be, e.g., a surface and/or a bead as noted.

The invention also provides kits for making the caged sensor, e.g., comprising a substrate, a first label, one or more first caging groups, and instructions for assembling the substrate, the first label, and the first caging groups to form the caged sensor, e.g., packaged in one or more containers. In a similar kit of the invention, a first label, one or more first caging groups, and instructions for assembling the first label, the first caging groups, and a substrate supplied by a user of the kit to form the caged sensor, packaged in one or more containers, are provided.

In one aspect, systems and/or apparatus comprising the caged sensors noted above and, e.g., components such as detectors, fluid handling apparatus, sources of uncaging energy or the like are a feature of the invention.

In an additional class of embodiments, a composition comprising a caged sensor is provided, e.g., a caged binding sensor for detecting binding of a binding target by its partner or a caged sensor for localizing the partner of a binding target. The caged sensor includes one or more molecules collectively comprising a binding target and a first label. Also included are one or more first caging groups associated with the one or more molecules, the presence of the first caging groups inhibiting (e.g., preventing) the binding target from binding to its partner. The binding target and its partner are capable of a stable interaction. In one class of embodiments, a first signal exhibited by the first label when the binding target is not bound to the partner is distinguishable from a second signal exhibited by the first label when the binding target is bound to the partner. In another class of embodiments, a first signal exhibited by the first label is not affected by binding of the binding target to the partner. All of the various optional configurations and features noted for the embodiments above apply here as well, e.g., for label configurations and signal types, appropriate uncaging energies (light, heat, sonic, etc.), use of photolabile caging components, location of the probes in cells or cell extracts (and resulting compositions), use of cellular and subcellular targeting and delivery modules, protein transduction domains, kits comprising the compositions or components for making the compositions and appropriate instructions, systems and apparatus comprising the probes, and the like.

An additional class of embodiments provides a composition comprising a caged nucleic acid probe, a caged antisense nucleic acid and a target nucleic acid, a caged biomolecular analog, a caged transcription factor, a caged antibody, a caged molecular decoy, or a caged aptamer. The caged nucleic acid probe comprises at least one probe nucleic acid that has a region of complementarity to a target nucleic acid. The caged probe includes a first label, wherein a first signal exhibited by the first label when the probe nucleic acid is not bound to the target nucleic acid is distinguishable from a second signal exhibited by the first label when the probe nucleic acid is bound to the target nucleic acid. The probe also includes one or more first caging groups associated with the probe nucleic acid, the first caging groups inhibiting (e.g., preventing) the probe nucleic acid from binding to the target nucleic acid. The caged nucleic acid probe optionally comprises any appropriate nucleic acid, e.g., an oligodeoxyribonucleotide or a peptide nucleic acid. The probe nucleic acid optionally comprises a molecular beacon. The at least one probe nucleic acid optionally comprises a plurality of probe nucleic acids, e.g., a first probe nucleic acid that comprises an acceptor fluorophore and a second probe nucleic acid that comprises a donor fluorophore, whereby binding of the first and second probe nucleic acids to the target nucleic acid brings the donor and acceptor fluorophores into proximity, permitting energy transfer between them and resulting in the second signal.

The caged antisense nucleic acid comprises an antisense nucleic acid having a region of complementarity to a target nucleic acid and one or more first caging groups associated with the antisense nucleic acid. The first caging groups inhibit (e.g., prevent) the antisense nucleic acid from binding to and inactivating the target nucleic acid. The antisense nucleic acid can be an RNA, DNA, PNA, or any other appropriate molecule.

The caged biomolecular analog comprises a molecule comprising one or more nonnatural nucleotides and/or one or more nonnatural amino acids and one or more caging groups associated with the molecule. The caged biomolecular analog optionally also includes one or more natural nucleotides and/ or one or more natural amino acids The caged transcription factor includes a transcription factor and one or more first caging groups associated with the transcription factor. The first caging groups inhibit (e.g., prevent) the transcription factor from regulating transcription from a cognate promoter. Example transcription factors include transcriptional activators and transcriptional repressors, including transcription factors that include a leucine zipper motif, a helix-loop-helix motif, an HMG domain, a helix-turn-helix motif, a homeo domain, a winged helix motif, a paired box domain, and/or a TEA domain. A preferred transcription factor is one that comprises at least one zinc finger motif, e.g., a $Cys_2His_2$-type zinc finger motif.

The caged antibody includes an antibody that binds an epitope, a cellular delivery module and/or at least one subcellular delivery module associated with the antibody, and one or more first caging groups associated with the antibody. The first caging groups inhibit (e.g., prevent) the antibody from binding to the epitope. The antibody can be, e.g., a monoclonal antibody, a single-chain antibody, or the like.

The caged molecular decoy comprises a molecular decoy and one or more first caging groups associated with the molecular decoy. The molecular decoy comprises, e.g., an amino acid, a polypeptide, a nitrogenous base, a nucleoside, a nucleotide, a nucleic acid, a carbohydrate, and/or a lipid. Optionally, the decoy is a nucleic acid, e.g., a double-stranded DNA or an RNA comprising a transcription factor binding sequence, or an RNA or DNA comprising a viral assembly sequence. The molecular decoy can bind a pathogenic protein or nucleic acid (e.g., a protein or nucleic acid required for viral assembly in a cell).

The caged aptamer comprises an aptamer that, in uncaged form, binds a ligand, but has one or more first caging groups associated therewith. The first caging groups inhibit (e.g., prevent) the aptamer from binding to the ligand.

All of the features for the embodiments above apply here as well, e.g., for label configurations and signal types, appropriate uncaging energies (light, heat, sonic, etc.), use of photolabile caging components, location of the caged molecules in cells or cell extracts (and resulting compositions), use of cellular and subcellular targeting and delivery modules, protein transduction domains, kits comprising the caged molecules or components for making the caged molecules and appropriate instructions, systems and apparatus comprising the caged molecules, and the like.

Another class of embodiments provides a cell comprising a caged ribozyme or a caged antibody. The caged ribozyme comprises a ribozyme and one or more first caging groups associated with the ribozyme. The first caging groups inhibit (e.g., prevent) the ribozyme from exhibiting an enzymatic activity. The caged antibody includes an antibody that binds an epitope and one or more first caging groups associated with the antibody. The first caging groups inhibit (e.g., prevent) the antibody from binding to the epitope. The antibody is optionally a monoclonal antibody, a single-chain antibody, or the like.

All of the features for the embodiments above apply here as well, e.g., for label configurations and signal types, appropriate uncaging energies (light, heat, sonic, etc.), use of photolabile caging components, use of cellular and subcellular targeting and delivery modules, protein transduction domains, kits comprising the caged molecules or components for making the caged molecules and appropriate instructions, systems and apparatus comprising the cell, and the like.

In an additional class of embodiments, a composition comprising a labeled modulator is provided. The modulator includes a modulator of an activity of a protein and a first label. A first signal exhibited by the first label when the modulator is not bound to the protein is distinguishable from a second signal exhibited by the first label when the modulator is bound to the protein. For example, the modulator can be an activator or an inhibitor (e.g., a cleavable inhibitor). The labeled modulator can be, e.g., a small molecule, a polypeptide, nucleic acid, or the like. The protein affected by the modulator can be, e.g., an enzyme (as noted above), a channel protein, a transporter, or the like. In one additional example, the enzyme is protein kinase C and the modulator is the inhibitor HB89. Similarly, any or all of the various label configurations noted above apply to this embodiment as well (e.g., the first label can be optical or fluorescent, etc.). Any of the caging groups and configurations noted above can be associated with or applied to the modulator to regulate activity of the modulator. Compositions comprising the modulator with and/or in cells, or cell components, apply to this embodiment as well. The use of additional labels in a manner similar to those noted for the above embodiments applies to this class of embodiments in a manner similar to that noted above. Similarly, the modulator can be associated with a cellular or subcellular delivery module as noted above (e.g., a protein transduction domain). Components and features for localizing the modulators on matrices (e.g., arrays) as with the embodiments above is also a feature of the invention. Systems and apparatus, e.g., similar to those noted above, that also include the labeled modulator are a feature of the invention.

As with the embodiments above, kits for making the labeled modulator are a feature of this embodiment, e.g., kits that include a modulator, a first label, and instructions for assembling the modulator and the first label to form the labeled modulator, packaged in one or more containers. In one aspect, a kit for making the labeled modulator comprising a first label and instructions for assembling the first label and a modulator supplied by a user of the kit to form the labeled modulator, packaged in one or more containers is provided. In another, a kit for making the caged labeled modulator comprising a modulator, a first label, one or more first caging groups, and instructions for assembling the modulator, the first label, and the first caging groups to form the caged labeled modulator, packaged in one or more containers is provided. In yet another, a kit for making the caged labeled modulator comprising a first label, one or more first caging groups, and instructions for assembling the first label, the first caging groups, and a modulator supplied by a user of the kit to form the caged labeled modulator, packaged in one or more containers is provided.

In an additional class of embodiments, the invention provides a composition comprising at least a first caged component and a second caged component. The first and second caged components can be uncaged by exposure to energy of the same type. Alternatively, the first caged component can be uncaged by exposure to energy of a first type and the second caged component can be uncaged by exposure to energy of a second type different from the first type. The various uncaging energies for the first and second types can be the same general type (e.g., where the energy of the first type is light of a first wavelength and the energy of the second type is light of a second wavelength) or they can be of different general types (e.g., light and heat or light and sonication energy). Similarly, the composition optionally comprises three or more caged components. The caged components can be, e.g., a caged sensor, a caged nucleic acid probe, a caged modulator, a caged interfering RNA, a caged antisense nucleic acid, a caged ribozyme, a caged biomolecular analog, a caged transcription factor, a caged molecular decoy, a caged antibody, a caged aptamer, a caged small molecule, a caged nucleoside triphosphate, a caged chelating agent, and/or a caged metal ion. The compositions can be formulated in any of the various states noted above, e.g., in cells, cell compartments, cell extracts, systems and devices and kits.

Another general class of embodiments provides a composition comprising a caged component, which caged component comprises a component, one or more first caging groups associated with the component, and a cellular delivery module associated with the component, which cellular delivery module can mediate introduction of the component into a cell. The caged components can be, e.g., any of those described or noted herein, e.g., a caged sensor (e.g., an enzyme or binding sensor), a caged nucleic acid probe, a caged modulator, a caged antisense nucleic acid, a caged ribozyme, a caged biomolecular analog, a caged transcription factor, a caged molecular decoy, a caged antibody, a caged aptamer, a caged interfering RNA or RNAi-based sensor, a caged polypeptide, a caged nucleic acid, a caged lipid, a caged carbohydrate, a caged small molecule, a caged metal ion, a caged nucleotide (e.g., a caged nucleoside triphosphate or caged cAMP), a caged chelating agent, a caged fluorescent dye, a caged second messenger, and/or a caged neurotransmitter.

In one class of embodiments, the cellular delivery module comprises a polypeptide, e.g., a PEP-1 peptide, an amphipathic peptide (e.g., an MPG or MPG$^{\Delta NLS}$ peptide), or a cationic peptide (e.g., a homopolymer of histidine, lysine, or D-arginine) that is covalently or non-covalently associated with the one or more molecules. In one embodiment, the cellular delivery module comprises a protein transduction domain, e.g., derived from an HIV-1 Tat protein, from a herpes simplex virus VP22 protein, and/or from a *Drosophila* antennapedia protein. In one aspect, the protein transduction domain is a model protein transduction domain (e.g., a homopolymer of D-arginine, e.g., 8-D-Arg). In another class of embodiments, the cellular delivery module associated with the component comprises a lipid, e.g., a fatty acid. For example, the component can be covalently attached to one or more myristoyl groups, e.g., via a photolabile linker.

Optionally, the cellular delivery module is covalently attached to the component. For example, the covalent attachment is optionally reversible by exposure to light of a preselected wavelength. As another example, the covalent attachment is optionally a disulfide or ester linkage that is reduced or cleaved once the sensor is inside a cell. In one aspect, the cellular delivery module is associated with one or more second caging groups, the presence of which prevents the cellular delivery module from mediating introduction of the component into a cell.

Essentially all of the features noted above, e.g., for various caged components, apply to this embodiment as well, as relevant. For example, the composition optionally also includes a cell, e.g., a cell comprising the caged component, and systems comprising the composition are also a feature of the invention.

In an additional class of embodiments, methods for using any or all of the above compositions in an appropriate assay are provided. Similarly, methods for making any of the above compositions (e.g., by coupling caging groups to the relevant moiety and, optionally, putting the resulting molecule into a cell) are provided.

In a first general class of embodiments, a method of assaying an activity of an enzyme is provided. The method includes contacting the enzyme and a caged sensor, by introducing the caged sensor into a cell. The caged sensor comprises one or more molecules collectively comprising a substrate for the enzyme and a first label, and one or more caging groups associated with the one or more molecules. The substrate is in a first state on which the enzyme can act, thereby converting the substrate to a second state. A first signal exhibited by the first label when the substrate is in its first state is distinguishable from a second signal exhibited by the first label when the substrate is in its second state. The caging groups inhibit the enzyme from acting upon the substrate. The assay is initiated by exposing the enzyme and the caged sensor to uncaging energy of a first type, whereby exposure to the uncaging energy frees the first component from inhibition by the first caging groups. The activity of the enzyme is then assayed as appropriate to the enzyme, e.g., by methods known in the art. Typically, the first and/or the second signal is detected.

A second general class of embodiments also provides a method of assaying an activity of an enzyme. The method includes contacting the enzyme and a caged sensor. The caged sensor comprises one or more molecules collectively comprising a substrate for the enzyme and a first label, and one or more caging groups associated with the one or more molecules. The substrate is in a first state on which the enzyme can act, thereby converting the substrate to a second state. The first state is not converted to the second state by cleavage by the enzyme. A first signal exhibited by the first label when the substrate is in its first state is distinguishable from a second signal exhibited by the first label when the substrate is in its second state. The caging groups inhibit the enzyme from acting upon the substrate. The assay is initiated by exposing the enzyme and the caged sensor to uncaging energy of a first type, whereby exposure to the uncaging energy frees the first component from inhibition by the first caging groups. The activity of the enzyme is then assayed as appropriate to the enzyme, e.g., by methods known in the art. Typically, the first and/or the second signal is detected. The method optionally includes contacting the enzyme and the caged sensor by introducing the caged sensor into a cell.

For either of these related general classes of embodiments, any of the above embodiments can be applied as well to the extent they are relevant. For example, exposing the enzyme and the caged sensor to uncaging energy of a first type optionally includes sonicating the enzyme and the caged sensor or exposing the enzyme and the caged sensor to light of a first wavelength. This exposure can be addressable, e.g., the enzyme and the caged sensor can be exposed to light of a first wavelength by exposing one or more preselected areas (e.g., wells in a microtiter plate, in any of the well configurations noted herein; or one or more channels in a microfluidic chip) comprising the relevant components to the light.

The preselected areas can be simultaneously or serially exposed to the uncaging energy. For example, the one or more preselected areas can comprise a plurality of the wells of a multiwell plate, and exposing the preselected areas to the light can comprise exposing the plurality of wells to the light simultaneously (similarly, sonication or thermal energy can be applied to one or more wells in series or simultaneously). Similarly, the one or more preselected areas can comprise a plurality of the channels of a microfluidic chip, wherein exposing the preselected areas to the light comprises exposing the plurality of channels to the light simultaneously. In another embodiment, the one or more preselected areas comprise one or more spots of a microarray. For example, the one or more preselected areas can comprise a plurality of the spots of the microarray, wherein exposing the preselected areas to the light comprises exposing the plurality of spots to the light simultaneously. In another embodiment, the one or more preselected areas comprise one or more regions of a cell, a tissue, or a body of an organism. Here the uncaging energy can be, e.g., light, heat, or other energy delivered by conventional techniques such as during MRI, PET or CAT scanning or by a laser emitting an appropriate wavelength, e.g., a laser coupled to a fiber optic delivery system.

Exposing the enzyme and the caged sensor to light of a first wavelength optionally comprises exposing the enzyme and the caged sensor to light such that the intensity of the light and the duration of exposure to the light are controlled so that a first portion of the caged first component (which can be a selected amount) is uncaged and a second portion of the caged first component remains caged. Put another way, the uncaging rate can be controlled. Furthermore, the uncaging step can be repeated until the components are depleted, providing multiple controlled reaction initiations for one set of reagents.

A plurality of caged components can be used in the assay. For example, the method can include contacting the enzyme and a second caged component comprising one or more second caging groups and exposing the second caged component to uncaging energy of a second type, whereby exposure to the uncaging energy frees the second component from inhibition by the second caging groups. The second caged component can, e.g., be required for initiation of the assay or for detection of the activity of the enzyme. The second caged component can be, e.g., a nucleoside triphosphate, ATP, a metal ion, a polypeptide (e.g., a phosphobinder or an antibody), a nucleic acid (e.g., a nucleic acid probe or an aptamer), a carbohydrate, and/or a lipid. As yet another example, the additional component that is caged can be required for termination of the assay (e.g., an inhibitor or a chelating agent, e.g., EDTA, EGTA, or citrate). As yet another example, the additional component can comprise a modulator, e.g., an activator or inhibitor of the enzyme or another enzyme involved or thought to be involved in the same pathway (as just one example, a caged inhibitor can be uncaged, followed by uncaging of a caged sensor). The methods thus allow initiation, detection, modulation and/or termination of the reaction to be conveniently and precisely controlled, temporally and/or spatially, since the various caging groups optionally respond to different uncaging conditions (e.g., different wavelengths of uncaging light, pH, temperature, etc.). Using a plurality of caged components can also permit multiplexing of enzyme assays. For example, the plurality of caged components can include a second sensor for detecting activity of a second enzyme. (Optionally, a third, fourth, etc. caged sensor can also be used).

The methods can use any of the sensor configurations, enzymes, modulators, and/or signal detection steps as noted above. The methods can include introducing any of the components noted above into cells (or into cell compartments or other features), or into tissues or organisms, or producing cell lysates, or the like. Contacting the enzyme with one or more reagents can include introducing the first caged component into an organism, or into serum, plasma, intercellular fluid, etc. The method is applicable to biochemical assays, cell lysate assays (prepared before or after addition of the first component), cell assays, organism assays or the like. Benefits of the methods include improved quantification, real-time results, and in vitro assay to organism assay translation.

In an additional class of embodiments, methods of assaying an intermolecular association between a first molecule and a second molecule that are capable of a stable interaction are provided. In the methods, the first and second molecules are contacted, wherein one or more caging groups are associated with at least the first molecule (and optionally the second). The caging groups prevents the association of the first and second molecules. The assay is initiated by exposing the first and second molecules to uncaging energy, whereby exposure to the uncaging energy frees the first and/or second molecule from inhibition by the caging groups. The association between the first and second molecules is then assayed. All of the above optional method variations apply to this method as well. Further, the various composition components noted above can be adapted for use in this method, as appropriate.

In an additional class of embodiments, methods of detecting a target nucleic acid are provided. In this class of methods, the target nucleic acid and at least one caged probe nucleic acid are contacted together. The caged probe nucleic acid includes a probe nucleic acid having one or more caging groups associated with the probe nucleic acid. The probe nucleic acid has a region of complementarity to a first strand of the target nucleic acid. The caging groups prevent the probe nucleic acid from binding to the first strand of the target nucleic acid. The method also includes exposing the caged probe nucleic acid and the target nucleic acid to uncaging energy, whereby exposure to the uncaging energy frees the probe nucleic acid from inhibition by the caging groups and permits the probe nucleic acid to bind to the first strand of the target nucleic acid. A binding-dependent signal from the probe nucleic acid is detected. All of the above optional method variations apply to this method as well. Further, the various composition components noted (particularly the caged nucleic acid embodiments) above can be adapted for use in this method, as appropriate.

In an additional related class of embodiments, methods of selectively inhibiting expression of a target nucleic acid in a cell are provided. In the methods, a caged antisense nucleic acid is introduced into the cell, the caged antisense nucleic acid comprising an antisense nucleic acid comprising a region of complementarity to the target nucleic acid and one or more caging groups associated with the antisense nucleic acid. The presence of the caging groups prevents the antisense nucleic acid from binding to and inactivating the target nucleic acid. The cell is exposed to uncaging energy, whereby exposure to the uncaging energy frees the antisense nucleic acid from inhibition by the caging groups and permits the antisense nucleic acid to inactivate the target nucleic acid. All of the above optional method variations apply to this method as well. For example, exposing the cell to uncaging energy optionally comprises exposing the cell to light of a first wavelength. Further, the various composition components noted above can be adapted for use in this method, as appropriate.

In yet an additional related class of embodiments, methods of activating a ribozyme are provided. In the methods, a caged ribozyme is provided, the caged ribozyme comprising a ribozyme and one or more caging groups. The presence of the caging groups prevents the ribozyme from exhibiting an enzymatic activity. The caged ribozyme is introduced into a cell. Exposing the caged ribozyme to uncaging energy frees the ribozyme from inhibition by the caging groups and permits the ribozyme to exhibit the enzymatic activity. All of the above optional method variations apply to this method as well. Further, the various composition components noted above (e.g., with respect to ribozymes) can be adapted for use in this method, as appropriate.

In still an additional related class of embodiments, methods of regulating the expression of a gene comprising a first promoter in a cell are provided. In the methods, a caged transcription factor is introduced into the cell. The caged transcription factor comprises a transcription factor capable of regulating transcription from the first promoter, and one or more caging groups associated with the transcription factor. The presence of the caging groups prevents the transcription factor from regulating transcription from the first promoter. Exposing the cell to uncaging energy frees the transcription factor from inhibition by the caging groups and permits the transcription factor to regulate transcription from the first promoter. All of the above optional method variations apply to this method as well. Further, the various composition components noted above (e.g., with respect to transcription factors) can be adapted for use in this method, as appropriate.

In yet an additional related class of embodiments, methods of regulating transcription of a gene are provided. The methods include introducing a caged direct transcriptional modulator into a cell, wherein the caged transcriptional modulator comprises a transcriptional modulator and one or more caging groups. The presence of the caging groups prevents the transcriptional modulator from affecting expression of the gene. Exposing the cell to uncaging energy frees the transcriptional modulator from inhibition by the caging groups and permits the transcriptional modulator to regulate transcription of the gene. All of the above optional method variations apply to this method as well. Further, the various composition components noted above (e.g., with respect to transcription factors) can be adapted for use in this method, as appropriate.

In an additional class of embodiments, methods of using a labeled modulator are provided. In the methods a protein and the labeled modulator are contacted. The protein has an activity and the labeled modulator comprises a modulator of the activity and a first label. A first signal exhibited by the first label when the modulator is not bound to the protein is distinguishable from a second signal exhibited by the first label when the modulator is bound to the protein. The first and/or second signal is detected. Optionally, the labeled modulator further includes one or more caging groups associated with the labeled modulator, where the presence of the caging groups prevents the labeled modulator from binding to the protein and/or affecting the activity of the protein. Optionally, the methods further includes exposing the protein and the caged labeled modulator to an uncaging energy, whereby exposure to the uncaging energy frees the labeled modulator from inhibition by the caging groups and permits the labeled modulator to bind to and affect the activity of the protein. All of the above optional method variations apply to this method as well. Further, the various composition components noted above (e.g., with respect to caged modulators) can be adapted for use in this method, as appropriate.

In an additional class of embodiments, methods of using a caged antibody are provided. In the methods, a caged antibody is introduced into a cell. The caged antibody comprises an antibody that binds an epitope and one or more caging groups. The presence of the caging groups prevents the antibody from binding to the epitope. Exposing the cell to uncaging energy frees the antibody from inhibition by the caging groups and permits the antibody to bind the epitope. All of the above optional method variations apply to this method as well. Further, the various composition components noted above (e.g., with respect to caged antibodies) can be adapted for use in this method, as appropriate.

In an additional class of embodiments, methods of using a plurality of caged components are provided. In the methods, at least a first caged component and a second caged component are contacted. The first caged component is uncaged by exposure to uncaging energy of a first type and the second caged component is uncaged by exposure to uncaging energy of a second type different from the first type. The caged components are exposed to uncaging energy of the first and second type. All of the above optional method variations apply to this method as well. Further, the various composition components noted above (e.g., with pluralities of caged components) can be adapted for use in this method, as appropriate.

In another class of embodiments, the invention provides methods of determining whether a test compound affects an activity of a GPCR. The methods can be used, for example, to screen for compounds affecting (directly or indirectly) the activity of the GPCR. In the methods, a cell comprising the GPCR is provided, and at least one caged component is introduced into the cell. The caged component comprises a component and one or more caging groups associated with the component. The cell and the test compound are contacted, and the cell is exposed to uncaging energy, which exposure to frees the component from the caging groups. A signal that provides an indication of the activity of the GPCR is detected from the component. Comparison with a signal from a like component in a cell comprising the GPCR and the component but not treated with the test compound, for example, can indicate whether the test compound increases, decreases, or does not affect activity of the GPCR.

In an additional aspect, methods of detecting modification of a substrate of interest are provided. In the methods, an initial substrate is introduced into a cell. The initial substrate is caged by association with one or more caging moiety that inhibits modification of the substrate in the cell. The initial substrate is uncaged in the cell by dissociating part or all of the caging moiety from the substrate to provide an uncaged substrate of interest, or by changing the conformation of the initial substrate or caging moiety, or any combination thereof. The uncaged substrate of interest is permitted to be modified in the cell and the resulting modified substrate is released from the cell, or fixed in the cell. One or more modification detection reagents is contacted to the modified substrate, resulting in a detectable signal, which is detected.

In several embodiments, the modified substrate is captured on one or more capture substrate prior to detecting the detectable signal. For example, the modified substrate optionally comprises one or more affinity moiety and the capture substrate optionally comprises one or more affinity capture moiety. The modified substrate is contacted to the capture substrate, whereby the affinity capture moiety binds the affinity moiety. The affinity moiety can include any of those biological or chemical or physical moieties that are commonly used for binding a cognate molecule, such as avidin, biotin, nucleic acids, antibodies, antibody ligands, polypeptides, polypeptide ligands, proteins, protein ligands, His tags, His tag binding moieties, Glutathione, GST, HA tags, a nucleic acid, or the like. The capture substrate can be any material comprising a surface suitable for attaching or complexing affinity capture reagents, e.g., microwell plates, beads, affinity columns, microscope slides, or the like.

The initial substrate is typically introduced into the cell by co-transfecting, into the cell, the initial substrate with one or more vector that comprises or encodes a substrate modification component. The substrate modification component modifies the uncaged substrate of interest. For example, the substrate modification component can include a catalytic molecule, such as an enzyme, a ribozyme, an oxidoreductase, a transferase, a hydrolase, a lyase, a ligase, an isomerase, a kinase, a phosphatase, a GTPase, an ATPase, a phosphodiesterase, a luciferase, an acetylase, a glycosylase, a ubiquitin-conjugating enzyme, a hydrogenase, a polymerase, a peroxidase, a protease, and/or a caspase. Similarly, the uncaged substrate of interest can be any appropriate substrate for such a catalytic molecule, e.g., an enzyme substrate, ribozyme substrate, kinase substrate, etc. The substrate of interest can be a specific substrate (acted on only by a single type of catalytic molecule), or a generic substrate (acted on by more than one member of a class of catalytic molecules).

The vector that is co-transfected with the substrate can include a nucleic acid that encodes the substrate modification component. Alternately, the vector can include the substrate modification component, e.g., the catalytic molecule itself, e.g., as a component of a vector system (e.g., as part of a viral or other vector). Use of vectors is optional in the invention, in that the cell can endogenously comprise the substrate modification component of interest. The substrate can also (additionally or alternatively) be associated with a cellular delivery agent to enhance transport of the substrate into the cell. Examples of appropriate cellular delivery agents include polypeptides, PEP-1 peptides, amphipathic peptides (e.g., an MPG or MPG$^{ANLS}$ peptide), cationic peptides, homopolymers of D-arginine, homopolymers of histidine, homopolymers of lysine, protein transduction domains, HIV-1 Tat proteins, herpes simplex virus VP22 proteins, Drosophila antennapedia proteins, lipofectamine, and the like.

Uncaging the substrate can include exposing the cell to an uncaging energy or substance, e.g., light, a change in pH, a change in heat, sonic energy, or the like. Once the substrate is uncaged, it can be modified in the cell, e.g., by incubating the cell with the substrate for between about 5 seconds and about 240 minutes or more after uncaging the substrate prior to said releasing or fixing. Releasing the modified substrate can typically include lysing the cell, but can also include other release mechanisms. For example, releasing the substrate can alternately include permitting the cell to release the substrate through endogenous mechanisms (e.g., exocytosis), or by permitting the substrate to be complexed in the cell with a cell transport molecule that facilitates release of the substrate from the cell.

The detection reagent can be any moiety that facilitates detection of the modified substrate. Examples include phosphobinders, antibodies that specifically bind to the modified substrate, nucleic acids that specifically bind to the modified substrate, aptamers that specifically bind to the modified substrate, micro or nano particles that bind to the modified substrate, or a combination thereof. The signal that is produced is detected by the appropriate method, e.g., performing a homogeneous assay, a heterogeneous assay, FRET, Q-FRET, TR-FRET, and/or fluorescence polarization. In several typical embodiments, the detector is an optical detector that detects an optically detectable signal. For example, in one typical embodiment, the detection reagent comprises a detection reagent label comprising a donor or acceptor moiety, and the modified substrate comprises a substrate label comprising a donor or acceptor moiety. Binding of the detection reagent to the modified substrate results in an increase or decrease in signal from the detection reagent label or the substrate label, or both. In one case, the donor or acceptor moiety on the detection reagent label transfers energy to the substrate label, or the substrate label transfers energy to the detection reagent label, in a proximity dependent manner.

These methods can also be adapted to provide a screen to identify modulators of the substrate modification component (e.g., modulators of one or more activity of the various catalytic molecules noted above). In the methods, one or more actual or potential modulator of a substrate modification component is added to the cell. Whether or to what extent the actual or potential substrate modulator modulates an activity of the substrate modification component on the uncaged substrate of interest is then determined, e.g., by comparison to a control experiment that is performed in an essentially similar fashion, except that either no modulator or a control modulator is added to the cell. Typically, the actual or potential modulator is incubated in the cell for between about 0.5 hours and about 72 hours prior to uncaging the substrate.

The cell can be treated in an appropriate fashion to permit use of the cell in any currently available system of interest, e.g., to provide for addition of any reagents, detection of signals, or the like. In one typical example, the cell is treated with trypsin and seeded into a microwell plate prior to uncaging the initial substrate. Subsequent operations can be performed in the microwell plate, e.g., where the plate comprises an affinity capture substrate, e.g., with the affinity moieties coated on the plate, or coated on beads that are added to the plate. Similarly, the cells can be flowed through microfluidic systems and signals detected there from using available microfluidic devices or systems.

Compositions, systems and kits for practicing these methods are also a feature of the invention. For example, the invention includes a composition that includes a cellular delivery agent, a caged substrate and a vector that comprises or encodes a substrate modification component. The substrate modification component modifies an uncaged substrate corresponding to the caged substrate. For example, the caged or uncaged substrate can be an enzyme substrate that comprises a target site that is bound or modified by the substrate modification component, as well as an affinity capture component. The vector, substrate modification component and cellular delivery agent can be any of those noted above with respect to the various methods of the invention. The composition can, of course, also include a cell that permits entry of the cellular delivery agent.

Similarly, in one aspect, the invention includes systems for practicing the methods herein. For example, a system of the invention includes an affinity capture substrate, and a cell or cell lysate comprising a modified enzyme substrate comprising an affinity capture moiety that can be specifically bound to the affinity capture substrate. The modified enzyme substrate comprises a modification detection site that indicates whether a substrate modification component has acted upon the substrate. The system also includes a modification detection reagent that specifically binds to the modification detection site, where binding of the modification detection reagent to the modified substrate produces a detectable signal. A detector that detects the detectable signal during operation of the system is also typically a feature of the invention.

The affinity capture substrate can include, e.g., a microwell plate, a bead, an affinity column, a microscope slide, or any other available substrate that can be functionalized by addition of an affinity capture reagent. The affinity capture reagent and modification detection reagent is any of those noted above. The detector can be any detector with a suitable signal receiver that can receive the detectable signal. Typical detectors include microscopes, CCD arrays, cameras, spectrophotometers, and/or any combination thereof. The system can be configured for detection of one or more activity of one or more actual or potential modulators of enzyme activity prior to detection by the modification detection reagent.

Similarly, a related or additional system of the invention includes a cell comprising a caged substrate of interest and a modification component, an actual or potential modulator of the modification component, a source of uncaging energy, a cell lysis or fixation module, a reporter that detects modifications to the substrate of interest, and a detector that detects a signal from the reporter. The system also includes a computer that includes system memory or computer readable media comprising system instructions that direct the system to: incubate the cell with the actual or potential modulator for a user selected period of time, uncage the caged substrate of interest by exposing the cell to the source of uncaging energy for a selected period of time, incubate the resulting energy-exposed cell that comprises a resulting uncaged substrate of interest for a user selected period of time, lyse or fix the cell with the cell lysis or fixation module, contact the resulting fixed cell or cell lysate with the reporter, and detect the signal from the reporter.

Kits comprising an affinity capture substrate, a caged substrate comprising an affinity capture moiety, and detection reagent that detects one or more modification to the caged substrate when in uncaged form are also a feature of the invention. Such kits can include instructional materials for using the other components of the kit, e.g., to practice any method herein, containers for holding kit components, suitable packaging components, or the like.

Any or all of the above compositions can be used singly or in combination, depending on the relevant assay. The above methods can be combined or practiced in tandem, and the methods can use the compositions, systems and/or apparatus noted above, as appropriate. Many additional aspects of the invention are discussed below.

BRIEF DESCRIPTION OF THE DRAWINGS

FIG. 19 schematically illustrates caging a sensor by covalent coupling of a photolabile group.

FIG. 36 schematically depicts uncaging a smaller region within a well of a microtiter plate. Panel A depicts cells (white stars) grown on the bottom of the well. Panel B depicts light exposure of a portion of the well (boxed area), which uncages a caged molecule inside the cells. At the same time, detection of a signal from the same portion of the well (from the cells containing the uncaged molecule, represented by black stars) is performed.

DEFINITIONS

Figure 1:
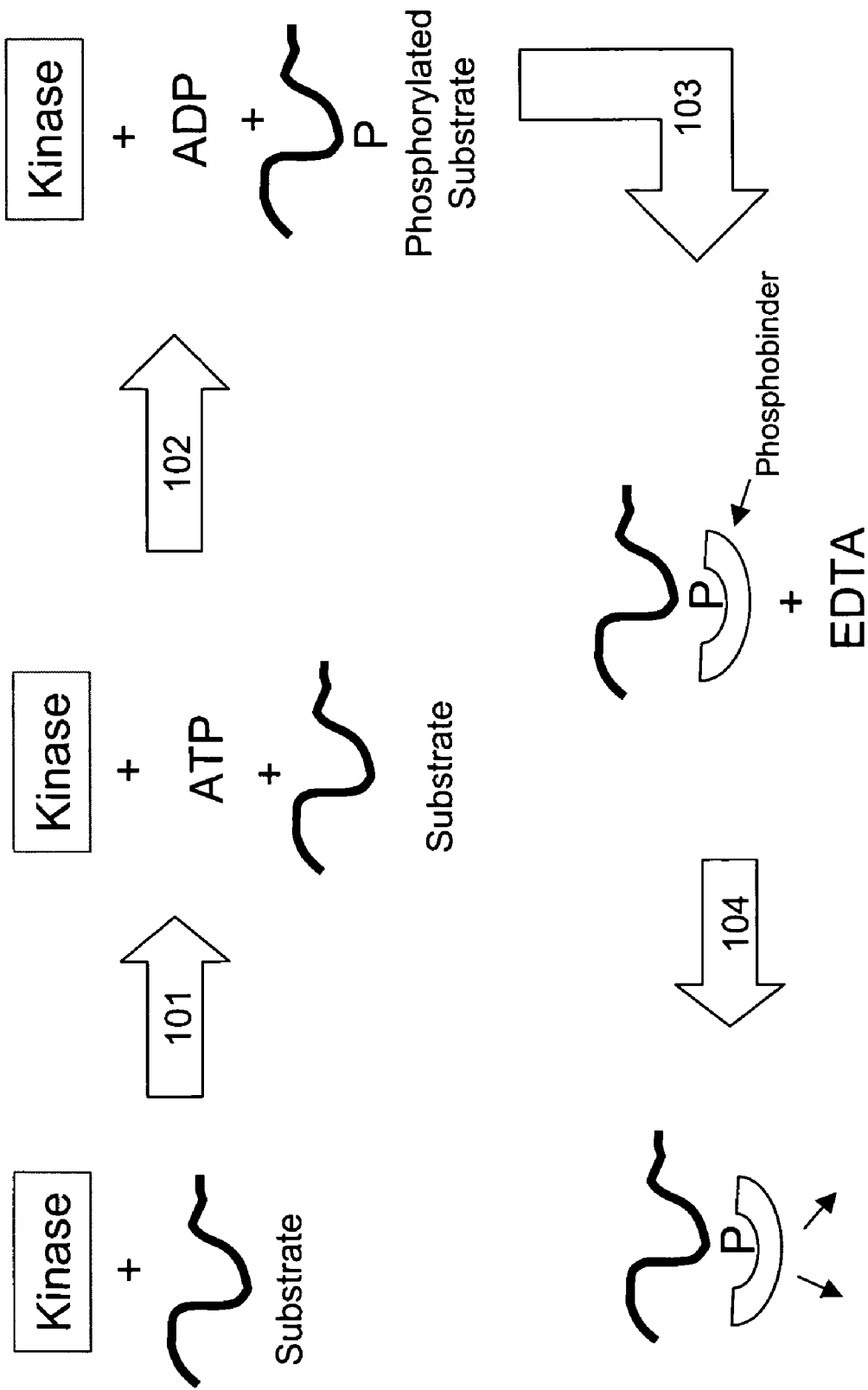
FIG. 1 schematically depicts a standard kinase assay in which the reaction is initiated by adding ATP.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an," and "the" include plural referents unless the context clearly dictates otherwise. Thus, for example, reference to "a protein" includes a plurality of proteins, reference to a "cellular delivery module" includes a plurality of cellular delivery modules, reference to "a cell" includes mixtures of cells, and the like.

An "aptamer" is a nucleic acid capable of interacting with a ligand. An aptamer can be, e.g., a DNA or RNA, and can be e.g. a chemically synthesized oligonucleotide. The ligand can be any natural or synthetic molecule, including, but not limited to, a resin, metabolites, nucleosides, nucleotides, drugs, toxins, transition state analogs, peptides, lipids, proteins, amino acids, nucleic acid molecules, hormones, carbohydrates, receptors, cells, viruses, bacteria and others. Interaction with a nucleic acid ligand includes interactions other than complementary base pairing along the length of the aptamer and the nucleic acid ligand.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see *Fundamental Immunology*, W. E. Paul, ed., Raven Press, N.Y. (1999), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include multiple or single chain antibodies, including single chain Fv (sFv or scFv) antibodies in which a variable heavy and a variable light chain are joined together (directly or through a peptide linker) to form a continuous polypeptide.

The activity of an enzyme can be "assayed," either qualitatively (e.g., to determine if the activity is present) or quantitatively (e.g., to determine kinetic and/or thermodynamic constants of the reaction). Similarly, an intermolecular association (e.g., a binding reaction between two molecules) can be "assayed," either qualitatively (e.g., to determine if the association occurs) or quantitatively (e.g., to determine kinetic and/or thermodynamic constants of the reaction, e.g., a dissociation constant).

A "caging group" is a moiety that can be employed to reversibly block, inhibit, or interfere with the activity (e.g., the biological activity) of a molecule (e.g., a polypeptide, a nucleic acid, a small molecule, a drug, etc.). The caging groups can, e.g., physically trap an active molecule inside a framework formed by the caging groups. Typically, however, one or more caging groups are associated (covalently or noncovalently) with the molecule but do not necessarily surround the molecule in a physical cage. For example, a single caging group covalently attached to an amino acid side chain required for the catalytic activity of an enzyme can block the activity of the enzyme. The enzyme would thus be caged even though not physically surrounded by the caging group. Caging groups can be, e.g., relatively small moieties such as carboxyl nitrobenzyl, 2-nitrobenzyl, nitroindoline, hydroxyphenacyl, DMNPE, or the like, or they can be, e.g., large bulky moieties such as a protein or a bead. Caging groups can be removed from a molecule, or their interference with the molecule's activity can be otherwise reversed or reduced, by exposure to an appropriate type of uncaging energy and/or exposure to an uncaging chemical, enzyme, or the like.

A "photoactivatable" or "photoactivated" caging group is a caging group whose blockage of, inhibition of, or interference with the activity of a molecule with which the photoactivatable caging group is associated can be reversed or reduced by exposure to light of an appropriate wavelength. For example, exposure to light can disrupt a network of caging groups physically surrounding the molecule, reverse a noncovalent association with the molecule, trigger a conformational change that renders the molecule active even though still associated with the caging group, or cleave a photolabile covalent attachment to the molecule, etc.

A "photolabile" caging group is one whose covalent attachment to a molecule is reversed (cleaved) by exposure to light of an appropriate wavelength. The photolabile caging group can be, e.g., a relatively small moiety such as carboxyl nitrobenzyl, 2-nitrobenzyl, nitroindoline, hydroxyphenacyl, DMNPE, or the like, or it can be, e.g., a relatively bulky group (e.g. a macromolecule, a protein) covalently attached to the molecule by a photolabile linker (e.g., a polypeptide linker comprising a 2-nitrophenyl glycine residue).

A "cellular delivery module" or "cellular delivery agent" is a moiety that can mediate introduction into a cell of a molecule with which the module is associated (covalently or noncovalently).

An "enzyme" is a biological macromolecule that has at least one catalytic activity (i.e., that catalyzes at least one chemical reaction). An enzyme is typically a protein, but can be, e.g., RNA. Known protein enzymes have been grouped into six classes under the Enzyme Commission classification scheme (see, e.g. the Commission's internet website at prowl-.rockefeller.edu/enzyme/enzyme.htm), namely, oxidoreductase, transferase, hydrolase, lyase, ligase, or isomerase. The activity of an enzyme can be "assayed," either qualitatively (e.g., to determine if the activity is present) or quantitatively (e.g., to determine kinetic and/or thermodynamic constants of the reaction).

An "epitope" is the specific region of an antigenic molecule that binds to an antibody.

The term "eukaryote" refers to organisms belonging to the phylogenetic domain Eucarya such as animals (e.g., mammals, insects, reptiles, birds, etc.), ciliates, plants, fungi (e.g., yeasts, etc.), flagellates, microsporidia, protists, etc. Additionally, the term "prokaryote" refers to non-eukaryotic organisms belonging to the Eubacteria (e.g., *Escherichia coli*, *Thermus thermophilus*, etc.) and Archaea (e.g., *Methanococcus jannaschii*, *Methanobacterium thermoautotrophicum*, *Halobacterium* species, etc.) phylogenetic domains.

"Expression of a gene" or "expression of a nucleic acid" means transcription of DNA into RNA (optionally including modification of the RNA, e.g., splicing), translation of RNA into a polypeptide (possibly including subsequent modification of the polypeptide, e.g., post-translational modification), or both transcription and translation, as indicated by the context.

The term "gene" is used broadly to refer to any nucleic acid associated with a biological function. Thus, genes include coding sequences and/or the regulatory sequences required for their expression. The term "gene" applies to a specific genomic sequence as well as to a cDNA or an MRNA encoded by that genomic sequence. Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one which regulates transcription in a specific tissue type or cell type, or types.

A "label" is a moiety that facilitates detection of a molecule. Common labels in the context of the present invention include fluorescent, luminescent, and/or colorimetric labels. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "modulator" enhances or inhibits an activity of a protein (e.g., a catalytic activity of an enzyme), either partially or completely. An "activator" enhances the activity (whether moderately or strongly). An "inhibitor" inhibits the activity (e.g., an inhibitor of an enzyme attenuates the rate and/or efficiency of catalysis), whether moderately or strongly. A modulator can be, e.g., a small molecule, a polypeptide, a nucleic acid, etc.

A "molecular beacon" (MB) is an oligonucleotide or PNA which, under appropriate hybridization conditions (e.g., free in solution), self-hybridizes to form a stem and loop structure. The MB has a label and a quencher at the termini of the oligonucleotide or PNA; thus, under conditions that permit intra-molecular hybridization, the label is typically quenched (or otherwise altered) by the quencher. Under conditions where the MB does not display intra-molecular hybridization (e.g., when the loop is bound to a target nucleic acid), the MB label is unquenched.

A "molecular decoy" is a molecule that binds a protein that is ordinarily intended for another binding target. For example, a nucleic acid comprising a TAR sequence (an HIV sequence that binds HIV TAT protein) acts as a TAT decoy, while sequences comprising RRE sequences (a sequence of HIV that binds REV protein) act as a REV decoy. Similarly, sequences comprising viral (e.g., HIV) packaging sites act as decoys for viral (e.g., HIV) packaging elements.

A nucleic acid that is "nuclease resistant" or "resistant to nuclease activity" is cleaved more slowly under typical reaction conditions for a given nuclease (e.g., a 5' to 3' nuclease and/or an endonuclease) than is a corresponding nucleic acid comprising only the four conventional deoxyribonucleotides (A, T, G, and/or C), or the four conventional ribonucleotides (U, A, G, and/or C), and phosphodiester linkages.

The term "nucleic acid" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA in solution, such as 2'-O-methylated oligonucleotides), and the like. A nucleic acid can be e.g., single-stranded or double-stranded. Unless otherwise indicated, a particular nucleic acid sequence of this invention encompasses complementary sequences, in addition to the sequence explicitly indicated. A nucleic acid (e.g., an oligonucleotide, a molecular beacon, an antisense nucleic acid, a nucleic acid molecular decoy, a nucleic acid binding sensor, an aptamer, a nucleic acid probe, or the like) of this invention is optionally nuclease resistant.

A "nucleic acid target" is a nucleic acid, or region thereof, that is to be detected and/or bound, or whose expression (transcription and/or translation) is to be affected.

An "oligonucleotide" is a polymer comprising two or more nucleotides. The polymer can additionally comprise non-nucleotide elements such as labels, quenchers, blocking groups, or the like. The nucleotides of the oligonucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like.

A "synthetic oligonucleotide" or a "chemically synthesized oligonucleotide" is an oligonucleotide made through in vitro chemical synthesis, as opposed to an oligonucleotide made either in vitro or in vivo by a template-directed, enzyme-dependent reaction.

A "peptide nucleic acid" (PNA) is a polymer comprising two or more peptide nucleic acid monomers. The polymer can additionally comprise elements such as labels, quenchers, blocking groups, or the like. The monomers of the PNA can be unsubstituted, unmodified, substituted or modified.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

A "protein transduction domain" is a polypeptide sequence that can mediate introduction of a covalently associated molecule into a cell. Protein transduction domains are typically short peptides (e.g., often less than about 16 residues). Example protein transduction domains have been derived from the HIV-1 protein TAT, the herpes simplex virus protein VP22, and the *Drosophila* protein antennapedia. Model protein transduction domains have also been designed.

A "quencher" is a moiety that alters a property of a label (typically, a fluorescent label) when it is in proximity to the label. The quencher can actually quench an emission, but it does not have to, i.e., it can simply alter some detectable property of the label, or, when proximal to the label, cause a different detectable property than when not proximal to the label. A quencher can be, e.g., an acceptor fluorophore that operates via energy transfer and re-emits the transferred energy as light. Other similar quenchers, called "dark quenchers," do not re-emit transferred energy via fluorescence.

A "ribozyme" is a catalytically active RNA molecule. It can operate in cis or trans.

A "subcellular delivery module" or "subcellular delivery agent" is a moiety that can mediate delivery and/or localization of an associated molecule to a particular subcellular location (e.g., a subcellular compartment, a membrane, and/or neighboring a particular macromolecule). The subcellular delivery module can be covalently or noncovalently associated with the molecule. Subcellular delivery modules include, e.g., peptide tags such as a nuclear localization signal or mitochondrial matrix-targeting signal.

"Uncaging energy" is energy that removes one or more caging groups from a caged molecule (or otherwise reverses the caging groups' blockage of the molecule's activity). As appropriate for the particular caging group(s), uncaging energy can be supplied, e.g., by light, sonication, a heat source, a magnetic field, or the like.

A "substrate" (as distinct from a capture substrate) is a molecule on which an enzyme acts. The substrate is typically supplied in a first state on which the enzyme acts, converting it to a second state.

A "substrate of interest" is a molecule or other moiety that is acted upon by a substrate modification component, resulting in a "modified substrate," or "modified substrate of interest." The modification can be a detectable modification, e.g., addition or removal of atoms or chemical groups from the substrate, e.g., addition or removal of a phosphate or other biologically relevant moiety of interest. A "specific substrate" is a substrate that is only acted on by a single type of substrate modification component, e.g., an enzyme substrate is specific when it is only recognized by a single type of enzyme (the single type can, optionally, include isoforms and allelic and species variants of the enzyme). A "generic" substrate is a substrate that is recognized by more than one type of substrate modification component.

A "capture substrate" is a material with a surface to which capture moieties can be attached. Example materials include glass and other ceramics, plastic, quartz and other minerals, metals, metalloids, porcelain, metal covered (e.g. sputtered) glass, and/or the like. A number of substrates, often derivatized to facilitate microarray generation (e.g., by improving printing performance on the array) are commercially available (see, e.g., silane slides from Sigma Chemical Co., the SuperClean™, SuperAmide™, and SuperAldehyde™ substrates from Telechem, International Inc., etc.). Examples of surfaces that the materials can be formed into include beads, plates, slides, microarrays, membranes, column matrices, microfluidic chips, and many others. "Capture moieties" include affinity moieties that specifically bind cognate moieties (e.g., ligands that are bound by ligand binding molecules, or ligand binding molecules that are bound by ligands). Capture moieties can also include non-specific capture moieties, such as negatively or positively charged molecules that attract their polar opposites, or the like. Methods of attaching molecules to surfaces is well known in the art, including, for example, silane-based chemistries, e.g., for attachment to glass or certain polymers. For example, see Leyden et al. (1980), "Symposium on Silylated Surfaces," Gordon & Breach; Arkles, Chemtech 7, 766 (1977); Plueddemann, *Silane Coupling Reagents*, Plenum, N.Y., 1982; and Kirk-Othmer Encyclopedia of Chemical Technology third and fourth editions, Martin Grayson, Executive Editor, Wiley-Interscience, John Wiley and Sons, NY (as available through 2003). Alternatively, the surface may be provided with a relatively inert coating, for example, using a siliconizing reagent, such as Aquasil™ or Surfasil™ (Pierce, Rockford, Ill.), or Sigmacote™ (Sigma Chemical Co., St. Louis, Mo.). Siliconizing reagents available from commercial manufacturers, such as Pierce (Rockford, Ill.) or Sigma Chemical Co. (St. Louis, Mo.), include organosilanes containing a hydrolyzable group, which can hydrolyze in solution to form a silanol which can polymerize and form a film over the surface, and can react with hydroxyl groups on the surface, such that the film is tightly bonded over the entire surface. Other examples of suitable coating chemistries for linking capture moieties include nickel-NTA coated surfaces, pegylated surfaces, or other treated surfaces.

A "caging moiety" is a moiety that inhibits access by a substrate modification component to a substrate of interest. Many particular caging moieties (e.g., caging groups) are described herein, including those that can be removed (e.g., by application of an uncaging energy or molecule) or reconfigured to reduce the displayed inhibition effect. That is, the caging moiety can be removed to uncage the substrate of interest, or it can be altered in configuration to uncage the substrate of interest, without actual removal.

A modified substrate is "released" from a cell when it exits the cell membrane and/or cell wall to go from the inside of the cell to the outside of the cell. It can be completely free of the cell when released, or can be located on or associated with the outside of the cell.

A substrate of interest/modified substrate of interest is "captured" on one or more capture substrate prior to detecting the detectable signal. This capture can be covalent or, more typically, non-covalent in nature. The substrate of interest is captured when it is retained on the capture substrate through one or more washes that are used to remove non-specifically bound components. The nature of the wash will vary depending on the nature of the substrate of interest and the association with the capture substrate. One of skill is fully able to design appropriate wash conditions for the relevant substrates and capture moieties of interest.

A "vector" is a compound or composition that includes or encodes one or more component of interest. Typical vectors include genetic vectors that include nucleic acids for the transmission of genetic information, as well as, optionally, accessory factors such as proteins, lipid membranes, associated proteins (e.g., capsid or other structural proteins). An example of a type of genetic vector is a viral vector that can include proteins, polysaccharides, lipids, genetic material (nucleic acids, optionally including DNA and/or RNA) and the like. Another example of a genetic vector is a plasmid. In one typical configuration, the vector is a viral vector or a plasmid that encodes the substrate modification component (e.g., the component is encoded in one or more open reading frame(s) of the vector). Many suitable vectors are well known and described, e.g., in Ausubel and Sambrook, both infra.

A variety of additional terms are defined or otherwise characterized herein.

DETAILED DESCRIPTION

This invention uses caged compounds (e.g., photolabile caged compounds) to precisely control the timing and location of biochemical, cell-lysate and cell-based reactions. For example, this invention features photoactivatable (photo-activated, PA) sensors, regulators and compounds suitable for monitoring signal transduction pathways in cells. The sensors are designed for simple operation and are suitable for a wide array of instruments (e.g., fluorescent instrument platforms).

The caged (e.g., PA) sensors and regulators are suitable for biochemical, cell-lysate, cell-based and serum-based assay formats. The sensors, regulators, and methods herein are suitable for applications in environmental analysis, food testing, clinical and basic research and drug discovery, for example.

Various caged compositions and methods of use thereof are described herein. For example, a novel concept of using PA compound(s) to simplify biochemical assays is described below. Instrument and consumable requirements, e.g., for PA sensors, regulators and compounds, are also described herein.

The advantages of using a caged (e.g., PA) assay format include: (1.) controlled activation of assay components (which permits development of novel homogenous assays); (2.) improved assay precision, achieved e.g., (a.) by reducing the number of fluidic handling steps in HTS assays—reducing number of assay steps (useful because, e.g., each additional pipetting step introduces more error into an assay), and/or (b.) by facilitating simultaneous activation of large numbers of assays within milliseconds; and (3.) simplified automation and design of miniaturized platforms by reducing the number of steps required. Finally, the caged (e.g., PA) assay format permits specific activation of an assay (or other reaction) in specific locations, e.g., a subset of wells or locations within a microarray, microfluidic and/or other miniaturized formats. For example, activation of specific locations separated by no more than about a micron is possible.

The caged assay format is suitable for enzyme based assay formats, and is also suitable for other assay formats, such as binding assays. Caged reaction formats are also suitable for controlling transcriptional regulation, inhibition of gene expression, ribozyme activation, and many other applications.

An additional advantage of using caged compounds in cell lysates and in cells, is that caging a molecule frequently renders the molecule more resistant to nucleases, proteases, lipases, and the like, thus extending its half-life in the cell or lysate. Caging a molecule which already possesses enhanced resistance to degradation (e.g., by a nuclease or protease, e.g., by incorporation of unnatural amino acids and/or nucleotides into the molecule) offers similar advantages in terms of molecule half-life in the cell or lysate (e.g., thus minimizing false-positive results from undesirable cleavage of a FRET-based sensor or probe, etc.).

Yet another advantage of using caged compounds in cells is that caging a toxic molecule (e.g., a molecule that has an adverse effect on a cell into which it is introduced) frequently protects the cell from the effect of the molecule. This permits compounds that might otherwise be too disruptive to the cell to be utilized in cell assays. The cell is not subject to the adverse effect of the compound until the compound is uncaged during the assay. Additionally, uncaging can be controlled such that only a portion of the caged compound is uncaged (e.g., by controlling light intensity and/or duration of exposure to light for a photoactivatable compound), further limiting toxicity.

Caged Sensors and Regulators

The invention provides a variety of caged sensors and regulators. For example, a first group of caged sensors, regulators and compounds is designed for use with protein kinases. Protein kinase substrates are ideal in cell sensor probes, since all signal transduction is regulated by this superfamily of enzymes (and ATP is the origin of all energy exchanged). Protein kinases represent the largest super family of homologous proteins with over 500+ (and possibly as many as 1000 or more) different mammalian members known to date. An even greater number is predicted from genome sequencing and analysis. See, e.g., Manning et al. "The Protein Kinase Complement of the Human Genome" *Science* 298: 1912-1934(2002); the internet at cellsignal.com/reference/pathway; and the internet at cellsignal.com/reference/kinase/index.asp.

Protein phosphorylation is recognized as the most important pathway of protein regulation in cells, operating by switching cellular activities from one state to another and, by regulating gene expression, cell proliferation and differentiation. It is the major mechanism by which cells respond to extracellular signals such as hormones and growth factors, and it controls all events at various stages of the cell cycle. Reversible protein phosphorylation is catalyzed by protein kinases and protein phosphatases. Dysfunctions in activities of protein kinases can lead to severe pathological states. Understanding the mechanisms of action of these enzymes assists in development of highly specific targeted drugs.

Kinase/cell sensors described herein do not require the addition of a separate detection reagent during the assay. The sensors change signal as soon as the peptide substrate is phosphorylated. The same kinase/cell sensor peptide substrate can thus be used for biochemical assays, cell-based assays, cell-lysate assays and whole organism assays. This feature provides for data that can be interpreted across various assay formats, reducing the errors produced when going from biochemical assays to cell lysate assays, cell-based assays, whole organism assays and ultimately into the clinic.

One of the most valuable capabilities of the kinase sensors herein is the "built in" control (e.g., light activation control) in activating the sensors. The kinase/cell sensor can be activated with precise spatial, temporal and dosage control. Furthermore, the assays can be multiplexed, e.g., by activating different PA sensors at different wavelengths. This also provides for control of the order of kinase sensor and/or regulator activation.

The substrates in the assays can be labeled (e.g., fluorescently tagged) at the N-terminus, C-terminus or even within the peptide substrate, to monitor phosphorylation events by kinases at serine, threonine and/or tyrosine amino acids. As stated above, the same substrate can be used for in vitro biochemical reactions, which has a definite advantage for drug discovery, since the specificity of the peptide and compound inhibition can be tested on a panel of kinases in a biochemical assay before use in a cell assay. This provides an opportunity to test phylogenetically related kinase families by linking structural relationship data to pathway information and consequent downstream gene expression data.

The use of the caging/uncaging approach is not limited to kinase assays. Other enzyme assays, such as those that rely on phosphatases and proteases, can also be used in the methods of the invention. Binding assays such as antibody assays, protein-to-protein and DNA-to-protein biochemical (or cellular, etc.) assays can also be practiced in accordance with the invention. Indeed, any biochemical reaction that has assay components that can be caged (e.g., caged by a photo removable, e.g., photolabile, group) can be used to reduce the number of steps in an assay in accordance with the invention. Photolabile or other removable groups can also be coupled directly to regulators of gene or enzyme activity.

Examples of inhibitor-regulators include protein kinase inhibitors. These inhibitors can consist of two or more amino acids that bind specifically to a specific kinase, preventing the kinase from activating its target. For example, a kinase-inhibiting compound (e.g., HB89 for PKC kinase) can be encaged in a protein complex that is photolabile. Upon exposure to light, the protein complex encaging the inhibitor dissociates and releases the active kinase inhibitor. As another example, RNAi and anti-sense nucleic acids can be used to shut down expression of specific gene or genes. Just as a gene or specific set of genes can be downregulated, e.g., a Zn-finger specific activator(s) can upregulate a gene or set of genes. These gene expression inhibitors or activators (regulators or modulators) can also be blocked with photolabile or other removable compounds to prevent regulator function until exposure to light or other uncaging energy.

In addition, through the use of caged (e.g., PA) sensors and regulators that are dual labeled, this invention allows "High Content Screening," e.g., quantifying a reaction (with one label) and locating the activity spatially in the cell (with another label).

Enzyme Sensors

In a first aspect, the invention provides a caged enzyme sensor for detecting an activity of an enzyme. The caged sensor includes one or more molecules collectively comprising a substrate for the enzyme, where the substrate is in a first state on which the enzyme can act, thereby converting the substrate to a second state. The second state is typically detectably distinguishable from the first state (e.g., by optic property, electromagnetic property, electrostatic charge, mass, secondary or tertiary structure, biochemical property, and/or intermolecular interactions, or the like; exemplary reactions include, but are not limited to, phosphorylation, cleavage, or other change in electrostatic charge or mass, among many others). The sensor preferably includes a first label, in which a first signal exhibited by the first label when the substrate is in its first state is distinguishable from a second signal exhibited by the first label when the substrate is in its second state. The caged sensor also includes one or more first caging groups associated with the one or more molecules, the first caging groups inhibiting (e.g., preventing) the enzyme from acting upon the substrate.

Thus, one general class of embodiments provides a composition comprising a cell that comprises a caged sensor for detecting an activity of an enzyme. The caged sensor includes one or more molecules, collectively comprising a substrate for the enzyme and a first label, and one or more first caging groups associated with the one or more molecules. The substrate is in a first state on which the enzyme can act, thereby converting the substrate to a second state. A first signal exhibited by the first label when the substrate is in its first state is distinguishable from a second signal exhibited by the first label when the substrate is in its second state. The first caging groups inhibit the enzyme from acting upon the substrate.

Depending on the application, the enzyme can be any of a variety of enzymes, e.g., an oxidoreductase, a transferase, a hydrolase, a lyase, a ligase, and/or an isomerase. The enzyme can be, e.g., a kinase, a phosphatase, a GTPase, an ATPase, a phosphodiesterase, a luciferase, an acetylase, a glycosylase, a ubiquitin-conjugating enzyme, a hydrogenase, a polymerase, and/or a peroxidase. In one embodiment, the enzyme is a protease (e.g., a caspase).

In one class of embodiments, the enzyme is a caspase. One polypeptide comprises the substrate for caspase and the first label and further comprises a second label or a quencher, where the first label and the second label or the quencher interact to produce the first signal when the substrate is intact. Cleavage of the substrate by caspase prevents the interaction of the first label and the second label or the quencher, thereby resulting in production of the second signal.

Any of a variety of configurations can be used for the polypeptides. In one embodiment, one of the first label and the second label or the quencher is located at the N-terminus of the polypeptide and the other of the first label and the second label or the quencher is located at the C-terminus of the polypeptide. Optionally, one label is a fluorophore and the other label is a quencher, e.g., in which the first and second labels are fluorophores that quench and unquench via FRET mediated phenomena. For example, the first label can be FITC and the second label rhodamine or coumarin.

In one embodiment the enzyme is caspase 3, the substrate comprises an Asp-Glu-Val-Asp motif, and the one or more first caging groups are located on one or more of the amino acid residues in the Asp-Glu-Val-Asp motif.

Another general class of embodiments provides a composition comprising a caged sensor for detecting an activity of an enzyme. The caged sensor includes one or more molecules, collectively comprising a substrate for the enzyme and a first label, and one or more first caging groups associated with the one or more molecules. The substrate is in a first state on which the enzyme can act, thereby converting the substrate to a second state. The first state is not converted to the second state by cleavage by the enzyme. A first signal exhibited by the first label when the substrate is in its first state is distinguishable from a second signal exhibited by the first label when the substrate is in its second state. The first caging groups inhibit the enzyme from acting upon the substrate. The composition optionally comprises the enzyme, a cell (e.g., a cell comprising the caged sensor and/or the enzyme) and/or a cell lysate.

In this general class of embodiments, the enzyme can be any of a variety of enzymes, providing that the first state of the substrate is not cleaved by the enzyme to form the second state. Thus, the enzyme is typically an oxidoreductase, a transferase, a ligase, and/or an isomerase. The enzyme can be a hydrolase or a lyase, for example, if the activity being assayed is one that does not involve cleavage of the substrate. The enzyme can be, e.g., a kinase, an acetylase, a ubiquitin-conjugating enzyme, a hydrogenase, or a polymerase.

The caged sensors of this invention are optionally caged enzyme-labile sensors other than those designed for detection of extracellular reporter enzyme activity such as those described in U.S. Pat. No. 5,981,207 to Burbaum et al. (Nov. 9, 1999).

For either of these related general classes of embodiments, the first caging groups can inhibit the enzyme from acting upon the substrate by at least about 50%, at least about 75%, at least about 90%, at least about 95%, or at least about 98%, as compared to the substrate in the absence of the first caging groups, or the first caging groups can prevent the enzyme from acting upon the substrate. For example, if the first caging groups inhibit the enzyme from acting upon the substrate by at least 90%, then at most 10% as much of the caged sensor as of a corresponding uncaged sensor would be converted to the second state under equivalent reaction conditions (concentrations of sensor and enzyme, reaction time, etc.) Typically, removal of or an induced conformational change in the first caging groups permits the enzyme to act upon the substrate.

In a first aspect, the first label is an optically (or spectroscopically) detectable label such as a fluorophore or other fluorescent label. However, non-optical labels can also be used. Thus, the first signal and/or the second signal can be, e.g., an optical signal, a fluorescent signal, a luminescent signal, a nonoptical signal, a magnetic signal, or the like, as appropriate to the assay. As one example, the first signal can be a fluorescent signal emitted at one wavelength and the second signal can be a fluorescent signal emitted at another wavelength. As another example, the first signal can be a fluorescent emission at one wavelength with a first intensity, and the second signal can be a fluorescent emission at the same wavelength but with a second intensity substantially greater or less than the first intensity (e.g., when emission by a fluorophore comprising the first label is quenched or unquenched). For example, the second intensity can be at least about 20%, at least about 50%, or at least about 100% greater or less than the first intensity.

The one or more first caging groups associated with the one or more molecules can be covalently or non-covalently attached to the one or more molecules. In a preferred aspect, the one or more first caging groups are photoactivatable (e.g., photolabile). For example, in one embodiment, the first caging groups can be removed by exposure to light with a wavelength between about 60 nm and about 400 nm, between about 400 nm and about 700 nm, and/or between about 700 nm and about 1000 nm (i.e., the light can be UV, near-UV, visible, near-infrared, and/or infrared). Other first caging groups are removable via input of different uncaging energies, e.g., the one or more first caging groups can be removable by sonication or application of heat or by altering environmental variables such as pH, ionic strength, or the like.

In the caged sensors herein, the first label and the substrate are optionally physically connected. The substrate can include, e.g., an amino acid, a polypeptide, a nitrogenous base, a nucleoside, a nucleotide, a nucleic acid, a carbohydrate, and/or a lipid. The substrate can be, e.g., a specific substrate, acted upon by a single enzyme (optionally including isoforms and allelic and species variants of the enzyme), or a generic substrate, acted upon by more than one type of enzyme or, more typically, more than one member of a class of enzymes (e.g., a universal kinase substrate, which can be phosphorylated by any of a group of kinases).

Kinase Sensors

In one class of embodiments, the enzyme of the caged sensor is a kinase, e.g., a protein kinase that phosphorylates tyrosine, serine and/or threonine. For example, one polypeptide can comprise the first label and the substrate for the kinase, where the substrate includes a serine, threonine, or tyrosine residue capable of being phosphorylated by the kinase. The first label is located at the serine, threonine, or tyrosine residue and exhibits the first signal when the residue is not phosphorylated and the second signal when the residue is phosphorylated. The one or more first caging groups are optionally located on one or more amino acid residues involved in binding the kinase and/or on a residue that can be phosphorylated by the kinase.

In one embodiment, one polypeptide comprises the substrate for the kinase and the first label and further comprises a second label or a quencher. The first label and the second label or the quencher interact to produce the first signal when the substrate is not phosphorylated. Phosphorylation of the substrate prevents the interaction of the first label and the second label or the quencher, resulting in production of the second signal. Optionally, the one or more first caging groups are located on one or more amino acid residues involved in binding the kinase and/or on a residue that can be phosphorylated by the kinase. One of the first label and the second label or the quencher can be located at the N-terminus of the polypeptide and the other of the first label and the second label or the quencher at the C-terminus of the polypeptide. Here again, one label can be a fluorophore and the other a quencher. For example, the first and second labels are optionally hydrophobic fluorophores, e.g., the first label can be FITC and the second label rhodamine or coumarin (listed by way of example only; a large number of other suitable fluorophores and quenchers are known in the art).

In one kinase-based sensor, phosphorylation of the substrate triggers a conformational change in the polypeptide, where the conformational change prevents interaction of the first label and the second label or the quencher.

In one embodiment, phosphorylation of the substrate results in binding of a phosphobinder to the phosphorylated substrate, the binding of the phosphobinder preventing the interaction of the first and the second label or the quencher. Optionally, the phosphobinder is associated with one or more second caging groups, the presence of which prevents the phosphobinder from binding the phosphorylated substrate. Indeed, one aspect of the invention is simply a caged phosphobinder. The second caging groups are optionally removable under different conditions than the first caging groups inhibiting phosphorylation of the substrate. In one embodiment, the phosphobinder is an antibody. Such antibodies are well known in the art, and many are commercially available, e.g., from Zymed Laboratories, Inc. or QIAGEN (www.qiagen.com). In other embodiments, the phosphobinder comprises an SH-2 domain, a PTB domain, a 14-3-3 domain, an FHA domain, a WD40 domain and/or a WW domain. These and other such domains are reviewed in e.g., Yaffe and Elia "Phosphoserine/threonine-binding domains" Curr Opin Cell Biol. (2001) 13(2): 131-8; Li et al. "The FHA domain mediates phosphoprotein interaction" J Cell Sci. (2000) 113 Pt 23:4143-9; the internet at cellsignal.comlreference/domain/index.asp; and the internet at mshri.on.ca/pawson/ww.html.

In another embodiment, one polypeptide comprises the substrate for the kinase and the first label. Optionally in this embodiment, the polypeptide further comprises a second label or a quencher and a phosphobinder; where the first label and the second label or the quencher do not interact when the substrate is not phosphorylated, thereby producing the first signal. Phosphorylation of the substrate results in intramolecular binding of the phosphobinder to the phosphorylated substrate, resulting in the interaction of the first label and the second label or the quencher, producing the second signal. Optionally, the one or more first caging groups are located on one or more amino acid residues involved in binding the kinase and/or on a residue that can be phosphorylated by the kinase. As with other embodiments, one of the first label and the second label or the quencher is optionally located at the N-terminus of the polypeptide and the other of the first label and the second label or the quencher is located at the C-terminus of the polypeptide. In this embodiment as well, one label can be a fluorophore and the other a quencher. The first and second labels can exhibit FRET.

Here as well, the phosphobinder is optionally associated with one or more second caging groups, the presence of which prevents the phosphobinder from binding the phosphorylated substrate. Optionally, the second caging groups are removable under different conditions than the first caging groups inhibiting phosphorylation of the substrate. The phosphobinder can be any of those noted above.

In one aspect, a first polypeptide comprises the substrate for the kinase and the first label while a second polypeptide comprises a second label or a quencher and a phosphobinder. The first label and the second label or the quencher do not interact when the substrate is not phosphorylated, thereby producing the first signal. Phosphorylation of the substrate results in intermolecular binding of the phosphobinder to the phosphorylated substrate, resulting in the interaction of the first label and the second label or the quencher, thereby producing the second signal. All of the features noted above, e.g., with respect to location of caging groups, labels, optional use of fluorophores and quenchers, FRET pairs, types of phosphobinders, differential removal of different caging groups, and the like, apply to this embodiment as well.

In a related embodiment, a first polypeptide comprises the substrate for the kinase and the first label while a second polypeptide comprises a phosphobinder. Phosphorylation of the substrate results in intermolecular binding of the phosphobinder to the phosphorylated substrate. Fluorescence polarization is used to detect binding of the phosphobinder to the phosphorylated substrate. All of the features noted above, e.g., with respect to location of caging groups, labels, types of phosphobinders, differential removal of different caging groups, and the like, apply to this embodiment as well, as applicable.

In an additional embodiment, one polypeptide comprises the substrate for the kinase, a second substrate, the first label, a third label, a fourth label or a quencher, and a phosphobinder. The substrate includes a serine, threonine, or tyrosine residue capable of being phosphorylated by the kinase. The second substrate is associated with one or more third caging groups, the presence of which prevents phosphorylation of the second substrate. The first label is located at the serine, threonine, or tyrosine residue and exhibits the first signal when the residue is not phosphorylated and the second signal when the residue is phosphorylated. The third label and the fourth label or the quencher do not interact when the second substrate is not phosphorylated, thereby producing a third signal. Phosphorylation of the second substrate results in intramolecular binding of the phosphobinder to the phosphorylated second substrate, resulting in the interaction of the third label and the fourth label or the quencher, thereby producing a fourth signal, the fourth signal being distinguishable from the first, second and third signals. Optionally, the one or more first caging groups are located on one or more amino acid residues involved in binding the kinase that phosphorylates the first substrate. The second substrate is optionally a target for the same kinase, but can be a target for a different kinase. The one or more first caging groups are optionally located on one or more amino acid residues involved in binding the kinase and/or on a residue that can be phosphorylated by the kinase. Optionally, the third caging groups preventing phosphorylation of the second substrate are removable under different conditions than the first caging groups inhibiting phosphorylation of the substrate. All of the features noted above, e.g., with respect to location of caging groups, labels, optional use of fluorophores and quenchers, FRET pairs, types of phosphobinders differential removal of different caging groups, and/or the like apply to this embodiment as well. For example, one of the third label and the fourth label or the quencher is optionally located at the C-terminus of the polypeptide and the other of the third label and the fourth label or the quencher is located within the polypeptide. The third and fourth labels are optionally fluorophores capable of exhibiting FRET.

Caged kinase sensors can be produced, e.g., by caging and optionally adding cellular and/or subcellular delivery modules, additional labels, and the like to kinase probes as described in e.g., *J. Mol. Screening*, vol. 5,1:23-30 (2000); *Anal Bioch.*, 244, 2: 340-6 (1997); *J. Biol. Chem.*, vol. 277, no.13:11527-532 (2002); *PNAS* vol. 98:15003-08 (2001); *Anal Sci.*, vol. 17: i1456-67 (2001); *Nature Bio.*, vol. 18:313-16 (2000); *Nat. Rev. Mol. Cell. Biol.*, 3:906-18 (2002); and U.S. Pat. No. 6,410,255 to Pollok et al. (Jun. 25, 2002) entitled "Optical probes and assays."

Intracellular Sensors

The invention optionally includes a composition comprising the caged sensor and a cell, e.g., where the sensor is located inside the cell. Alternately, the sensor can be located in (e.g., as part of) a cell lysate. The cell can be, e.g., a prokaryotic cell (e.g., a eubacterial or an archaebacterial cell) such as an *Escherichia coli* cell, or a eukaryotic cell, e.g., a mammalian cell or a yeast cell.

Optionally, for any of the above embodiments, the one or more molecules are associated with a cellular delivery module that can mediate introduction of the sensor into a cell. For example, the cellular delivery module optionally comprises a polypeptide, e.g., a PEP-1 peptide, an amphipathic peptide (e.g., an MPG or MPG$^{\Delta NLS}$ peptide), or a cationic peptide (e.g., a homopolymer of histidine, lysine, or D-arginine) that is covalently or non-covalently associated with the one or more molecules. In one embodiment, the cellular delivery module comprises a protein transduction domain, e.g., derived from an HIV-1 TAT protein, from a herpes simplex virus VP22 protein, and/or from a Drosophila antennapedia protein. In one aspect, the protein transduction domain is a model protein transduction domain (e.g., a homopolymer of D-arginine, e.g., 8-D-Arg).

Optionally, the cellular delivery module is covalently attached to the one or more molecules. For example, the covalent attachment is optionally reversible by exposure to light of a preselected wavelength. As another example, the covalent attachment is optionally a disulfide or ester linkage that is reduced or cleaved once the sensor is inside a cell.

Optionally, the cellular delivery module associated with the one or more molecules comprises a lipid, e.g., a fatty acid. For example, the one or more molecules can be covalently attached to one or more myristoyl groups, e.g., via a photolabile linker.

In certain embodiments, the cellular delivery module can also serve as a caging group. For example, the cellular delivery module can be covalently attached to the one or more molecule (e.g., by a photolabile linker). The cellular delivery module can mediate introduction of the one or more molecules into the cell, where the presence of the cellular delivery module inhibits (e.g., prevents) the substrate from being acted on by the enzyme until the cellular delivery module is removed (e.g., by exposing the cell to light of an appropriate wavelength to cleave the photolabile linker).

In one aspect, the cellular delivery module is associated with one or more additional fourth caging groups, the presence of which prevents the cellular delivery module from mediating introduction of the sensor into a cell.

Optionally, the one or more molecules are associated with at least one subcellular delivery module, e.g., comprising a polypeptide, a nucleic acid (e.g., DNA, RNA and/or PNA), and/or a carbohydrate. For example, the subcellular delivery module can mediate localization of the sensor to a membrane (e.g., a plasma membrane, a nuclear or other organellar membrane), a mitochondrion, a peroxisome, a nucleus, an endoplasmic reticulum, a Golgi, a vesicle, a lysosome, an endosome, and/or a chloroplast. Thus, the subcellular delivery module optionally comprises a mitochondrial matrix-targeting sequence, a nuclear localization signal, a signal peptide, an ER retention signal, a peroxisomal targeting motif, a chloroplast stromal targeting sequence, a transmembrane domain, and/or a lipid attachment site. Optionally, the subcellular delivery module comprises a binding domain that mediates localization of the sensor by binding to a target protein. The subcellular delivery module can be covalently or non-covalently attached to the one or more molecules, e.g., a covalent attachment reversible by exposure to light of a preselected wavelength or by reduction or enzymatic cleavage within the cell. In one aspect, the subcellular delivery module is associated with one or more fifth caging groups, the presence of which prevents the subcellular delivery module from mediating subcellular localization of the sensor.

Additional Features of Sensors

For any of the above embodiments, the one or more molecules can further comprise a fifth label, the fifth label exhibiting a unique fifth signal, the fifth signal being independent of the state of the substrate. For example, the fifth label can be a fluorophore, a quantum dot, or the like. The fifth label can be used, for example, for co-localization of the sensor or for normalization of transfection/transduction efficiency when the sensor is introduced into a cell.

Optionally, in the embodiments herein, the caged sensor is bound to a matrix (e.g., electrostatically, covalently, directly or via linker). In one aspect, the matrix is a surface and the sensor is bound to the surface at a predetermined location within an array comprising other sensors. In one embodiment, the matrix comprises a bead (e.g., color-coded or otherwise addressable).

For example, in one matrix embodiment, the caged sensor comprises a first oligonucleotide, the first oligonucleotide being complementary to a second oligonucleotide, the second oligonucleotide being bound to a matrix. The matrix can be, e.g., a surface (e.g., an array) and/or a bead as noted.

Kits

The invention also provides kits for making the caged sensor, e.g., comprising a substrate, a first label, one or more first caging groups, and instructions for assembling the substrate, the first label, and the first caging groups to form the caged sensor, e.g., packaged in one or more containers. In a similar kit of the invention, a first label, one or more first caging groups, and instructions for assembling the first label, the first caging groups, and a substrate supplied by a user of the kit to form the caged sensor, packaged in one or more containers, are provided.

Systems

In one aspect, systems and/or apparatus comprising the caged sensors noted above and, e.g., components such as detectors, fluid handling apparatus, sources of uncaging energy, or the like are a feature of the invention.

Other caged enzyme sensors

In a related aspect, other sensors that detect an enzymatic activity can be caged. For example, sensors such as those described in Giuliano et al. (2003) *Modern Drug Discovery* 6:33-37, wherein the subcellular localization of the sensor changes when the enzyme acts on the substrate, can be caged as described herein.

Binding Sensors

In an additional class of embodiments, compositions comprising caged sensors are provided. A caged sensor includes one or more molecules collectively comprising a binding target and a first label. Also included are one or more first caging groups associated with the one or more molecules, the first caging groups inhibiting (e.g., preventing) the binding target from binding to its partner, wherein the binding target and the partner are capable of a stable interaction (distinct from the extremely transient interaction typical between an enzyme and its substrate). Typically, the partner does not enzymatically act upon and then promptly release the binding target. Rather, the binding target and the partner form a relatively stable, detectable complex with each other.

The caging groups can result in at least about 50%, at least about 75%, at least about 90%, at least about 95%, or at least about 98% inhibition of binding between the binding target and the partner, as compared to the binding target in the absence of the first caging groups, or can prevent the binding target from binding to its partner. Typically, removal of or an induced conformational change in the caging groups permits the binding target to bind to its partner.

In one class of embodiments, a first signal exhibited by the first label when the binding target is not bound to the partner is distinguishable from a second signal exhibited by the first label when the binding target is bound to the partner. This type of binding sensor can be used, for example, for detecting binding of the binding target by its partner. Such binding sensors can be used to study essentially any intermolecular (or even intramolecular) binding event. To name only a few examples, binding sensors can be used to examine protein-protein interactions, protein-nucleic acid interactions, enzyme-cofactor binding, or lipid binding.

For example, the first label can be an optically (or spectroscopically) detectable label such as a fluorophore or other fluorescent label. However, non-optical labels can also be used. Thus, as appropriate to the assay, the first signal and/or the second signal can be, e.g., an optical signal, a fluorescent signal, a luminescent signal, a nonoptical signal, a magnetic signal, or the like. As one example, the first signal can be a fluorescent signal emitted at one wavelength and the second signal can be a fluorescent signal emitted at another wavelength. As another example, the first signal can be a fluorescent emission at one wavelength with a first intensity, and the second signal can be a fluorescent emission at the same wavelength but with a second intensity substantially greater or less than the first intensity (e.g., when emission by a fluorophore comprising the first label is quenched or unquenched). For example, the second intensity can be at least about 20%, at least about 50%, or at least about 100% greater or less than the first intensity.

In an alternative class of embodiments, a first signal exhibited by the first label (e.g., a fluorophore or quantum dot) is not affected by binding of the binding target to the partner. This type of sensor can be used, for example, for localizing the partner of a binding target within a living cell.

The sensor can optionally also comprise a second label (e.g., a fluorophore or quantum dot) that exhibits a unique third signal which is independent of binding of the binding target to its partner (e.g., for localization of the sensor, normalization, or the like).

The binding target can comprise, without limitation, one or more of: an amino acid, a polypeptide, an antibody, a nitrogenous base, a nucleoside, a nucleotide, a nucleic acid, a carbohydrate, a lipid, or a drug. Similarly, the partner can comprise, without limitation, one or more of: an amino acid, a polypeptide, an antibody, a nitrogenous base, a nucleoside, a nucleotide, a nucleic acid, a carbohydrate, or a lipid. In one example embodiment, the binding target comprises an antibody and the partner comprises an epitope recognized by the antibody. As another example, the binding target can comprise a polypeptide comprising an SH-2 domain, a PTB domain, a 14-3-3 domain, an FHA domain, a WD40 domain and/or a WW domain, and the partner can comprise a phosphorylated polypeptide. In yet another example embodiment, the partner comprises a protein and the binding target comprises a modulator of an activity of the protein (e.g., an activator or an inhibitor, e.g., a small molecule or peptide inhibitor; see, e.g., Feller and Kardinal (2000) *FASEB* 14:1529; Gallouzi and Steitz (2001) *Science* 294:1895; Schutze-Redelmeiner (1996) *J. Immunol.* 157:650-655; and Pooga (1998) *Nat. Biotech.*, 16:857-861). In yet another example embodiment, the binding target comprises at least one probe nucleic acid comprising a region of complementarity to a target nucleic acid, and the partner comprises the target nucleic acid.

The composition optionally also includes the partner, a cell (e.g., a cell comprising the sensor and/or the partner), and/or a cell lysate.

All of the various optional configurations and features noted for the enzyme sensor embodiments above apply here as well. Additionally, all of the features for the embodiments above apply here as well, e.g., for label configurations and signal types, appropriate uncaging energies (light, heat, sonic, etc.), use of covalently or non-covalently attached caging groups (e.g., photolabile caging components), location of the probes in cells or cell extracts (and resulting compositions), use of cellular and subcellular targeting and delivery modules, protein transduction domains, kits comprising the compositions or components for making the compositions and appropriate instructions, matrices (e.g., arrays comprising the sensors), systems and apparatus comprising the probes, and the like.

Nucleic Acid Probes

In an additional class of embodiments, a composition comprising a caged nucleic acid probe is provided. The caged nucleic acid probe comprises at least one probe nucleic acid that has a region of complementarity to a target nucleic acid. The caged probe includes a first label, wherein a first signal exhibited by the first label when the probe nucleic acid is not bound to the target nucleic acid is distinguishable (e.g., by wavelength and/or intensity) from a second signal exhibited by the first label when the probe nucleic acid is bound to the target nucleic acid. The probe also includes one or more first caging groups associated with the probe nucleic acid, the first caging groups inhibiting (e.g., preventing) the probe nucleic acid from binding to the target nucleic acid.

The caging groups can inhibit the probe nucleic acid from binding to the target nucleic acid by at least about 50%, at least about 75%, at least about 90%, at least about 95%, or at least about 98%, as compared to the probe nucleic acid in the absence of the first caging groups, or the caging groups can prevent the probe nucleic acid from binding to the target nucleic acid. Typically, removal of or an induced conformational change in the caging groups permits the probe nucleic acid to bind to the target nucleic acid.

In one class of embodiments, the at least one probe nucleic acid comprises one probe nucleic acid. In other embodiments, the least one probe nucleic acid comprises a plurality of probe nucleic acids. For example, the at least one probe nucleic acid can comprise two probe nucleic acids, each of which comprises a region of complementarity to the target nucleic acid (e.g., dual molecular beacons in which the first label is on one probe nucleic acid and a quencher is on the second probe nucleic acid).

All of the features for the embodiments above apply here as well, e.g., for label configurations and signal types, appropriate uncaging energies (light, heat, sonic, etc.), use of covalently or non-covalently attached caging groups (e.g., photolabile caging components), use of cellular and subcellular targeting and delivery modules (e.g., protein transduction domains), kits comprising the compositions or components for making the compositions and appropriate instructions, matrices, systems and apparatus comprising the probes, and the like. It should be noted that the composition optionally also includes the target nucleic acid, a cell lysate, and/or a cell, e.g., a cell comprising the caged nucleic acid probe and/or the target nucleic acid. In addition, it is worth noting that the caged nucleic acid probe optionally comprises any appropriate nucleic acid, e.g., an oligodeoxyribonucleotide or a peptide nucleic acid. Similarly, the probe nucleic acid optionally comprises a molecular beacon.

In brief, a molecular beacon (MB) is an oligonucleotide or PNA that when free in solution self-hybridizes to form a stem and loop structure. The MB has the first label and a quencher at the termini of the oligonucleotide or PNA. Thus, under conditions that permit intra-molecular hybridization, the first label is typically quenched (or otherwise altered) by the quencher, thereby resulting in production of the first signal. Under conditions where the MB does not display intra-molecular hybridization (e.g., when the probe nucleic acid comprising the loop is bound to the target nucleic acid), the first label is unquenched, thereby resulting in production of the second signal. The quencher can be, e.g., a dark quencher or an acceptor fluorophore. Details regarding standard methods of making and using MBs are well established in the literature. See, e.g., Tyagi et al. *Nature Biotech.* 14:303-8 (1996); Tyagi et al., *Nature Biotech.* 16:49-53 (1998); *Anal Chem* (2001) 73:5544-50; Sokol et al. (1998) "Real time detection of DNA:RNA hybridization in living cells" *Proc. Natl. Acad. Sci.* U.S.A. 95:11538-11543; Fang et al. (1999) "Designing a novel molecular beacon for surface-immobilized DNA hybridization studies" *J. Am. Chem. Soc.* 121:2921-2922; U.S. Pat. No. 5,925,517; U.S. Pat. No. 6,150,097; and U.S. Pat. No. 6,037,130.

Optionally, the caged MB can comprise one or more non-natural nucleotides. For example, the nonnatural nucleotides can be included to increase nuclease resistance and/or to enhance specificity of the beacon. As one example, the stem of the MB can comprise, at complementary positions of the two strands of the stem, at least one pair of nonnatural nucleotides that base pair with each other but that do not Watson-Crick base pair with the bases typical to biological DNA or RNA (i.e., A, C, G, T, or U). Uncaged molecular beacons comprising such nonnatural nucleotides in their stem are also a feature of the invention. Examples of nonnatural nucleotides include, but are not limited to, Locked-NucleicAcid™ nucleotides (available from Exiqon A/S, on the internet at exiqon.com; see, e.g., SantaLucia Jr. (1998) *Proc Natl Acad Sci* 95:1460-1465) and isoG, isoC, isoA, isoT, and other nucleotides used in the AEGIS system (Artificially Expanded Genetic Information System, available from EraGen Biosciences, on the internet at eragen.com; see, e.g., U.S. Pat. Nos. 6,001,983, 6,037,120, 6,140,496).

In a related class of embodiments, the at least one probe nucleic acid comprises a first probe nucleic acid and a second probe nucleic acid. The first probe nucleic acid comprises a first region of complementarity to the target nucleic acid and the first label, and the second probe nucleic acid comprises a second region of complementarity to the target nucleic acid and a third label. The first label is an acceptor fluorophore, and the third label is a donor fluorophore. Binding of the first and second probe nucleic acids to the target nucleic acid brings the donor and acceptor fluorophores into proximity, permitting energy transfer between them and resulting in the second signal.

The first and second probe nucleic acids can be non-self-complementary. In other embodiments, however, the first probe nucleic acid and/or the second probe nucleic acid forms a stem-loop structure when not bound to the target nucleic acid. Typically, one arm of the stem and the loop comprise the region of complementarity to the target nucleic acid. The first probe nucleic acid and/or the second probe nucleic acid optionally also include a quencher. Optionally, the first and/or second probe nucleic acids comprise one or more nonnatural nucleotides.

Use of such dual nucleic acid probes is described in, e.g., WO2003000933A1 entitled "Dual resonance energy transfer nucleic acid probes" by Bao et al.; US20020177157 entitled "Pairs of nucleic acid probes with interactive signaling moieties and nucleic acid probes with enhanced hybridization efficiency and specificity" by Luo et al.; Sueda et al. (2000) Bioconj. Chem. 11:827-831; and Sueda et al. (2002) Bioconj. Chem. 13:200-205.

Caged nucleic acid probes can be used for detection of essentially any desired target nucleic acid, including for example a DNA or RNA target, e.g., in a cell, in a cell lysate, in vitro, on a solid support. As one specific example, a caged molecular beacon can be employed for in vivo monitoring of gene expression inside a cell (e.g., the MB probe nucleic acid can be complementary to an mRNA, e.g., a highly-expressed mRNA).

Antisense Nucleic Acids

In a related embodiment, the invention provides a composition comprising a caged antisense nucleic acid and a target nucleic acid. The antisense nucleic acid has a region of complementarity to the target nucleic acid and one or more first caging groups associated with the antisense nucleic acid. The first caging groups inhibit (e.g., prevent) the antisense nucleic acid from binding to and inactivating the target nucleic acid. The antisense nucleic acid can be an RNA, DNA, a PNA, or any other appropriate molecule.

The caging groups can inhibit the antisense nucleic acid from binding to and inactivating the target nucleic acid by at least about 50%, at least about 75%, at least about 90%, at least about 95%, or at least about 98%, as compared to the antisense nucleic acid in the absence of the first caging groups, or the caging groups can prevent the antisense nucleic acid from binding to and inactivating the target nucleic acid. Typically, removal of or an induced conformational change in the caging groups permits the antisense nucleic acid to bind to and inactivate the target nucleic acid.

Any of the features noted above apply to this embodiment as well, e.g., appropriate uncaging energies (light, heat, sonic, etc.), use of covalently or non-covalently attached caging groups (e.g., photolabile caging groups), use of cellular and subcellular targeting and delivery modules (e.g., protein transduction domains), kits comprising the compositions or components for making the compositions and appropriate instructions, matrices, systems and apparatus comprising the antisense nucleic acids, and the like. It will be appreciated that the composition optionally also includes a cell, e.g., a cell comprising the caged antisense nucleic acid.

Use of antisense nucleic acids is well known in the art. Typically, a nucleic acid comprising a nucleotide sequence in a complementary, antisense orientation with respect to a coding (sense) sequence of an endogenous gene is introduced into a cell. A duplex can form between the antisense sequence and its complementary sense sequence, resulting in inactivation of the gene. The antisense nucleic acid can inhibit gene expression by forming a duplex with an RNA transcribed from the gene, by forming a triplex with duplex DNA, etc. An antisense nucleic acid can be produced, e.g., for any gene whose coding sequence is known or can be determined, by a number of well-established techniques (e.g., chemical synthesis of an antisense PNA or oligonucleotide (optionally including modified nucleotides and/or linkages that increase resistance to degradation or improve cellular uptake) or in vitro transcription). Antisense nucleic acids and their use are described, e.g., in U.S. Pat. No. 6,242,258 to Haselton and Alexander (Jun. 5, 2001) entitled "Methods for the selective regulation of DNA and RNA transcription and translation by photoactivation"; U.S. Pat. No. 6,500,615; U.S. Pat. No. 6,498,035; U.S. Pat. No. 6,395,544; U.S. Pat. No. 5,563,050; E. Uhlmann and A. Pepan, Chem. Rev. 90 (1990) 543; P. D. Cook, Anti-Cancer Drug Design 6 (1991) 585; J. Goodchild, Bioconjugate Chem. 1 (1990) 165; S. L. Beaucage and R. P. Iyer, Tetrahedron 49 (1993) 6123; and F. Eckstein, Ed., "Oligonucleotides and Analogues—A Practical Approach," IRL Press (1991).

Biomolecular Analogs

Another class of embodiments provides a caged biomolecular analog comprising a molecule comprising one or more nonnatural nucleotides and/or one or more nonnatural amino acids and one or more caging groups associated with the molecule. Essentially all of the features noted for the embodiments above apply to this embodiment as well, except that the relevant caged molecule is the biomolecular analog. In addition, it is worth noting that the caged biomolecular analog optionally further comprises one or more natural nucleotides and/or one or more natural amino acids. Similarly, the biomolecular analog can be chemically synthesized.

The natural nucleotides include the four deoxyribonucleotides naturally occurring in DNA (dA, dC, dG, and dT) and the four ribonucleotides naturally occurring in RNA (A, C, G, and U), while the natural amino acids include the 20 amino acids naturally occurring in most proteins (A, C, D, E, F, G, H, I, K, L, M, N, P, Q, R, S, T, V, W, and Y). Naturally occurring modified versions of these nucleotides and amino acids are also natural nucleotides. Nonnatural (unnatural) nucleotides and amino acids encompass all other nucleotides and amino acids (e.g., D-amino acids, chemically modified nucleotides or amino acids that can be synthesized in vitro but that are not found in nature, beta-amino acids, homo-amino acids, cyclic amino acids, and derivatives of the natural amino acids such as ring-substituted Phe and Tyr derivatives). A variety of unnatural nucleotides and amino acids can be synthesized and/or are commercially available. See, e.g., Sigma Chem-Files vol. 1 no. 5 (2001) and vol. 2 no. 4 (2002).

All of the features for the embodiments above apply here as well, e.g., for label configurations and signal types, appropriate uncaging energies (light, heat, sonic, etc.), use of covalently or non-covalently attached caging groups (e.g., photolabile caging components), use of cellular and subcellular targeting and delivery modules (e.g., protein transduction domains), kits comprising the compositions or components for making the compositions and appropriate instructions, matrices, systems and apparatus comprising the biomolecular analogs, and the like. It is worth noting that the composition optionally also includes a cell lysate and/or a cell, e.g., a cell comprising the caged biomolecular analog.

Transcription Factors

Compositions comprising caged transcription factors are also a feature of the invention. For example, the caged transcription factors can include a transcription factor and one or more first caging groups associated with the transcription factor. The first caging groups inhibit (e.g., prevent) the transcription factor from regulating transcription from a cognate promoter. Example transcription factors include transcriptional activators and transcriptional repressors, including transcription factors that include a leucine zipper motif, a helix-loop-helix motif, an HMG domain, a helix-turn-helix motif, a homeo domain, a winged helix motif, a paired box domain, and/or a TEA domain. A preferred transcription factor is one that comprises at least one zinc finger motif, e.g., a $Cys_2His_2$-type zinc finger motif. Many transcription factors are known in the art, including many that do not comprise one of the domains listed herein. Essentially any transcription factor can be used in the present invention.

The caging groups can inhibit the transcription factor from regulating transcription from the cognate promoter by at least about 50%, at least about 75%, at least about 90%, at least about 95%, or at least about 98%, as compared to the transcription factor in the absence of the first caging groups, or the caging groups can prevent the transcription factor from regulating transcription from the cognate promoter. Typically, removal of or an induced conformational change in the caging groups permits the transcription factor to regulate transcription from the cognate promoter.

All of the features for the embodiments above apply here as well, e.g., for label configurations and signal types. As with the embodiments above, the caged transcription factor is optionally located inside a cell. Thus, the composition optionally also includes a cell comprising the caged transcription factor, e.g., a prokaryotic cell (e.g., a eubacterial or an archaebacterial cell) such as an *Escherichia coli* cell, or a eukaryotic cell, e.g., a mammalian cell or a yeast cell. The various configurations for caging groups (associated here with the transcription factor) are also features of the invention, as is the use of cellular delivery modules that can mediate introduction of the caged transcription factor into a cell. The caged transcription factor is optionally associated with at least one subcellular delivery module in any of the configurations noted above, though nuclear delivery is generally the most relevant configuration. The caged transcription factor is optionally bound to a matrix in any of the configurations noted above. Kits comprising the caged transcription factors, or components for making caged transcription factors and any of the additional kit features noted above apply here as well. For example, a kit for using the caged transcription factor is a feature of the invention. The kit comprises the caged transcription factor and instructions for using the caged transcription factor (e.g., instructions for introducing the caged transcription factor into a cell and uncaging it to thereby induce expression of a protein whose gene is under control of the cognate promoter), packaged in one or more containers. The kit optionally further comprises one or more cells and/or plasmids (e.g., an expression plasmid comprising the cognate promoter, a multiple cloning site for ease of insertion of a coding sequence to be over-expressed under control of the cognate promoter, or the like).

The caged transcription factor of this invention can be used, e.g., to regulate (upregulate or downregulate) expression of any gene comprising the cognate promoter in any cell type. For example, the caged transcription factor can be used to regulate over-expression of a protein (e.g., a toxic protein whose expression interferes with cell viability), e.g., for purification from *Escherichia coli*, yeast, or the like. The composition optionally also includes the cognate promoter, e.g., a plasmid comprising the cognate promoter.

Molecular Decoys

In yet another embodiment, the invention provides compositions comprising caged molecular decoys. The caged molecular decoy comprises a molecular decoy and one or more first caging groups associated with the molecular decoy. The molecular decoy comprises, e.g., an amino acid, a polypeptide, a nitrogenous base, a nucleoside, a nucleotide, a nucleic acid, a carbohydrate, and/or a lipid. Optionally, the decoy is a nucleic acid, e.g., a double-stranded DNA or an RNA comprising a transcription factor binding sequence (e.g., a palindromic doubled-stranded DNA comprising a CREB (5'TGACGTCA3') or TRE (5'TGACTCA 3') binding element that acts as a dominant negative by competitively binding the respective transcription factor. See, e.g., Lunblad et al. (1998) *J Biol Chem* 273:19251-58 and Kusmoki et al. (2002) *Nature Structural Biol* 9:252-56). Alternatively, the decoy is a nucleic acid (e.g., an RNA or DNA) comprising a viral assembly sequence. Optionally, the decoy is a protein, e.g., a protein that can bind a pathogenic protein or nucleic acid (e.g., a protein or nucleic acid required for viral assembly in a cell). The composition optionally also includes the transcription factor, pathogenic protein or nucleic acid, or other molecule to which the molecular decoy binds and/or a cell (e.g., a cell comprising the molecular decoy and/or the molecule to which it binds).

All of the above optional configurations regarding label configuration, caging group configurations, inclusion of targeting elements, inclusion in cellular and non-cellular compositions, matrices, systems, and the like are equally applicable to the caged molecular decoy embodiments. For example, the molecular decoy can comprise a first label, e.g., a label whose signal changes when the molecular decoy binds its target (e.g., the molecular decoy can comprise the first label and a quencher, or the first label and a second label that interacts with the first via FRET, such that the signal from the first label provides an indication of molecular decoy-target binding and thus an indication of inhibition of the target). Similarly, kits for making the caged molecular decoys are also a feature of the invention.

Aptamers

In an additional class of embodiments, a composition comprising a caged aptamer is provided. The aptamer, in uncaged form, binds a ligand, but has one or more first caging groups associated therewith. The first caging groups inhibit (e.g., prevent) the aptamer from binding to the ligand. All of the above optional configurations regarding label configuration, caging group configurations, inclusion of targeting elements, inclusion in cellular and non-cellular compositions, and the like are equally applicable to the caged aptamer embodiments. Similarly, matrices and systems comprising the aptamers are features of the invention, as are kits for making the caged aptamers. It is worth noting that the composition can also include the ligand.

The caging groups can inhibit the aptamer from binding to the ligand by at least about 75%, at least about 90%, at least about 95%, or at least about 98%, as compared to the aptamer in the absence of the first caging groups, or the caging groups can prevent the aptamer from binding to the ligand. Typically, removal of or an induced conformational change in the caging groups permits the aptamer to bind the ligand.

Aptamers can be selected, designed, etc. for binding various ligands by methods known in the art. For example, aptamers are reviewed in Sun S. "Technology evaluation: SELEX, Gilead Sciences Inc." *Curr Opin Mol Ther.* 2000 February; 2(1): 100-5; Patel D J, Suri A K. "Structure, recognition and discrimination in RNA aptamer complexes with cofactors, amino acids, drugs and aminoglycoside antibiotics" *J Biotechnol.* 2000 March, 74(1):39-60; Brody E N, Gold L. "Aptamers as therapeutic and diagnostic agents" *J Biotechnol.* 2000 March, 74(1):5-13; Hermann T, Patel D J. "Adaptive recognition by nucleic acid aptamers" *Science* 2000 Feb 4, 287(5454):820-5; Jayasena SD. "Aptamers: an emerging class of molecules that rival antibodies in diagnostics" *Clin*

Chem. 1999 September, 45(9): 1628-50; and Famulok M, Mayer G. "Aptamers as tools in molecular biology and immunology" *Curr Top Microbiol Immunol.* 1999, 243:123-36.

Antibodies

An additional feature of the invention is a caged antibody, e.g., an antibody that binds an epitope and one or more first caging groups associated with the antibody. One embodiment provides a composition comprising a caged antibody that includes an antibody that binds an epitope, a cellular delivery module and/or at least one subcellular delivery module associated with the antibody, and one or more first caging groups associated with the antibody. The first caging groups inhibit (e.g., prevent) the antibody from binding to the epitope. The composition optionally also includes the epitope and/or a cell, e.g., a cell comprising the caged antibody and/or the epitope.

In a related embodiment, a cell comprising a caged antibody is provided. The caged antibody comprises an antibody that binds an epitope and one or more first caging groups associated with the antibody. The first caging groups inhibit (e.g., prevent) the antibody from binding to the epitope. The cell optionally also includes the epitope.

For either of these related embodiments, the antibody can be, e.g., a monoclonal antibody, a single-chain antibody, or the like. The antibody can be labeled, e.g., in any of the basic configurations noted above. The first caging groups can be associated with the antibody in any of the configurations noted above. The caged antibody can be associated with a cellular delivery module or a subcellular delivery module as above. The caged antibody, whether in the cell or not, can be in an array in any of the basic configurations herein.

The caging groups can inhibit the antibody from binding to the epitope by at least about 50%, at least about 75%, at least about 90%, at least about 95%, or at least about 98%, as compared to the antibody in the absence of the first caging groups, or the caging groups can prevent the antibody from binding to the epitope. Typically, removal of or an induced conformational change in the caging groups permits antibody to bind to the epitope.

Kits for making the caged antibody comprising an antibody, one or more first caging groups, and instructions for assembling the antibody and the first caging groups to form the caged antibody, packaged in one or more containers are a feature of the invention. Similarly, kits for making the caged antibody comprising one or more first caging groups and instructions for assembling the first caging groups and an antibody supplied by a user of the kit to form the caged antibody, packaged in one or more containers are a feature of the invention. In an additional aspect, kits for making the caged antibody comprising an antibody, one or more first caging groups, one or more cellular delivery modules and/or at least one subcellular delivery module, and instructions for assembling the antibody, the first caging groups, and the delivery modules to form the caged antibody, packaged in one or more containers are a feature of the invention. Similarly, kits for making caged antibody comprising one or more first caging groups, one or more cellular delivery modules and/or at least one subcellular delivery module, and instructions for assembling the first caging groups, the delivery modules, and an antibody supplied by a user of the kit to form the caged antibody, packaged in one or more containers are provided. Systems and apparatus comprising the caged antibodies are a feature of the invention.

Ribozymes

Caged ribozymes are an additional feature of the invention. In one class of embodiments, a caged ribozyme, comprising a ribozyme and one or more first caging groups associated with the ribozyme, is provided. The first caging groups inhibit (e.g., prevent) the ribozyme from exhibiting an enzymatic activity. Essentially all of the features noted above, e.g., for nucleic acid probes and antisense nucleic acids, apply to this embodiment as well, except that the relevant caged molecule is the ribozyme. It is worth noting that the caged ribozyme can be located inside a cell. One class of embodiments provides a cell comprising a caged ribozyme. Similarly, the ribozyme can be associated with a cellular delivery module and/or a subcellular delivery module, whether the caged ribozyme is in the cell or not.

The caging groups can inhibit the enzymatic activity of the ribozyme by at least about 50%, at least about 75%, at least about 90%, at least about 95%, or at least about 98%, as compared to the ribozyme in the absence of the first caging groups, or the caging groups prevent the ribozyme of from exhibiting the enzymatic activity. Typically, removal of or an induced conformational change in the caging groups permits the ribozyme to exhibit the enzymatic activity.

RNAi

Another class of embodiments provides a caged interfering RNA. The caged interfering RNA includes an RNA having at least one double-stranded region, the double-stranded region comprising a sense strand and a complementary antisense strand. The caged interfering RNA also includes one or more first caging groups associated with the RNA. The first caging groups prevent the RNA from initiating RNA interference in a cell comprising the RNA. In one embodiment, the RNA comprises a first polyribonucleotide comprising the sense strand and a second polyribonucleotide comprising the antisense strand. In another embodiment, the RNA comprises a self-complementary polyribonucleotide (e.g., a hairpin). In either case, the double-stranded region optionally comprises fewer than about 25 base pairs, fewer than about 50 base pairs, fewer than about 150 base pairs, fewer than about 250 base pairs, fewer than about 500 base pairs, fewer than about 1000 base pairs, or fewer than about 1500 base pairs. Although a double-stranded region comprising about 20-25 base pairs is typically sufficient to initiate RNAi, longer regions may be convenient or desirable in certain applications (e.g., double-stranded RNAs longer than 25 bp can stimulate the immune system, which can be advantageous in certain applications).

As with any or all of the embodiments above describing caged molecule embodiments, considerations regarding optional caged RNA location (in a cell or cell lysate, etc.), configurations of the caging groups (covalent, non-covalent, photoactivatable, photoremovable, non-photo removable, etc.), association of the RNA with cellular delivery modules or subcellular delivery modules, cell targeting molecules or moieties, incorporation of the RNAs into matrices, and the like apply to this embodiment as well. Kits for making the caged RNA (e.g., comprising an RNA, one or more first caging groups, and instructions for assembling the RNA and the first caging groups to form the caged RNA, packaged in one or more containers, and/or one or more first caging groups and instructions for assembling the first caging groups and an RNA supplied by a user of the kit to form the caged RNA, packaged in one or more containers) are also a feature of the invention. Optionally, any of the various systems and devices noted above can be applied here as well, e.g., including the caged RNAs of this class of embodiments. Similarly, the RNA (e.g., the sense strand and/or the antisense strand) can optionally comprise one or more labels, and can optionally also comprise one or more quenchers (e.g., an acceptor fluorophore or a dark quencher). For example, the sense strand can comprise a first label and the antisense strand a second label. The two labels can be, e.g., different, non-interacting fluorophores with distinct emission spectra (e.g., red and green, such that the double-stranded RNA is yellow while the single strands are red and green). As another example, the two labels can be a fluorophore and a quencher (e.g., two fluorophores that quench and unquench via FRET-mediated phenomena). See, e.g., Byrom et al. "Visualizing siRNA in mammalian cells: Fluorescence analysis of the RNAi effect" *Ambion TechNotes* 9(3).

Caging the interfering RNA allows, e.g., precise control over the timing of gene silencing by controlling initiation of RNA interference (also called RNAi or RNA-mediated interference). Use of RNAi for inhibiting gene expression in a number of cell types (including, e.g., mammalian cells) and organisms is well described in the literature, as are methods for determining appropriate interfering RNA(s) to target a desired gene and for generating such interfering RNAs. For example, RNA interference is described e.g., in US patent application publications 20020173478, 20020162126, and 20020182223 and in Hannon G. J. "RNA interference " *Nature*. 2002 Jul. 11,418(6894):244-51; Ueda R. "RNAi: a new technology in the post-genomic sequencing era" *J Neurogenet*. 2001, 15(3-4):193-204; Ullu et al. "RNA interference: advances and questions" *Philos Trans R Soc Lond B Biol Sci*. 2002 Jan. 29, 357(1417):65-70; and Schmid et al. "Combinatorial RNAi: a method for evaluating the functions of gene families in Drosophila" *Trends Neurosci*. 2002 Feb., 25(2):71-4. A kit for producing interfering RNAs is commercially available, e.g., from Ambion, Inc. (on the internet at ambion.com, the Silencer™ siRNA construction kit). Kits for labeling such RNAs are available from the same source.

Labeled Modulators

In another class of embodiments, a composition comprising a labeled modulator is provided. The modulator includes a modulator of an activity of a protein and a first label. A first signal exhibited by the first label when the modulator is not bound to the protein is distinguishable from a second signal exhibited by the first label when the modulator is bound to the protein. For example, the binding-dependent signal from the first label can be based on FRET (e.g., between the first label and a quencher) that is induced or disrupted by modulator binding to the protein target. As another example, a fluorescent first label can be shielded within a binding pocket of the modulator's protein target, thus producing binding-dependent signals.

The caging groups can inhibit the modulator from binding to the protein and/or affecting the activity of the protein by at least about 50%, at least about 75%, at least about 90%, at least about 95%, or at least about 98%, as compared to the modulator in the absence of the first caging groups, or the first caging groups can prevent the modulator from binding to the protein and/or affecting the activity of the protein. Typically, removal of, or an induced conformational change in, the first caging groups permits the modulator to bind to the protein and/or to affect the activity of the protein.

The modulator can be, for example, an activator or an inhibitor (e.g., a competitive inhibitor, a noncompetitive inhibitor, a reversible inhibitor, an irreversible inhibitor, and/or a cleavable inhibitor that blocks the active site following cleavage, e.g., by a protease). The labeled modulator can be, e.g., a small molecule, a polypeptide, a nucleic acid, a carbohydrate, or the like. The protein affected by the modulator can be, e.g., an enzyme, a channel protein, a transporter, or the like. In one example, the enzyme is protein kinase C and the modulator is the inhibitor HB89. The various optional configurations and features for the embodiments above apply here as well. For example, any or all of the various label configurations noted above apply to this embodiment also (e.g., the first label can be optical or fluorescent, etc.). Any of the caging groups and configurations noted above can be associated with or applied to the modulator to regulate activity of the modulator. Compositions comprising the modulator with and/or in cells, or with cell components, apply to this embodiment as well. The composition optionally also includes the protein. The use of additional labels in a manner similar to those noted for the above embodiments applies to this class of embodiments in a manner similar to that noted above. Similarly, the modulator can be associated with a cellular or subcellular delivery module as noted above. As with the embodiments above, kits for making the labeled or caged labeled modulator, and matrices, systems and apparatus that include the labeled modulator, are a feature of the invention.

Use of a labeled modulator provides many advantages. For example, the ability to determine, by monitoring the first and/or second signals, the location within a cell where activation or inhibition of the target protein's activity is occurring and/or a more accurate measurement of the time between the occurrence of inhibition of the target and a downstream effect. Use of a caged labeled modulator provides the additional advantages of controlling the timing, location, etc. of modulation of the protein's activity.

Modulators of protein activity have been well described in the art. See, e.g., *J Biol Chem* (2002) 277:41014-22; *PNAS* (1998) 95:1568-1573; U.S. Pat. No. 5,998,580 to Fay et al. (Dec. 7, 1999) entitled "Photosensitive caged macromolecules"; U.S. Pat. No. 6,043,065 to Kao et al. (Mar. 28, 2000) entitled "Photosensitive organic compounds that release 2,5,-di(tert-butyl) hydroquinone upon illumination"; and Llopis et al. "Ligand-dependent interactions of coactivators steroid receptor coactivator-1 and peroxisome proliferator-activated receptor binding protein with nuclear hormone receptors can be imaged in live cells and are required for transcription" *PNAS* (2000) 97:4363-4368.

Compositions with Two or More Caged Components

Caged compounds, including the caged sensors and regulators of this invention, can be used in various combinations. Thus, in one class of embodiments, the invention provides a composition comprising at least a first caged component and a second caged component. Typically, the first caged component can be uncaged by exposure to energy of a first type and the second caged component can be uncaged by exposure to energy of a second type different from the first type. The various uncaging energies for the first and second types can be the same general type (e.g., where the energy of the first type is light of a first wavelength and the energy of the second type is light of a second wavelength) or they can be of different general types (e.g., light and heat or light and sonication energy). Alternatively, the first caged component and the second caged component can be uncaged by exposure to energy of the same type (e.g., the first and second caged components can be uncaged by light of a given wavelength). As noted, caged components can also be uncaged by changes in pH or ionic strength or by other environmental changes. The composition optionally comprises three or more caged components. The caged components can be, e.g., any of those noted above, e.g., a caged sensor (e.g., an enzyme or binding sensor), a caged nucleic acid probe, a caged modulator, a caged antisense nucleic acid, a caged ribozyme, a caged biomolecular analog, a caged transcription factor, a caged molecular decoy, a caged antibody, a caged aptamer, and/or a caged interfering RNA or RNAi-based sensor (e.g., as described above or in U.S. Patent Application 60/484,785, filed Jul. 3, 2003 and in U.S. patent application Ser. No. 10/716,393, filed of even date herewith, entitled "RNAi-based sensors, caged interfering RNAs, and methods of use thereof" by Nguyen and McMaster). Other caged components include, but are not limited to, a caged polypeptide, a caged nucleic acid, a caged lipid, a caged carbohydrate, a caged small molecule, a caged metal ion, a caged nucleotide (e.g., a caged nucleoside triphosphate or caged cAMP), a caged chelating agent, a caged fluorescent dye, a caged second messenger, and/or a caged neurotransmitter. See, e.g., Haughland (2003) *Handbook of Fluorescent Probes and Research Products* Ninth Edition or the current Web Edition, available from Molecular Probes, Inc.; and Shigeri et al. (2001) "Synthesis and application of caged peptides and proteins" Pharmacology & Therapeutics 91:85-92). A number of caged compounds, including, for example, caged nucleotides, caged Ca2+, caged chelating agents, caged neurotransmitters, and caged luciferin, are commercially available, e.g., from Molecular Probes, Inc. (on the internet at (www.) molecularprobes.com). The caged components can be in essentially any combination; e.g., two or more caged sensors, a caged sensor and a caged modulator, a caged sensor and a caged chelating agent, a caged interfering RNA and a caged nucleic acid probe, two or more caged nucleic acid probes, a caged antisense nucleic acid and a caged nucleic acid probe, a caged sensor and a caged nucleic acid probe, a caged sensor and a caged interfering RNA and a caged nucleic acid probe, or a caged transcription factor and a caged nucleic acid probe, to list only a few examples. The compositions can be formulated in any of the various states noted above, e.g., in cells, cell compartments, cell extracts, matrices, systems, and devices and kits.

As noted, the composition optionally comprises a cell. In some embodiments, a single cell comprises the first and second caged components. In a related class of embodiments, a first cell comprises the first caged component and a second cell comprises the second caged component (e.g., in a mixed culture of first and second cells). In yet another related class of embodiments, a cell comprises the first caged component, and the second caged component is outside the cell (e.g., in a culture medium, an extracellular space, or the like).

In some embodiments, the first and second (and optionally third, etc.) caged components are not physically connected. For example, one molecule can comprise the first component (caging groups and/or delivery modules can be covalently and/or noncovalently associated with the first component), while a second molecule can comprise the second component (caging groups and/or delivery modules can be covalently and/or noncovalently associated with the second component). In other embodiments, the first and second (and optionally third etc.) caged components are physically connected. For example, the first and second caged components can be connected by a linker (which can optionally be caged). The linker can, for example, be a photolabile or otherwise cleavable linker. For example, a single molecule can comprise the first component (with associated caging groups), a photolabile linker, and the second component (with associated caging groups), and can optionally further comprise one or more cellular and/or subcellular delivery modules. (It is worth noting that in some instances, a caged component can also function as a delivery module.) Such physically connected caged components can comprise, e.g., a polypeptide, a polypeptide joined to a nucleic acid (e.g., DNA, RNA and/or PNA), a nucleic acid (e.g., a nucleic acid comprising two nucleic acid probes), different types of nucleic acids, or the like (as only a few examples, the molecule can comprise a DNA and a polypeptide, a PNA and a polypeptide, or a DNA, a PNA and a polypeptide).

Use of physically connected components provides a significant advantage for use in cellular assays, in that the components are introduced into the cell in a predetermined molar ratio. For example, if a molecule comprising two linked sensors is introduced into cells, each cell will receive a one to one ratio of the sensors even though the concentration of the sensors may be different for different cells.

Caged Components with Cellular Delivery Modules

As noted, caged substances can be conveniently introduced into cells by cellular delivery modules associated with the caged substances. Thus, one general class of embodiments provides a composition comprising a caged component, which caged component comprises a component, one or more first caging groups associated with the component, and a cellular delivery module associated with the component, which cellular delivery module can mediate introduction of the component into a cell. The caged components can be, e.g., any of those described or noted herein, e.g., a caged sensor (e.g., an enzyme or binding sensor), a caged nucleic acid probe, a caged modulator, a caged antisense nucleic acid, a caged ribozyme, a caged biomolecular analog, a caged transcription factor, a caged molecular decoy, a caged antibody, a caged aptamer, a caged interfering RNA or RNAi-based sensor, a caged polypeptide, a caged nucleic acid, a caged lipid, a caged carbohydrate, a caged small molecule, a caged metal ion, a caged nucleotide (e.g., a caged nucleoside triphosphate or caged cAMP), a caged chelating agent, a caged fluorescent dye, a caged second messenger, and/or a caged neurotransmitter.

In one class of embodiments, the cellular delivery module comprises a polypeptide, e.g., a PEP-1 peptide, an amphipathic peptide (e.g., an MPG or MPG$^{\Delta NLS}$ peptide), or a cationic peptide (e.g., a homopolymer of histidine, lysine, or D-arginine) that is covalently or non-covalently associated with the one or more molecules. In one embodiment, the cellular delivery module comprises a protein transduction domain, e.g., derived from an HIV-1 TAT protein, from a herpes simplex virus VP22 protein, and/or from a *Drosophila* antennapedia protein. In one aspect, the protein transduction domain is a model protein transduction domain (e.g., a homopolymer of D-arginine, e.g., 8-D-Arg).

Optionally, the cellular delivery module associated with the component comprises a lipid, e.g., a fatty acid. For example, the component can be covalently attached to one or more myristoyl groups, e.g. via a photolabile linker.

Optionally, the cellular delivery module is covalently attached to the component. For example, the covalent attachment is optionally reversible by exposure to light of a preselected wavelength. As another example, the covalent attachment is optionally a disulfide or ester linkage that is reduced or cleaved once the sensor is inside a cell.

In one aspect, the cellular delivery module is associated with one or more second caging groups, the presence of which prevents the cellular delivery module from mediating introduction of the component into a cell.

Essentially all of the features noted above, e.g., for various caged components, apply to this embodiment as well, as are relevant. For example, the composition optionally also includes a cell, e.g., a cell comprising the caged component, and systems comprising the composition are also a feature of the invention.

Methods

Other embodiments herein provide methods for using any or all of the above compositions, e.g., in an appropriate assay. Similarly, methods for making any of the above compositions (e.g., by coupling caging groups to the relevant moiety and, optionally, putting the resulting molecule into a cell) are also features of the invention.

Enzyme Assays

In a first general class of embodiments, a method of assaying an activity of an enzyme is provided. The method includes contacting the enzyme and a caged sensor, by introducing the caged sensor into a cell. The caged sensor comprises one or more molecules collectively comprising a substrate for the enzyme and a first label, and one or more caging groups associated with the one or more molecules. The substrate is in a first state on which the enzyme can act, thereby converting the substrate to a second state. A first signal exhibited by the first label when the substrate is in its first state is distinguishable from a second signal exhibited by the first label when the substrate is in its second state. The caging groups inhibit the enzyme from acting upon the substrate. The assay is initiated by exposing the enzyme and the caged sensor to uncaging energy of a first type, whereby exposure to the uncaging energy frees the first component from inhibition by the first caging groups. The activity of the enzyme is then assayed as appropriate to the enzyme, e.g., by methods known in the art. Typically, the first and/or the second signal is detected.

A second general class of embodiments also provides a method of assaying an activity of an enzyme. The method includes contacting the enzyme and a caged sensor. The caged sensor comprises one or more molecules collectively comprising a substrate for the enzyme and a first label, and one or more caging groups associated with the one or more molecules. The substrate is in a first state on which the enzyme can act, thereby converting the substrate to a second state. The first state is not converted to the second state by cleavage by the enzyme. A first signal exhibited by the first label when the substrate is in its first state is distinguishable from a second signal exhibited by the first label when the substrate is in its second state. The caging groups inhibit the enzyme from acting upon the substrate. The assay is initiated by exposing the enzyme and the caged sensor to uncaging energy of a first type, whereby exposure to the uncaging energy frees the first component from inhibition by the first caging groups. The activity of the enzyme is then assayed as appropriate to the enzyme, e.g., by methods known in the art. Typically, the first and/or the second signal is detected. The method optionally includes contacting the enzyme and the caged sensor by introducing the caged sensor into a cell.

For either of these related general classes of embodiments, any of the above embodiments can be applied as well, to the extent they are relevant. For example, exposing the enzyme and the caged sensor to uncaging energy of a first type optionally includes sonicating the enzyme and the caged sensor or exposing the enzyme and the caged sensor to light of a first wavelength. This exposure can be addressable, e.g., the enzyme and the caged sensor can be exposed to light of a first wavelength by exposing one or more preselected areas (e.g., wells in a microtiter plate, in any of the well configurations noted herein; or one or more channels in a microfluidic chip) comprising the relevant components to the light.

The preselected areas can be simultaneously or serially exposed to the uncaging energy. For example, the one or more preselected areas can comprise a plurality of the wells of a multiwell plate, and exposing the preselected areas to the light can comprise exposing the plurality of wells to the light simultaneously (similarly, sonication or thermal energy can be applied to one or more wells in series or simultaneously). Similarly, the one or more preselected areas can comprise a plurality of the channels of a microfluidic chip, wherein exposing the preselected areas to the light comprises exposing the plurality of channels to the light simultaneously. In another embodiment, the one or more preselected areas comprise one or more spots of a microarray. For example, the one or more preselected areas can comprise a plurality of the spots of the microarray, wherein exposing the preselected areas to the light comprises exposing the plurality of spots to the light simultaneously. In another embodiment, the one or more preselected areas comprise one or more regions of a cell, a tissue, or a body of an organism. Here the uncaging energy can be, e.g., light, heat, or other energy delivered by conventional techniques such as during MRI, PET or CAT scanning or by a laser emitting an appropriate wavelength, e.g., a laser coupled to a fiber optic delivery system.

Exposing the enzyme and the caged sensor to light of a first wavelength optionally comprises exposing the enzyme and the caged sensor to light such that the intensity of the light and the duration of exposure to the light are controlled so that a first portion of the caged first component (which can be a selected amount) is uncaged and a second portion of the caged first component remains caged. Put another way, the uncaging rate can be controlled. Furthermore, the uncaging step can be repeated until the components are depleted, providing multiple controlled reaction initiations for one set of reagents.

A plurality of caged components can be used in the assays herein. For example, the method can include contacting the enzyme and a second caged component comprising one or more second caging groups and exposing the second caged component to uncaging energy of a second type, whereby exposure to the uncaging energy frees the second component from inhibition by the second caging groups. The second caged component can, e.g., be required for initiation of the assay or for detection of the activity of the enzyme. The second caged component can be, e.g., a nucleoside triphosphate, ATP, a metal ion, a polypeptide (e.g., a phosphobinder or an antibody), a nucleic acid (e.g., a nucleic acid probe or an aptamer), a carbohydrate, and/or a lipid. As yet another example, the additional component that is caged can be required for termination of the assay (e.g., an inhibitor or a chelating agent, e.g., EDTA, EGTA, or citrate). As yet another example, the additional component can comprise a modulator, e.g., an activator or inhibitor of the enzyme or another enzyme involved, or thought to be involved, in the same pathway (as just one example, a caged inhibitor can be uncaged, followed by uncaging of a caged sensor). The methods thus allow initiation, detection, modulation and/or termination of the reaction to be conveniently and precisely controlled, temporally and/or spatially, since the various caging groups optionally respond to different uncaging conditions (e.g., different wavelengths of uncaging light, pH, temperature, etc.).

Using a plurality of caged components can also permit multiplexing of enzyme assays. For example, the plurality of caged components can include a second sensor for detecting activity of a second enzyme. (Optionally, a third, fourth, etc. caged sensor can also be used). The first and second sensors can either be uncaged under the same conditions, to permit simultaneous activation of the sensors, or under different conditions, to permit simultaneous or independent activation of the sensors. Typically, the second sensor emits enzyme activity-dependent signal(s) distinguishable from the signal emitted by the first sensor. The sensors can optionally be bound to a matrix (e.g., a surface or a bead) or be tagged (e.g., with a unique oligonucleotide) for binding to such a matrix. Use of multiplex assays allows the activity of two or more enzymes to be monitored simultaneously. One example application includes detecting when during the cell cycle a particular enzyme is active; a sensor for the enzyme can be multiplexed in a cellular assay (even with an asynchronous culture) with sensors for other enzymes whose cell-cycle dependent activity patterns have already been established (e.g., kinases such as PKC).

The various uncaging energies for the different caged components can be of the same type (e.g., light of the same wavelength) or different types. These different types of uncaging energies can be the same general type (e.g., where the energy of one type is light of a first wavelength and the energy of another type is light of a second wavelength) or they can be of different types (e.g., light and heat or light and sonication energy).

The methods can include introducing any of the components noted above (e.g., the caged sensor) into cells (or into subcellular compartments or other features), or into tissues or organisms, or producing cell lysates, or the like. Contacting the enzyme with one or more reagents can include introducing the first caged component into an organism, or into serum, plasma, intercellular fluid, etc. The method is applicable to biochemical assays, cell lysate assays (prepared before or after addition of the first component) cell assays, organism assays or the like. Benefits of the methods include improved quantification, real-time results, and in vitro assay to cell assay and/or to organism assay translation.

The methods are also applicable to multiplexed assays. For example, for each of the assays to be multiplexed, a caged sensor can be bound to a matrix (e.g., a surface, e.g., an array, or a bead) or can be configured to be captured on a matrix (e.g., the caged sensor can comprise a first oligonucleotide complementary to a second oligonucleotide bound to the matrix, e.g., in an array of such oligonucleotides). Assays can be multiplexed in vitro (e.g., using arrays of enzyme sensors) or in vivo (e.g., by introducing caged enzyme sensors comprising oligonucleotides into a cell, uncaging the sensors, lysing the cells, capturing the sensors on a matrix comprising complementary oligonucleotides, and detecting signal(s) from the sensors).

The methods can use any of the sensor configurations, enzymes, modulators, signal detection steps, and/or the like, as noted above. Thus, for example, the caged sensor can include a specific or a generic substrate. It is worth noting that in embodiments in which the caged sensor and the enzyme are contacted in a cell, the enzyme can be endogenous to the cell or can be transiently or stably expressed (e.g., overexpressed) in the cell by introducing a vector encoding the enzyme into the cell. It is worth noting that in embodiments in which the caged sensor includes a generic substrate and the enzyme is overexpressed in the cell, the majority of the modifications to the substrate that are detected will be due to the overexpressed enzyme.

Additional Methods

In an additional class of embodiments, methods of using a caged sensor are provided. In the methods, a caged sensor is provided. The caged sensor comprises one or more molecules collectively comprising a binding target and a first label. One or more first caging groups are associated with the one or more molecules, the first caging groups inhibiting (e.g., preventing) the binding target from binding to its partner. The caged sensor and the partner are contacted and exposed to uncaging energy, whereby exposure to the uncaging energy frees the sensor from the caging groups and permits the binding target to bind the partner. All of the above optional method variations apply to this method as well. Further, the various composition components noted above can be adapted for use in this method, as appropriate. The methods can be used, e.g., to localize the partner within a cell, or to assay an intermolecular association.

In one example class of embodiments, methods of assaying an intermolecular association between a first molecule and a second molecule that are capable of a stable interaction with each other are provided. In the methods, the first and second molecules are contacted, wherein one or more caging groups are associated with at least the first molecule (and optionally the second). The caging groups inhibit (e.g., prevent) the association of the first and second molecules. The assay is initiated by exposing the first and second molecules to uncaging energy, whereby exposure to the uncaging energy frees the first and/or second molecule from inhibition by the caging groups. The association between the first and second molecules is then assayed, e.g., with techniques established in the art. All of the above optional method variations apply to this method as well. Further, the various composition components noted above can be adapted for use in this method, as appropriate.

In an additional class of embodiments, methods of detecting a target nucleic acid are provided. In this class of methods, the target nucleic acid and at least one caged probe nucleic acid are contacted together (e.g., one caged probe nucleic acid or a plurality of caged probe nucleic acids). The caged probe nucleic acid includes a probe nucleic acid having one or more caging groups associated with the probe nucleic acid. The probe nucleic acid has a region of complementary to a first strand of the target nucleic acid. The caging groups inhibit (e.g., prevent) the probe nucleic acid from binding to the first strand of the target nucleic acid. The method also includes exposing the caged probe nucleic acid and the target nucleic acid to uncaging energy, whereby exposure to the uncaging energy frees the probe nucleic acid from inhibition by the caging groups and permits the probe nucleic acid to bind to the first strand of the target nucleic acid. A binding-dependent signal from the probe nucleic acid is detected. All of the above optional method variations apply to this method as well. Further, the various composition components noted (particularly the caged nucleic acid probe embodiments) above can be adapted for use in this method, as appropriate.

In yet an additional class of methods of the invention, methods of selectively inhibiting expression of a gene in a cell are provided. In the methods, a caged RNA is introduced into the cell. The caged RNA includes an RNA comprising at least one double-stranded region in which each strand comprises a region of complementarity to at least a portion of the gene. The caged RNA comprises one or more caging groups associated with the RNA, the caging groups inhibiting (e.g., preventing) the RNA from initiating RNA interference in the cell. RNA interference is initiated by exposing the cell to uncaging energy (e.g., light of a predetermined wavelength), freeing the RNA from the caging groups. All of the above optional method variations apply to this method as well. Further, the various composition components noted (particularly the caged RNA interference embodiments) above can be adapted for use as appropriate in this method.

The invention also includes other methods of selectively inhibiting expression of a gene in a cell. In the methods, a first caged DNA and a second caged DNA are introduced into the cell. The first caged DNA includes a first DNA encoding a sense RNA and one or more caging groups. The second caged DNA comprises a second DNA encoding an antisense RNA and one or more caging groups. The caging groups inhibit (e.g., prevent) transcription of the first and second DNAs, the first and second DNAs each comprising at least a portion of the gene, and the sense and antisense RNAs being at least partially complementary and able to form a duplex over at least a portion of their lengths. RNA interference is initiated by generating double-stranded RNA by exposing the cell to uncaging energy, whereby exposure to the uncaging energy frees the first and second DNAs from the caging groups and permits transcription of the first and second DNAs to occur. All of the above optional method variations apply to this method as well. Further, the various composition components noted above can be adapted for use in this method, as appropriate. It is worth noting that the first and second DNAs can optionally be included on a single plasmid (see, e.g., US patent application publication 20020182223).

In an additional related class of embodiments, methods of selectively inhibiting expression of a target nucleic acid in a cell are provided. In the methods, a caged antisense nucleic acid is introduced into the cell, the caged antisense nucleic acid comprising an antisense nucleic acid comprising a region of complementarity to the target nucleic acid and one or more caging groups associated with the antisense nucleic acid. The caging groups inhibit (e.g., prevent) the antisense nucleic acid from binding to, and inactivating, the target nucleic acid. The cell is exposed to uncaging energy, whereby exposure to the uncaging energy frees the antisense nucleic acid from inhibition by the caging groups and permits the antisense nucleic acid to inactivate the target nucleic acid. All of the above optional method variations apply to this method as well. For example, exposing the cell to uncaging energy optionally comprises exposing the cell to light of a first wavelength. Further, the various composition components noted above can be adapted for use in this method, as appropriate.

In yet an additional related class of embodiments, methods of activating a ribozyme are provided. In the methods, a caged ribozyme is provided, the caged ribozyme comprising a ribozyme and one or more caging groups. The caging groups inhibit (e.g., prevent) the ribozyme from exhibiting an enzymatic activity. The caged ribozyme is introduced into a cell. Exposing the caged ribozyme to uncaging energy frees the ribozyme from inhibition by the caging groups and permits the ribozyme to exhibit the enzymatic activity. All of the above optional method variations apply to this method as well. Further, the various composition components noted above (e.g., with respect to ribozymes) can be adapted for use in this method, as appropriate.

In still an additional related class of embodiments, methods of regulating the expression of a gene comprising a first promoter in a cell are provided. In the methods, a caged transcription factor is introduced into the cell. The caged transcription factor comprises a transcription factor capable of regulating transcription from the first promoter, and one or more caging groups associated with the transcription factor. The caging groups inhibit (e.g., prevent) the transcription factor from regulating transcription from the first promoter. Exposing the cell to uncaging energy frees the transcription factor from inhibition by the caging groups and permits the transcription factor to regulate transcription from the first promoter. All of the above optional method variations apply to this method as well. Further, the various composition components noted above (e.g., with respect to transcription factors) can be adapted for use in this method, as appropriate.

In yet an additional related class of embodiments, methods of regulating transcription of a gene are provided. The methods include introducing a caged direct transcriptional modulator into a cell, wherein the caged transcriptional modulator comprises a transcriptional modulator (e.g., a molecular decoy, a transcription factor, or a transcription factor binder or modulator, e.g., a nuclear binding receptor enzyme) and one or more caging groups. The caging groups inhibit (e.g., prevent) the transcriptional modulator from affecting expression of the gene. Exposing the cell to uncaging energy frees the transcriptional modulator from inhibition by the caging groups and permits the transcriptional modulator to regulate transcription of the gene. All of the above optional method variations apply to this method as well. Further, the various composition components noted above (e.g., with respect to transcription factors and molecular decoys) can be adapted for use in this method, as appropriate.

In an additional class of embodiments, methods of using a labeled modulator are provided. In the methods, a protein and the labeled modulator are contacted. The protein has an activity and the labeled modulator comprises a modulator of the activity and a first label. A first signal exhibited by the first label when the modulator is not bound to the protein is distinguishable from a second signal exhibited by the first label when the modulator is bound to the protein. The first and/or second signal is detected. Optionally, the labeled modulator further includes one or more caging groups associated with the labeled modulator, where the caging groups inhibit (e.g., prevent) the labeled modulator from binding to the protein and/or affecting the activity of the protein. Optionally, the methods further includes exposing the protein and the caged labeled modulator to an uncaging energy, whereby exposure to the uncaging energy frees the labeled modulator from inhibition by the caging groups and permits the labeled modulator to bind to and affect the activity of the protein. All of the above optional method variations apply to this method as well. Further, the various composition components noted above (e.g., with respect to caged modulators) can be adapted for use in this method, as appropriate.

In an additional class of embodiments, methods of using a caged antibody are provided. In the methods, a caged antibody is introduced into a cell. The caged antibody comprises an antibody that binds an epitope and one or more caging groups. The caging groups inhibit (e.g., prevent) the antibody from binding to the epitope. Exposing the cell to uncaging energy frees the antibody from inhibition by the caging groups and permits the antibody to bind the epitope. All of the above optional method variations apply to this method as well. Further, the various composition components noted above (e.g., with respect to caged antibodies) can be adapted for use in this method, as appropriate.

In an additional class of embodiments, methods of using a caged biomolecular analog are provided. In the methods, a caged biomolecular analog is provided. The caged biomolecular analog comprises a biomolecular analog and one or more caging groups associated with the biomolecular analog, the biomolecular analog comprising a molecule comprising one or more nonnatural nucleotides and/or one or more nonnatural amino acids. Exposing the caged biomolecular analog to uncaging energy frees the biomolecular analog from inhibition by the caging groups. All of the above optional method variations apply to this method as well. Further, the various composition components noted above (e.g., with respect to caged biomolecular analogs) can be adapted for use in this method, as appropriate.

In an additional class of embodiments, methods of using a caged molecular decoy are provided. In the methods, a caged molecular decoy and a protein are contacted. The caged molecular decoy comprises a molecular decoy that binds the protein and one or more caging groups associated with the molecular decoy, the caging groups inhibiting (e.g., preventing) the molecular decoy from binding to the protein. Exposing the caged molecular decoy to uncaging energy frees the molecular decoy from inhibition by the caging groups and permits the molecular decoy to bind the protein. All of the above optional method variations apply to this method as well. Further, the various composition components noted above (e.g., with respect to caged molecular decoys) can be adapted for use in this method, as appropriate.

In an additional class of embodiments, methods of using a caged aptamer are provided. In the methods, a caged aptamer and a ligand are contacted. The caged aptamer comprises an aptamer that binds the ligand and one or more caging groups associated with the aptamer, the caging groups inhibiting (e.g., preventing) the aptamer from binding to the ligand. Exposing the caged aptamer to uncaging energy frees the aptamer from inhibition by the caging groups and permits the aptamer to bind the ligand. All of the above optional method variations apply to this method as well. Further, the various composition components noted above (e.g., with respect to caged aptamers) can be adapted for use in this method, as appropriate.

In an additional class of embodiments, methods of using a plurality of caged components are provided. In the methods, a first caged component and at least a second caged component are contacted. The first caged component is uncaged by exposure to uncaging energy of a first type and the second caged component is uncaged by exposure to uncaging energy of a second type, the same as or different from the first type. The first and second caged components can be uncaged simultaneously or sequentially, as desired. The caged components are exposed to uncaging energy of the first and second type. All of the above optional method variations apply to this method as well. Further, the various composition components noted above (e.g., with pluralities of caged components) can be adapted for use in this method, as appropriate.

Introduction and Uncaring of Caged Substrates into Cells, and Release of Uncaged Substrates from Cells As described throughout, a caged substrate of interest is optionally introduced into a cell, uncaged, incubated with a substrate modification component (e.g., enzyme, ribozyme, etc.), and the effect on the uncaged substrate of interest is detected. Optionally, the effect of a modulator on the activity of the substrate modification component is detected, e.g., to provide a screen for modulators of substrate modification components. In general, these approaches can be performed entirely in the cell, or detection of modifications to the substrate of interest can be performed after cell lysis and/or fixation. Several sections herein describe detection of the substrate of interest in a cell, e.g., a living cell. In this section, methods and related compositions, kits and systems are further described for those procedures in which the cell is lysed or fixed prior to detection of the substrate of interest. To the extent that the discussion in this section relates to features that are generally applicable to the other methods, systems, compositions and kits herein, it will be appreciated that these features can be applied to such other methods, systems, compositions and kits.

Methods

Methods of detecting modification(s) of a substrate of interest are provided. In several of the methods herein, an initial substrate is typically first introduced into a cell. The initial substrate can be any substrate noted herein, e.g., an enzyme substrate, e.g., a kinase substrate, an oxidoreductase substrate, a transferase substrate, a hydrolase substrate, a lyase substrate, a ligase substrate, an isomerase substrate, a phosphatase substrate, a GTPase substrate, an ATPase substrate, a phosphodiesterase substrate, a luciferase substrate, an acetylase substrate, a glycosylase substrate, a ubiquitin-conjugating enzyme substrate, a hydrogenase substrate, a polymerase substrate, a peroxidase substrate, a protease substrate, and/or a caspase substrate, or another substrate of interest, such as a ribozyme substrate, nucleic acid, RNAi, or the like. It will be appreciated that such substrates are ubiquitous targets of interest in molecular medicine, as they can be used to monitor the activity of substrate modification components such as enzymes, antibodies, ribozymes, nucleic acids, and the like. These substrate modification components provide an underlying biochemical basis for many forms of disease, as well as being indicators useful for disease diagnosis and prognosis and for testing potential and actual therapeutic agents of interest.

In most cases, the initial substrate is caged by association with one or more caging moiety that inhibits modification of the substrate in the cell. Any of the caging moieties noted herein, or generally available in the art, are applicable to the subject class of methods. The initial substrate is uncaged in the cell by dissociating part or all of the caging moiety from the substrate to provide an uncaged substrate of interest, or by changing the conformation of the initial substrate or caging moiety, or any combination thereof, as discussed generally herein. The uncaged substrate of interest is modified in the cell by incubation with a substrate modification component, which can, e.g., be co-introduced with the caged substrate, or can be separately introduced, or can be endogenous to the cell.

The initial substrate can be introduced into the cell by co-transfecting, into the cell, the initial substrate with one or more vector that comprises or encodes a substrate modification component. This is not actually necessary, however, as the substrate modification component can be separately introduced into the cell, or the substrate modification component can be endogenous to the cell of interest. Where the substrate modification component is separately introduced (e.g., stably expressed in a cell line), or co-introduced, the vector used for the introduction optionally comprises one or more positive or negative selectable marker (e.g., an antibiotic resistance gene, a CAT gene, a gene that encodes a fluorescent or luminescent marker such as green fluorescence protein, Lac Z or the like) to permit selection of cells that express the substrate modification component of interest for analysis. The vector can also include or encode control molecules that can be used to normalize assay results across assays by providing an indication of the presence and expression level of the vector in a cell of interest.

In general, the substrate modification component modifies the uncaged substrate of interest, but has a substantially reduced activity on the caged substrate, permitting the modification reaction to be "turned on" at a selected time, e.g., after the cell has been incubated a sufficient time to permit expression of the substrate modification component and/or to experience the effects of any modulator or potential modulator of activity of the substrate modification component. The substrate modification component can be essentially any molecule or complex of molecules that has activity on the substrate of interest. Examples of such complexes include substrate binders (molecules or complexes that change the substrate by binding to it, e.g., antibodies, nucleic acids, polypeptides, or the like) and substrate modifiers (molecules that add or remove substrate components, e.g., by cleavage, addition of atoms or molecules to the substrate, etc.). Examples include catalytic molecules, such as enzymes, ribozymes, oxidoreductases, transferases, hydrolases, lyases, ligases, isomerases, kinases, phosphatases, GTPases, ATPases, phosphodiesterases, luciferases, acetylases, glycosylases, ubiquitin-conjugating enzymes, hydrogenases, polymerases, peroxidases, proteases, caspases and the like. Typically, the uncaged substrate of interest is any appropriate cognate substrate for a selected catalytic molecule, e.g., an enzyme substrate, ribozyme substrate, kinase substrate, etc.

The substrate of interest can be a specific substrate (acted on only by a single type of catalytic molecule), or a generic substrate (acted on by more than one member of a class of catalytic molecules). For example, the generic substrate can be recognized by more than one type of enzyme, or, more typically, more than one member of a class of enzymes. For example, the substrate can be a protease substrate that is recognized by several different proteases. For example, several serine proteases recognize conserved generic substrates. For examples of generic (sometimes termed "universal") substrates, see, e.g., Ross et al. (2002) "A non-radioactive method for the assay of many serine/threonine-specific protein kinases" *Biochem. J.* 366, 977-981; and Pinna and Ruzzene (1996) *Biochimica et Biophysica Acta* 1314 191-225. The use of generic substrates can simplify assay design by permitting a relatively small number of substrates to serve as targets for analysis of a relatively large number of substrate modification components.

The vector that is co-transfected with the substrate can include a nucleic acid that encodes the substrate modification component. Alternately, the vector can include the substrate modification component, e.g., the catalytic molecule itself, e.g., as a component of a vector system (e.g., as part of a viral or other vector). Use of vectors is optional in the invention, in that the cell can endogenously comprise the substrate modification component of interest. Typical vectors include genetic vectors that include nucleic acids for the transmission of genetic information, as well as, optionally, accessory factors such as proteins, lipid membranes, associated proteins (e.g., capsid or other structural proteins). An example of a type of genetic vector is a viral vector that can include any of: proteins, polysaccharides, lipids, genetic material (nucleic acids, optionally including DNA and/or RNA) and/or the like. Another example of a genetic vector is a plasmid. In one typical configuration, the vector is a viral vector or a plasmid that encodes the substrate modification component (e.g., the component is encoded in one or more open reading frame(s) of the vector). Many suitable vectors are well known and described, e.g., in Ausubel and Sambrook, both supra. Other useful references, e.g. for cell isolation and/or culture (e.g., for subsequent substrate purification) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

Accordingly, the vector can be, for example, in the form of a plasmid, a bacterium, a virus, a naked polynucleotide, a conjugated polynucleotide, or the like. The vectors and/or initial substrate can be introduced into cells and/or microorganisms by standard methods including electroporation (see, e.g., From et al., *Proc. Natl. Acad. Sci.* USA 82, 5824 (1985)), infection by viral vectors, and high velocity ballistic penetration by small particles with the nucleic acid either within the matrix of small beads or particles or on the surface (see, Klein et al., *Nature* 327, 70-73 (1987)). In a preferred embodiment, the initial substrate and/or vector can also (additionally or alternatively) be associated with a cellular delivery agent to enhance transport of the substrate into the cell. Examples of appropriate cellular delivery agents include polypeptides, e.g., PEP-1 peptides, amphipathic peptides (e.g., an MPG or $MPG^{\Delta NLS}$ peptide), cationic peptides (e.g., homopolymers of D-arginine, homopolymers of histidine, homopolymers of lysine), protein transduction domains, HIV-1 TAT proteins, herpes simplex virus VP22 proteins, Drosophila antennapedia proteins, lipofectamine, and the like. See, e.g., the section titled "In vivo and in vitro cellular delivery" below.

In the class of methods under discussion, the resulting modified substrate is released from the cell, e.g., by cell lysis (e.g., using detergents, acid, base, or other standard methods, e.g., as taught in Ausubel or Sambrook or Freshney, all supra) or is fixed in the cell by conventional cell fixation methods. One or more modification detection reagent is contacted to the modified substrate, resulting in a detectable signal, which is detected. This detection can be a liquid phase detection, with the detection reagent and the modified substrate both being in solution, or the detection reagent or modified substrate can be fixed to, or captured on, a solid substrate.

In several useful embodiments, the modified substrate is captured on one or more capture substrate prior to detecting the detectable signal. For example, the modified substrate optionally comprises one or more affinity moiety and the capture substrate optionally comprises one or more cognate affinity capture moiety. The affinity moiety or capture moiety can include any of those biological or chemical or physical moieties that are commonly used for binding a cognate molecule, such as avidin, biotin, complementary nucleic acids, antibodies and antibody ligands, polypeptides and polypeptide ligands, proteins and protein ligands, His tags and His tag binding moieties, Glutathione and GST, HA tags and binders, or the like.

The modified substrate is contacted to the capture substrate, whereby the affinity capture moiety binds the affinity moiety. The capture substrate can be any material comprising a surface suitable for attaching or complexing affinity capture reagents, e.g., microwell plates, beads, affinity columns, microscope slides, dipsticks (e.g., a single dipstick or a device with pins spaced to fit in the wells of a multiwell plate; see, e.g., Jianbing et al. (2003) *Chinese Science Bulletin* 48:1903-1905 and Smits et al. (1999) *J Clin Microbiol* 37:4179-4182), or the like. The capture substrate material is chosen to match available instrumentation, e.g., to facilitate detection by using the capture substrate in conventional instrumentation such as microwell plate readers, microfluidic instruments, microchip readers, array readers and/or the like. In general, capturing one or more materials onto a solid phase capture substrate provides the ability to remove non-specific components through standard washing procedures. Such washing procedures are well known for a variety of cognate binding molecules. For example, an extensive guide to the hybridization of nucleic acids is found in Tijssen (1993) Laboratory Techniques in Biochemistry and Molecular Biology—Hybridization with Nucleic Acid Probes part I chapter 2, "Overview of principles of hybridization and the strategy of nucleic acid probe assays," (Elsevier, N.Y.), as well as in Ausubel, supra. Hames and Higgins (1995) Gene Probes 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis, labeling, detection and quantification of DNA and RNA, including oligonucleotides. Similarly, Ausubel and a number of other basic texts describe standard protein detection (e.g., antibody or antibody ligand detection processes, including various substrate hybridization and washing processes, e.g., R.

Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods*, 2nd Edition Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein; Borrebaeck (ed.) (1995) *Antibody Engineering, 2nd Edition* Freeman and Company, NY (Borrebaeck); McCafferty et al. (1996) *Antibody Engineering, A Practical Approach* IRL at Oxford Press, Oxford, England (McCafferty), Paul (1995) *Antibody Engineering Protocols* Humana Press, Towata, N.J. (Paul); Paul (ed.), (1999) *Fundamental Immunology. Fifth edition* Raven Press, N.Y.; Coligan (1991) *Current Protocols in Immunology* Wiley/Greene, NY; Harlow and Lane (1989) *Antibodies: A Laboratory Manual Cold Spring Harbor Press*, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497. Appropriate procedures for capturing cognate molecules to a surface and detecting them are widely available, whether the molecules are nucleic acids, proteins, polysaccharides, lipids, and/or other moieties of interest. Another advantage to solid phase capture, as noted, is a simplified ability to use existing instrumentation to detect substrates of interest.

Uncaging the substrate can include exposing the cell to an uncaging energy or substance, e.g., light, a change in pH, a change in heat, sonic energy, or the like. Once the substrate is uncaged, it can be modified in the cell, e.g., by incubating the cell with the substrate for between about 5 seconds and about 240 minutes (e.g., between about 5 minutes and about 120 minutes) or more after uncaging the substrate prior to said releasing or fixing. Releasing the modified substrate can typically include lysing the cell, but can also include other release mechanisms. For example, releasing the substrate can alternately include permitting the cell to release the substrate through endogenous mechanisms (e.g., exocytosis), or by permitting the substrate to be complexed in the cell with a cell transport molecule that facilitates release of the substrate from the cell.

The detection reagent can be any moiety that facilitates detection of the modified substrate. Examples include phosphobinders, antibodies that specifically bind to the modified substrate, nucleic acids that specifically bind to the modified substrate, aptamers that specifically bind to the modified substrate, micro or nano particles that bind to the modified substrate, or a combination thereof. The signal that is produced is detected by the appropriate method, e.g., performing a homogeneous assay, a heterogeneous assay, FRET, Q-FRET, TR-FRET, and/or fluorescence polarization. FRET (Fluorescence Resonance Energy Transfer) is a non-radiative energy transfer phenomenon in which two fluorophores with overlapping emission and excitation spectra, when in sufficiently close proximity, experience energy transfer by a resonance dipole induced dipole interaction. The phenomenon is commonly used to study the binding of analytes such as nucleic acids, proteins and the like. FRET is a distance dependent excited state interaction in which emission of one fluorophore is coupled to the excitation of another which is in proximity (close enough for an observable change in emissions to occur). Some excited fluorophores interact to form excimers, which are excited state dimers that exhibit altered emission spectra (e.g., phospholipid analogs with pyrene sn-2 acyl chains). See, e.g., Haugland (1996) *Handbook of Fluorescent Probes and Research Chemicals* Published by Molecular Probes, Inc., Eugene, Oreg. e.g., at chapter 13). For example, in one embodiment, the substrate of interest can comprise a first label and the detection reagent can comprise a second label, wherein, for example, the first label comprises an acceptor FRET moiety and the second label comprises a donor FRET moiety. The acceptor moiety comprises a quencher moiety, wherein the quencher moiety can be selected from, e.g., a group consisting of: fluorophores, Dabsyl, Black-hole™, QSY™, and an Eclipse Dark Quencher. Similarly, the donor moiety is optionally selected from a group consisting of: Xanthene dyes, Cyanine dyes, Metal-Ligand Complexes, Coumarin dyes, BODIPY dyes, and Pyrene dyes, and the like. See also, Haugland (2003) *Handbook of Fluorescent Probes and Research Chemicals Ninth Edition* Published by Molecular Probes, Inc., Eugene, Oreg. In Q-FRET, when a quencher such as Dabcyl and a fluorophore such as coumarin are located near each other, their proximity guides the emission of the fluorophore. See, e.g., Dubertret et al. (2001) Nature Biotech. 19:365-370; see also the internet at prozyme.com and IDTdna.com.

In several typical embodiments, the detector is an optical detector that detects an optically detectable signal. Examples of available detectors include microscopes, CCD arrays, cameras, spectrophotometers, microplate plate readers, array readers, microfluidic device instrumentation and the like. For example, fluorescence based signals can be monitored, e.g., in laser activated fluorescence detection systems which employ a laser light source at an appropriate wavelength for activating the fluorescent indicator within the system. Fluorescence is then detected using an appropriate detector element, e.g., a photomultiplier tube (PMT), CCD array, camera, or the like. Similarly, for screens employing calorimetric signals, spectrophotometric detection systems may be employed which direct a light source at the sample and provide a measurement of absorbance or transmissivity of the sample. See also *The Photonics Design and Applications Handbook*, books 1, 2, 3 and 4, published annually by Laurin Publishing Co., Berkshire Common, P.O. Box 1146, Pittsfield, Mass. for common sources for optical components.

In one example embodiment, the detection reagent comprises a detection reagent label comprising a donor or acceptor moiety, and the modified substrate comprises a substrate label comprising a donor or acceptor moiety. Binding of the detection reagent to the modified substrate results in an increase or decrease in signal from the detection reagent label or the substrate label, or both. In one case, the donor or acceptor moiety on the detection reagent label transfers energy to the substrate label, or the substrate label transfers energy to the detection reagent label, in a proximity dependent manner. This energy transfer can be via FRET, or can be via other energy transfer phenomena.

These methods can also be adapted to provide a screen to identify modulators of the substrate modification component (e.g., modulators of one or more activity of the various catalytic molecules noted above). This is a useful platform for identifying compounds that have activity on the substrate modification compounds, which, in turn, is useful in identifying lead compounds for further biological analysis, identification of inhibitors or activators of enzyme activity for biological or industrial purposes, and the like. In the methods, one or more actual or potential modulator of a substrate modification component is added to the cell. This addition can be before or after introduction of the initial substrate and substrate modification component, and can be before or after uncaging of the initial substrate. However, in the most typical format, the initial substrate and substrate modification component are introduced and the substrate modification component is expressed. The potential modulator is then added, e.g., by applying the potential modulator to a culture comprising the cell, or by using any of the methods herein or generally available to deliver the modulator to the cell. The cell is then incubated with the modulator for a given period of time to permit the potential modulator to act on the substrate modification component. The length of time of the incubation can be varied to provide time course data on the effects of the potential modulator, or single course measurements can be made. Potential modulators that are thought to have an indirect mode of action (e.g., transcriptional activators or repressors) can be incubated for longer periods of time than those thought to have direct modes of action (e.g., potential agonists or antagonists of the substrate modification component). Typically, the actual or potential modulator is incubated in the cell for between about 0.5 hours and about 72 hours prior to uncaging the substrate. Whether, or to what extent, the actual or potential modulator modulates an activity of the substrate modification component on the uncaged substrate of interest is determined, e.g., by comparison to a control experiment that is performed in an essentially similar fashion, except that either no modulator or a control modulator with a known activity (positive or negative) is added to the cell.

The cell can be treated in an appropriate fashion to permit use of the cell in any currently available system of interest, e.g., to provide for addition of any reagents, detection of signals, or the like. In one typical example, the cell is treated with trypsin and seeded into a microwell plate prior to uncaging the initial substrate. Subsequent operations can be performed in the microwell plate, e.g., where the plate comprises an affinity capture substrate, e.g., with the affinity moieties coated on the plate, or coated on beads that are added to the plate. Similarly, the cells can be flowed through microfluidic systems and signals detected there from using available microfluidic devices or systems.

Compositions, Systems and Kits

In addition to the methods, compositions, systems and kits, e.g., for practicing the methods, are also a feature of the invention. In review of the foregoing methods, it will be appreciated, for example, that the invention includes a composition that includes a cellular delivery agent, a caged substrate and a vector that comprises or encodes a substrate modification component. The composition can, of course, also include a cell that permits entry of the cellular delivery agent. Thus, in a related aspect, the invention includes a composition that comprises a cell, a cellular delivery agent, a caged substrate and a vector. The invention can also include, e.g., a composition that includes a cell, a cellular delivery agent, an uncaged substrate in the cell and a vector that comprises or encodes the substrate modification component in the cell. The vector, substrate modification component and cellular delivery agent can be any of those noted above with respect to the various methods of the invention.

Similarly, in one aspect, the invention includes systems for practicing the methods and/or using the compositions herein. These systems can be integrated into a single device, or can comprise multiple separate system elements. A system of the invention can include the affinity capture substrate, and a cell or cell lysate comprising a modified enzyme substrate (the substrate that has been acted on by the substrate modification component), e.g., where the modified substrate includes an affinity capture moiety that can be specifically bound to the affinity capture substrate (to provide for a solid phase assay, as noted in more detail above). The modified enzyme substrate comprises a modification detection site that indicates whether a substrate modification component has acted upon the substrate (e.g., a cleavage site, a phosphorylation site, a region that is bound by the substrate modification component, or the like). The system also includes a modification detection reagent that specifically binds to the modification detection site, where binding of the modification detection reagent to the modified substrate produces a detectable signal. This can take any available detection reagent form, e.g., a detection reagent comprising any of the various labels noted above. The portion of the detection reagent that recognizes the modified substrate is any of those noted above, including cognate molecules for ligands, antibodies, proteins, peptides, nucleic acids, or the like. A detector that detects the detectable signal during operation of the system is also typically a feature of the invention (e.g., microscope, spectrophotometer, plate reader, etc., as noted above). The features of the system can include any of those noted above with respect to the methods and compositions.

As noted above, the affinity capture substrate can include, e.g., a microwell plate, a bead, an affinity column, a microscope slide, an array substrate, or any other available substrate that can be functionalized by addition of an affinity capture reagent. The affinity capture reagent and modification detection reagent is any of those noted above. The detector can be any detector with a suitable signal receiver that can receive the detectable signal. Typical detectors include microscopes, CCD arrays, cameras, spectrophotometers, photomultipliers, and/or any combination thereof. The system can be configured for detection of one or more activity of one or more actual or potential modulators of enzyme activity prior to detection by the modification detection reagent.

It will be appreciated that a related or additional system of the invention includes a cell comprising a caged substrate of interest and a modification component, an actual or potential modulator of the modification component, a source of uncaging energy (light, heat, pH, etc.), a cell lysis or fixation module, a reporter that detects modifications to the substrate of interest, and a detector that detects a signal from the reporter. The various system components can be any of those noted above in the context of the methods. The lysis or fixation module can include high throughput fluid handling components such as conventional robotic and/or pipettor systems, and/or microfluidic systems for transferring cells, lysis or fixation reagents, or the like. Many automated high throughput systems are commercially available and can be adapted to the present invention by including the appropriate system elements as set forth herein. For example, a variety of automated systems are available from the Zymark Corporation (Zymark Center, Hopkinton, Mass.), which utilize various Zymate systems (see also the internet at zymark.com), which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). Microfluidic systems have established the potential for automation and laboratory productivity increases as well. In these microfluidic systems, automated fluid handling and other sample manipulations are controlled at the microscale level. Such systems are now commercially available. For example, the Hewlett-Packard (Agilent Technologies) HP2100 bioanalyzer utilizes Lab-Chip™ technology to manipulate extremely small sample volumes. In this "lab-on-a-chip," system, sample preparation, fluid handling and biochemical analysis steps are carried out within the confines of a microchip. The chips have microchannels fabricated, e.g., in glass, providing interconnected networks of fluid reservoirs and pathways. The Caliper High Throughput Screening System (see, e.g., the internet at calipertech.comlproducts/index.htm) provides an interface between standard library formats and chip technologies (see, generally, the internet at calipertech.com).

Essentially any of the reagents or cells in the system can be laid out in an array to increase system throughput as well. Any of a variety of array configurations can be used in the systems herein. One common array format for use in the modules herein is a microwell plate, in which the array is embodied in the wells of a microwell plate. Such plates are commercially available and can be ordered in a variety of well sizes and numbers of wells per plate, as well as with any of a variety of functionalized surfaces for binding of assay or array components. Common trays include the ubiquitous 96 well plate, with 384 and 1536 well plates also in common use. In addition to liquid phase arrays, components can be stored in solid phase arrays and, as described in some detail above, solid phase arrays can be used to capture modified substrates using capture substrates. These arrays fix materials in a spatially accessible pattern (e.g., a grid of rows and columns) onto a solid substrate such as a membrane (e.g., nylon or nitrocellulose), a polymer or ceramic surface, a glass or modified silica surface, a metal surface, or the like. In addition to providing a convenient surface for analysis, components can also be accessed subsequently from the array, e.g., by local rehydration (e.g., using a pipette or other fluid handling element) and fluidic transfer, or by scraping the array or cutting out sites of interest on the array.

While arrays are most often thought of as physical elements with a specified spatial-physical relationship, the present invention can also make use of "logical" arrays, which do not have a straightforward spatial organization. For example, a computer system can be used to track the location of one or several components of interest (modified substrates, reagents for substrate analysis, etc.) which are located in or on physically disparate components. The computer system creates a logical array by providing a "look-up" table of the physical location of array members. Thus, even components in motion can be part of a logical array, as long as the members of the array can be specified and located.

The systems herein also optionally include a computer that includes system memory or computer readable media comprising system instructions that direct the system to manipulate the other components of the system. For example, in one embodiment, the system instructions provide instructions to: incubate the cell with the actual or potential modulator for a user selected period of time, uncage the caged substrate of interest by exposing the cell to the source of uncaging energy for a selected period of time, incubate the resulting energy-exposed cell that comprises a resulting uncaged substrate of interest for a user selected period of time, lyse or fix the cell with the cell lysis or fixation module, contact the resulting fixed cell or cell lysate with the reporter, and detect the signal from the reporter.

Kits comprising an affinity capture substrate (e.g., a streptavidin coated plate), a caged substrate comprising an affinity capture moiety (e.g., biotin), and a detection reagent that detects one or more modification to the caged substrate when in uncaged form are also a feature of the invention. Such kits can include instructional materials for using the other components of the kit, e.g., to practice any method herein, containers for holding kit components, suitable packaging components, or the like. Kits can also include control expression vectors, e.g., encoding a known substrate modification component (e.g., a known kinase) that can be used in control assays in conjunction with a vector of interest, which can, optionally, be supplied by the user. Kits can also include reagents useful in practicing the methods herein, e.g., lysis buffers, wash buffers, detection reagents (e.g., anti-phosphoantibodies for kinase detection, and/or second labeled antibodies that bind the anti-phosphoantibodies) and the like.

One of skill will appreciate a variety of additional modifications to the above that can be practiced according to the present invention. For example, multiple substrates can be transduced into cells and analyzed in a multiplex assay that tests the activity of several different substrate modification components (e.g., multiple kinase enzymes) on multiple different substrates (e.g., multiple different substrates). Peptides can be fluorescently labeled prior to introduction into cells to provide for normalized cell delivery. Plasmids can be made to produce the substrate modification component of interest and one or more additional proteins or nucleic acids that can be used to normalize assay results.

Example Systems and Methods

Figure 62:
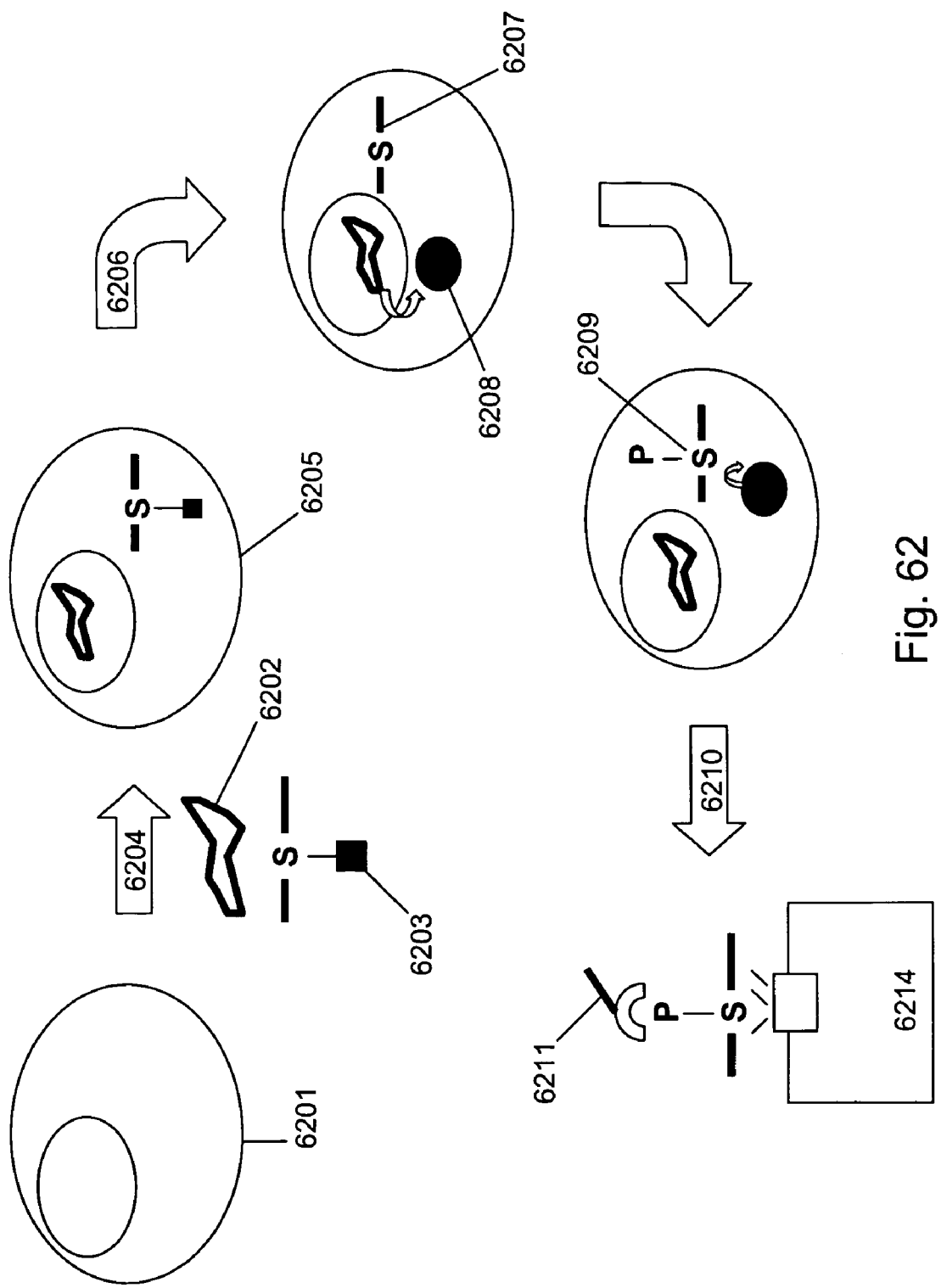
FIG. 62 schematically illustrates an example assay using a caged kinase substrate.

FIG. 62 provides an example assay for the above methods and compositions. As shown, cell 6201 is co-transfected in step 6204 with expression vector 6202 that encodes a substrate modification component, and initial substrate of interest 6203. Co-transfection of the caged substrate and vector can be done as shown, but is not necessary, in that the vector can be transduced separately, or the cell can simply provide the relevant substrate modification component as an endogenous cell component. However, overall assay precision can be improved in some cases by co-transfection. While a single cell is depicted for example purposes, it will be appreciated that batch transfection can, and typically is, performed to minimize experimental variation. It is also worth noting that minimal amounts of initial substrate 6203 can be used, as the assay format is highly sensitive (e.g., the limit of detection can be as low as femto to picomolar range against a background 50 µl of cell lysate from 5000 cells).

In the depicted example, expression vector 6202 encodes a kinase and initial substrate 6203 is a caged kinase substrate. Resulting transduced cell 6205 is incubated for a selected period of time to permit expression of kinase 6208 (e.g., about 24 hours-expression typically begins 16-72 hours after transfection, depending on the genes and cell types at issue), and then treated with light or other uncaging energy (sonication, heat, pH etc.) in step 6206 to uncage initial substrate 6203 to produce uncaged substrate 6207. For example, the light exposure can be, e.g., from about 10-60 seconds, depending on the media being used, the intensity of the uncaging energy and the like.

Optionally, one or more modulators or potential modulators can be added to the cell prior or subsequent to step 6206 to detect effects of the modulator or potential modulator on any modification component of interest. Similarly, cell or cells 6205 can be treated in any of the ways that cells are typically treated in culture, e.g., trypsinized and distributed into a microwell plate or plates or into one or more flasks for incubations and/or further processing and analysis steps. Further, cell 6205 is incubated for a selected period of time to permit kinase (or, in other examples, other substrate modification component(s)) 6208 to act on substrate 6207, e.g., between about 1 second and about 24 hours, e.g., about 5 seconds-240 minutes or 5-120 minutes (time course experiments can be run to determine the time-dependent effects of kinase 6208, or other substrate modification components of interest in other examples). Kinase 6208 phosphorylates substrate 6207 to produce phosphorylated modified substrate 6209.

Figure 63:
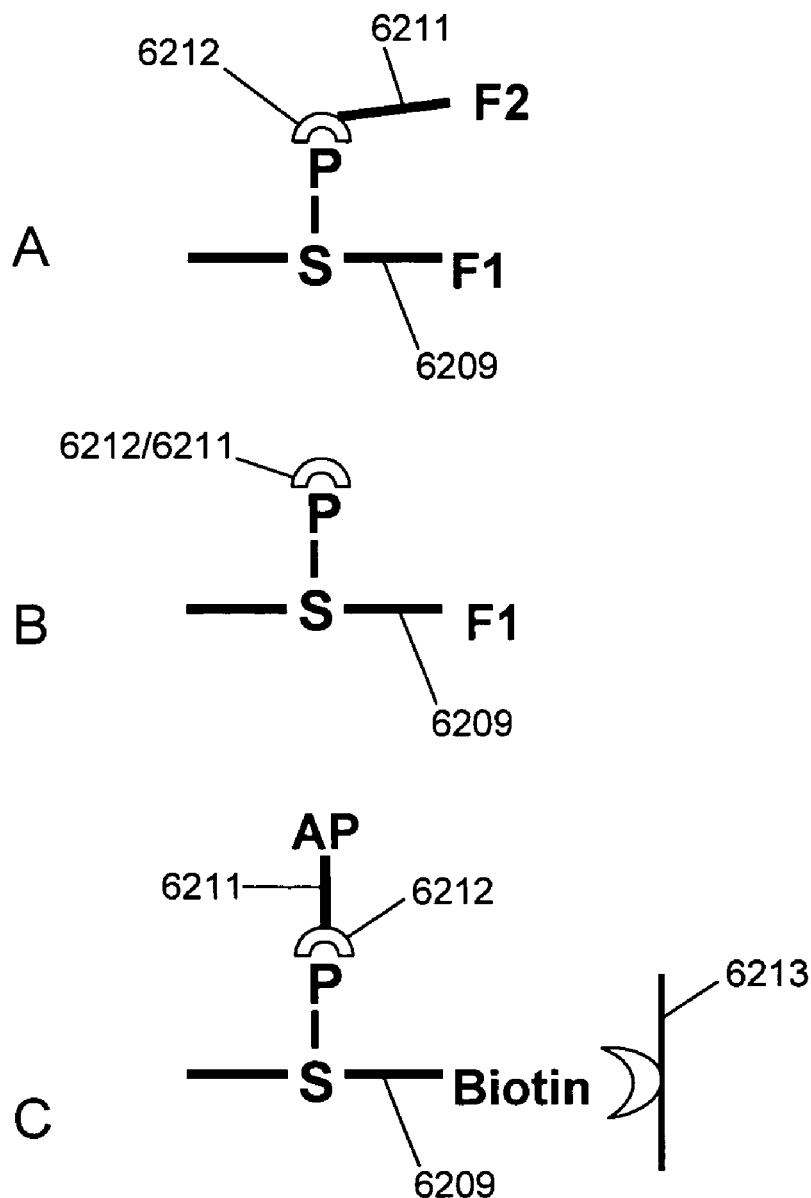
FIG. 63 Panels A-C schematically illustrate example approaches to detecting a phosphorylated kinase substrate.

In step 6210, cell 6205 is lysed or fixed to stop the reaction of kinase 6208 on substrate 6207. Phosphorylation sensitive reporter 6211 is contacted to substrate 6209 to detect the phosphorylation state of substrate 6209. Various approaches for this detection are shown in FIG. 63. As shown, homogeneous solution phase assays such as FRET, Q-FRIET or TR-FRET (Panel A) or fluorescence polarization (Panel B), or a heterogeneous assay that comprises a solid phase upon which substrate 6209 is bound, e.g., through a streptavidin-biotin linkage as shown in Panel C, can be used. In Panel A, reporter 6211 comprises a quencher, Eu or acceptor fluorescent moiety ("F2") while 6209 comprises a donor fluorescent moiety ("F1"). It will be appreciated that F1 and F2 can be reversed in alternate embodiments. Reporter 6211 also comprises phosphobinder domain 6212 (e.g., an antibody, metal ion, affinity chromatography moiety such as IMAC, etc.). In Panel B, reporter 6211 does not comprise a separate label, but still comprises phosphobinder domain 6212 and detection is performed, e.g., by measuring a change in rotation brought about by binding, e.g., using fluorescence polarization. Panel C shows a heterogenous assay, in which substrate 6209 is bound to streptavidin-coated plate 6213 through a biotin linkage. Reporter 6211 comprises phosphobinder domain 6212 (e.g., an anti-phospho antibody, e.g., detected with an alkaline phosphatase conjugated secondary antibody and a chemiluminecescent, colorimetric or fluorescent substrate, e.g., a CSPD™ substrate and Sapphire II™ enhancer available from Applied Biosystems, on the internet at appliedbiosystems. com).

In certain embodiments, immunofluorescent detection is used, in which cells are fixed and substrate 6209 is detected using a phosphoantibody. Other detection possibilities include polyarginine binding to substrate 6209, use of unnatural ATP analogs followed by chemical conjugation to biotin (e.g., use of a modified ATP with a thio-R group on the phosphate in the assay results in the kinase transferring a thio-phosphate onto the substrate, such that various reporters such as biotin, fluorescent labels, or enzymes can then be conjugated to the thio group; see, e.g., the internet at chromagen.com/polaris.htm), or various phosphorylation-dependent substrate protection strategies. For example, certain peptide substrates can be protected from protease digestion by incorporation of a phosphate, which will result in maintaining F1 on substrate 6209 (and cleavage of F1 from 6209 in unphosphorylated, unprotected substrates). Similarly, phosphorylated peptides have a difference in charge which permits electrophoretic resolution of substrate 6209 from substrate 6207. A variety of other methods of detecting phosphorylated substrates are commonly known in the art and can be adapted to practice of the present invention.

In any case, detection of reporter 6211 can be performed with detector 6214 (e.g., a microscope, spectrophotometer, CCD array, or the like).

Caging Groups

A large number of caging groups, and a number of reactive compounds that can be used to covalently attach caging groups to other molecules, are well known in the art. Examples of photolabile caging groups include, but are not limited to: nitroindolines; N-acyl-7-nitroindolines; phenacyls; hydroxyphenacyl; brominated 7-hydroxycoumarin-4-ylmethyls (e.g., Bhc); benzoin esters; dimethoxybenzoin; meta-phenols; 2-nitrobenzyl; 1-(4,5-dimethoxy-2-nitrophenyl)ethyl (DMNPE); 4,5-dimethoxy-2-nitrobenzyl (DMNB); alpha-carboxy-2-nitrobenzyl (CNB); 1-(2-nitrophenyl)ethyl (NPE); 5-carboxymethoxy-2-nitrobenzyl (CMNB); (5-carboxymethoxy-2-nitrobenzyl)oxy) carbonyl; (4,5-dimethoxy-2-nitrobenzyl)oxy) carbonyl; desoxybenzoinyl; and the like. See, e.g., U.S. Pat. No. 5,635,608 to Haugland and Gee (Jun. 3, 1997) entitled "α-carboxy caged compounds"; *Neuro* 19, 465 (1997); *J Physiol* 508.3, 801 (1998); *Proc Natl Acad Sci USA* 1988 September, 85(17): 6571-5 *J Biol Chem* 1997February 14, 272(7):4172-8; *Neuron* 20, 619-624, 1998; *Nature Genetics*, vol. 28:2001:317-325; *Nature*, vol. 392,1998:936-941; Pan, P., and Bayley, H. "Caged cysteine and thiophosphoryl peptides" *FEBS Letters* 405:81-85(1997); Pettit et al. (1997) "Chemical two-photon uncaging: a novel approach to mapping glutamate receptors" *Neuron* 19:465-471; Furuta et al. (1999) "Brominated 7-hydroxycoumarin-4-ylmethyls: novel photolabile protecting groups with biologically useful cross-sections for two photon photolysis" *Proc. Natl. Acad. Sci.* 96(4):1193-1200; Zou et al. "Catalytic subunit of protein kinase A caged at the activating phosphothreonine" *J. Amer. Chem. Soc.* (2002) 124:8220-8229; Zou et al. "Caged Thiophosphotyrosine Peptides" *Angew. Chem. Int. Ed.* (2001) 40:3049-3051; Conrad II et al. "p-Hydroxyphenacyl Phototriggers: The reactive Excited State of Phosphate Photorelease" *J. Am. Chem. Soc.* (2000) 122:9346-9347; Conrad II et al. "New Phototriggers 10: Extending the π,π* Absorption to Release Peptides in Biological Media" *Org. Lett.* (2000) 2:1545-1547; Givens et al. "A New Phototriggers 9: p-Hydroxyphenacyl as a C-Terminus Photoremovable Protecting Group for Oligopeptides" *J. Am. Chem. Soc.* (2000) 122:2687-2697; Bishop et al. "40-Aminomethyl-2,20-bipyridyl-4-carboxylic Acid (Abc) and Related Derivatives: Novel Bipyridine Amino Acids for the Solid-Phase Incorporation of a Metal Coordination Site Within a Peptide Backbone" *Tetrahedron* (2000) 56:4629-4638; Ching et al. "Polymers As Surface-Based Tethers with Photolytic triggers Enabling Laser-Induced Release/Desorption of Covalently Bound Molecules" *Bioconjugate Chemistry* (1996) 7:525-8; *BioProbes Handbook*, 2002 from Molecular Probes, Inc.; and *Handbook of Fluorescent Probes and Research Products*, Ninth Edition or Web Edition, from Molecular Probes, Inc, as well as the references below. Many compounds, kits, etc. for use in caging various molecules are commercially available, e.g., from Molecular Probes, Inc. (on the internet at molecularprobes.com).

A caging group optionally comprises a first binding moiety that can bind to a second binding moiety. For example, a commercially available caged phosphoramidite [1-N-(4,4'-Dimethoxytrityl)-5-(6-biotinamidocaproamidomethyl)-1-(2-nitrophenyl)-ethyl]-2-cyanoethyl-(N,N-diisopropyl)-phosphoramidite (PC Biotin Phosphoramadite, from Glen Research Corp., on the internet at glenres.com) comprises a photolabile group and a biotin (the first binding moiety in this example). A second binding moiety, e.g., streptavidin or avidin, can thus be bound to the caging group, increasing its bulkiness and its effectiveness at caging. In certain embodiments, a caged component comprises two or more caging groups each comprising a first binding moiety, and the second binding moiety can bind two or more first binding moieties simultaneously. For example, the caged component can comprise at least two biotinylated caging groups; binding of streptavidin to multiple biotin moieties on multiple caged component molecules links the caged components into a large network. Cleavage of the photolabile group attaching the biotin to the component results in dissociation of the network.

Figure 57:
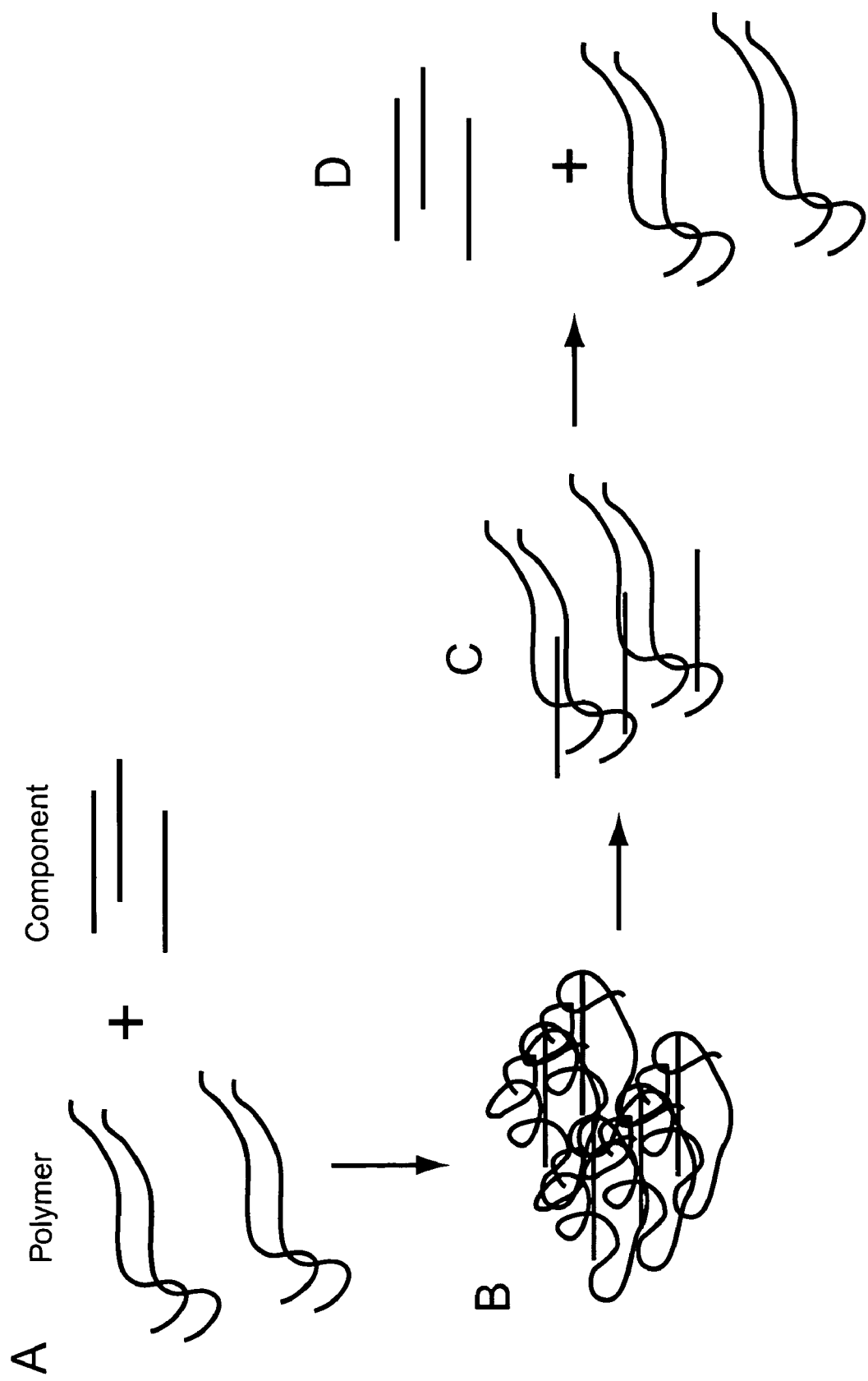
FIG. 57 schematically illustrates use of an environmentally responsive polymer as a noncovalently associated caging group.
Figure 58:
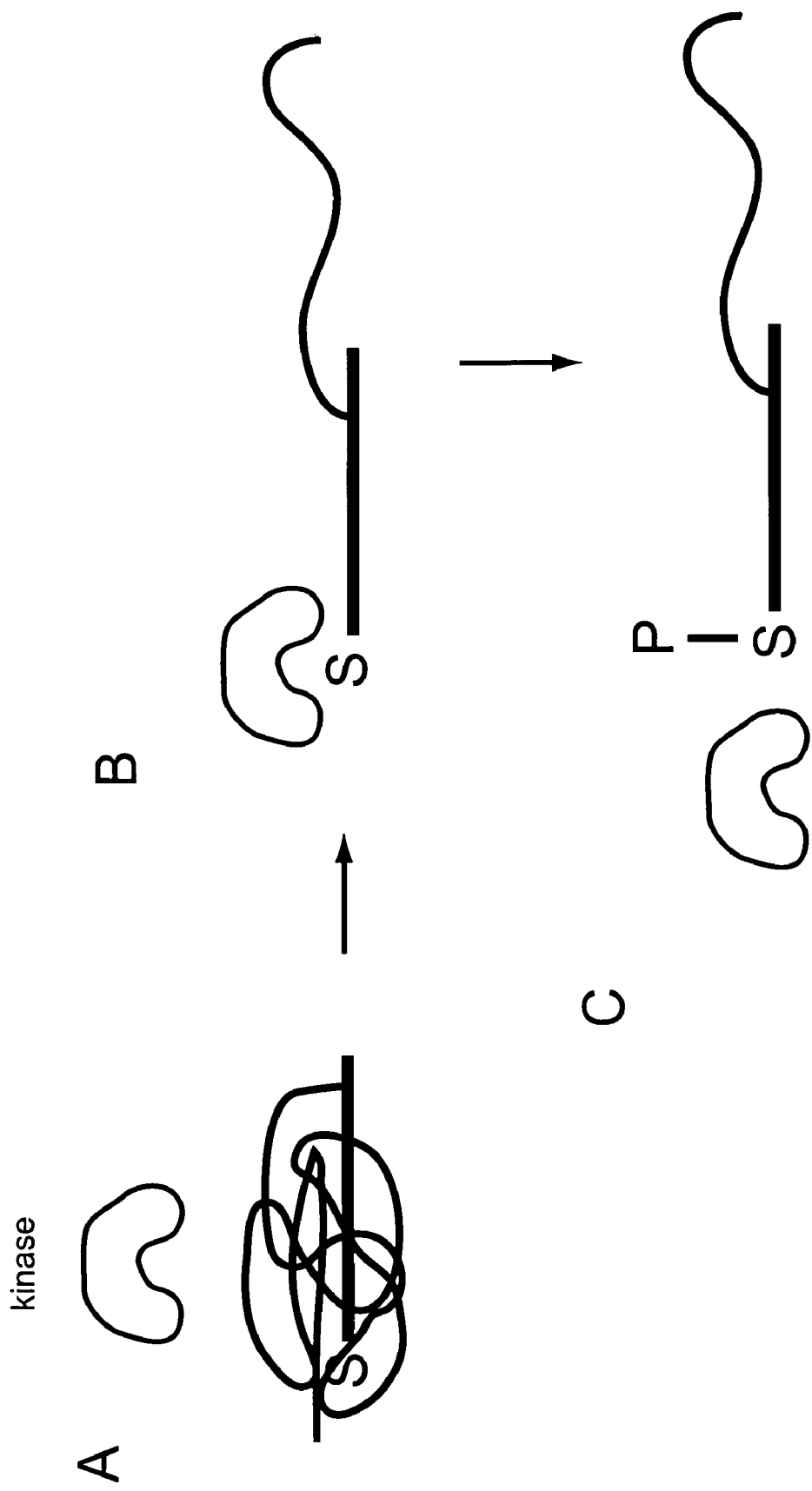
FIG. 58 schematically illustrates use of an environmentally responsive polymer as a covalently associated caging group.

Environmentally responsive polymers suitable for use as caging groups have also been described. Such polymers undergo conformational changes induced by light, an electric or magnetic field, a change in pH and/or ionic strength, temperature, or addition of an antigen or saccharide, or other environmental variables. For example, Shimoboji et al. (2002) "Photoresponsive polymer-enzyme switches" *Proc. Natl. Acad. Sci. USA* 99:16,592-16,596 describes polymers that undergo reversible conformational changes in response to light. Such polymers can, e.g., be used as photoactivatable caging groups. See also, Ding et al. (2001) "Size-dependent control of the binding of biotinylated proteins to streptavidin using a polymer shield" *Nature* 411:59-62; Miyata et al. (1999) "A reversibly antigen-responsive hydrogel" *Nature* 399:766-769; Murthy et al. (2003) "Bioinspired pH-responsive polymers for the intracellular delivery of biomolecular drugs" *Bioconjugate Chem.* 14:412-419; and Galaev and Mattiasson (1999) "'Smart' polymers and what they could do in biotechnology and medicine" *Trends Biotech.* 17:335-340. FIGS. 57 and 58 schematically illustrate use of environmentally responsive polymers as caging groups. FIG. 57 illustrates noncovalent association of a polymer with a component to be caged (e.g., an enzyme sensor, a nucleic acid probe, etc.). In its folded conformation, the polymer physically surrounds and traps the component (Panel B). The caged component is optionally introduced into a cell, an in vitro assay, or the like. A conformational change in the polymer induced by light, pH, temperature, or the like results in release of the component from the unfolded conformation of the polymer (Panel D). FIG. 58 illustrates covalent association of a polymer with a component, a serine kinase sensor in this example. In its folded conformation, the polymer blocks access to the serine residue phosphorylated by a serine kinase (Panel A). A conformational change in the polymer induced by light, pH, temperature, or the like permits access to the serine (Panel B).

An alternative method for caging a molecule is to enclose the molecule in a photolabile vesicle (e.g., a photolabile lipid vesicle), optionally including a protein transduction domain or the like. Similarly, the molecule can be loaded into the pores of a porous bead which is then encased in a photolabile gel.

Caged polypeptides (including e.g. peptide substrates and proteins such as antibodies or transcription factors) can be produced, e.g., by reacting a polypeptide with a caging compound or by incorporating a caged amino acid during synthesis of a polypeptide. See, e.g., U.S. Pat. No. 5,998,580 to Fay et al. (Dec. 7, 1999) entitled "Photosensitive caged macromolecules"; Kossel et al. (2001) PNAS 98:14702-14707; Trends Plant Sci (1999) 4:330-334; *PNAS* (1998) 95:1568-1573; *J Am Chem Soc* (2002) 124:8220-8229; *Pharmacology & Therapeutics* (2001) 91:85-92; and *Angew Chem Int Ed Engl* (2001) 40:3049-3051. A photolabile polypeptide linker (e.g., for connecting a protein transduction domain and a sensor, or the like) can, for example, comprise a photolabile amino acid such as that described in U.S. Pat. No. 5,998,580, supra.

Caged nucleic acids (e.g., DNA, RNA or PNA, including e.g., probes, ribozymes or aptamers) can be produced by reacting the nucleic acids with caging compounds or by incorporating a caged nucleotide during synthesis of a nucleic acid. See, e.g., U.S. Pat. No. 6,242,258 to Haselton and Alexander (Jun. 5, 2001) entitled "Methods for the selective regulation of DNA and RNA transcription and translation by photoactivation"; *Nature Genetics* (2001) 28: 317-325; and *Nucleic Acids Res.* (1998) 26:3173-3178.

Caged modulators (e.g., inhibitors and activators), small molecules, etc. can be similarly produced by reaction with caging compounds or by synthesis. See, e.g., *Trends Plant Sci* (1999) 4:330-334; *PNAS* (1998) 95:1568-1573; U.S. Pat. No 5,888,829 to Gee and Millard (Mar. 30, 1999) entitled "Photolabile caged ionophores and method of using in a membrane separation process"; U.S. Pat. No. 6,043,065 to Kao et al. (Mar. 28, 2000) entitled "Photosensitive organic compounds that release 2,5,-di(tert-butyl) hydroquinone upon illumination"; U.S. Pat. No. 5,430,175 to Hess et al. (Jul. 4, 1995) entitled "Caged carboxyl compounds and use thereof"; U.S. Pat. No. 5872243; and *PNAS* (1980) 77:7237-41. A number of caged compounds, including for example caged nucleotides, caged Ca2+, caged chelating agents, caged neurotransmitters, and caged luciferin, are commercially available, e.g., from Molecular Probes, Inc. (on the internet at molecularprobes.com).

Useful site(s) of attachment of caging groups to a given molecule can be determined by techniques known in the art. For example, a molecule with a known activity can be reacted with a caging compound. The resulting caged molecule can then be tested to determine if its activity is sufficiently abrogated. As another example, amino acid residues central to the activity of a protein (e.g., active site residues of an enzyme, residues located at a binding interface, or the like) can be identified by routine techniques such as scanning mutagenesis, sequence comparisons and site-directed mutagenesis, or the like. Such residues can then be caged, and the activity of the caged protein can be assayed to determine the efficacy of caging.

Appropriate methods for uncaging caged molecules are also known in the art. For example, appropriate wavelengths of light for removing many photolabile groups have been described; e.g., 300-360 nm for 2-nitrobenzyl, 350 nm for benzoin esters, and 740 nm for brominated 7-hydroxycoumarin-4-ylmethyls (two-photon) (see, e.g., references herein). Conditions for uncaging any caged molecule (e.g., the optimal wavelength for removing a photolabile caging group) can be determined according to methods well known in the art. Instrumentation and devices for delivering uncaging energy are likewise known (e.g., sonicators, heat sources, light sources, and the like). For example, well-known and useful light sources include e.g., a lamp, a laser (e.g., a laser optically coupled to a fiber-optic delivery system) or a light-emitting compound.

In Vivo and in Vitro Cellular Delivery

Caged and/or labeled molecules (e.g., sensors and regulators) can be introduced into cells by traditional methods such as lipofection, electroporation, calcium phosphate precipitation, particle bombardment, microinjection and/or optofection. Such delivery can be accomplished without uncaging and thereby activating the molecules. For example, PA sensors and regulators are not active during the delivery processes until exposed to light.

Delivery of molecules by exposing cells to pulses of laser beam (laserfection or laser transfection) has also been described, as have delivery by pinocytosis or use of streptolysin-O (SLO). As another example, a kit from Active Motif utilizing the PEP-1peptide as a delivery system for proteins ranging from a small peptide to a large IgG antibody is commercially available (Chariot ™, on the internet at activemotif.com). However, these methods require manipulation of the cells, e.g., adding and removing transfection materials, pretreating cells, and special apparatus and equipment, etc.

While the methods above are suitable for introducing molecules (e.g., PA sensors and regulators) into cells, this invention features a simpler and more effective method of introducing molecules (e.g., PA sensors and regulators) into the cell. In this method, the caged molecule (e.g., sensor or regulator) is coupled to a peptide delivery sequence found to be taken-up naturally by cells (see, FIG. 21). For example, sensors and/or regulators can be coupled to the HIV TAT sequence, which most cells naturally uptake. The chimeric probe can simply be, e.g., added to cell culture or injected into the animal for delivery.

That is, the caged and/or labeled molecule is optionally associated (covalently or non-covalently) with a cellular delivery module that can mediate its introduction into the cell. The cellular delivery module is typically, but need not be, a polypeptide, for example, a PEP-1 peptide, an amphipathic peptide, e.g., an MPG peptide (see, Simeoni et al. (2003) "Insight into the mechanism of the peptide-based gene delivery system MPG: Implications for delivery of siRNA into mammalian cells" *Nucl Acids Res* 31: 2717-2724), a cationic peptide (e.g., a homopolymer of lysine, histidine, or D-arginine), or a protein transduction domain (a polypeptide that can mediate introduction of a covalently associated molecule into a cell). See, e.g., Lane (2001) *Bioconju Chem.*, 12:825-841; Bonetta (2002) *The Scientist* 16:38; and *Curr Opin Mol Ther* (2000) 2:162-7. For example, a caged sensor can be covalently associated with a protein transduction domain (e.g., an HIV TAT sequence, which most cells naturally uptake, or a short D-arginine homopolymer, e.g., 8-D-Arg, eight contiguous D-arginine residues). The protein transduction domain can be covalently attached directly to the sensor, or can be indirectly associated with the sensor (for example, the protein transduction domain can be covalently coupled to a bead or to a carrier protein such as BSA, which is in turn coupled to the sensor, e.g., through a photolabile or cleavable linker. The protein transduction domain-coupled caged sensor can simply be, e.g., added to cell culture or injected into an animal for delivery. (Note that TAT and D-arginine homopolymers, for example, can alternatively be noncovalently associated with the caged sensor and still mediate its introduction into the cell.)

A number of polypeptides capable of mediating introduction of associated molecules into a cell are known in the art and can be adapted to the present invention. See, e.g., the references above and Langel (2002) *Cell Penetrating Peptides* CRC Press, Pharmacology & Toxicology Series.

Caged and/or labeled molecules (e.g., sensors or regulators) can also be introduced into cells by covalently or non-covalently attached lipids, e.g., by a covalently attached myristoyl group. Lipids used for lipofection are optionally excluded from cellular delivery modules in some embodiments.

As one example, kinase sensors can be introduced into a cell by any of several methods, including, without limitation, PEP-1, laser transfection, and direct coupling of a TAT peptide or like sequence. Depending on the format, cells can require minutes to hours to take in the sensor.

To extend the example, a PA kinase sensor can be introduced into specific tissues, e.g., by coupling to viral proteins, laser transfection or gold particle bombardment. The tissue can then be exposed to light to activate the kinase sensor and the tissue can be lysed and a signal from the sensor (e.g., a fluorescent signal) can be measured. As another example, lymphocytes having an introduced PA kinase sensor can be examined with a capillary detection system. The PA sensor is activated and measured when it passes a light source and detector. Other caged and/or labeled molecules can similarly be introduced into specific tissues and/or cell types (e.g., explanted or in an organism). See, e.g., Robbins et al. (2002) "Peptide delivery to tissues via reversibly linked protein transduction sequences" *Biotechniques* 33:190-192 and Rehman et al. (2003) "Protection of islets by in situ peptide-mediated transduction of the Ikappa B kinase inhibitor Nemo-binding domain peptide" *J Biol Chem* 278:9862-9868.

The cell into which a caged and/or labeled molecule (e.g., a sensor or regulator of this invention) is introduced can be a prokaryotic cell (e.g., an archaebacterial cell or a eubacterial cell, e.g., an *Escherichia coli* cell) or a eukaryotic cell (e.g., a yeast or a mammalian cell). The cell can be, e.g., in culture or in a tissue, fluid, etc. and/or from or in an organism.

The cell delivery modules optionally can be caged and/or can be released from the associated molecule (e.g., by placement of a photolabile linkage, a disulfide or ester linkage that is reduced or cleaved in the cell, or the like, between the cell delivery module and the molecule).

The amount of a caged component delivered to a cell can optionally be controlled by controlling the number of cellular delivery modules associated with the caged component. For example, increasing the ratio of 8-D-Arg to caged component can increase the percentage of caged component that enters the cell.

Subcellular Delivery

Caged and/or labeled molecules (e.g., sensors and regulators) can be delivered to specific locations within cells—e.g., a membrane, nucleus, Golgi apparatus or even a specific target—using, e.g., peptides, nucleic acids or proteins as delivery tags. For example, peptides such as PEP-1 migrate through the cell membrane and are transported to the nucleus. Similarly, chloroplast transit sequences can be used to target the chloroplast.

Figure 21A:
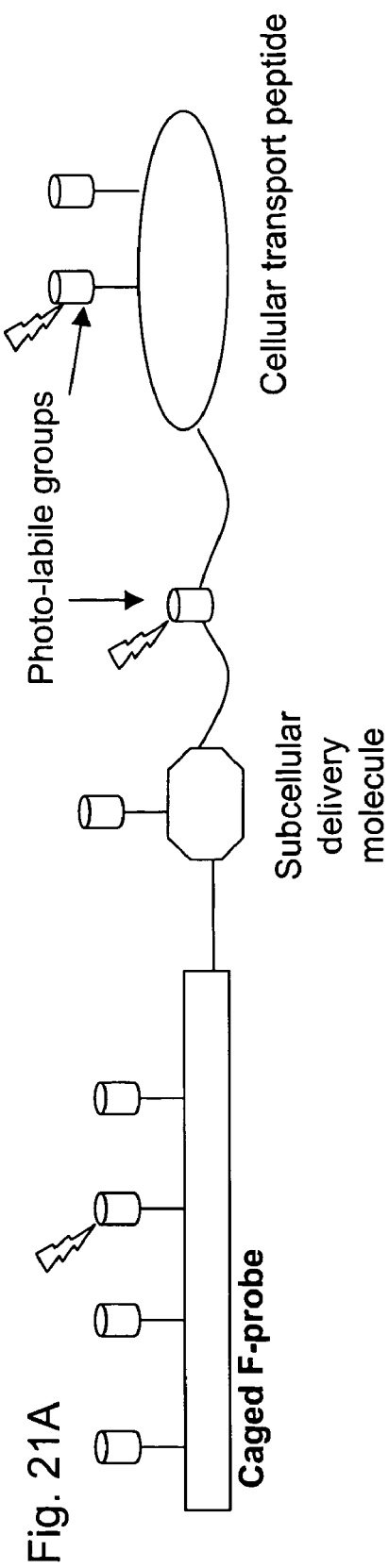
FIG. 21 schematically depicts general designs for photo activated probes (Panel A) and regulators (Panel B).
Figure 21B:
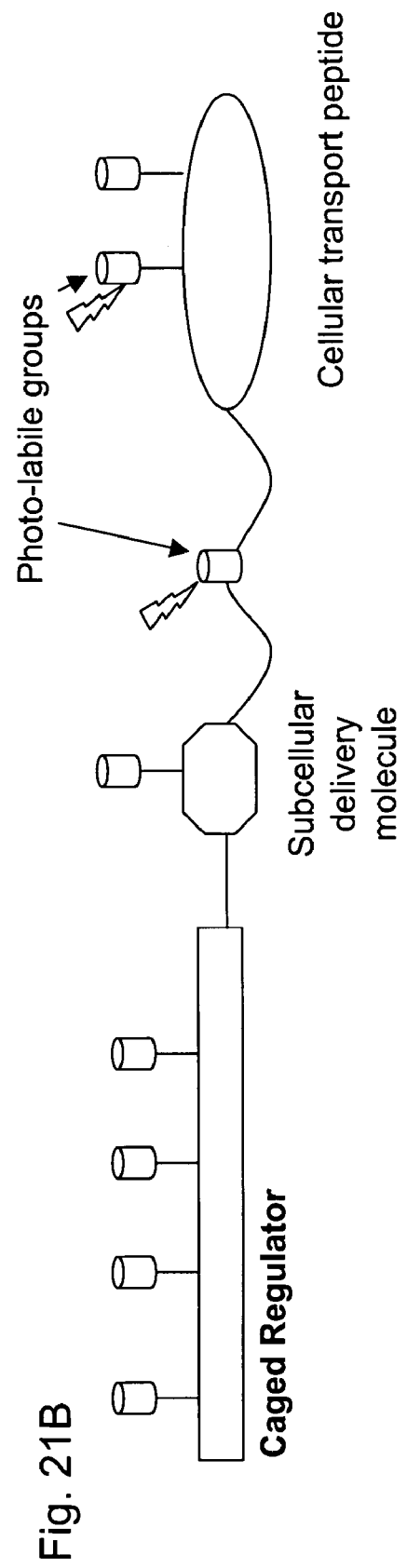
Figure 22:
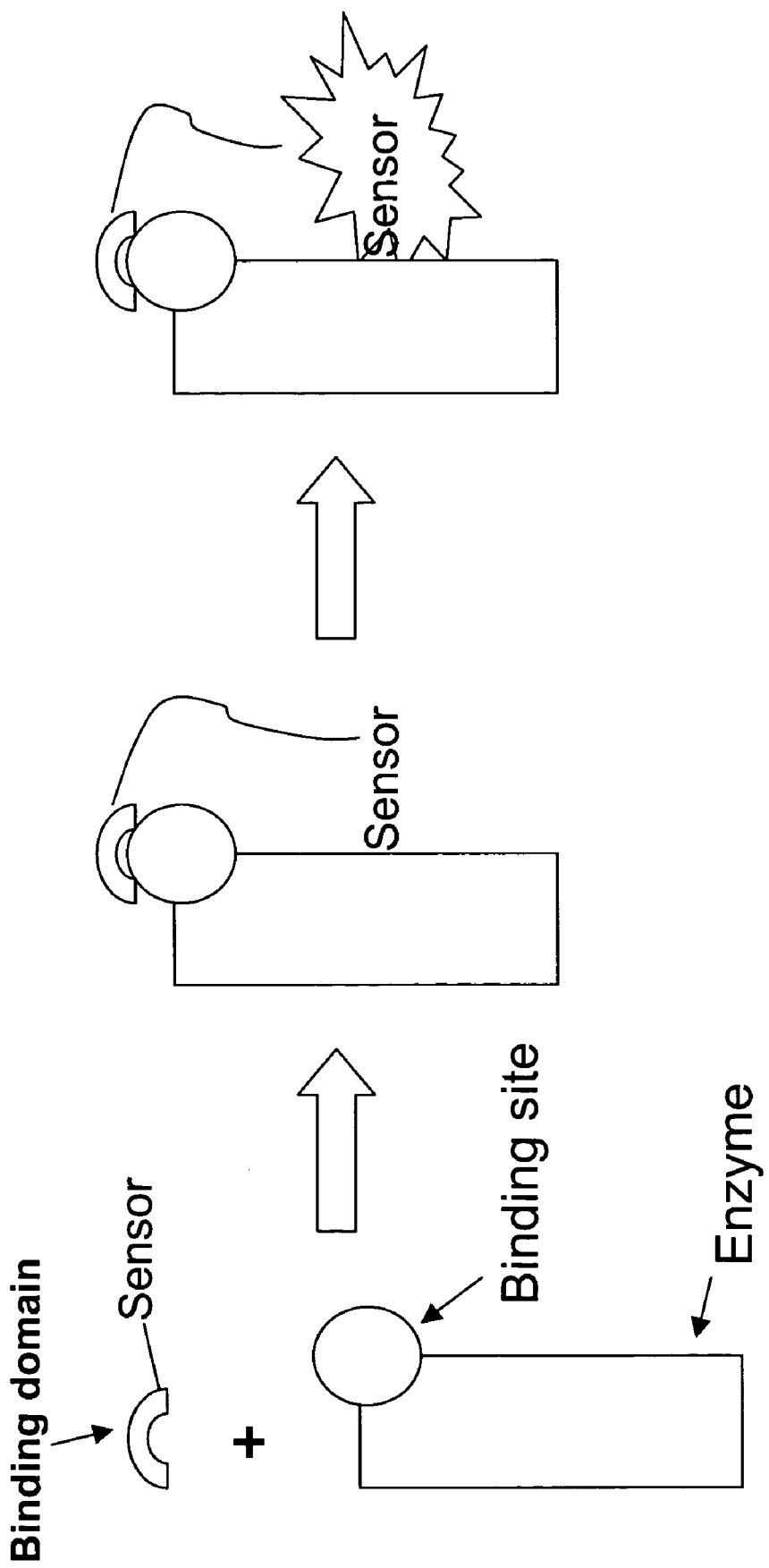
FIG. 22 schematically depicts specific cellular localization of a sensor using a binding domain.

For example, a kinase sensor can be coupled directly with another peptide or protein for specific delivery of the sensor to a specific location within the cell where kinase reaction may occur; e.g., coupling a peptide sensor to PEP-1 can deliver the peptide into the nucleus. FIG. 21 illustrates linkage of a caged probe (e.g., peptide, nucleic acid, or ribozyme) or caged regulator (e.g., peptide, small molecule, protein, RNAi, or antisense) to a subcellular delivery module and to a cellular delivery module (e.g., protein or binding domain). As illustrated, the linkage can be photolabile. Similarly, adaptor proteins and binding domain can be used to bring the sensor close to the activity site within the cell. FIG. 22 shows linkage of a binding domain to a sensor. The binding domain binds to its target-binding site. The sensor then measures the target activity. Alternatively, the binding domain can bind to a surrogate target that locates close to the "true" target of the sensor.

Figure 20:
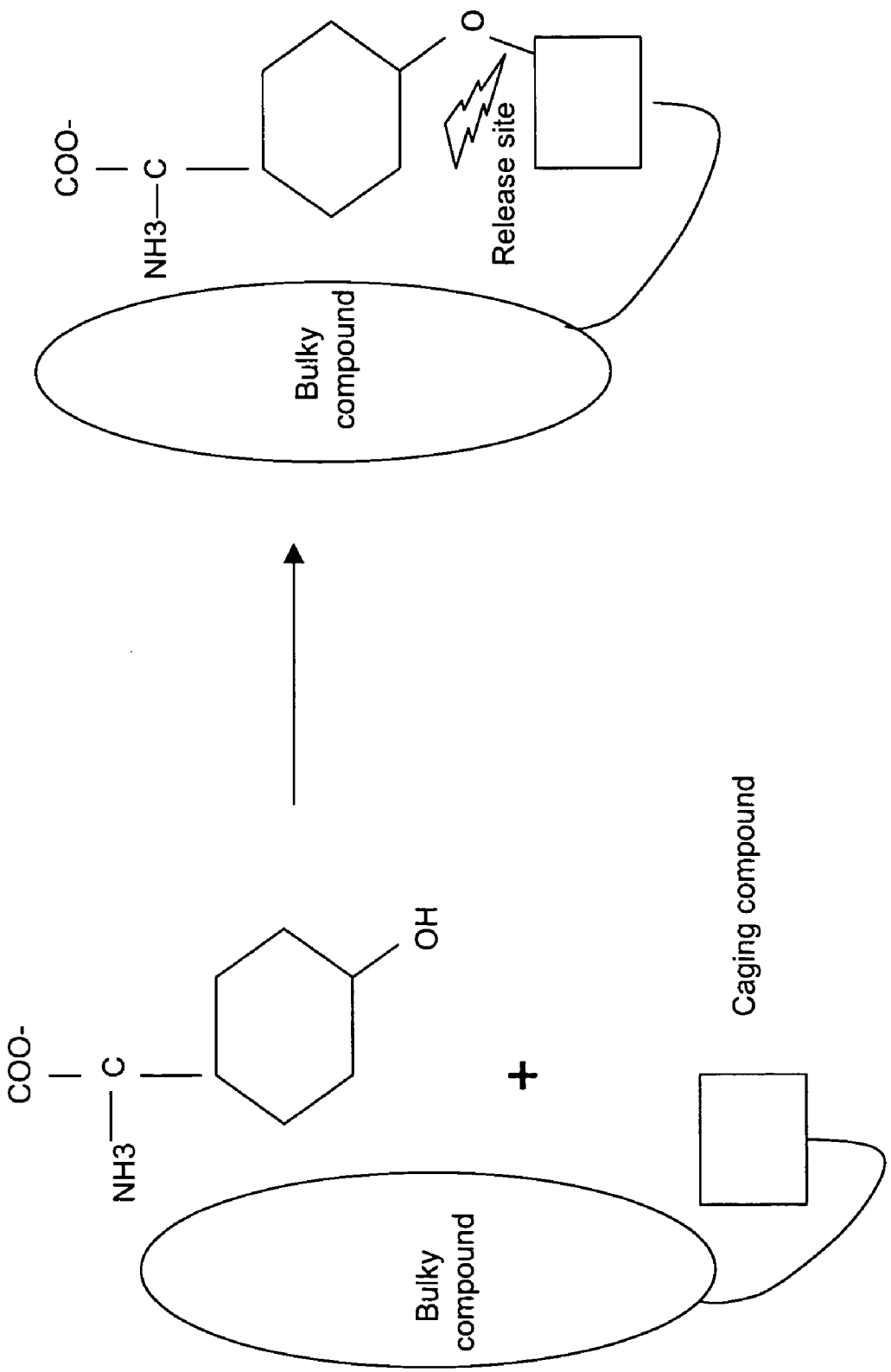
FIG. 20 schematically illustrates caging a sensor by covalent coupling of a photolabile group plus a bulky group.

The subcellular delivery molecules optionally can be caged (e.g., photo-activated) and/or can be released from the molecule (e.g., by having photolabile group, a disulfide or ester linkage, or the like, between the molecule and the subcellular delivery molecule, as shown in the photolabile sensor example in FIG. 20).

The caged and/or labeled molecule is optionally associated (covalently or non-covalently) with a subcellular delivery module that mediates subcellular localization of the molecule. Such localization can be, for example, to a membrane (e.g., the plasma membrane, the nuclear membrane, the inner or outer mitochondrial membrane, or any other organellar membrane) and/or an organelle or compartment thereof (e.g., a mitochondrion, a peroxisome, a nucleus, an endoplasmic reticulum, a Golgi, a vesicle, a lysosome, an endosome, or a chloroplast). The subcellular delivery module can comprise one or more peptide sequences such as a mitochondrial matrix-targeting sequence, a nuclear localization signal, a signal peptide, an ER retention signal (e.g., a KDEL sequence), a peroxisomal targeting motif (e.g., a C-terminal SKL sequence), a chloroplast stromal targeting sequence, a transmembrane domain, a lipid attachment site (e.g., a GPI attachment site, a prenylation or myristoylation sequence, or the like), or the like. See, e.g., *Molecular Biology of the Cell* (3rd ed.) Alberts et al., Garland Publishing, 1994; and *Molecular Cell Biology* (4th ed.) Lodish et al., W H Freeman & Co, 1999. Similarly, localization can be to a target protein; that is, the subcellular delivery module can comprise a binding domain that binds the target protein. For example, an enzyme sensor can be localized by association of the sensor with a binding domain that binds the enzyme or a binding domain that binds a protein localizing near the enzyme.

As noted, certain delivery modules can mediate both cellular and subcellular delivery. For example, the PEP-1 peptide can mediate introduction of a caged molecule into a cell and can also mediate delivery of the caged molecule into the nucleus. Similarly, a short D-arginine homopolymer (e.g., 8-D-Arg, eight contiguous D-arginine residues; see, e.g., Mitchell et al. (2000) *J. Pept. Res.* 56:318-25) can mediate both cellular and nuclear delivery of an associated caged and/or labeled molecule. For example, 8-D-Arg can be covalently linked through a disulfide linker to a caged molecule. The 8-D-Arg module mediates entry of the caged molecule into a cell, where the linker is reduced in the reducing environment of the cytoplasm, freeing the caged molecule from the 8-D-Arg module. The caged molecule can remain in the cytoplasm, or can be delivered to a specific subcellular location if a subcellular delivery module is associated with the molecule. Alternatively, a non-reducible linker can be used, such that the 8-D-Arg module mediates entry of the caged molecule into a cell, remains associated with the molecule, and mediates its entry into the nucleus.

As another example, the caged and/or labeled molecules of this invention (e.g., sensors or regulators) can include an endosomal release agent to assist in achieving their desired subcellular localization. For example, an interfering RNA is typically most effective at initiating RNAi when it is localized to the cytoplasm. Thus, if a method that results in localization of the interfering RNA to the endosome is used to introduce the RNA into the cell (e.g., lipofection, certain protein transduction domains, and the like), performance of the interfering RNA can be improved by including an endosomal release agent on the RNA (e.g., HA-2, PEI, or a dendrimer). See, e.g., *Journal of Controlled Release* (1999) 61:137-143; *J Biol Chem* 277:27135-43; *Proc Natl Acad Sci* 89:7934-38; and *Bioconjugate Chem* (2002) 13:996-1001.

Labels

The compositions of this invention optionally include one or more labels, e.g., optically detectable labels, such as fluorescent or luminescent labels, and/or non-optically detectable labels, such as magnetic labels. A number of fluorescent labels are well known in the art, including but not limited to, quantum dots, hydrophobic fluorophores (e.g., rhodamine and fluorescein), and green fluorescent protein (GFP) and variants thereof (e.g., cyan fluorescent protein and yellow fluorescent protein). See, e.g., *Handbook of Fluorescent Probes and Research Products*, Ninth Edition or Web Edition, from Molecular Probes, Inc. Likewise, a variety of fluorophore/quencher combinations, using e.g., fluorescence resonance energy transfer (FRET)-based quenching, non-FRET based quenching, or wavelength-shifting harvester molecules, are known. Example combinations include cyan fluorescent protein and yellow fluorescent protein, terbium chelate and TRITC (tetrarhodamine isothiocyanate), europium chelates and allophycocyanin, europium cryptate and Allophycocyanin, fluorescein and tetramethylrhodamine, IAEDANS and fluorescein, EDANS and DABCYL, fluorescein and DABCYL, fluorescein and fluorescein, BODIPY FL and BODIPY FL, and fluorescein and QSY 7 dye. Nonfluorescent acceptors such as DABCYL and QSY 7 and QSY 33 dyes have the particular advantage of eliminating background fluorescence resulting from direct (i.e., nonsensitized) acceptor excitation. See, e.g., U.S. Pat. Nos. 5,668,648; 5,707,804; 5,728,528; 5,853,992; and 5,869,255 to Mathies et al. for a description of FRET dyes.

For use of quantum dots as labels for biomolecules, see, e.g., Dubertret et al. (2002) *Science* 298:1759; *Nature Biotechnology* (2003) 21:41-46; and *Nature Biotechnology* (2003) 21:47-51.

Other optically detectable labels can also be used in the invention. For example, gold beads can be used as labels and can be detected using a white light source via resonance light scattering. See, e.g. the internet at geniconsciences.com. Suitable non-optically detectable labels are also known in the art. For example, magnetic labels can be used in the invention (e.g., 3 nm superparamagnetic colloidal iron oxide as a label and NMR detection; see, e.g., *Nature Biotechnology* (2002) 20:816-820).

Labels can be introduced to molecules, e.g. polypeptides, nucleic acids, and small molecules, during synthesis or by postsynthetic reactions by techniques established in the art. Similarly, signals from the labels (e.g., absorption by and/or fluorescent emission from a fluorescent label) can be detected by essentially any method known in the art. For example, multicolor detection, detection of FRET (including, e.g., time-resolved or TR-FRET), and the like, are well known in the art. FRET was briefly described above. As another example, fluorescence polarization can be used. Briefly, in the performance of such fluorescent binding assays, a typically small, fluorescently labeled molecule, e.g., a ligand, antigen, etc., having a relatively fast rotational correlation time, is used to bind to a much larger molecule, e.g., a receptor protein, antibody etc., which has a much slower rotational correlation time. The binding of the small labeled molecule to the larger molecule significantly increases the rotational correlation time (decreases the amount of rotation) of the labeled species, namely the labeled complex over that of the free unbound labeled molecule. This has a corresponding effect on the level of polarization that is detectable. Specifically, the labeled complex presents much higher fluorescence polarization than the unbound, labeled molecule.

Generally, the fluorescence polarization level is calculated using the following formula:

$$P=[I_1-I_2]/[I_1+I_2]$$

where $I_1$ is the fluorescence detected in the plane parallel to the excitation light, and 12 is the fluorescence detected in the plane perpendicular to the excitation light. References which discuss fluorescence polarization and/or its use in molecular biology include Perrin (1926) "Polarization de la lumiere de fluorescence. Vie moyenne de molecules dans l'etat excite" *J Phys Radium* 7:390; Weber (1953) "Rotational Brownian motion and polarization of the fluorescence of solutions" *Adv Protein Chem* 8:415; Weber (1956) *J Opt Soc Am* 46:962; Dandliker and Feigen (1961) "Quantification of the antigen-antibody reaction by the polarization of fluorescence" *Biochem Biophys Res Commun* 5:299; Dandliker and de Saussure (1970) "Fluorescence polarization in immunochemistry" *Immunochemistry* 7:799; Dandliker et al.

(1973) "Fluorescence polarization immunoassay. Theory and experimental method" *Immunochemistry* 10:219; Levison et al. (1976) "Fluorescence polarization measurement of the hormone-binding site interaction" *Endocrinology* 99:1129; Jiskoot et al. (1991) "Preparation and application of a fluorescein-labeled peptide for determining the affinity constant of a monoclonal antibody-hapten complex by fluorescence polarization" *Anal Biochem* 196:421; Wei and Herron (1993) "Use of synthetic peptides as tracer antigens in fluorescence polarization immunoassays of high molecular weight analytes" *Anal Chem* 65:3372; Devlin et al. (1993) "Homogeneous detection of nucleic acids by transient-state polarized fluorescence" *Clin Chem* 39:1939; Murakami et al. (1991) Fluorescent-labeled oligonucleotide probes detection of hybrid formation in solution by fluorescence polarization spectroscopy" *Nuc. Acids Res* 19:4097; Checovich et al. (1995) "Fluorescence polarization—a new tool for cell and molecular biology" *Nature* 375:354-256; Kumke et al. (1995) "Hybridization of fluorescein-labeled DNA oligomers detected by fluorescence anisotropy with protein binding enhancement" *Anal Chem* 67:21, 3945-3951; and Walker et al. (1996) "Strand displacement amplification (SDA) and transient-state fluorescence polarization detection of mycobacterium tuberculosis DNA" *Clinical Chemistry* 42:1, 9-13.

Arrays

In an array on a matrix (e.g., a surface), each nucleic acid, polypeptide, modulator, etc. is bound (e.g., electrostatically or covalently bound, directly or via a linker) to the matrix at a unique location. Methods of making, using, and analyzing such arrays (e.g., microarrays) are well known in the art, including methods of using arrays by overlaying the arrays with cells into which the components of the array can be introduced. See, e.g., U.S. Pat. No. 6,197,599; Ziauddin and Sabatini "Microarrays of cells expressing defined cDNAs" *Nature* 2001 May 3, 411(6833):107-10; and Falsey et al. *Bioconjug. Chem.* (2001) 12:346-53.

Molecular Biological Techniques

In practicing the present invention, many conventional techniques in molecular biology, microbiology, and recombinant DNA technology are optionally used (e.g., for making and/or manipulating nucleic acids and polypeptides of the invention). These techniques are well known, and detailed protocols for numerous such procedures (including, e.g., in vitro amplification of nucleic acids, cloning, mutagenesis, transformation, protein expression, and the like) are described in, for example, Berger and Kimmel, *Guide to Molecular Cloning Techniques, Methods in Enzymology* volume 152 Academic Press, Inc., San Diego, Calif. ("Berger"); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla.

Oligonucleotide Synthesis

In general, synthetic methods for making oligonucleotides and PNAs (including labeled oligos and PNAs) is well known. For example, oligonucleotides can be synthesized chemically according to the solid phase phosphoramidite triester method described by Beaucage and Caruthers (1981), *Tetrahedron Letts.*, 22(20):1859-1862, e.g., using a commercially available automated synthesizer, e.g., as described in Needham-VanDevanter et al. (1984) *Nucleic Acids Res.*, 12:6159-6168. Synthesis of PNAs and modified oligonucleotides (e.g., oligonucleotides comprising 2'-O-methyl nucleotides and/or phosphorothioate, methylphosphonate, or boranophosphate linkages) are described in e.g., *Oligonucleotides and Analogs* (1991), IRL Press, New York; Shaw et al. (1993), *Methods Mol. Biol.* 20:225-243; Nielsen et al. (1991), *Science* 254:1497-1500; and Shaw et al. (2000) *Methods Enzymol.* 313:226-257.

Oligonucleotides, including modified oligonucleotides (e.g., oligonucleotides comprising fluorophores and quenchers, unnatural nucleotides, 2'-O-methyl nucleotides, and/or phosphorothioate, methylphosphonate, or boranophosphate linkages) can also be ordered from a variety of commercial sources known to persons of skill. There are many commercial providers of oligo synthesis services, and thus, this is a broadly accessible technology. Any nucleic acid can be custom ordered from any of a variety of commercial sources, such as The Midland Certified Reagent Company (on the internet at mcrc.com), The Great American Gene Company (on the internet at genco.com), ExpressGen Inc. (on the internet at expressgen.com), QIAGEN (oligos.qiagen.com), and many others. PNAs can be custom ordered from any of a variety of sources, such as PeptidoGenic (pkim@ccnet.com), HTI Bio-products, Inc. (on the internet at htibio.com), BMA Biomedicals Ltd (U.K.), Bio•Synthesis, Inc., and many others. A variety of commercial suppliers produce standard and custom molecular beacons, including Cruachem (cruachem.com), Oswel Research Products Ltd. (UK; oswel.com), Research Genetics (a division of Invitrogen, Huntsville Ala. (resgen.com)), the Midland Certified Reagent Company (Midland, Tex.; mcrc.com) and Gorilla Genomics, LLC (Alameda, Calif.).

A variety of nuclease-resistant nucleic acids can optionally be created, e.g., comprising modified nucleotides and/or modified internucleotide linkages such as those currently used in the synthesis of antisense oligonucleotides. For example, a nuclease resistant oligonucleotide can comprise one or more 2'-O-methyl nucleotides. For example, an oligonucleotide comprising standard deoxyribonucleotides can also comprise one or more 2'-O-methyl nucleotides (e.g., at its 5' end), or an oligonucleotide can consist entirely of 2'-O-methyl nucleotides. As another example, a nuclease resistant oligonucleotide can comprise one or more phosphorothioate linkages (oligonucleotides comprising such linkages are sometimes called S-oligos). An oligonucleotide can comprise, e.g., only phosphorothioate linkages or a mixture of phosphodiester and phosphorothioate linkages. In other embodiments, the oligonucleotide comprises one or more methylphosphonate linkages, one or more boranophosphate linkages, or the like. Combinations of typical nuclease resistance modification strategies can also be employed. For example, a nuclease resistant oligonucleotide can comprise both 2'-O-methyl nucleotides and phosphorothioate linkages.

Polypeptide Production

Polypeptides can optionally be produced by expression in a host cell transformed with a vector comprising a nucleic acid encoding the desired polypeptide(s). Expressed polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography, for example. Protein refolding steps can be used, as desired, in completing configuration of the mature protein. Finally, high performance liquid chromatography (HPLC) can be employed in the final purification steps. See, e.g., the references noted above and Deutscher, *Methods in Enzymology Vol.* 182: *Guide to Protein Purification*, Academic Press, Inc. N.Y. (1990); Sandana (1997) *Bioseparation of Proteins*, Academic Press, Inc.; Bollag et al. (1996) *Protein Methods, 2$^{nd}$ Edition* Wiley-Liss, NY; Walker (1996) *The Protein Protocols Handbook* Humana Press, NJ; Harris and Angal (1990) *Protein Purification Applications: A Practical Approach* IRL Press at Oxford, Oxford, U.K.; Scopes (1993) *Protein Purification: Principles and Practice 3$^{rd}$ Edition* Springer Verlag, NY; Janson and Ryden (1998) *Protein Purification: Principles, High Resolution Methods and Applications. Second Edition* Wiley-VCH, NY; and Walker (1998) *Protein Protocols on CD-ROM* Humana Press, NJ.

Alternatively, cell-free transcription/translation systems can be employed to produce polypeptides encoded by nucleic acids. A number of suitable in vitro transcription and translation systems are commercially available. A general guide to in vitro transcription and translation protocols is found in Tymms (1995) *In vitro Transcription and Translation Protocols: Methods in Molecular Biology* Volume 37, Garland Publishing, NY.

In addition, polypeptides (including, e.g., polypeptides comprising fluorophores and quenchers and/or unnatural amino acids) can be produced manually or by using an automated system, by direct peptide synthesis using solid-phase techniques (see, e.g., Stewart et al. (1969) *Solid-Phase Peptide Synthesis*, WH Freeman Co, San Francisco; Merrifield J (1963) *J. Am. Chem. Soc.* 85:2149-2154). Exemplary automated systems include the Applied Biosystems 431A Peptide Synthesizer (Perkin Elmer, Foster City, Calif.). If desired, subsequences can be chemically synthesized separately, and combined using chemical methods to provide full-length polypeptides.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Photo-Activated Sensors and Regulators

Sensors can be, e.g., fluorescent probes whose fluorescent intensity changes when the probes bind to specific targets or are modified with chemical groups. The sensors can be substrates of an enzyme, or binding targets of nucleic acids, or protein molecules, or any of the other formats noted herein. The sensors can be used e.g., for monitoring gene expression or activity of specific protein targets within a cell, cell lysate, in vitro biochemical assay, serum, plasma, CSF and/or intercellular fluids or the like.

Regulators can be molecules that either activate or inhibit specific enzymatic or other biochemical activity in a biochemical, cell-lysate, cell-based or serum assays. The regulator can be a peptide, small molecule, nucleic acid or any other noted herein.

By attaching or otherwise incorporating photolabile groups to sensors and regulators, the activities of the sensors and regulators are blocked until the photolabile groups are released by exposure to light of an appropriate wavelength. Accordingly, photolabile (and other PA) sensors and regulators are sensors and regulators whose activities can be controlled (e.g., temporally, spatially, or otherwise) by light.

In addition to photolabile groups, the sensors and regulators can be attached to molecules that assist in transportation of the sensors and regulators into cells. The sensors and regulators can also be attached to moieties that deliver sensors and regulators into specific sub-cellular locations such as nuclei, chloroplast, cell membrane, mitochondria, etc.

Figure 23C:
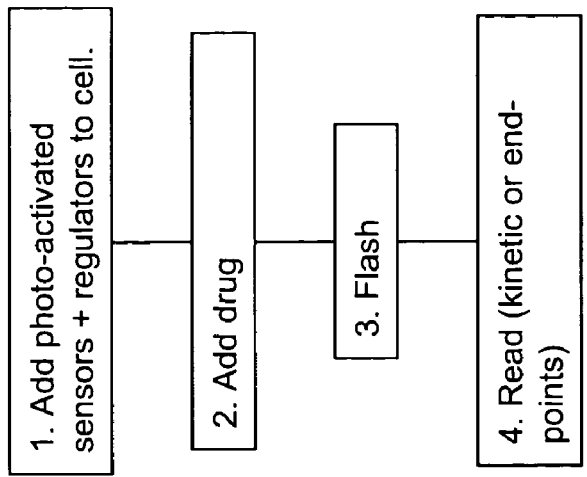
FIG. 23 depicts flowcharts illustrating the workflow for assays using photoactivatable sensors and/or regulators in three formats: biochemical (Panel A), cell-lysate (Panel B) and cell-based (Panel C).
Figure 23B:
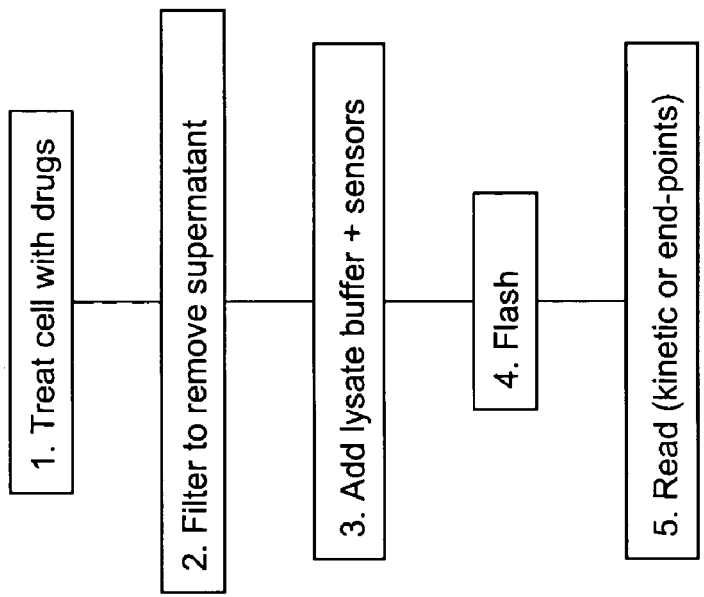
Figure 23A:
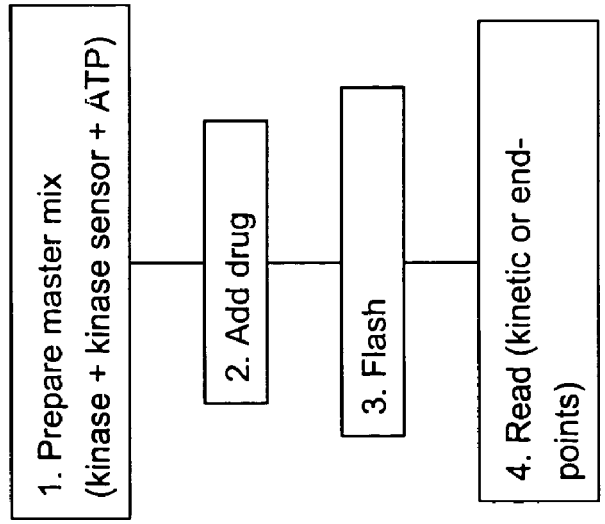

The applications of PA sensors and regulators in cellular assays can involve some or all of the following components: fluorescent probe and regulator, peptide delivery elements, photo-activation elements, and/or cellular or cell localization elements. Specific details of each component are described herein. The general workflow of photo-activated sensors is illustrated, e.g., in FIG. 23.

Using Photo-Activation to Control the Timing of Assays

Great progress has been made in the area of high throughput screening (HTS) of drugs due to the development of robotic/automation complemented by simple mix-and-read assay formats (see, e.g. *Modern Drug Discovery*, July 2002 38). The new trend in HTS is miniaturization and increased number of wells per plate—going from 96 to 384 to 1,536 to 10,000 or more wells. Liquid handling is an important component of the process. The delivery of fluid can be inaccurate and slow. This problem is particularly acute in kinetic assays, where the reaction in the first well to be initiated will start before the second well receives the final assay component to start the reaction. The present invention uses caging strategies, e.g., to block an assay until all reaction components are present in all reactions to be initiated. The use of light or other appropriate uncaging energies initiates all assays simultaneously.

Photolabile caged compounds have been described, e.g., in Neuro 19, 465 (1997); *J Physiol* 508.3, 801 (1998); Proc Natl Acad Sci USA 1988 September, 85(17):6571-5; *J Biol Chem* 1997 Feb 14, 272(7):4172-8; *Neuron* 20,619-624, 1998; *Nature Genetics*, vol. 28:2001:317-325; *Nature*, vol. 392, 1998:936-941; and *BioProbes Handbook*, 2002 from Molecular Probes, Inc. Many have been developed for fluorescent microscopy applications. For example, there are four major common photo cleavable groups—o-nitrobenzyl, bezoin, o-cinnamoyl and m-nitrophenyl photochemistry. These photolabile groups are coupled to various molecules to temporarily mask the biochemical activity of the molecules. A wide range of caged molecules is commercially available, including, without limitation,—NPE-caged ATP, NPE-caged Ins 1,2,5-P3, DMNP-caged EDTA, and caged amino acids. Caged metals, ions, amino acids, peptides and DNA have been demonstrated.

Photolabile groups can be cleaved away with light, e.g., light ranging from 260-360 nm. As another example, longer wavelength caged compounds have been developed for use with light at 460-500 nm. Photo-cleavage can happen within milliseconds of exposure to light.

In a photo-activated assay, assay components can be premixed and remain inert until activated by exposure to light of specific wavelength. Strategic coupling of photoactivatable (e.g., photolabile) groups inactivates one or several assay components.

The assay components that contain photolabile or other photoactivatable group(s) are referred to as photo-activated (PA) components. The PA component(s) can be used to start, stop and/or modulate the assay reaction. For example, PA-ATP can be used to start a kinase reaction and PA-EDTA can be used to stop the kinase reaction. Increasing or decreasing the releasing of PA component can alter the behavior of the reaction. The release of PA component is controlled by the light intensity, exposure period or number of exposures. This feature can be used to repeat the same assay without multiple steps of reagent addition. In addition, the kinetics of the assay can be tuned based on the initial reaction. Furthermore, one can achieve location specific control of assays by tuning light to a specific geographic location, e.g., a specific well of a microtiter plate or a specific spot of a well or slide.

Different PA components can be activated at different wavelengths, permitting the development of multiplexed and/or multifunctional and/or multi-step assays. This is accomplished, e.g., by using photolabile groups that are susceptible to different wavelengths of light. This capability permits, e.g., the control of sub-reactions within an assay. A great number of homogenous mix-and-read assays utilize two types of reagents—reagents used for the reaction (e.g., enzymes) and reagents used for detection after the reaction (e.g., labels). In the present invention, all these reagents can be combined and activated in accordance to the relevant assay workflow. The advantage here is that all assay components can be mixed together, reducing the number of liquid handling steps (which can contribute to poor assay results or inconsistencies).

In summary, the advantages of using PA assay format include at least the following: (1.) The ability to control precisely the timing of activation of assay components, facilitating the development of novel homogenous assays; (2.) Improved assay precision; (3) Reduced numbers of fluidic handling steps in HTS assays, e.g., that reduce the number of assay steps (each fluid-handling step can introduce error into an assay); (4.) Simultaneous activation of a large number of assays within roughly a millisecond time frame (e.g., shining light on one or more plates comprising large numbers of assays); (5.) Simplified automation and design of miniaturized platforms by reducing the number of steps required for performing an assay; (6.) Location specific activation of assay, e.g., a subset of wells or other locations within a microarray, microfluidic device and/or others miniaturized formats (e.g., activation of a specific location separated by about 1, 5, 10, 30, 50, or 100 microns or more is relatively straightforward in light-directed approaches); (7.) The PA assay format is extremely adaptable to different biochemical assays, being suitable for enzyme-based assays, binding assays and many others.

PA Kinase Assays

Figure 2:
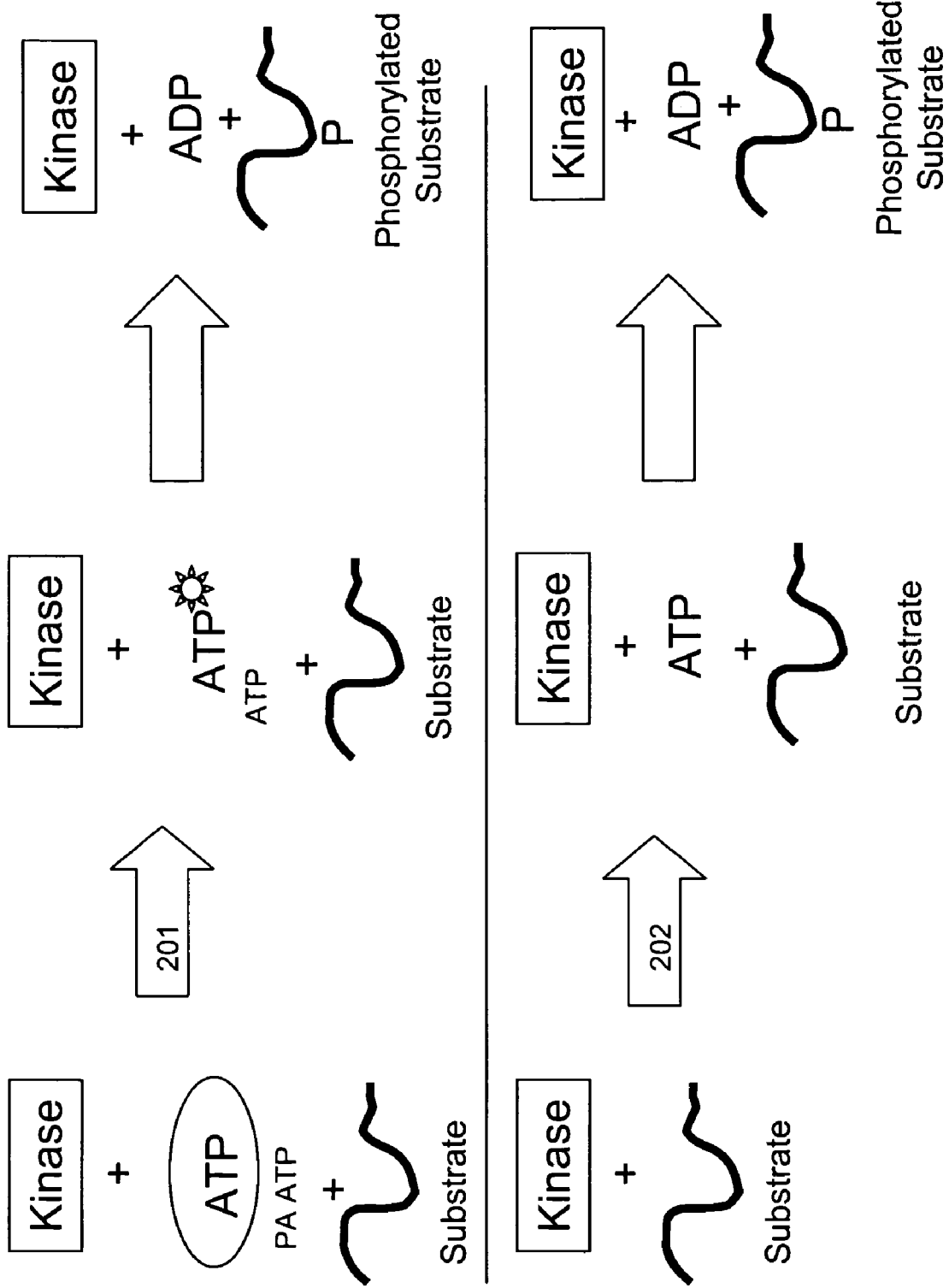
FIG. 2 Panel A schematically depicts a photo activated kinase assay in which the reaction is initiated by uncaging caged ATP. Panel B schematically depicts a standard kinase assay in which the reaction is initiated by adding ATP.
Figure 3:
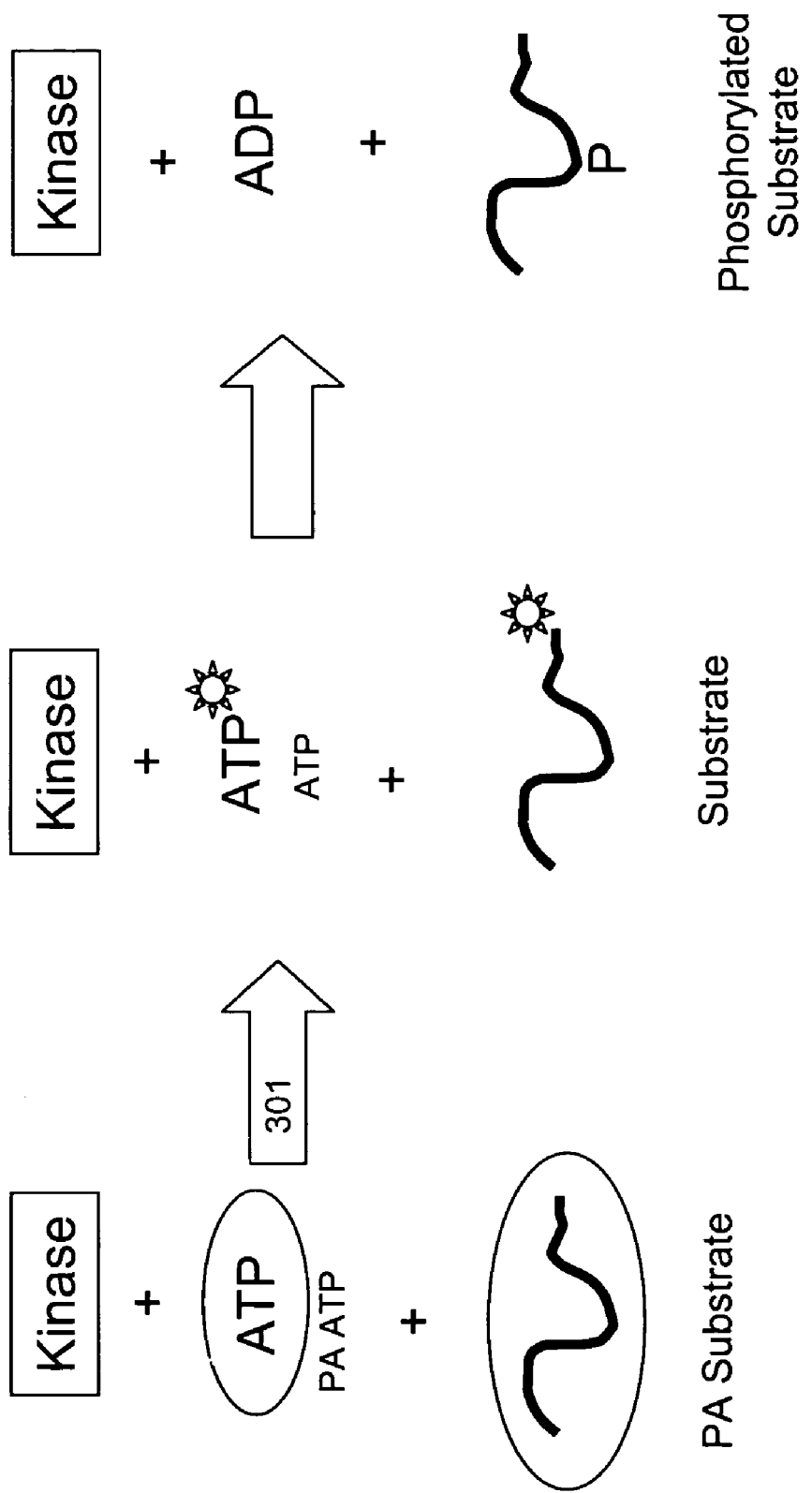
FIG. 3 schematically depicts a photo activated kinase assay in which the reaction is initiated by uncaging caged substrate (and optionally also caged ATP).
Figure 5:
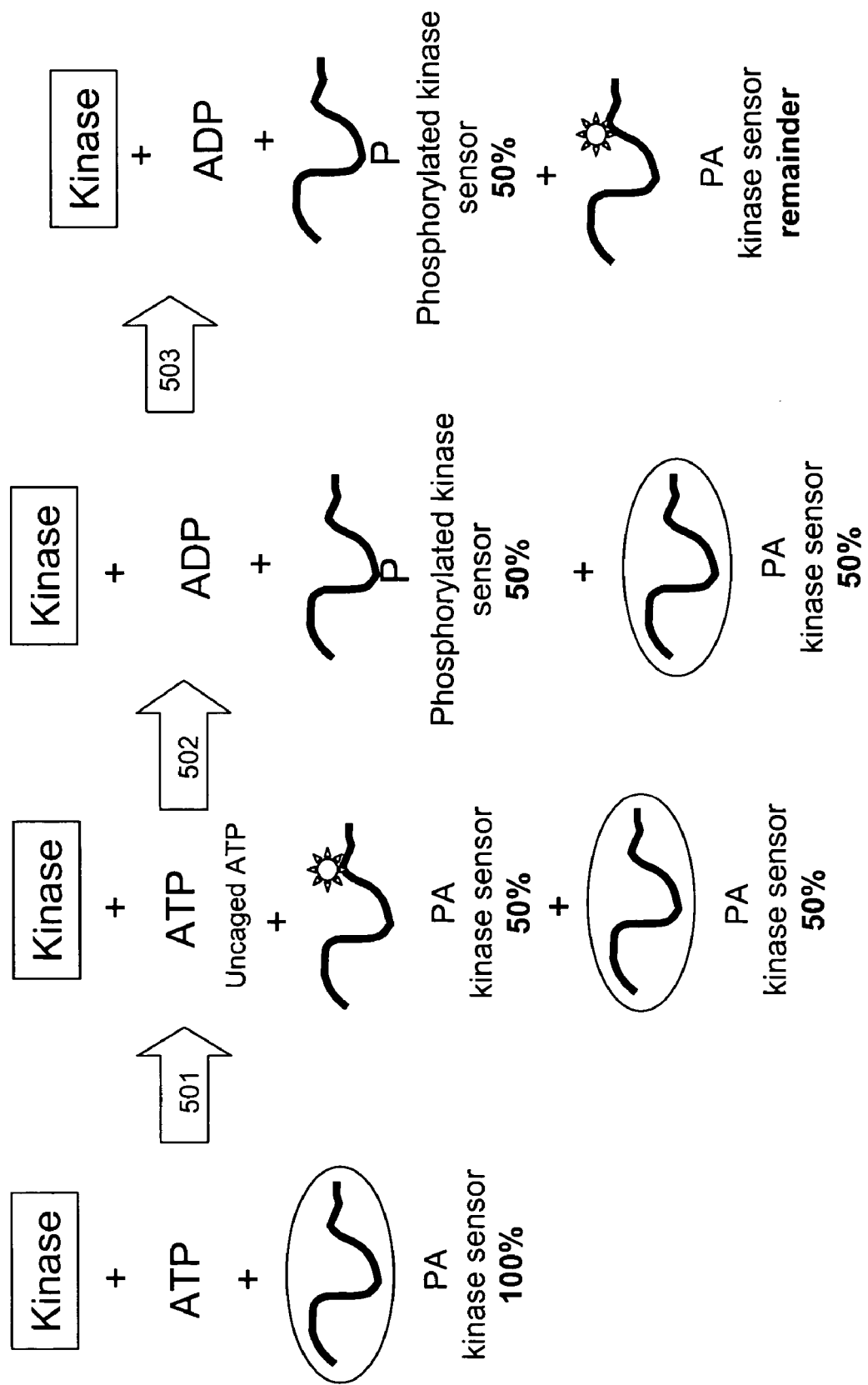
FIG. 5 schematically depicts controlled release of PA compound by light exposure.

To illustrate these benefits, an example kinase enzyme assay is described below. FIG. 1 illustrates a typical kinase assay. ATP or kinase is typically added to start the reaction. In this example, the reaction is initiated by adding ATP by pipette in step 101. The substrate is phosphorylated in step 102, and the phosphorylated substrate is detected by adding detection reagent (e.g., phosphobinders such as anti-phospho Tyr, Ser, or Thr antibodies, metal chelators, or SH2, FHA or WW binding domains, plus EDTA) in step 103, before the reaction is read in step 104 (e.g., by fluorescence polarization, FRET, or use of a fluorophore/quencher pair). By adding PA-ATP or PA-peptide substrate in an assay mix comprising all components, multiple steps can be combined (see, FIGS. 2 and 3). Instead of starting the reaction by adding ATP or kinase, the entire reaction including a caged component is mixed and the start of the reaction is triggered by illumination at a specific wavelength. For example, FIG. 2 Panel A depicts a PA kinase assay in which the reaction is initiated by uncaging PA caged ATP, e.g., by exposure to 300 nm light in step 201; a standard kinase assay in which the reaction is initiated by addition of ATP by pipette in step 202 is shown for comparison in Panel B. FIG. 3 depicts a PA kinase assay in which both ATP and the substrate are caged. The reaction is initiated, e.g., by exposure to 300 nm light in step 301 to uncaged the PA-ATP and PA-substrate. The amount of PA substrate or ATP released from caging can be controlled with light intensity. For example, FIG. 5 depicts a PA kinase assay in which release of substrate is controlled. 100% of the PA kinase sensor is initially caged. A portion (e.g., 50%) of the sensor is uncaged, e.g., by exposure to 300 nm light in step 501. The uncaged sensor is phosphorylated in step 502 and optionally detected. A second portion (e.g., the remainder) of the caged sensor is uncaged, e.g., by re-exposure to 300 nm light in step 503. The ATP is optionally also caged.

Figure 4:
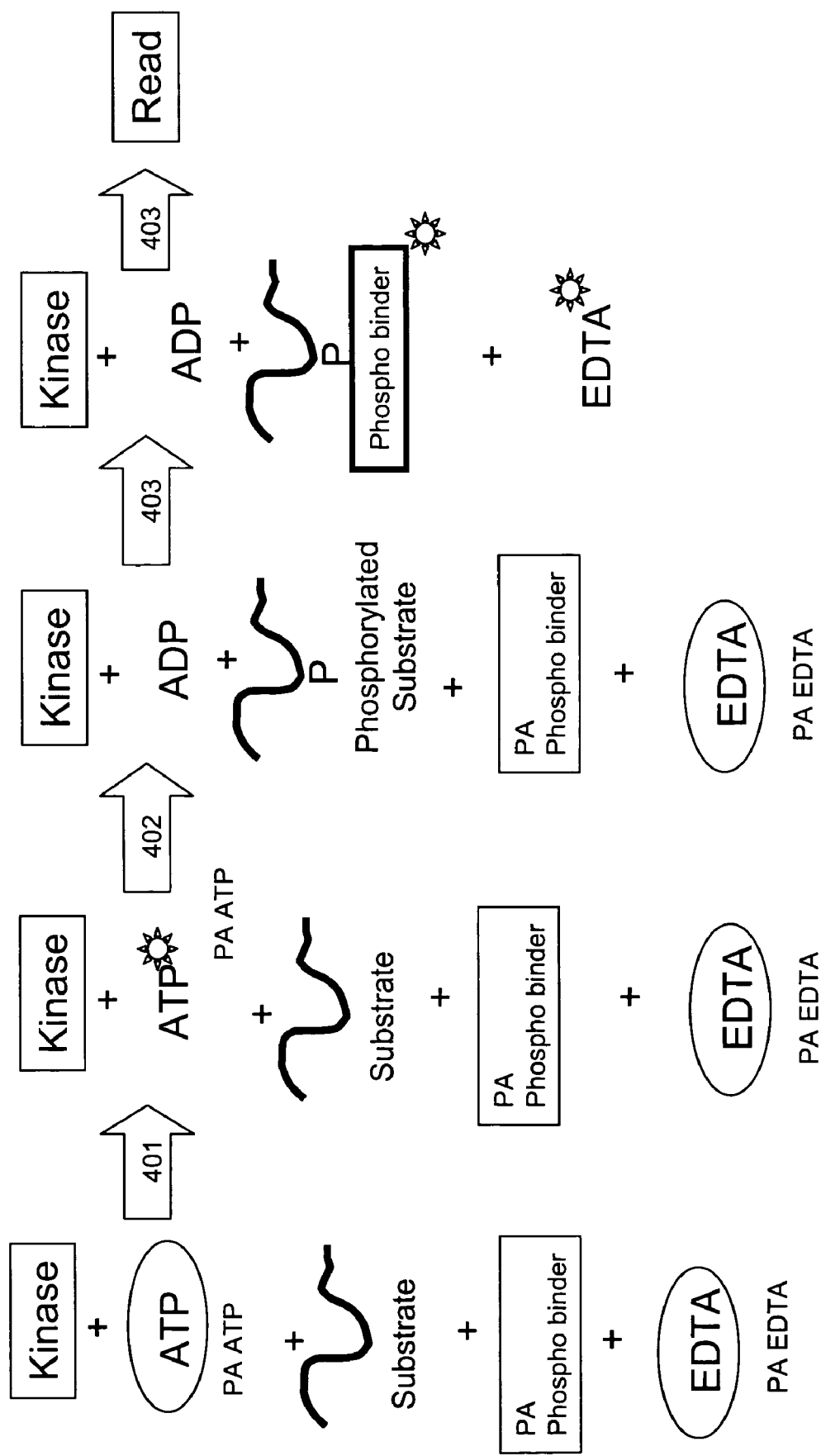
FIG. 4 schematically depicts controlled triggering and detection of the kinase reaction, using PA compounds uncaged by different wavelengths.

In addition, different assay components can be masked with caging groups that are susceptible to different photo cleavage wavelengths. In this case, a controlled activation, e.g., of specific substrate, can be performed. A novel assay using this approach is illustrated in FIG. 4. In this example, there are two PA assay components—ATP and phosphobinder (e.g., antibodies, metal chelator or phospho-binding domain). The kinase reaction is started when PA-ATP is exposed to UV light at 300 nm in step 401. The kinase phosphorylates the substrate in step 402. Thereafter, the detection reaction can be started by exposing the reaction to light at 460 nm in step 403, which uncages the phosphobinder. Results of the assay are read in step 404. As shown, a third assay component is optionally also caged (e.g., EDTA). In this example, all components of the assay are premixed so that minimal pipetting steps are required. A specific component is used and activated in an order dictated by the assay sequence. There are two pipetting steps in this assay compare to four pipetting steps in a conventional assay as illustrated in FIG. 1. Assay precision is improved by reducing fluid handling (e.g., pipetting) steps. This is especially important for low volume assays, e.g., in nanoliter scale and miniature well applications (e.g., 1536 well plates and beyond) or microfluidic platforms (see also, FIGS. 24 and 25).

Lastly, the parallel triggering of assays in multiple wells greatly improves data reproducibility for assays monitoring reaction kinetics (within an experiment or between experiments).

As already noted, the use of PA compound is not limited to kinase assays. It can used with other enzymatic assays, including, without limitation, phosphatase, luciferase or protease assays. It can also be applied to binding assays such as antibody, protein-to-protein and DNA-to-protein assays. Basically, any assay component can be caged, e.g., with photoactivatable (e.g., photolabile) groups, to reduce the number of steps in an assay's workflow, e.g., in biochemical reactions.

For example, photolabile groups can be coupled directly to sensors or regulators as described herein. The sensor is masked until exposed to light. For example, FIG. 19 illustrates linking a caging compound covalently to an amino acid or nucleic acid. Similarly, FIG. 20 illustrates linking a bulky and large interfering group to a nucleic acid, protein or other chemical group. Connecting the bulky group and the sensor is a photolabile group that cleaves when exposed to light. The sensor is functional when the bulky interfering group is released.

Fluorescent Probes (Sensors)

An example of a fluorescent probe (an "F-probe") is a kinase probe, e.g., a peptide-based sensor that changes its fluorescent property when a phosphate group is added to a specific amino acid. This sensor can be caged, e.g., with a photolabile group, to prevent it from being phosphorylated by the kinase. Upon exposure to light, the photolabile group falls off and the sensor becomes active, i.e., ready to be phosphorylated by the kinase. See, FIG. 3. This method can be applied to kinase probes developed for in vivo monitoring of kinase activity. See also, *J Mol Screening*, vol. 5,1:23-30 (2000); *Anal Bioch*, 244, 2:340-6 (1997); *J Biol Chem*, vol. 277, no.13: 11527-532 (2002); *PNAS* vol. 98, no. 26:15003-08 (2001); *Anal Sci*, vol. 17: i1456-67 (2001); and *Nature Bio*, vol. 18:313-16 (2000).

Many kinase assays have been developed to measure the phosphorylation activity of kinases. A typical biochemical kinase assay is illustrated in FIG. 1. It consists of two stages (reaction and detection). The first stage involves the addition of all components except ATP or kinase. The reaction is activated by the addition of ATP or kinase. After the reaction stage, the detection reagent is added to detect the phosphorylation on the peptide substrate. The detection methods can range from using phospho-specific antibodies, metal chelator, ATP-analog, measuring remaining ATP in combination with fluorescent polarization, FRET, LANCE, SPA, luciferase and others. See also, *BioProbes Handbook*, 2002 from Molecular Probes, Inc.; *J Mol Screening*, vol. 7,1:3-10 (2002); *Anal Bioch*, 269: 94-104 (1999); *J Mol Screening*, vol. 5,1:23-30 (2000); and *Anal Bioch*, 244, 2: 340-6 (1997). Unfortunately, this assay is not suitable for cell lysates, or for assays within cells or living animals (due to the presence of endogenous ATP and/or kinases). In drug discovery, ideally, a common assay would be used from primary screening, to secondary screening, to in vivo animal studies. This way the data can be compared consistently. The present invention provides this ability by overcoming the problems associated with inherent cellular materials.

The use of the kinase sensors of the invention in biochemical assays also permits kinetic measurement(s). The shape of the kinetic response curve provides additional information about drug binding to kinase—whether permanently bound or binding with specific on/off rate. The PA feature of the PA kinase sensor permits precise and uniform activation of biochemical reactions from thousands of wells within a single micro titer plate.

The kinetic measurement and precise activation of biochemical kinase assay also applies for cell-based assays. In a cell-based assay, the ability to control the timing of phosphorylation of the kinase sensor is crucial since the introduction of kinase sensor into cells in multiple wells of a microtiter plate has to be synchronized. When the sensor is not caged, phosphorylation reactions in different wells would likely start at different time, causing inconsistency in measurement. Hence, PA kinase sensors improve the precision of cell-based assays by allowing the experimenter to control the timing of activation. This is more important for assays based on kinetic measurement.

Photo-Activated Kinase, Phosphatase, Caspase, and Other Sensors

Figure 6:
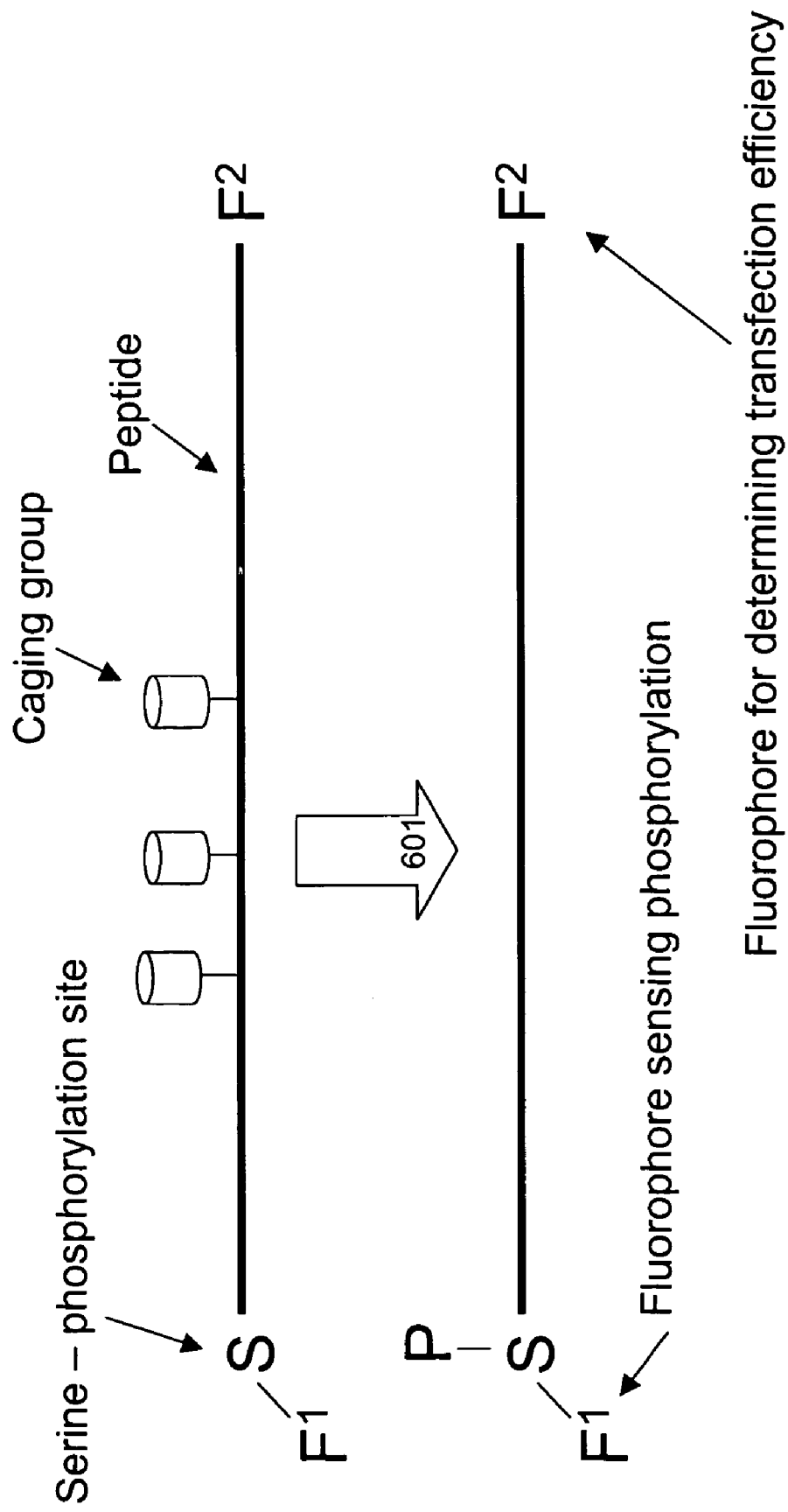
FIG. 6 schematically illustrates kinase sensor design 1.

FIG. 6 describes PA sensor 1, in which a fluorophore is located at the site of the amino acid where the phosphorylation occurs. The caging compound is located on the kinase-binding site. A second fluorophore is optionally included in the sensor to allow normalization to adjust for different transfection efficiency. The fluorophore at the phosphorylation site will exhibit a change in signal intensity upon the phosphorylation event (e.g., an increased intensity of emission). A photolabile caged compound can be photo cleaved by light of a specific wavelength (e.g., 340-420 nm). Uncaging by exposure to light and phosphorylation of the sensor by the kinase occur in step 601.

Figure 7:
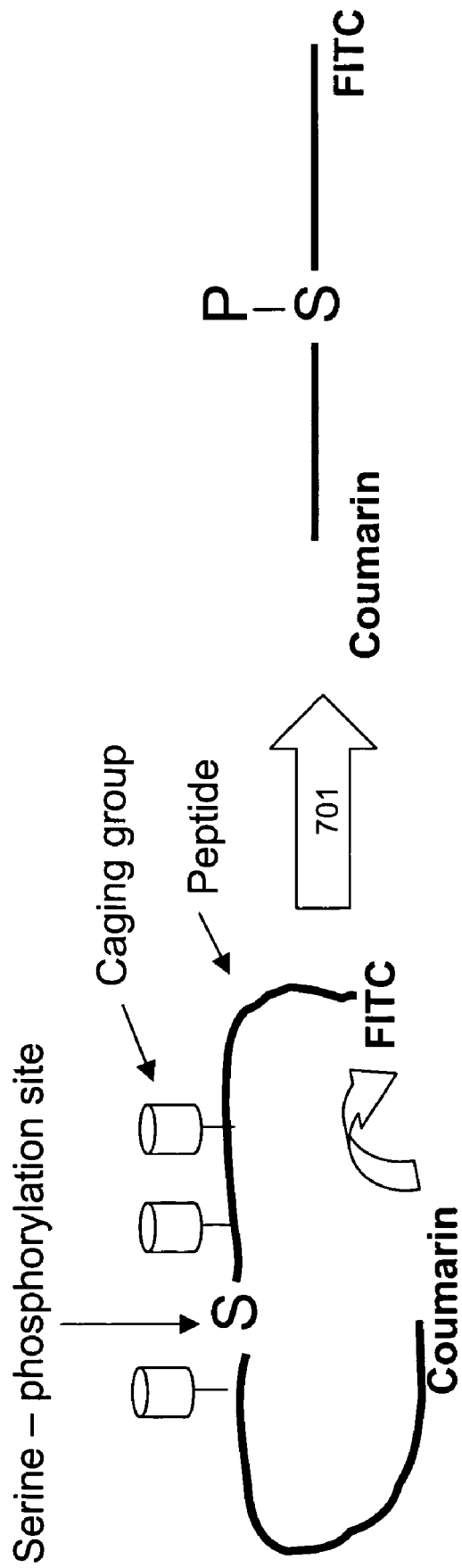
FIG. 7 schematically illustrates kinase sensor design 2.

FIG. 7 illustrates PA sensor 2, wherein the phosphorylation of a kinase substrate causes the decoupling of two hydrophobic fluorophores such as FITC and coumarin or Rhodamine. The caging compound is located at key kinase binding amino acids. Uncaging by exposure to light and phosphorylation of the sensor by the kinase occur in step 701.

Figure 8:
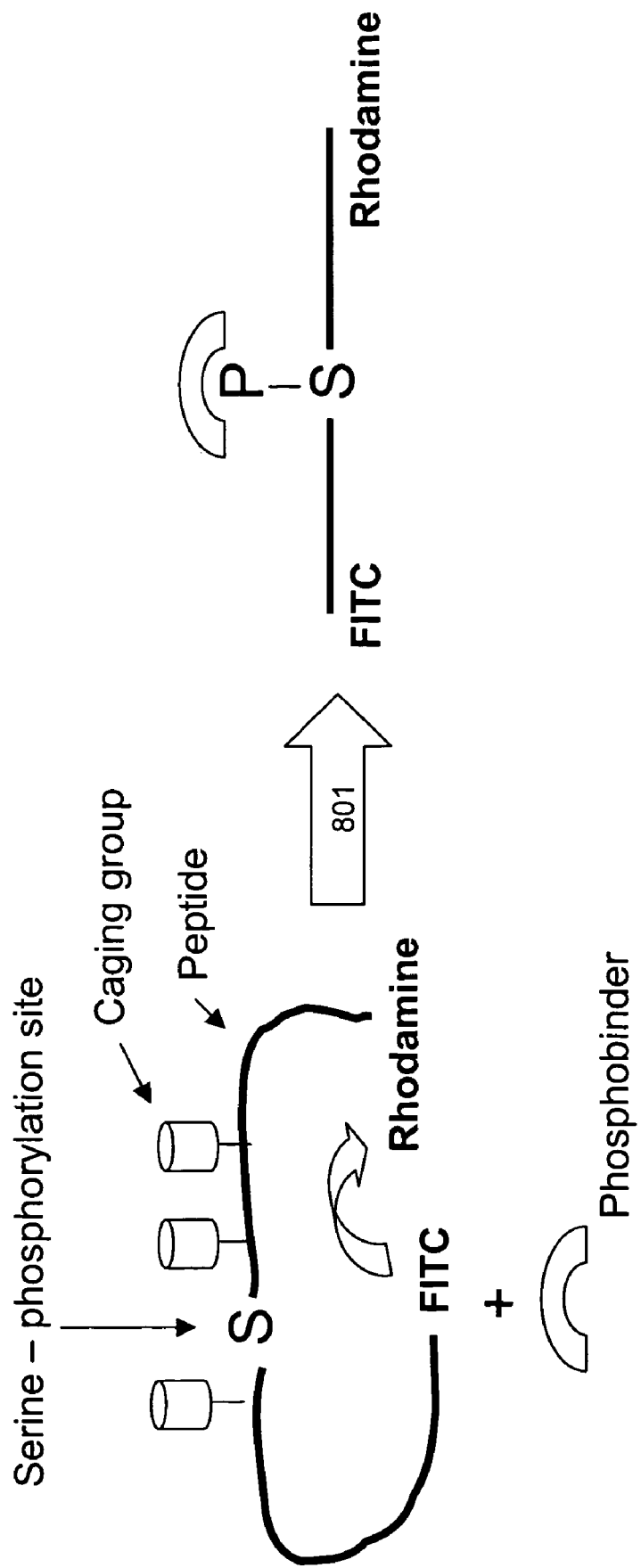
FIG. 8 schematically illustrates kinase sensor design 3.

FIG. 8 illustrates PA sensor 3 wherein the interaction of two hydrophobic dyes is interrupted when the substrate is phosphorylated and a specific binder (a phosphobinder) binds to the phosphorylated substrate. The phosphobinder can also be coupled with caging compound for selective activation of PA sensor and the phosphobinder (using different wavelengths to activate different PA assay components, see FIG. 4). The phosphobinder can be an antibody, a binding domain such as SH-2, 14-3-3, FHA, WW, etc. Uncaging by exposure to light, phosphorylation of the sensor by the kinase, and binding between the phosphobinder and the phosphorylated sensor occur in step 801.

Figure 9:
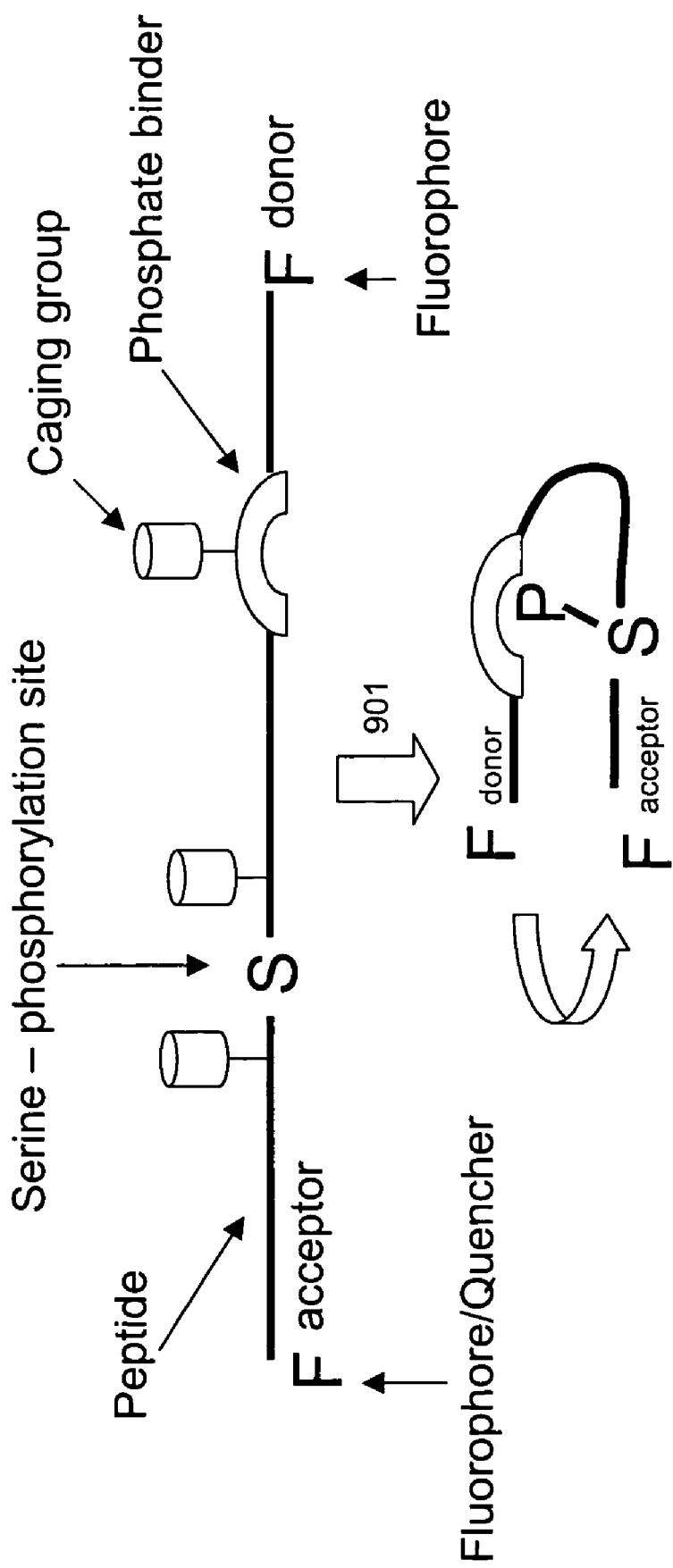
FIG. 9 schematically illustrates kinase sensor design 4.

FIG. 9 shows PA sensor 4. Here the kinase sensor contains the phosphobinder (antibody or phosphobinding domain such as FHA), a kinase specific substrate and FRET or fluorophore/quencher pair located at the end of the sensor. Upon phosphorylation, the binding domain binds to phosphorylation site and brings the FRET pair or a fluorophore/quencher pair together to induce FRET or quenching activity. An example of a suitable FRET pair is Europium and APC. The caging compound is located at key amino acid to prevent kinase binding and phosphorylation. The phosphobinder can also be caged to prevent binding to other phosphorylated groups within cells to minimize background. Different caging groups, which are photolabile at different wavelengths, can be used for precise control of the assay process. Uncaging by exposure to light, phosphorylation of the sensor by the kinase, and binding between the phosphobinder and the phosphorylated serine occur in step 901.

Figure 10:
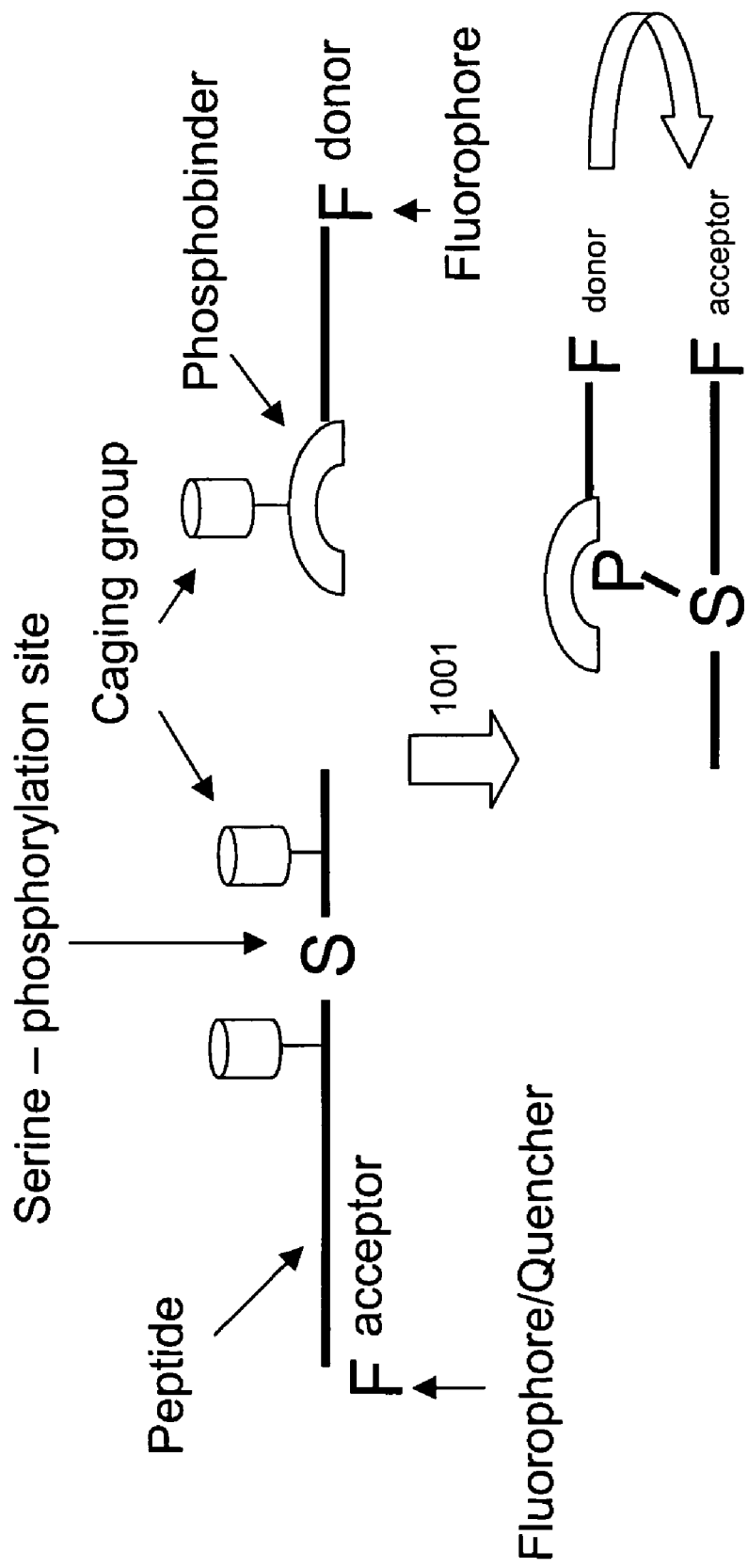
FIG. 10 schematically illustrates kinase sensor design 6.

FIG. 10 shows PA sensor 6. It is similar to design 4 except that the phosphobinder is not covalently attached to the kinase substrate. Signal is generated only when the phosphobinder locates the kinase substrate labeled with specific fluorescent donor. No signal is observed when the phosphobinder binds to unlabeled phosphorylated targets. Either a donor/acceptor or fluorophore/quencher pair can be used (e.g., a Eu chelate/quencher pair). Uncaging by exposure to light, phosphorylation of the sensor by the kinase, and binding between the phosphobinder and the phosphorylated sensor occur in step 1001.

Figure 11:
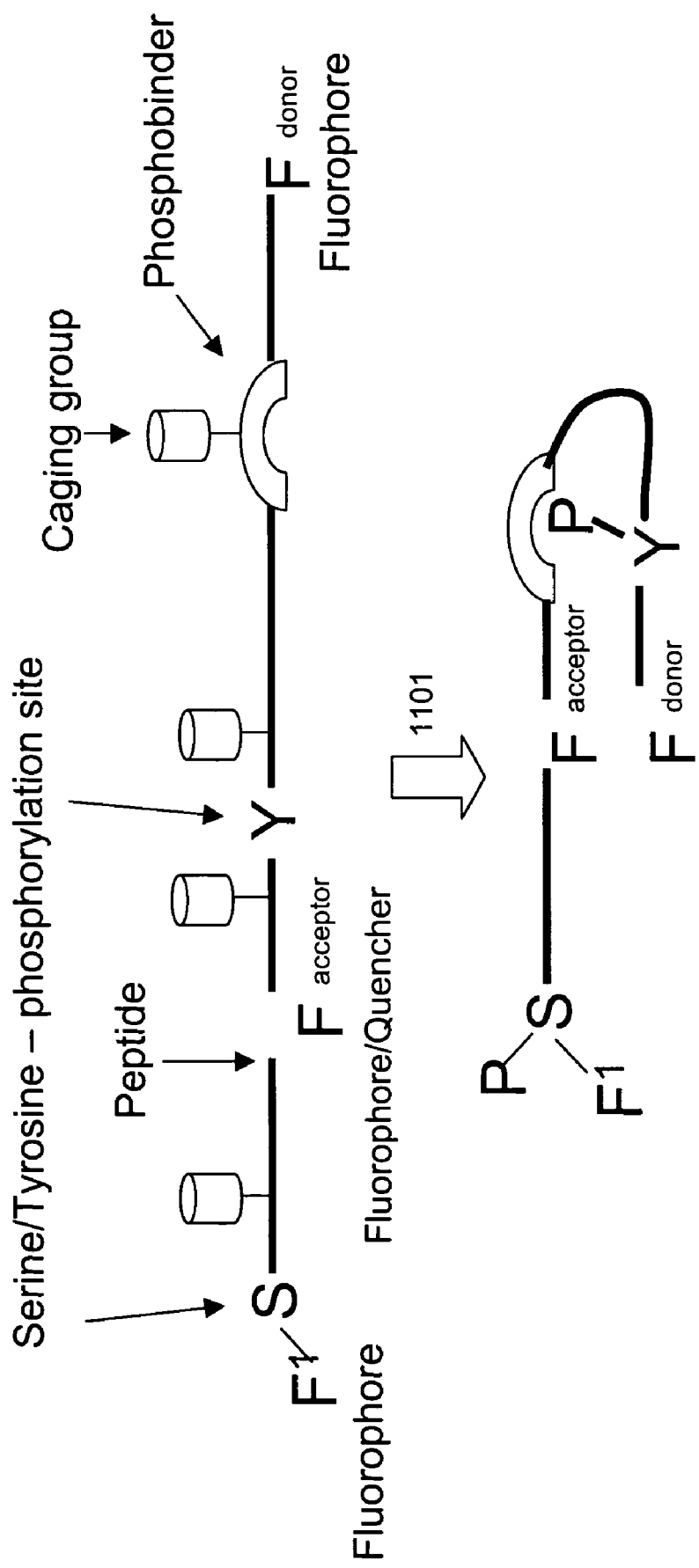
FIG. 11 schematically illustrates kinase sensor design 5, for detecting dual phosphorylation.

FIG. 11 shows PA sensor 5. Here the sensor can detect dual phosphorylation. Most kinases are phosphorylated at multiple sites. For example, AKT is phosphorylated at tyrosine and serine sites. This probe is a combination of design 1 (see, FIG. 6) and design 4 (see, FIG. 9). Phosphorylation at serine (located at amino-terminus) generates one type of signal while phosphorylation at tyrosine generates another. Phosphorylation of both sites will generate both signals (e.g., with non-overlapping fluorophores). Again, the caging compound is strategically located. Uncaging by exposure to light, phosphorylation of the sensor by the kinase(s), and binding between the phosphobinder and the phosphorylated tyrosine occur in step 1101.

Figure 12:
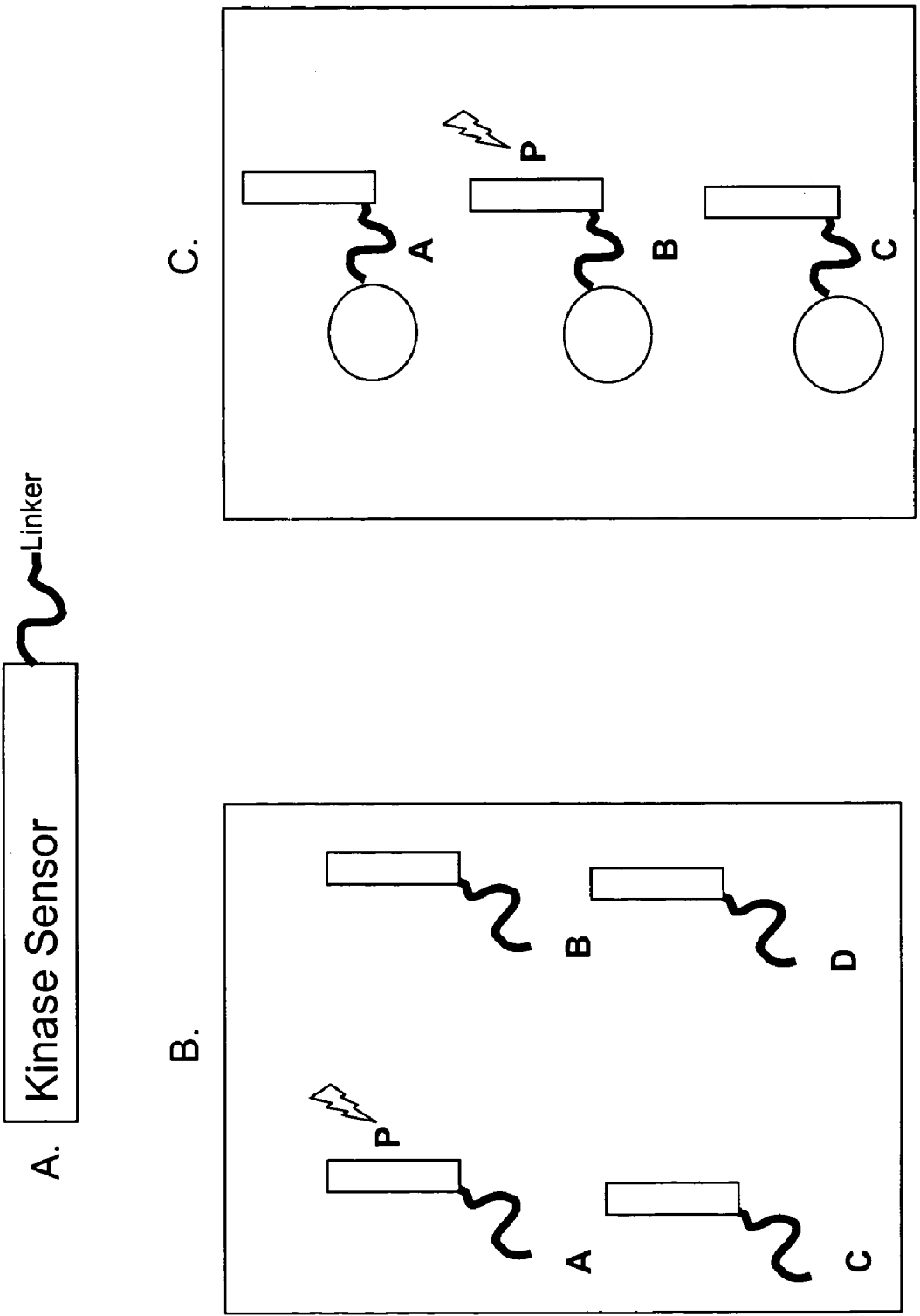
FIG. 12 schematically depicts one design for multiplex kinase sensors. Panel A depicts a kinase sensor with linker. Panel B depicts a micro-array of PA kinase sensors. Panel C depicts color-coded or bar-coded microspheres with PA kinase sensors.

PA kinase sensors can be multiplexed in an assay. For example, in FIG. 12, kinase sensors are arranged in an array and then exposed to a specific kinase or group of kinases. PA kinase sensors can be coupled to bar-coded beads (microtransmitter, color-dyed beads, nano-crystal, etc.) and the specific signal from each sensor can be mapped with specific bar code. Multiplexing in biochemical assay, cell lysate and cell is possible. For a cell, bar-coded beads are suitable. The signature of each bead can be mapped to a specific location within the cell and the corresponding signal detected. The entire cell can be lysed and the bead collected. The bead+ sensor can then be read, e.g., using a standard flow cytometer.

Figure 13:
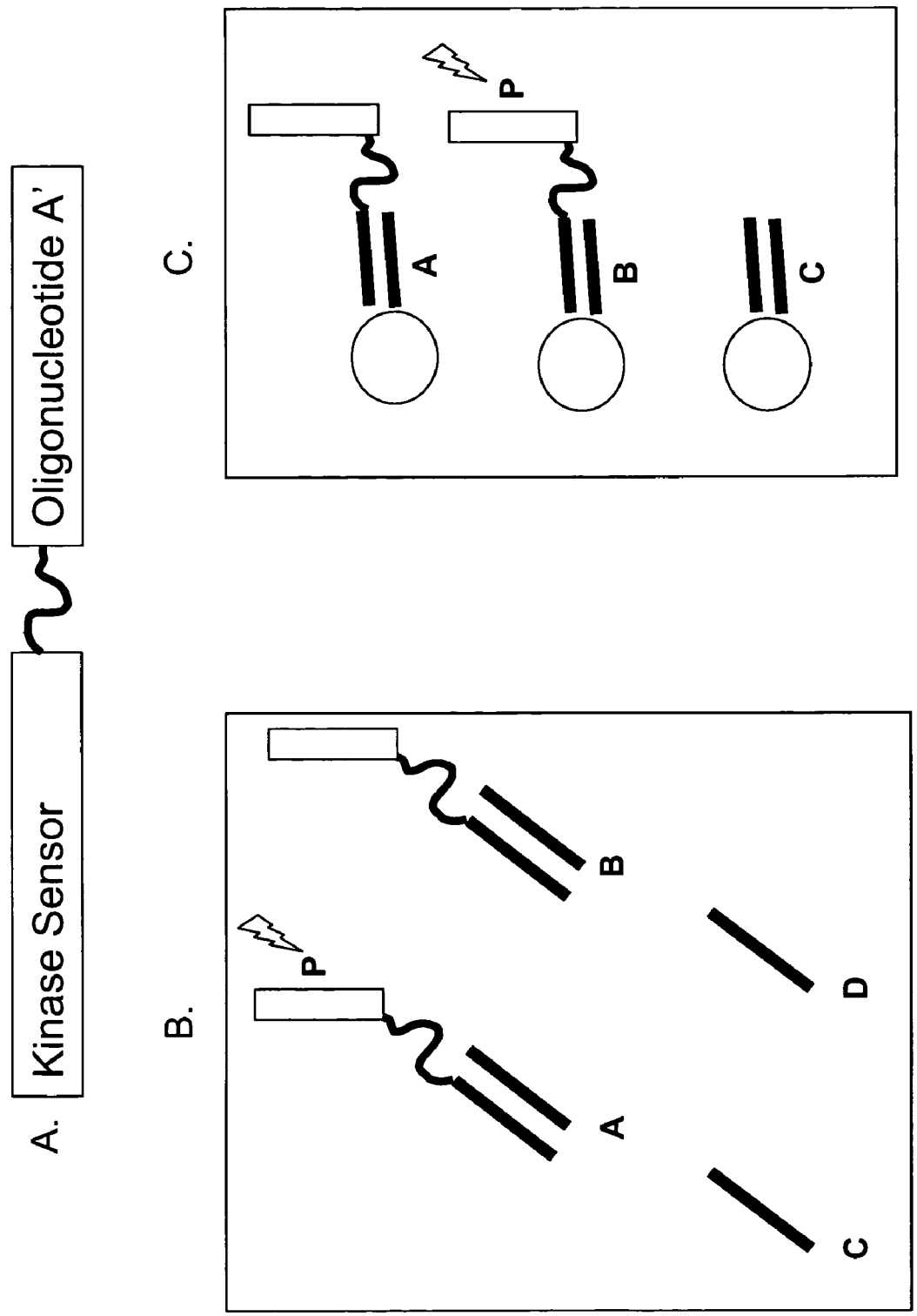
FIG. 13 schematically depicts another design for multiplex kinase sensors. Panel A depicts a kinase sensor coupled with an oligonucleotide. Panel B depicts a microarray with oligo capturing probes. Panel C depicts color-coded or bar-coded microspheres with oligo capturing probes.

In another variation, the PA kinase sensor can be coupled with an oligo. A microarray containing complementally oligonucleotides can be used to capture the PA sensors at specific locations (see, FIG. 13). Alternatively, a bar-coded bead can be coupled with an oligo capturing probe to pull out the specific kinase sensor.

For in vivo analysis of specific kinases, cells can be fixed, e.g., with glutaraldehyde and lysed; a specific kinase probe can be used to fish out the kinase and sensor for evaluation (e.g., via mass spectrometry).

Figure 14:
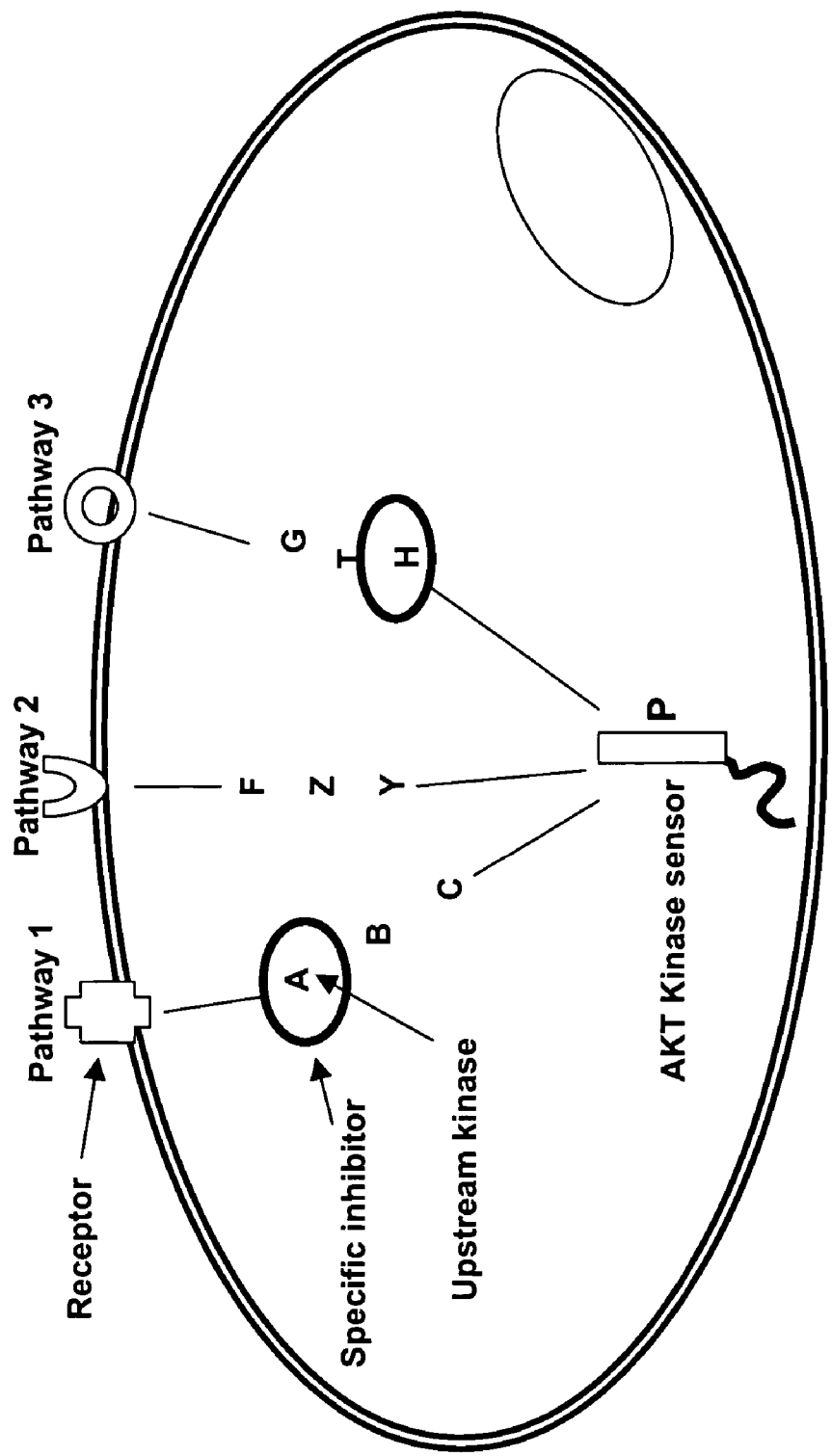
FIG. 14 schematically illustrates use of a kinase sensor in combination with inhibitors to study signaling pathways.

A panel of kinase sensors can be used to study the effect of drug compounds on pathways within the cell, in combination with chemical, peptide, anti-sense, RNAi and other specific inhibitors of specific target. An example is illustrated in FIG. 14 wherein three pathways are capable of activating the AKT. The activation of AKT can be measured using AKT PA sensor. Upon blocking pathways 1 and 3 with specific inhibitors (ovals) of upstream kinases, a drug can be evaluated for its effect on pathway 2 by measuring the signal of the AKT sensor. Alternatively, pathways 1 and 2 can be inhibited and the drug effect on pathway 3 can be determined. The drug's effect on specific kinases can also be determined by using sensors of upstream kinases in pathway 3. Hence, the investigator can determine the mode of action and specific effect of a drug within the cell by combining kinase sensors and inhibitors.

Figure 15B:
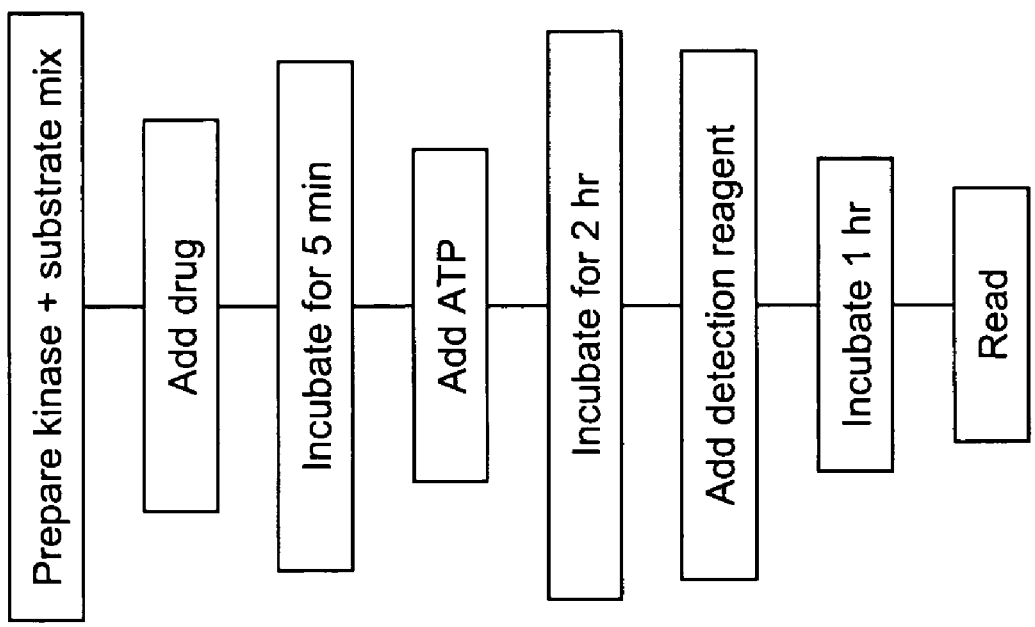
FIG. 15 depicts flowcharts illustrating the workflow for a PAC kinase sensor assay (Panel A) compared to a current HTS kinase assay (Panel B).
Figure 15A:
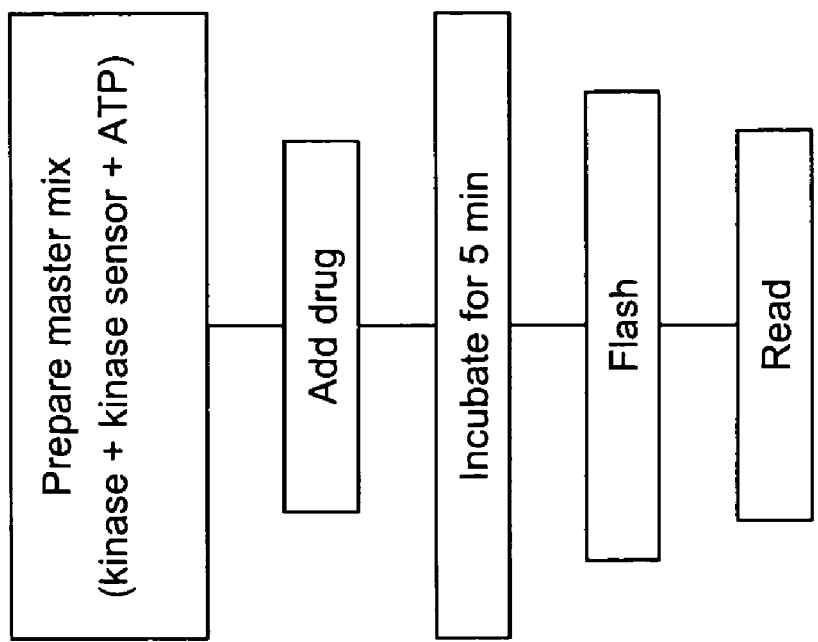

Photo-activated kinase sensors significantly simplify HTS kinase assays (see, a comparison of workflows between traditional and proposed PA kinase sensor in FIG. 15). The PAC kinase assay requires two pipetting steps and one reagent, while the current HTS kinase assay requires four pipetting steps and three separate reagents.

Other post-translational modifications (e.g., ubiquination, glycosylation and acetylation) can also be measured using similar FRET designs described above.

Figure 16:
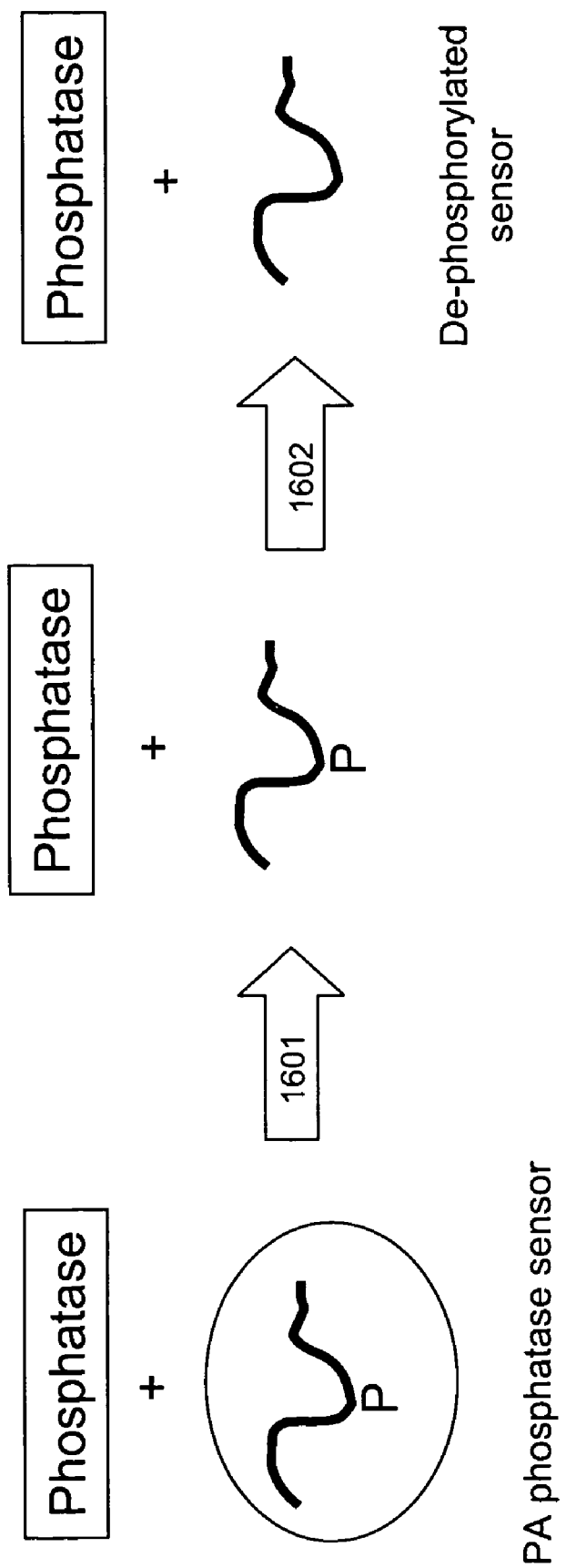
FIG. 16 schematically depicts a phosphatase sensor.

Sensors similar to the kinase sensors above can also be used to measure phosphatase activity (FIG. 16). In this case the peptide substrate is pre-phosphorylated by chemical or biochemical synthesis. Synthesis of other peptides incorporating 1-(2-nitrophenyl)ethyl caged phosphoserine, threonine, and tyrosine has been reported. See e.g. impulse.lms.mit.edu/caged.html. The PA phosphatase sensor is uncaged, e.g., by exposure to 300 nm light, in step 1601, and dephosphorylated by the phosphatase in step 1602.

Figure 17:
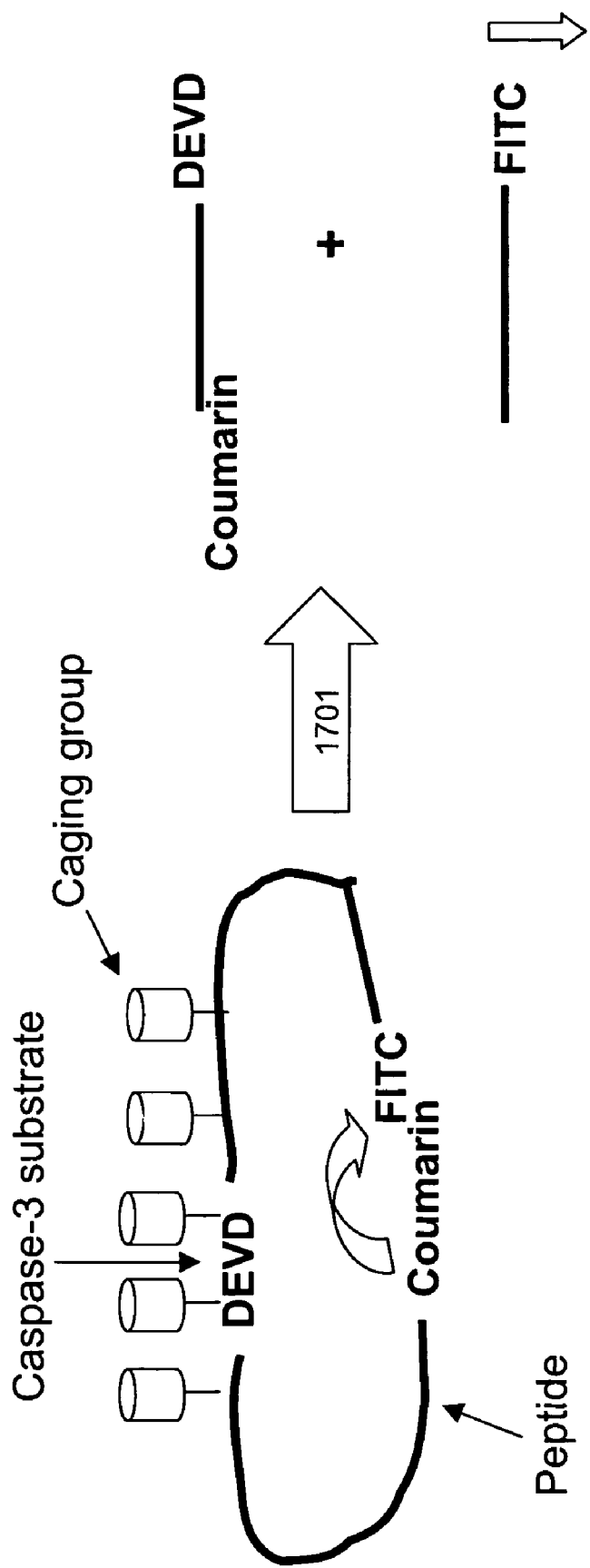
FIG. 17 schematically depicts a photoactivatable caspase 3 sensor.

Other PA sensors are also possible, such as protease sensors and caspase sensors (FIG. 17). For example, a caspase substrate is labeled at one end with FITC and another with coumarin. In an uncleaved sensor, FRET of coumarin to FITC occurs. Upon uncaging (e.g., by exposure to 340-420 nm light) and cleavage by caspase 3 in step 1701, coumarin is decoupled from FITC-eliminating FRET. Caspase 3 cleaves peptide sequence Asp-Glu-Val-Asp (DEVD) (e.g., *EMBO Reports*, vol. 1, no 3, pp266-270, 2000; and *Cell Death Differ* (2001) 8:30-7). Other sensors based on caspase specific substrates (and other protease specific substrates) are possible.

Figure 18:
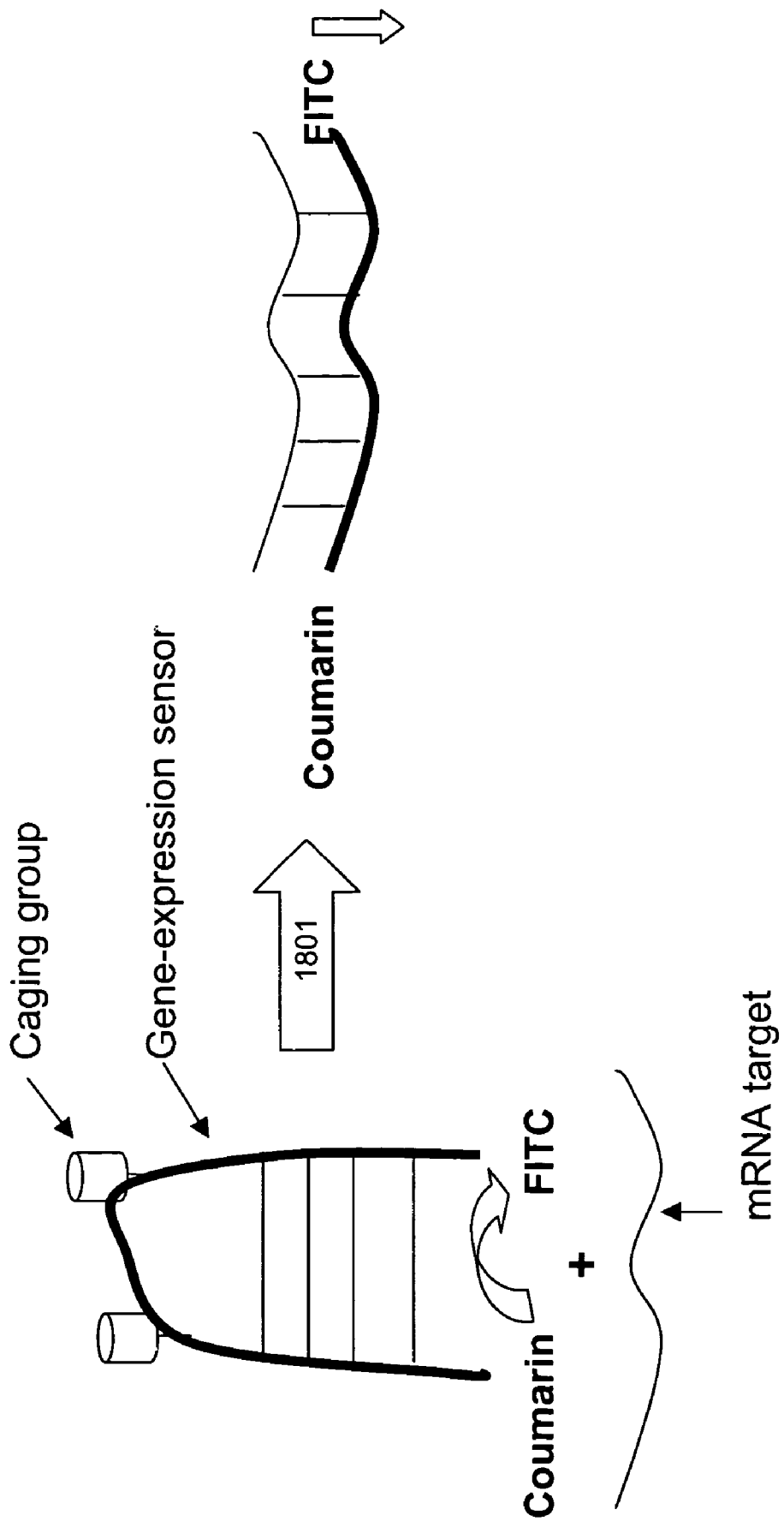
FIG. 18 schematically depicts a photoactivated (photoactivatable) gene expression sensor.

PA sensors can also be used for measuring gene expression. For example, as shown in FIG. 18, hairpin-loop DNA probes are end-labeled with FITC and coumarin to create a FRET probe. FRET is eliminated when the gene-expression sensor binds to a complementary target within cell, cell lysate or biochemical assay (*Anal Chem.*, 73(22):5544-50, 2001). Light exposure to uncage the gene expression sensor and hybridization of the sensor to the mRNA target occurs in step 1801.

All sensors described above can be photo-activated, e.g., by coupling with photolabile compounds or with protective groups with photolabile linkers.

There are several schemes for caging sensors with photolabile groups so that the sensors are inactivated until exposed to light. FIG. 19 illustrates a method using a caging compound to covalently link onto amino acid side chain (Tyr in this example) or nucleic acid. FIG. 20 illustrates linking a bulky covering group of nucleic acid, protein or other chemical group. Connecting this group with the sensor is a photolabile group that cleaves when exposed to light. The bulky group, which interferes with the sensor activity, is released from the sensor.

PA Regulators

PA regulators (e.g., modulators) are molecules that either activate or inhibit a specific protein (or other) activity. They can be peptides, nucleic acids, proteins, small molecules, or others. They are caged and inactivated using methods described above.

For example, protein kinase inhibitors can be regulators. These inhibitors (e.g., a peptide) may bind to a specific kinase and prevent the kinase from activating its target. Using the method described in FIG. 19 or 20, photolabile group(s) can be added to inactivate the kinase inhibitor. For example, a kinase inhibiting compound such as HB89 for PKC kinase can be encaged in a protein complex that is photolabile. Upon exposure to light, the protein complex+drug dissociates and releases the active kinase inhibitor. See, FIGS. 19 and 20. PA activators can also be developed using similar caging schemas described in FIGS. 19 and 20.

Caged sensors and regulators can also be activated by means other than light. Labile chemicals responding to magnetic, sonication, temperature, chemicals, or other uncagers can potentially be used as caging compound for sensors and regulators.

RNAi and anti-sense oligonucleotides can be used to shut down expression of specific gene or genes. These gene expression inhibitors can also be caged, e.g., surrounded with photolabile compound, to prevent its function until exposure to light.

Activators such as zinc finger transcriptional activators can be used to activate expression of specific gene. The zinc finger function can also be controlled by light activation.

PA Sensors: Constructs and Methods for Measuring RNA Transcripts in Living Cells Current methods for measuring mRNA transcripts from cells (such as Northern blot, quantitative PCR, microarray, branch DNA, and in situ hybridization) require the cells to be lysed or fixed. In addition, most methods require MRNA purification and reverse transcription. Furthermore, these methods involve multi-step processing that contributes to high intra- and inter-assay variation. Consequently, the current methods do not provide live, dynamic and location-specific imaging and measurements of MRNA, because the cells are exposed to environmental changes.

Figure 45:
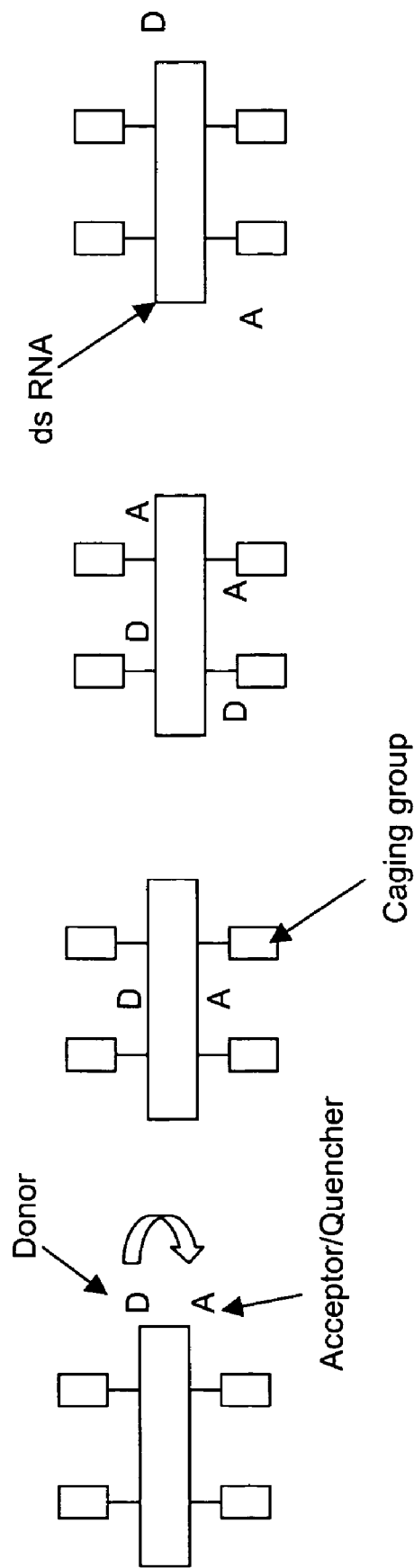
FIG. 45 schematically illustrates a caged siRNA that can be used, e.g., as a probe for mRNA.
Figure 46:
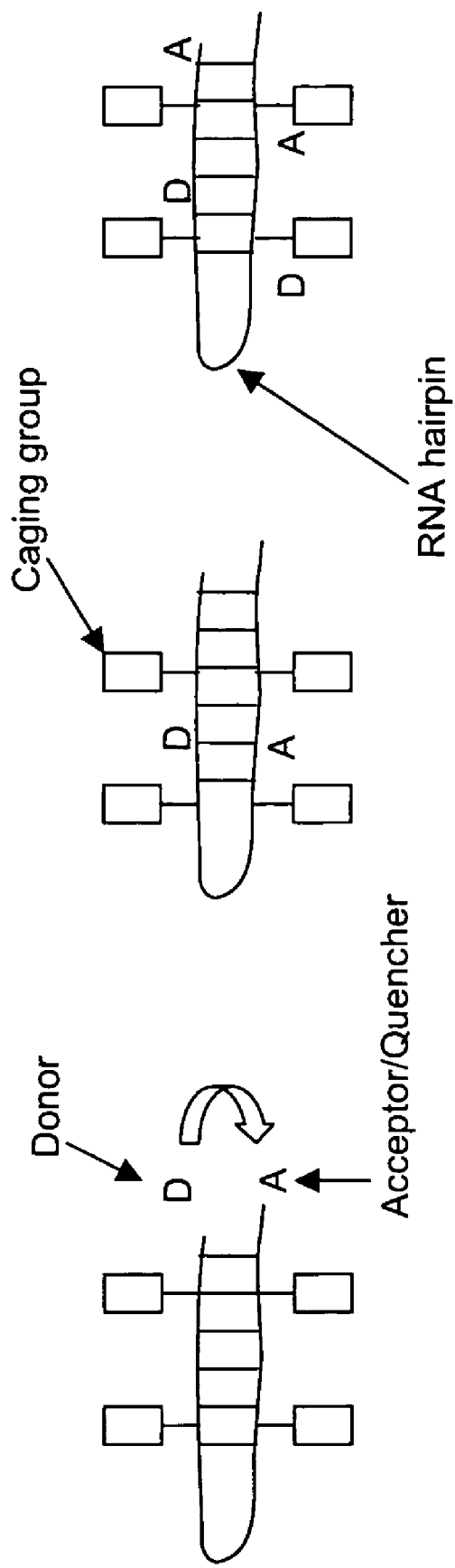
FIG. 46 schematically illustrates a caged shRNA that can be used, e.g., as a probe for mRNA.
Figure 47:
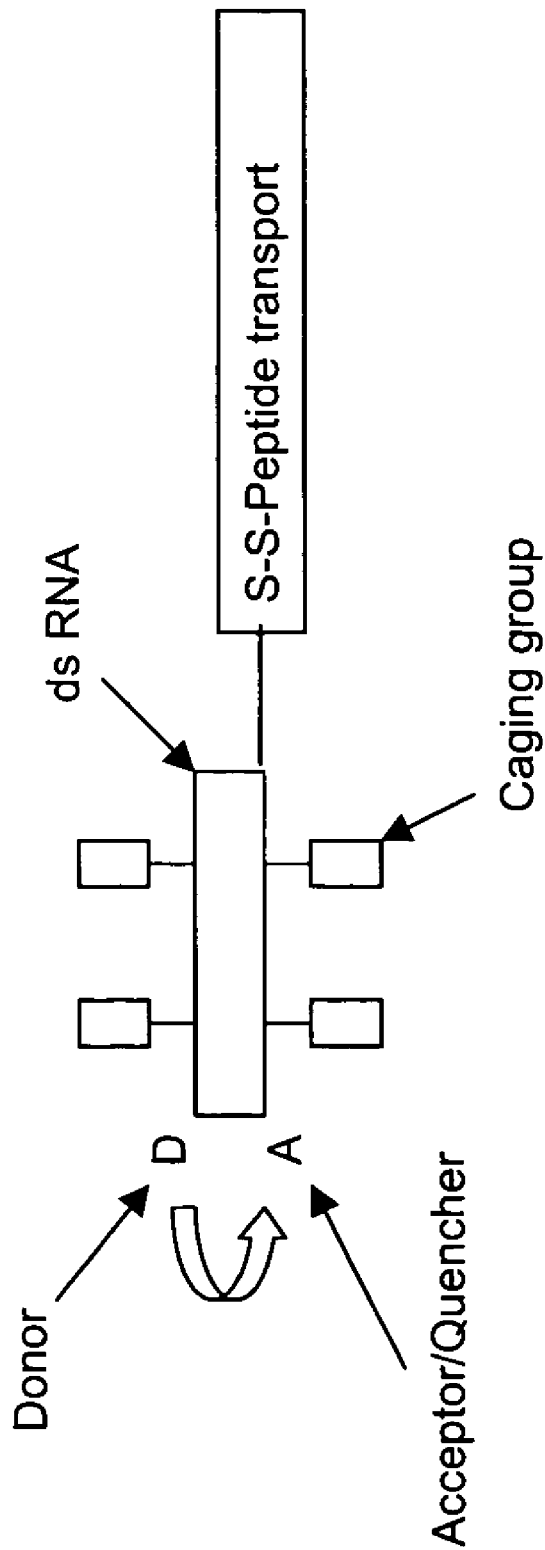
FIG. 47 schematically depicts a caged siRNA linked with a peptide transport moiety.

In one aspect, the present invention provides sensors for detecting and measuring mRNA in living cells (a.k.a. PAC probes for mRNA) and methods of controlling activation of such mRNA sensors in living cells. In one class of embodiments, the sensor is attached to one or more photolabile groups that protect the sensor from extra-cellular and intra-cellular degradation and, at the same time, inactivate the sensor. Upon exposure to light of a specific wavelength, the photolabile groups detach from the sensor and the sensor becomes active. The MRNA sensors include one or more labels (e.g., that interact via FRET or ET, e.g., a donor/acceptor or fluorophore/quencher combination) on, e.g., molecular beacons (see, FIGS. 37-40 and 42) or RNAs that can initiate RNAi (e.g., siRNA, shRNA; FIGS. 45-47). The signal from the sensor is used to detect and measure mRNA in living cells. Splice variants of mRNAs, for example, can also be analyzed using both MB and interfering RNA approaches.

Traditional or novel delivery methods can be used to introduce a sufficient quantity of MRNA sensors into cells. A high throughput uncaging device, such as those described herein, can be used to activate sensors, e.g., in cells grown in a microtiter plate. This invention also features methods of detecting and measuring mRNA with such sensors in living cells.

The ability to monitor immediate changes in MRNA levels in living cells facilitates the development of a broad range of cell-based assays for basic research, pharmaceutical industries, clinical and agricultural diagnostics. For example, a specific GPCR or kinase cell-based assay can be developed for screening lead compounds using PAC Probe for monitoring mRNAs downstream of the GPCR or kinase. Actual transcript or surrogate transcript (marker) response to modulation of specific pathways by the compounds can be monitored in living cells.

An example PAC probe for an mRNA comprises a molecular beacon (MB) (see, e.g., W Tan (2001) *Anal. Chem.* 73:5544; A Gerwirtz *PNAS* 95:11538; G Bao (2001) *BED* vol. 50, Bioengineering conference ASME; W Tan (2001) *Angw. Chem. Int. Ed.* 40:402) or an interfering RNA (e.g., siRNA, shRNA) (see, e.g., Watanabe (Jan. 13, 2003) *Scientist* 17(1): 36; D Engelke (2002) *Nature Biotech* 29:505; *Trends in Biotech* 20:49 (2002)); one or more caging groups, e.g., photolabile caging groups (see, e.g., FR Haselton JBC 274:20895; H Okamoto (2001) and *Nature Genetics* 28:317); and optionally a cellular and/or subcellular delivery module, e.g., a peptide delivery module such as TAT or Antp (see, e.g., D Lane *Bioconjugate Chemistry* 12:825).

Molecular Beacons (MB)

Figure 37:
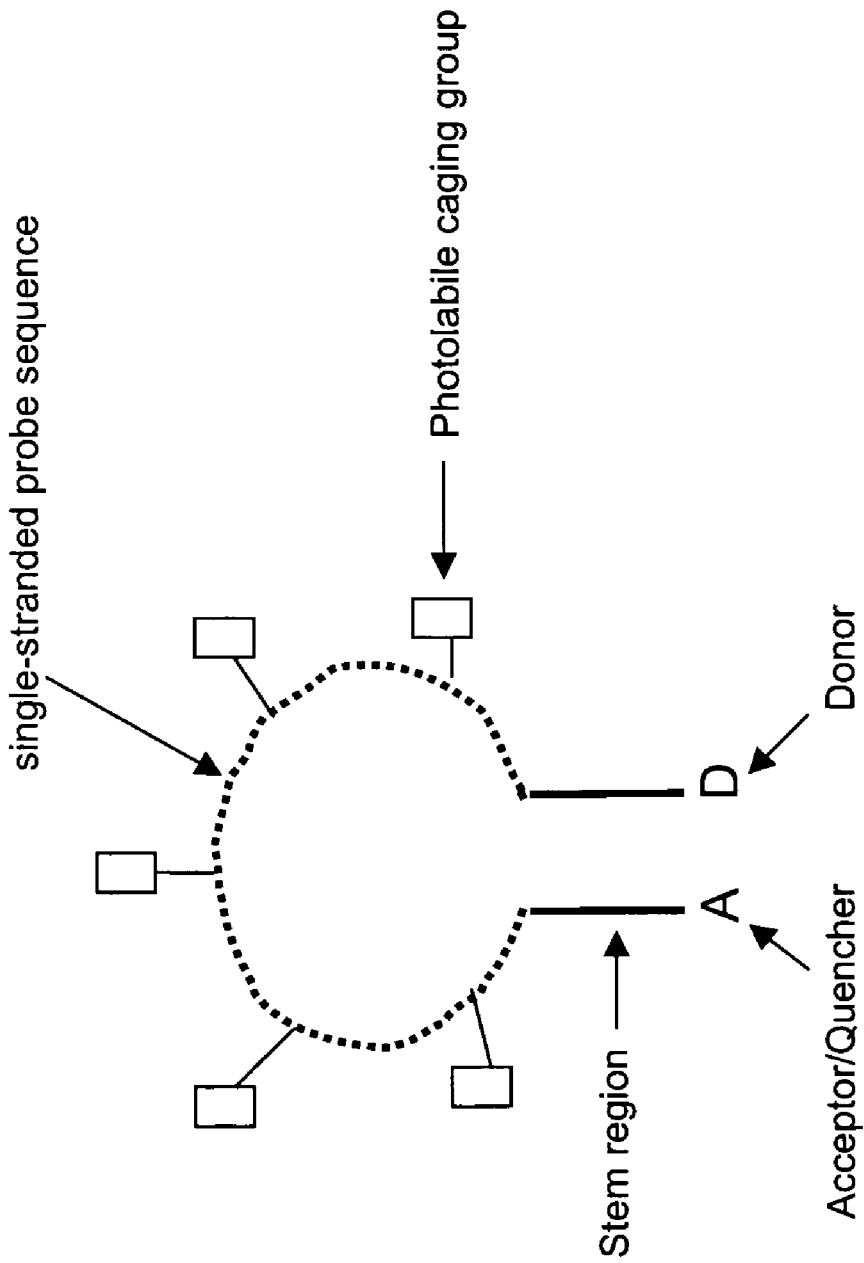
FIG. 37 schematically illustrates a caged molecular beacon, which can be used, for example, as a caged sensor for measuring mRNA in living cells.
Figure 38:
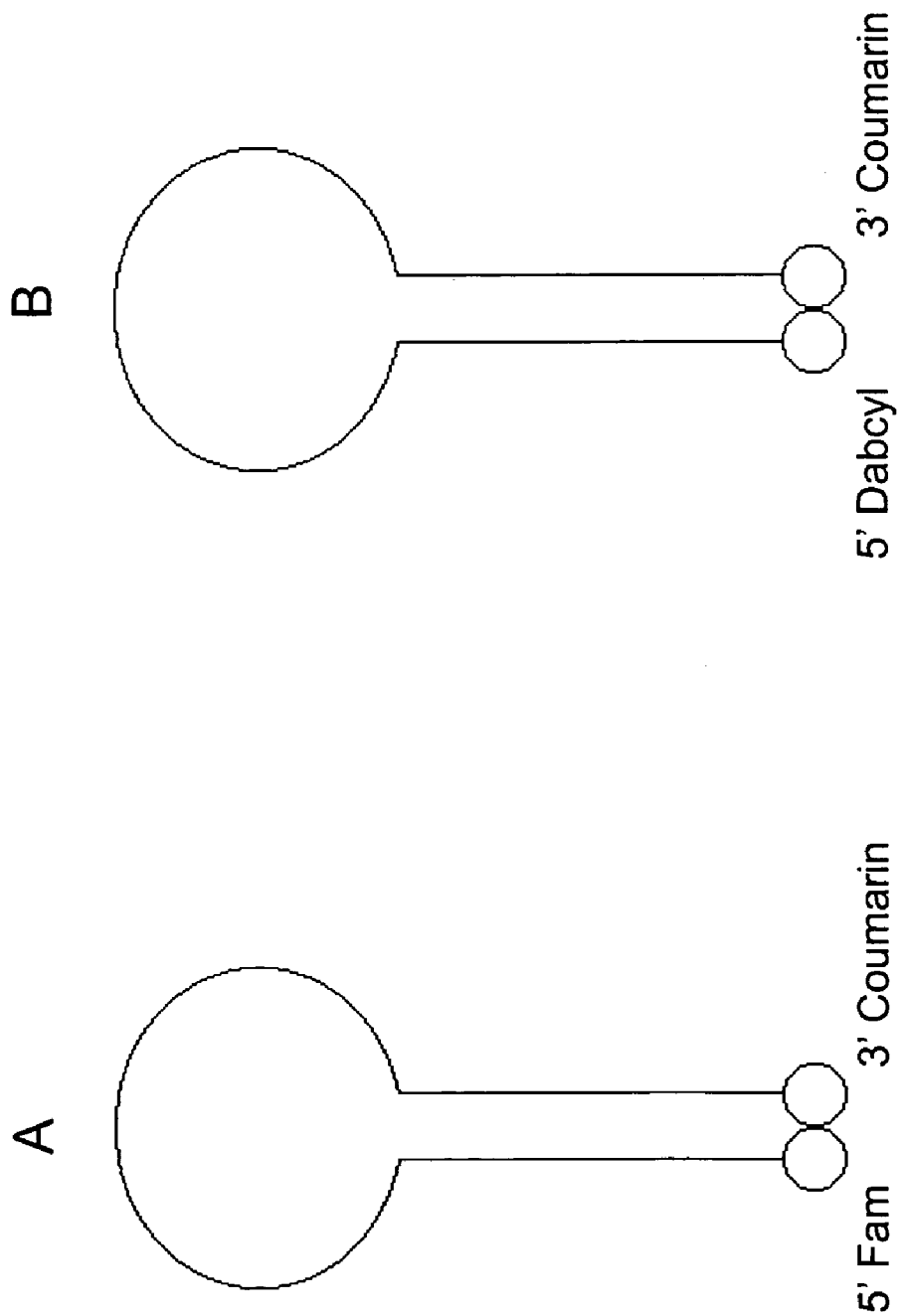
FIG. 38 Panel A schematically illustrates a dual-labeled FRET molecular beacon, in which the quencher is an acceptor fluorophore. Panel B schematically illustrates a fluorophore-quencher MB in which the quencher does not fluoresce.

FIGS. 37 and 38 illustrate an mRNA PAC probe that comprises a single stranded loop and a double stranded stem, e.g., comprising approximately 5 to 8 GC pairs. The entire structure can be protected and inactivated by caging groups, e.g., photolabile groups, attached at the phosphate backbone (the phosphate group or the ribose) and/or the bases.

Figure 40:
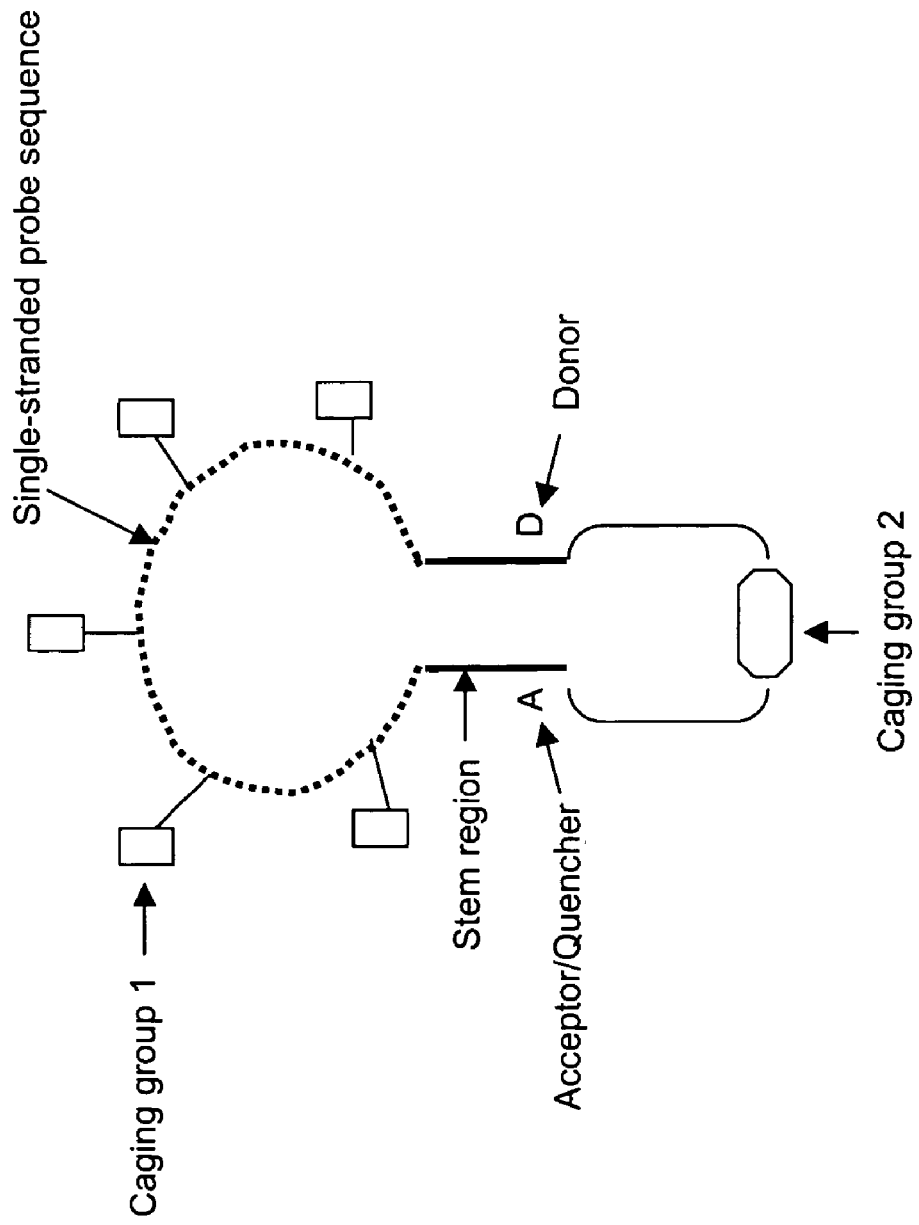
FIG. 40 schematically depicts a caged molecular beacon, which can be used, for example, as a caged sensor for measuring mRNA in living cells. In this example, a photolabile group prevents unfolding of the MB stem region.

FIG. 40 describes another approach to inactivating a MB sensor, wherein a photolabile linker (see, FIG. 40, caging group 2) prevents the unfolding of the stem of the MB until it is exposed to light. One or more caging groups can optionally be attached to the molecular beacon loop (see, FIG. 40, caging group 1), to prevent the loop from binding to the complementary target sequence and/or to protect the MB from degradation.

The 5' and 3' ends of the MB are typically linked with a fluorophore/quencher pair, for example, a fluorescent dye/ dark quencher pair, a combination of FRET dyes such as coumarin and FITC, or a combination such as Europium and APC that permits application of time-resolved fluorescence (TRF) or Fluorescence Lifetime Imaging Microscopy (FLIM) techniques (see, e.g., *Fluorescent and Luminescent Probes for Biological Activity*, edited by WTZ Watson, Academic Press, 2nd edition, 1999).

Figure 41:
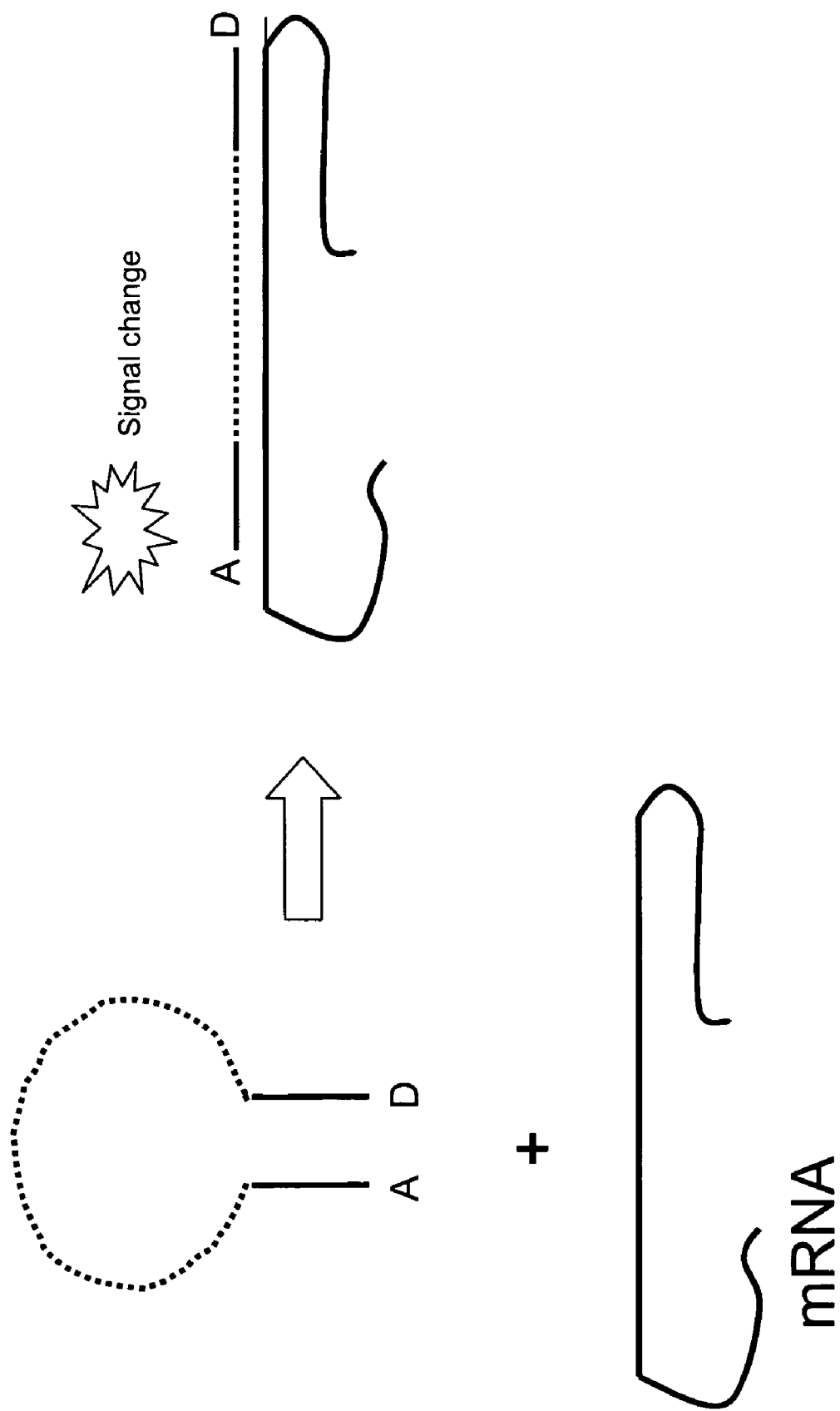
FIG. 41 schematically illustrates how a molecular beacon functions, e.g., in measuring mRNA in living cells.

When a MB binds to its target, the attached reporter molecules (e.g., fluorophore/quencher or acceptor/donor) at both ends are separated and a signal is generated and observed (see, FIG. 41). Detection of multiple MRNA species within a single cell and/or sample is made possible by using different reporter combinations as described above (e.g., multiple fluorophores that emit at distinct wavelengths).

Figure 39:
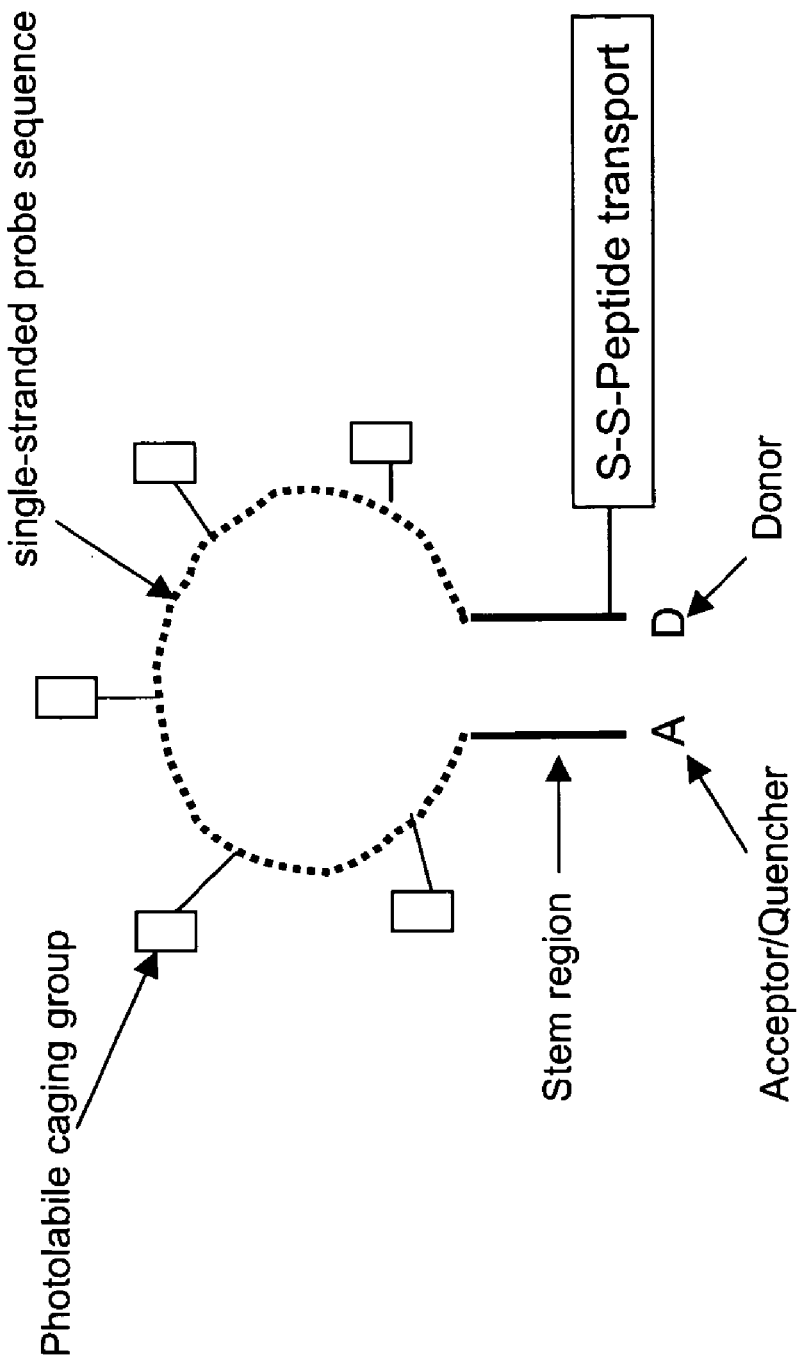
FIG. 39 schematically depicts an RNA sensor with a peptide transport moiety. In this example, a disulfide linker connects a molecular beacon with a polypeptide cellular delivery module.

FIG. 39 illustrates a MB linked with a peptide delivery module for transporting the MB into the cell. In this example, a disulfide linker connects the MB with the peptide. Upon entering the cell, the disulfide linker is cleaved and the MB is released from the peptide. A variety of peptide delivery modules can be used, including, without limitation, TAT sequence, 8-D-arg homopolymer, amphiphilic peptide, and Antp from Drosophila homeobox. Other methods can also be used for transporting MB into cells, such as calcium phosphate and lipofection.

Figure 42:
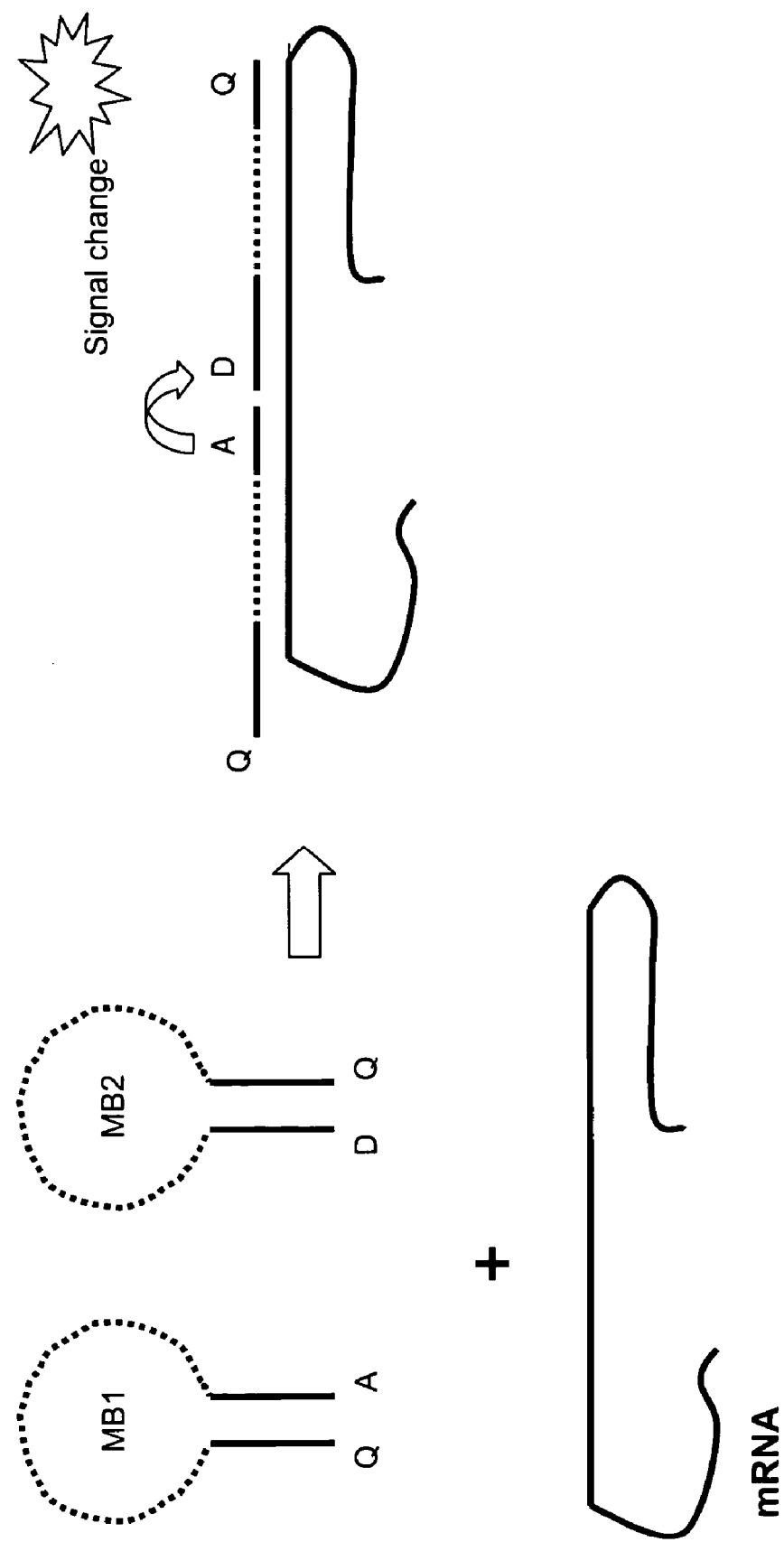
FIG. 42 schematically depicts dual molecular beacons, e.g., for measuring mRNA in living cells.
Figure 43:
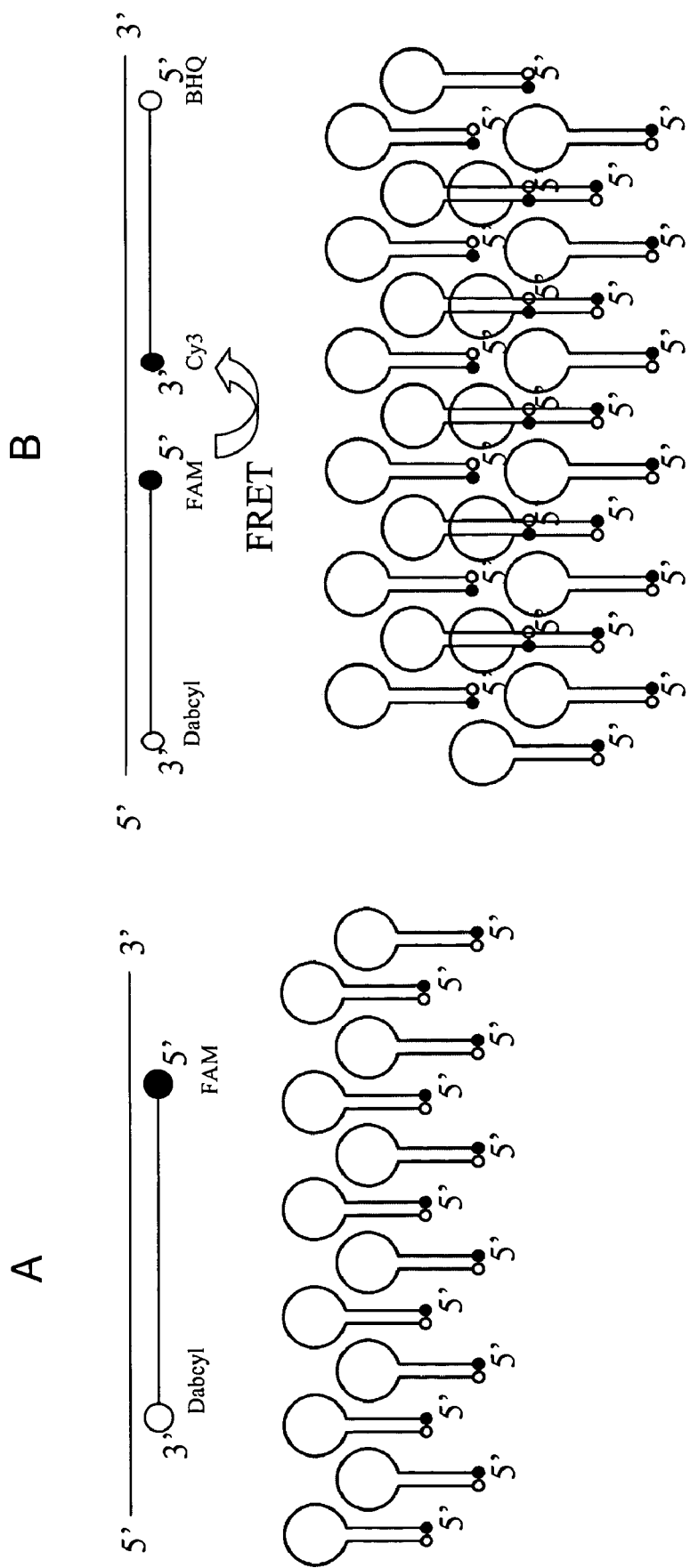
FIG. 43 schematically depicts target detection using a single beacon (Panel A) versus dual beacons (Panel B). The beacons are typically caged.

FIGS. 42 and 43 outline the use of multiple MBs for detecting a single target. In FIG. 42, a donor fluorophore (D) is located on MB2 and an acceptor fluorophore (A) is located on MB1. When both bind to a specific target, the acceptor and donor are located next to each other and FRET event occurs. Detection of a signal from the acceptor after stimulation of the donor indicates that binding of the dual MBs has occurred, placing the acceptor and donor in close proximity, and indicating the presence of the specific target. MB1 and/or MB2 optionally include a quencher (Q, which can be the same or different for the two beacons). FIG. 43 illustrates the difference between single versus dual MBs for detection of a single target.

Figure 44:
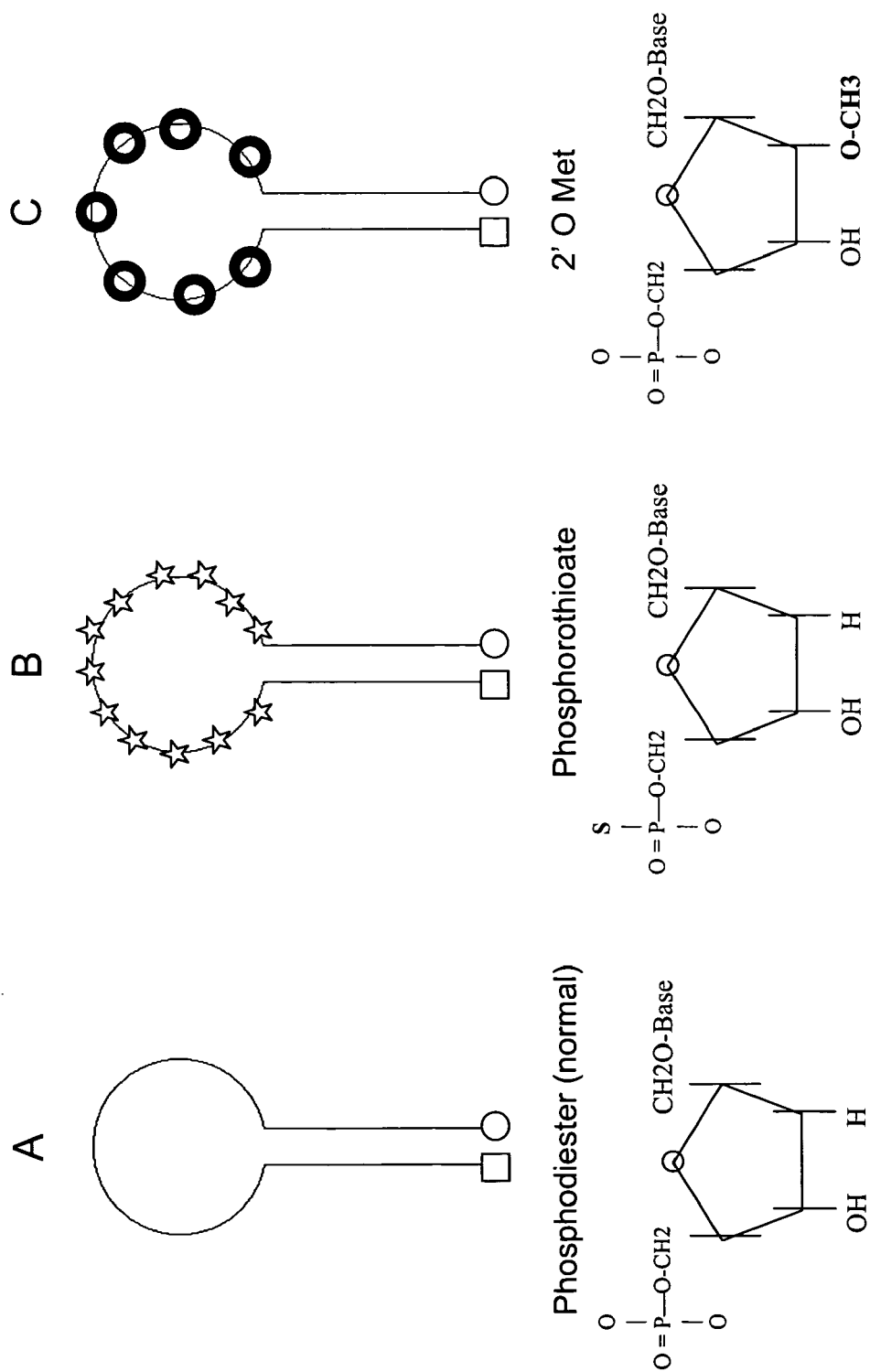
FIG. 44 schematically depicts a molecular beacon including only phosphodiester bonds (Panel A), a molecular beacon also including phosphorothioate bonds (Panel B), and a molecular beacon including 2'-O-methyl nucleotides (Panel C). Use of these or similar nucleotide analogs can minimize nuclease digestion of molecular beacons in living cells.

Modified nucleotides can optionally be incorporated into MBs to reduce degradation in cells. See, FIG. 44. For example, the loop region of MB can be protected from nuclease digestion by using a phosphate backbone analog such as phosphorothioate. As another example, the stem region can be protected from nuclease degradation by using a modified nucleotide, for example, a 2'-O-methyl nucleotide such as 2'-O-Methylinosine. Caging groups also protect MB against nuclease digestion.

RNAi

FIG. 45 describes a small interfering RNA (siRNA, also known as short interfering RNA) structure used for detecting MRNA in living cells. The siRNA can be, for example, a 21-25 mer double-stranded RNA. Other lengths and/or optional overhangs (e.g., two nucleotide 3' overhangs) can also be used. A reporter combination (e.g., two non-interacting fluorophores, or typically a fluorophore/quencher or donor/acceptor pair) is linked at the 5' and 3' ends of one strand or at the ends of opposite strands. The reporter molecules can also be within the siRNA, either on the same strand or on opposite strands of the double stranded siRNA. The reporters can be, e.g., a combination of FRET dyes such as coumarin and FITC or a combination such as europium and APC that permits application of time-resolved fluorescence (TRF) techniques.

An interfering RNA can be caged, e.g., with photolabile groups, at the phosphates, riboses and/or bases to protect it to and inactivate its function. It can optionally be linked to a delivery module, e.g., a peptide delivery module (for example, 8-D-Arg, Antp, Pep-1, or the like), e.g., with a disulfide linker as illustrated in FIG. 47. Other established delivery approaches can also be used, e.g., lipofection.

FIG. 46 shows another type of interfering RNA for measuring mRNA, e.g., a short hairpin RNA (shRNA, also called small hairpin RNA; e.g., *Nature Genetics* 33:396). For example, a shRNA can have about 60-70 nt that form a hairpin, e.g., with a 25-30 mer double-stranded region and an 8 mer single-stranded loop. A reporter pair (e.g., a donor and an acceptor fluorophore that interact via FRET, or a fluorophore/quencher pair, e.g., a fluorophore/dark quencher) can be attached for signaling the presence of a specific RNA transcript. As in the previous example, the shRNA can be caged, e.g., with photolabile caging groups.

Figure 48:
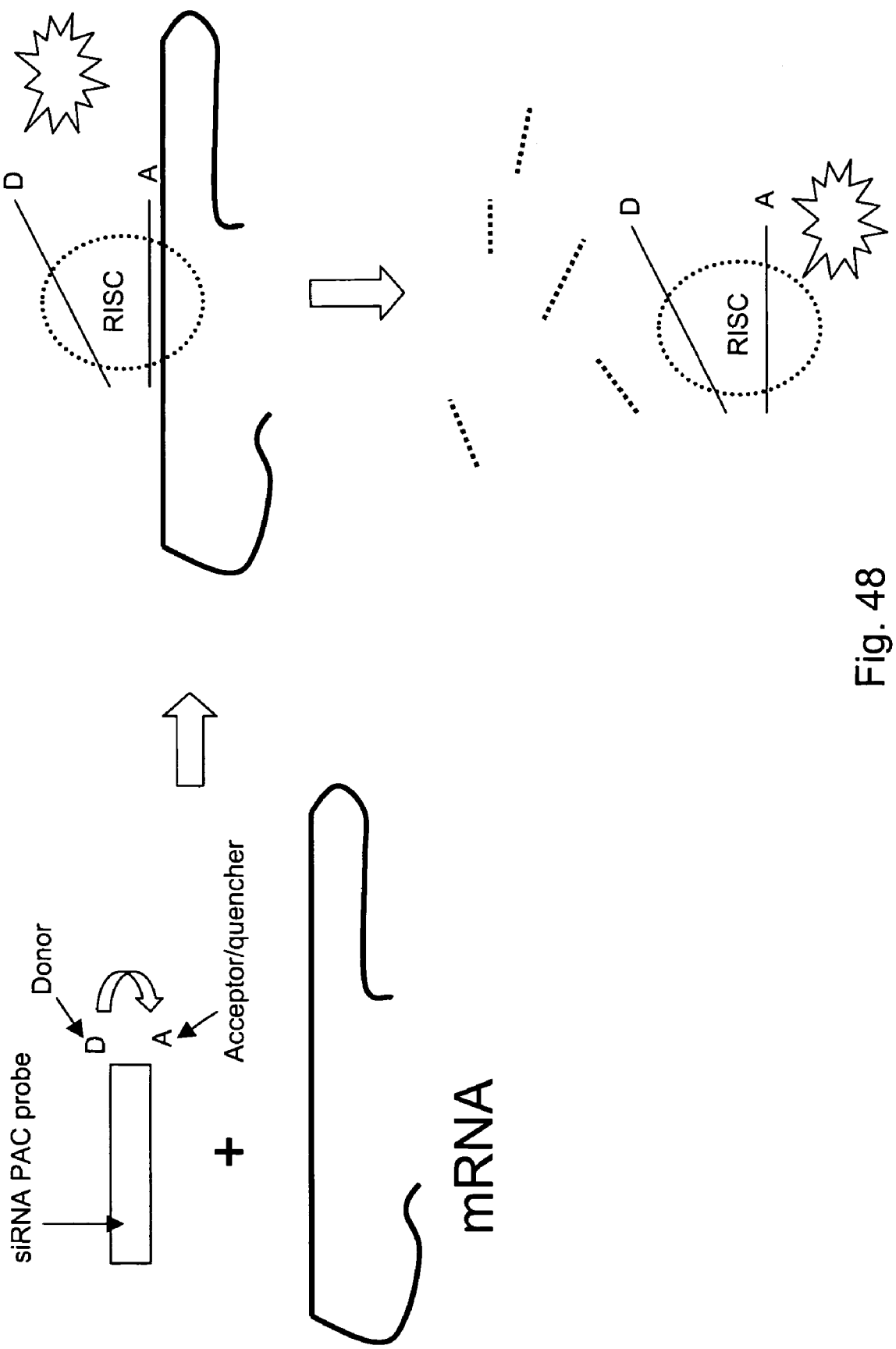
FIG. 48 schematically illustrates measurement of MRNA with a FRET siRNA.

FIG. 48 shows the detection of mRNA using an interfering RNA PAC probe. The siRNA is incorporated into the RISC complex, and the antisense strand guides cleavage of the target mRNA (promoting its degradation). Strand separation of the interfering RNA probe leads to the separation of the reporter molecules on the RNA, resulting in a detectable signal or change in signal (as indicated by the starburst symbol). Multiple mRNA transcripts can be analyzed using interfering RNAs with different reporter molecules (e.g., fluorophores that emit at different wavelengths).

Figure 49:
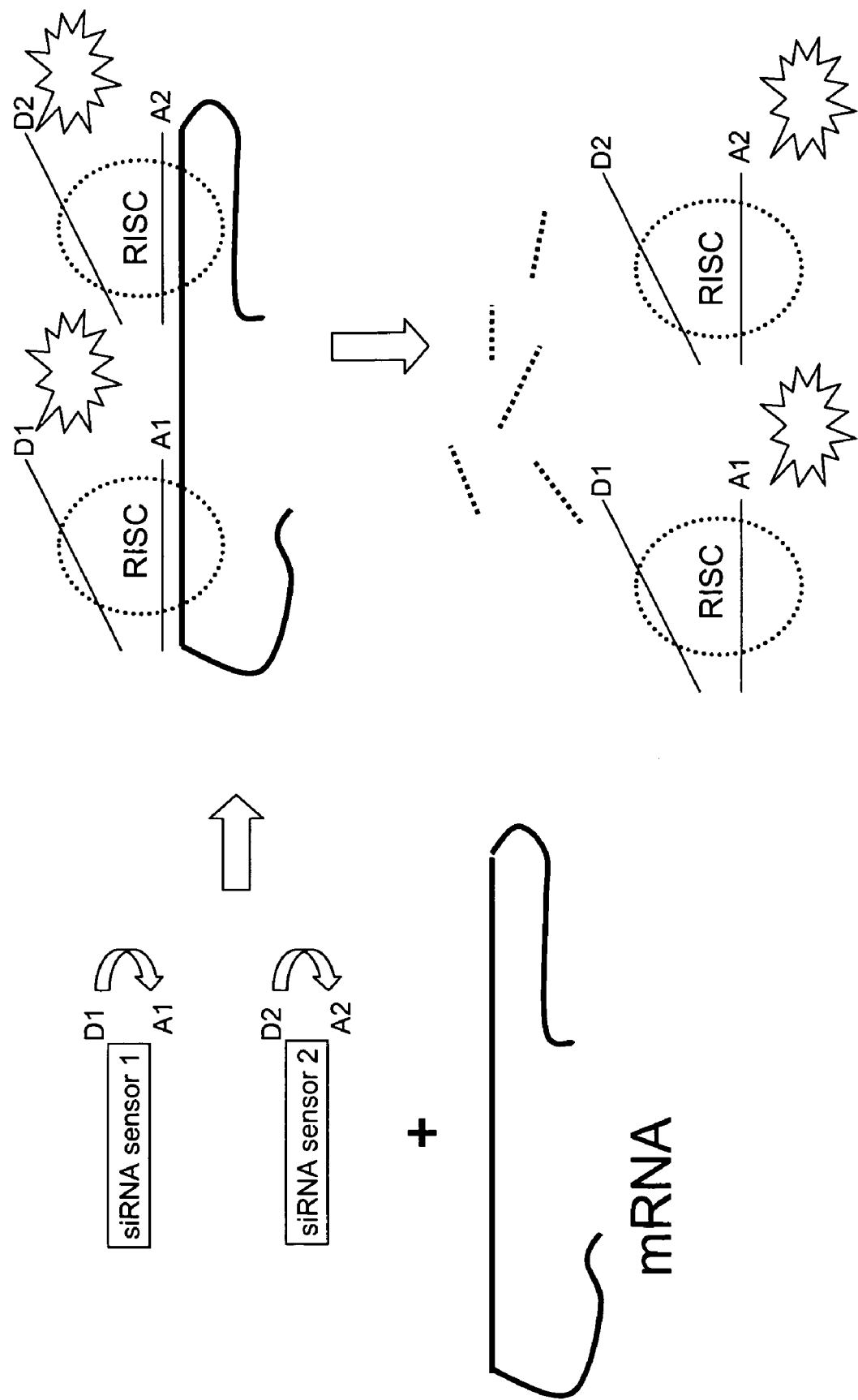
FIG. 49 schematically illustrates the use of multiple siRNAs per target gene.

FIG. 49 shows the detection of a single target using multiple (e.g., two or more) interfering RNA sensors. The different interfering RNAs typically emit distinguishable signals before and/or after initiation of RNAi. Detection specificity is improved using this design, because an actual signal or signal change (indicating degradation of the specific target mRNA) is recorded only when signals from both interfering RNAs are observed at about the same time.

Applications

Figure 50:
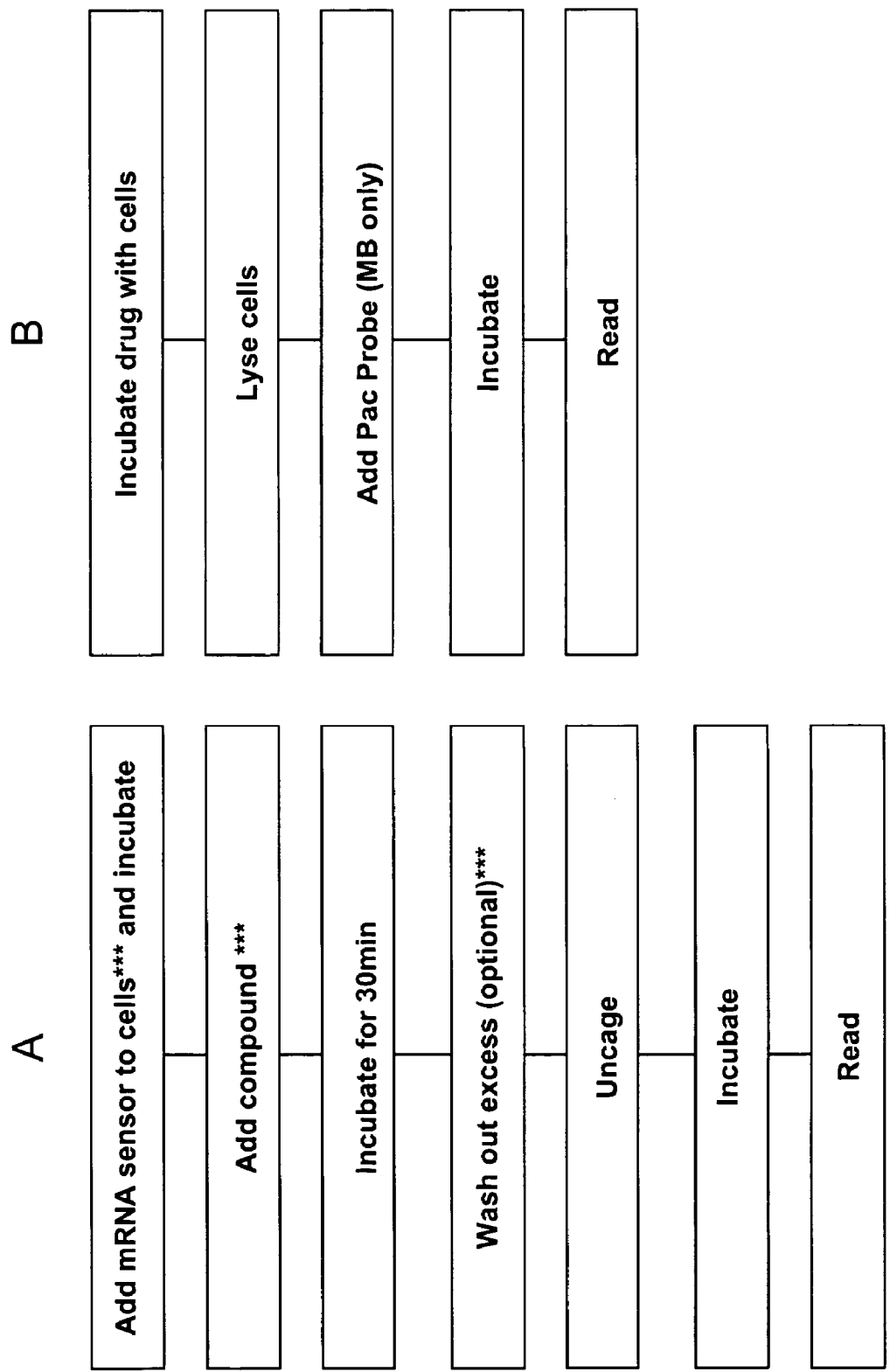
FIG. 50 depicts flowcharts illustrating example workflows for assays using photoactivatable MRNA sensors in two formats: live cell assay (Panel A) and cell-lysate assay (Panel B).

FIG. 50 shows example workflows for mRNA measurement using the sensors of this invention, where the effect of a compound (drug, agonist, antagonist, etc. affecting or potentially affecting an upstream signaling molecule) on mRNA level is monitored. There are minimal fluidic handling steps and reagents required. A photolabile PAC probe can be uncaged by exposing to a light source (e.g., in an uncaging device such as those described herein). Detection of MRNA in cell lysate is also possible with MB PAC probe.

A PAC probe for MRNA can be used to measure amount of mRNA transcript and location of mRNA processing in living cells. When performing quantitative analysis, a MB or interfering RNA for house-keeping RNA can optionally be used to normalize for variable target(s). Deviation between different cells can be corrected if one or more dual-labeled FRET MBs or interfering RNAs, for example, are used instead of a dark quencher/fluorophore probe format. With a dual-labeled FRET probe (i.e., a probe with a donor fluorophore and an acceptor fluorophore, where the donor and acceptor are capable of exhibiting FRET), at least two different signals can be obtained, i.e., the FRET signal (emission by the acceptor following stimulation of the donor) and the acceptor signal (emission by the acceptor following stimulation of the acceptor) using different excitation wavelengths, e.g., produced by different lasers, to stimulate the donor and acceptor. The ratio of these two signals can be taken, e.g., to normalize for transfection efficiency of the probe.

Figure 51:
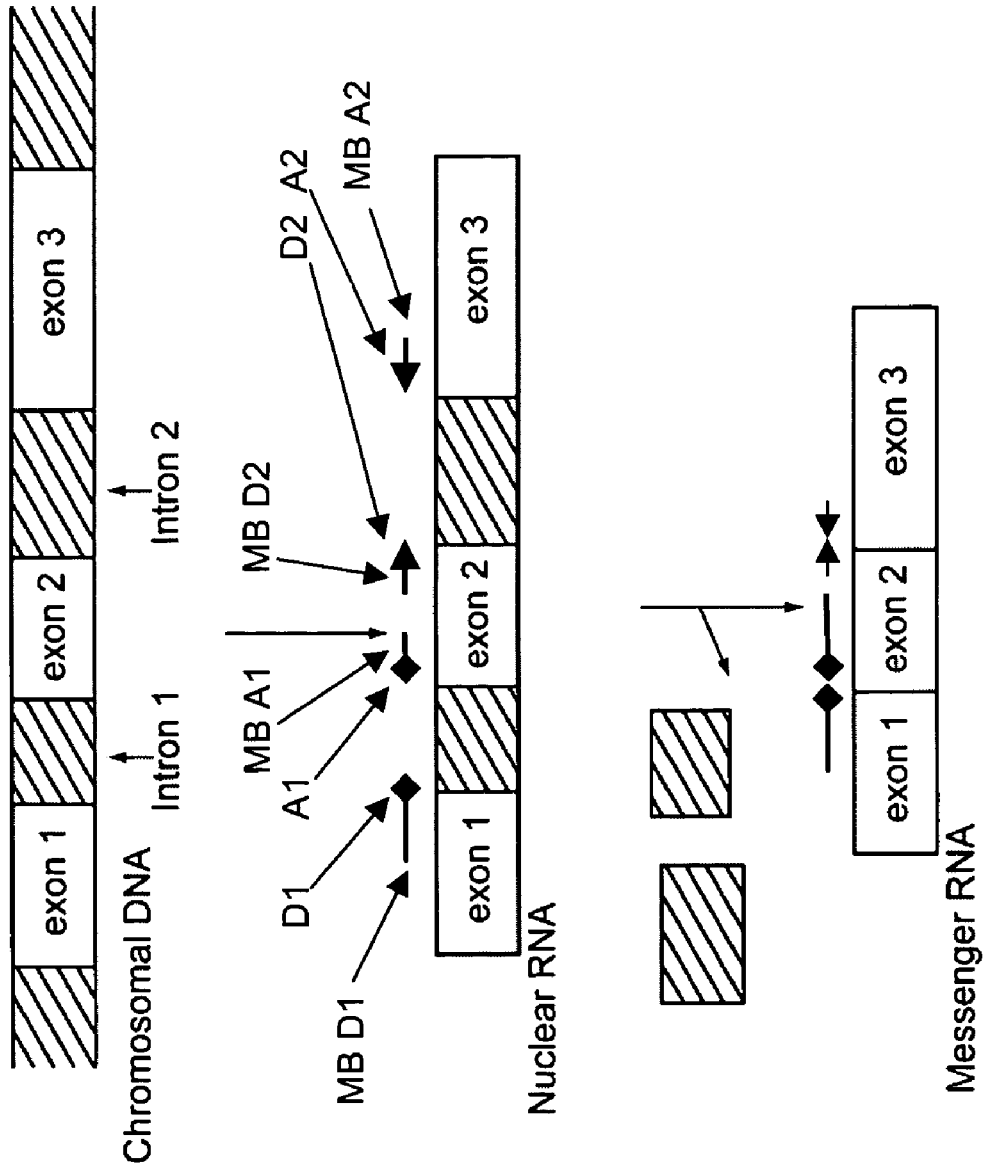
FIG. 51 schematically depicts the detection of splice variants with dual molecular beacons.

As noted, either MB or interfering RNA PAC probes can be used to analyze splice variants (including, e.g., in living cells). For example, FIG. 51 illustrates the detection of splice variants using dual MBs (see, FIG. 42). When dual MBs are used to monitor splice variants, one beacon locates at the end of one exon while another beacon locates at beginning of another exon. When the intervening intron is removed and both exons are stitched together, each of the two beacons binds to its target sequence and they locate within a few (e.g. 4-5) nucleotides from each other. Examples of genes with a variety of splice variants are beta-actin and cyclic nucleotide phosphodiesterases (see, *Current Opinion in Cell Biology* (2000) 12:174-179), among many others. Multiple pairs of dual MBs can be used simultaneously (typically, the signal produced by one pair of dual MBs is distinguishable from those produced by other pairs). In the example in FIG. 51, a nuclear RNA containing three exons and two introns is transcribed from chromosomal DNA. The nuclear RNA is spliced to form the MRNA, which in this example includes all three exons and no introns., Two pairs of dual MBs are utilized; splice donor MB D1 and splice acceptor MB A contain donor fluorophore D1 and acceptor fluorophore/quencher A1, respectively, while splice donor MB D2 and splice acceptor MB A2 contain donor fluorophore D2 and acceptor fluorophore/quencher A2, respectively. When the MBs bind the nuclear RNA, the donors and the acceptors/quenchers are too far apart to interact; however, when the MBs bind the MRNA, the donors and the acceptors/quenchers are in proximity and interact.

Figure 52:
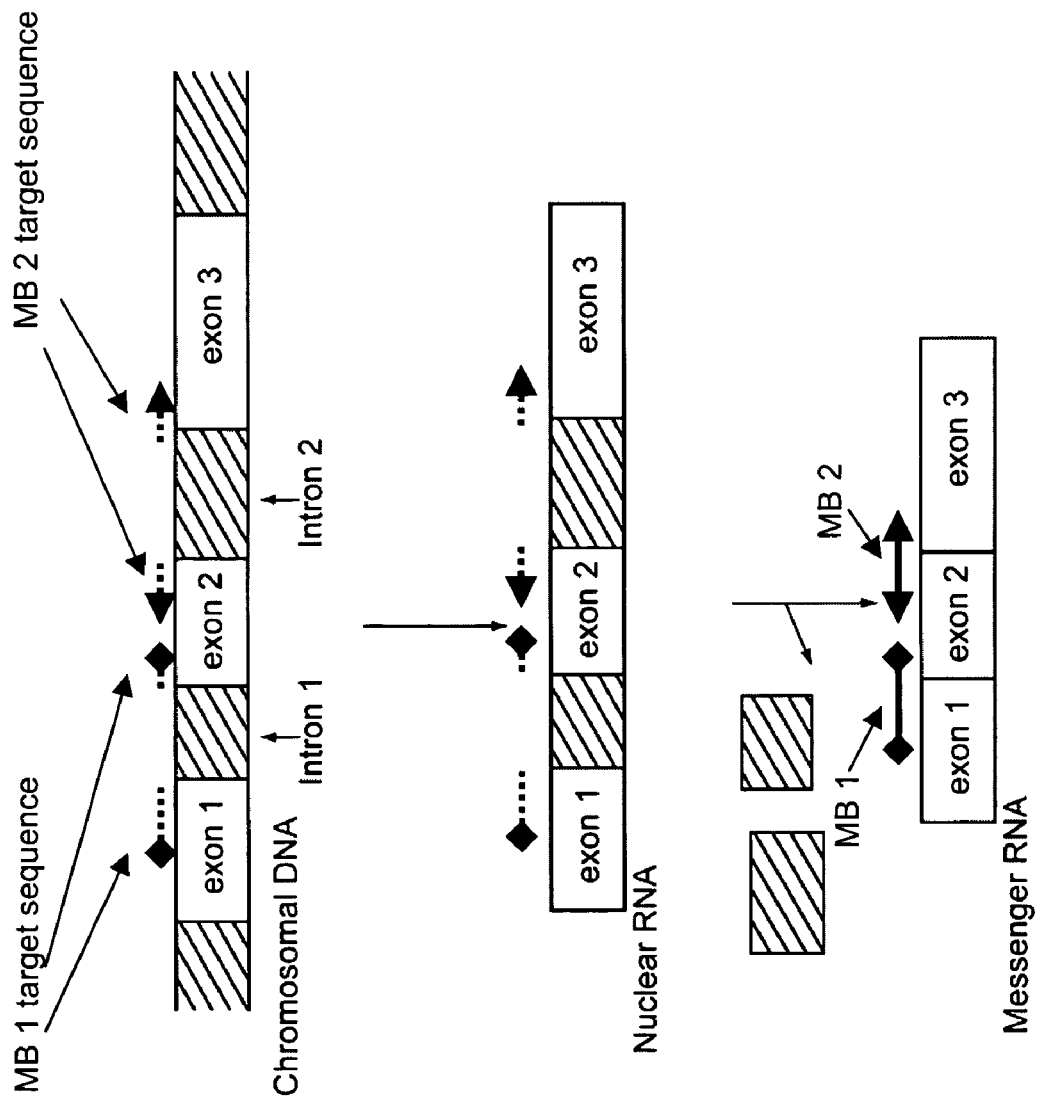
FIG. 52 schematically depicts the detection of splice variants with multiple single molecular beacons, each of which is designed to span a splice junction.
Figure 53:
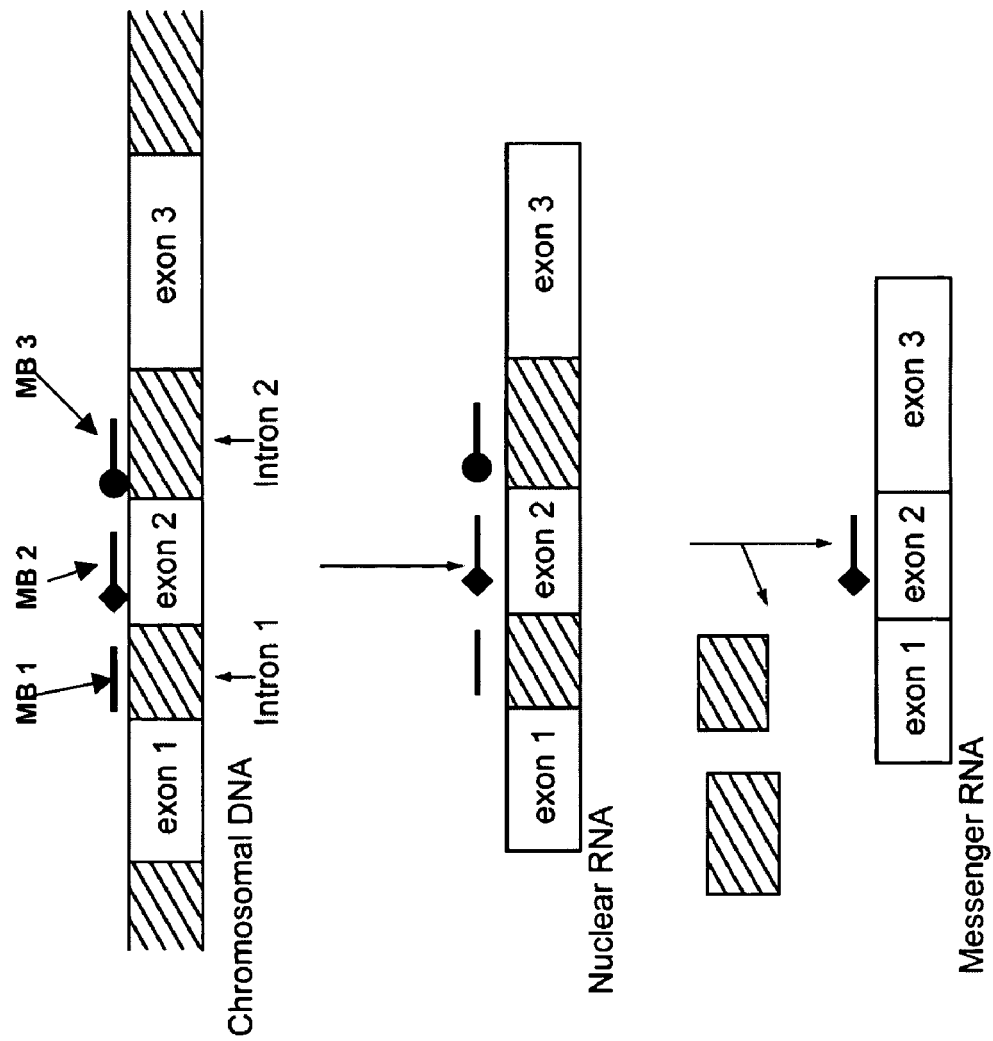
FIG. 53 schematically depicts the detection of splice variants with multiple single molecular beacons that do not span splice junctions.

Single MBs can also be used to analyze splice variants, when different fluorophores are employed to differentiate the binding of multiple single beacons. For example, FIG. 52 shows MBs designed to bind at the splice junctions. In this example, a nuclear RNA containing three exons and two introns is transcribed from chromosomal DNA. The nuclear RNA is spliced to form the mRNA, which in this example includes all three exons and no introns. Each MB's target sequence spans from one exon to another exon—minus the intron region. Since each MB spans a splice junction, the MB binds to its respective target only when the appropriate exons are juxtaposed in a spliced product (i.e., MB1 and MB2 bind the mRNA but not the nuclear RNA). Typically, each MB emits a unique signal (e.g., each MB can comprise a fluorophore that emits at a distinct wavelength). As another example, FIG. 53 shows MBs designed to be within the intron or exon regions and not the splice junction (each MB typically emits a unique signal). Again in this example, a nuclear RNA containing three exons and two introns is transcribed from chromosomal DNA. The nuclear RNA is spliced to form the mRNA, which in this example includes all three exons and no introns. MB1 binds in intron 1, MB2 binds in exon 2, and MB3 binds in intron 2. Thus, all three MBs bind the nuclear RNA, but only MB2 binds the mRNA and produces a signal.

Figure 54:
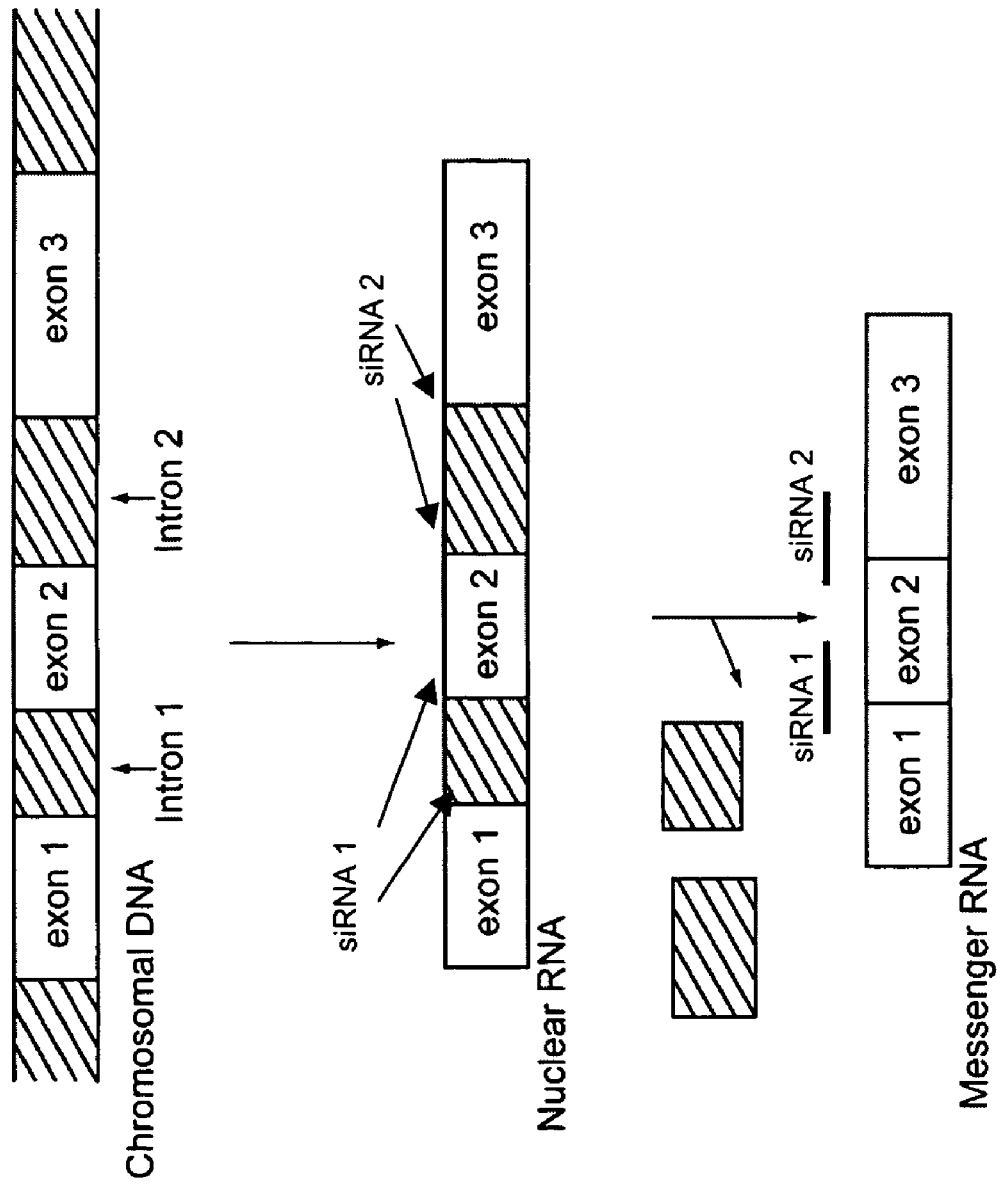
FIG. 54 schematically depicts the detection of splice variants with siRNA sensors that span splice junctions.

Interfering RNAs can also be used to analyze alternatively spliced mRNAs. For example, a siRNA probe can be designed to recognize the splice junction. One or more such siRNAs can be used to detect various isoforms. For example, FIG. 54 illustrates how multiple siRNAs can be used to determine splice variants. A nuclear RNA containing three exons and two introns is transcribed from chromosomal DNA. The nuclear RNA is spliced to form the mRNA, which in this example includes all three exons and no introns. A siRNA is designed to be at the splice junction. The isoform with the correct splice variant is digested. Similarly, siRNA can be made to bind to the exon regions and not between the splice junctions, or a siRNA can be designed against an intron.

Splice variants containing the intron are digested and result in a signal from the siRNA probe.

The above and additional RNAi-based sensors are described in U.S. Patent Application 60/484,785, filed Jul. 3, 2003, which is hereby incorporated by reference in its entirety.

Example Systems of the Invention

HTS Instruments and Micro Fluidic Devices for Using PA Sensors, Regulators and Compounds Advantages of using a PA assay format over a non-PA assay format have been described (e.g., fewer fluidic handling steps are required, etc.). Instrument platforms ranging from fluorescent microtiter plate readers, to flow cytometers, to laser scanning cytometers and other fluorescent measurement instruments are suitable for the PA assay format. The only requirement is the ability to illuminate at the desired wavelength(s) that photo-activates the photocaged sensors, regulators or compounds (and for non-PA caged sensors, regulators or compounds, even this is not required). At the same time, for convenience, the instrument can usually measure the sensor signal. For multiplex PA assays, the instrument should be able to resolve locations and/or bar-coded beads, or other features appropriate to the assay.

The component in which the assay is performed (the "assay carrier") for the PA assay reaction ideally has light transmission capability for the photolabile group and transmission capability for the sensor signal. For example, the assay carrier can be a microtiter plate. For cell-based assays, a UV transmissible clear bottomed assay carrier is typically preferred (e.g., for photoactivatable caging groups removed by UV light).

Figure 24:
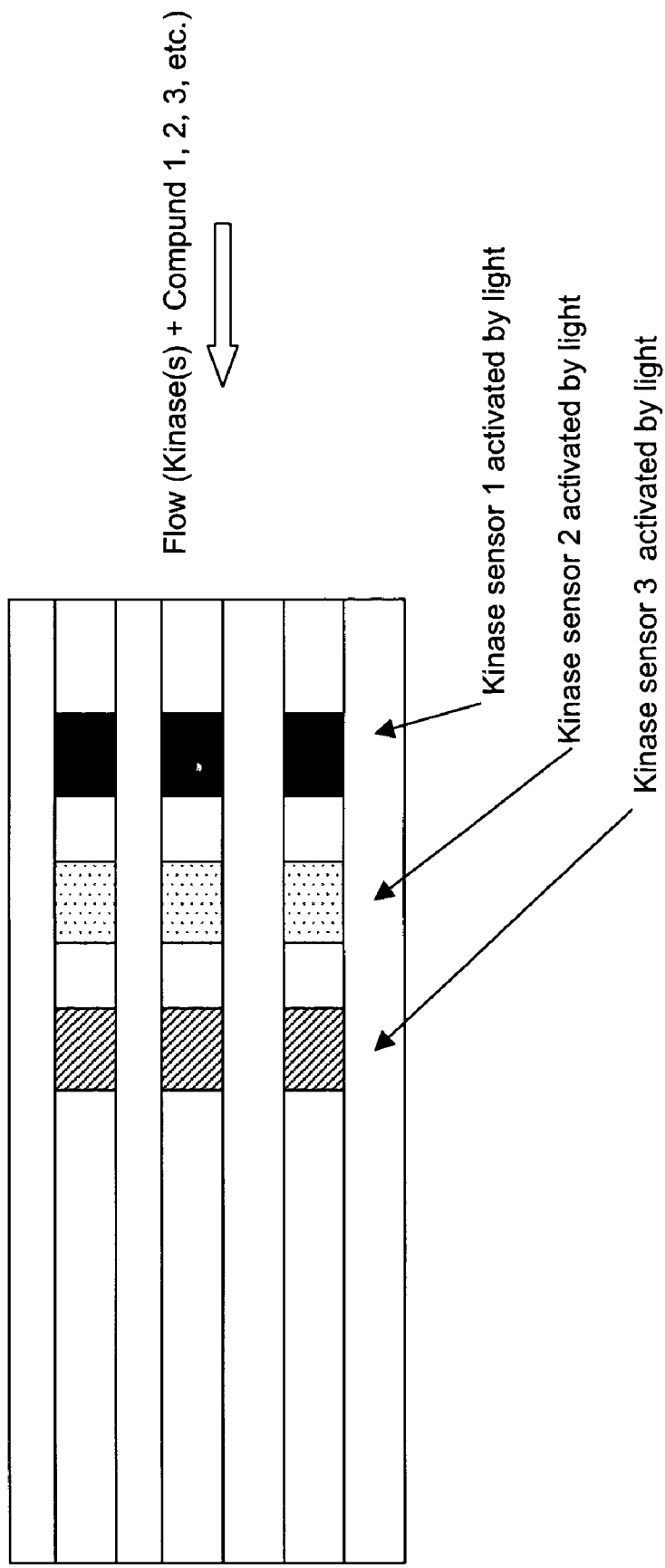
FIG. 24 schematically depicts a HTS microfluidic kinase assay using PA kinase sensors. Sensor 1 is represented by a solid box, sensor 2 by a dotted box, and sensor 3 by a hatched box.

The PA assay format is suitable for microfluidic and miniature platforms. For example, FIG. 24 illustrates the advantage of location specific activation of PA biochemical assays. Here, each channel of a miniaturized chip is coupled with a PA kinase sensor at multiple locations. As illustrated, drug compound 1 (2, 3, etc.) is introduced into the channel, which contains necessary components of a kinase assay (e.g., one or more kinases; direction of flow is indicated by the open arrow). Kinase reaction is activated at a specific location in the channel by illuminating the location (e.g., kinase sensor 1 can be activated by light in the filled region, kinase sensor 2 in the dotted region, and kinase sensor 3 in the cross-hatched region). The signal from kinase sensor can be read immediately (cf., for kinase peptide substrate, add detection reagent for detecting phosphorylated substrate). Compound 1 is flushed out after the reaction. Compound 2 is tested by repeating steps 1-3, except by illuminating another section of the channel to activate the relevant kinase sensor. Compound 3 is tested by repeating these steps. The steps are repeated until no more kinase sensor remains in the channel. The channel is scanned to detect signal. Signal at each location indicates compound inhibition or activation of the kinase. As another example, different concentrations of a single compound can be used instead of different compounds to determine IC-50 (e.g., starting with the lowest concentration). Real time or kinetic reads are possible with this kinase sensor.

Figure 25B:
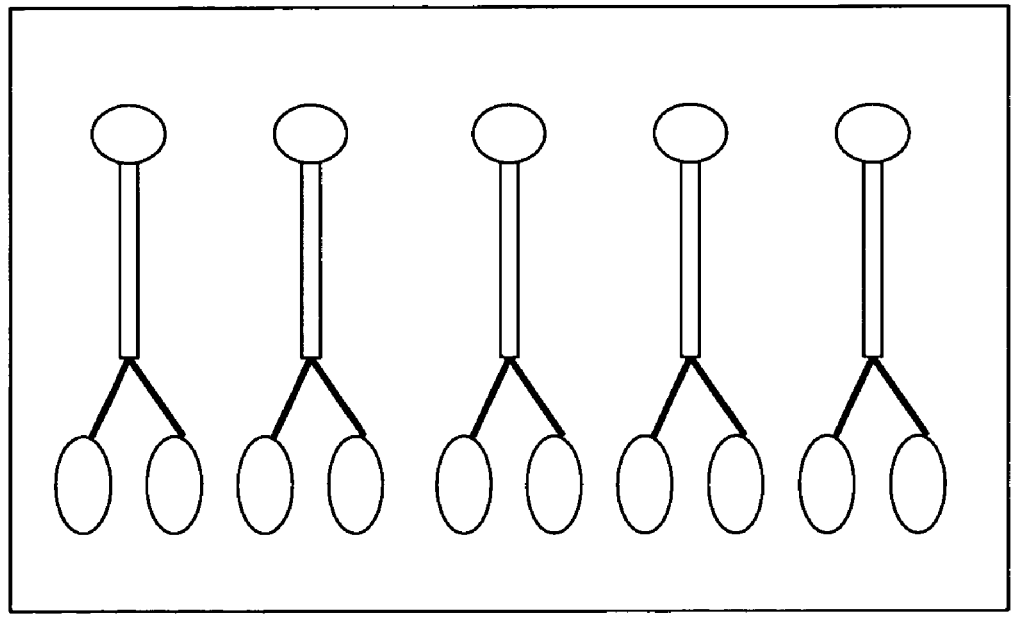
FIG. 25 schematically depicts a multiplex kinase assay using Y-shaped channels in a microfluidic chip. Panel A depicts a single channel, Panel B depicts an array of Y-channels.
Figure 25A:
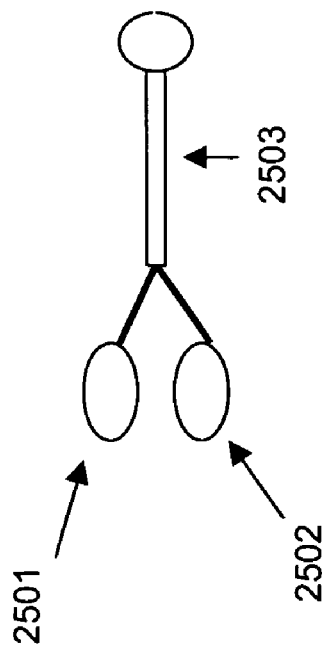

FIG. 25 illustrates photo activation of a reaction in a Y-shaped channel (Panel A) of a microfluidic chip (Panel B). Simultaneous activation of multiple channels with millisecond precision is possible. The materials used in the chip permit light transmission at the Y-channel location. Alternatively, a focused light source can be aimed at the Y channel for specific location activation. Advantages include evaporation control in the Y-channel and simultaneous activation using a caged compound. Solutions (drug and master kinase assay mix) can be delivered to holes 2501 and 2502, respectively, and sucked into channel 2503 by capillary or vacuum, then mixed by sonication, shaking or temperature (e.g., heating). The reaction is light-activated and read. The kinase sensor permits read-out of the assay.

Device for Photoactivation and Detection of Biochemical and Cell-Based Assays

Caged molecules have been used in microscopy studies of cells. There are commercial devices for uncaging samples on microscope slides. For example, Photonics Micropoint System and Prairie Technology fluorescent microscope adaptors have been used to activate caged calcium ions or EDTA for studying ion channels and voltage clamps in a single cell. However, there is no commercially available system for uncaging samples in test tube, microtiter plate, or other formats. Researchers resort to homemade xenon or mercury flash or UV lamps, which are highly non-uniform, irreproducible from run-to-run, not user friendly and unsafe to use. They are not integrated with a reader and are not made for high throughput applications.

This invention describes an uncaging device that triggers photoactivatable biochemical and cell-based assays and that optionally also detects signals from the assays. Photoactivatable assays contain caged molecules whose activities are muted by the attachment of photoactivatable (e.g., photolabile) chemical groups. When exposed to uncaging light, the photolabile groups fall off and the uncaged molecule becomes functionally active, setting off the reaction and generating signals.

Preferably, the uncaging device produces light of specific wavelength and intensity aiming at specific locations. For example, the device can initiate a photoactivatable reaction over an area ranging from about a nanometer to about a meter in size. It can trigger a single reaction or many reactions, with a spatial resolution of, e.g., 1 millimeter, 500 microns, 100 microns, 50 microns, 20 microns, 10 microns, or less. It can trigger photoactivatable reactions at high speed, preferably within 100 milliseconds, 10 milliseconds, 1 millisecond, 100 microseconds, 10 microseconds, 1 microsecond, 100 nanoseconds, 10 nanoseconds, or 1 nanosecond or less, for example. The uncaging device also has the capability of detecting the signal from the reaction in synchrony with the triggering event.

In a preferred embodiment, this device is coupled with a robotic liquid handling machine to provide an integrated platform for bioassays, including high throughput screening of compound libraries in drug discovery or clinical diagnosis of patient samples.

The design, uses and advantages of photoactivatable sensors and regulators in living cell and biochemical assays have been described herein. Photolabile caged sensors include peptide, nucleic acid and other molecules that have photolabile groups attached. In some embodiments, these sensors are covalently linked with photolabile groups that shield the sensors from enzymatic degradation within the cell and that also prevent the sensors from being active. Such shielding or protection of sensors is referred as to caging. Upon exposure to light of a specific wavelength, the photolabile groups detach from the sensors, which in turn become active. This process is referred to as uncaging. Photoactivatable caged regulators (inhibitors or activators) can also be uncaged using light of specific wavelength.

Instrument Functions and Capabilities

This invention features an uncaging instrument that can have a plurality of the following capabilities: (1) Photo-activate biochemical and cell based assays and detect at the same time (see, FIGS. 26-30); (2) Uncage in standard reaction formats such as 96, 384 and 1536 well microtiter plates (see, FIG. 31 Panel A); (3) Uncage other reaction formats such as two-dimensional microarrays of cells or biochemical assays (see, FIG. 31 Panel B), three-dimensional microarrays of cells or biochemical assays (see, FIG. 31 Panel C), assays within micro channels of micro fluidic systems (see, FIG. 31 Panel D) or flow channels of flow cytometers (see, FIG. 32), etc.; (4) Control energy, wavelength, time, location (x, y, z) and dimension of illumination for uncaging and detection (see, FIG. 30); (5) Illuminate from different orientations, e.g., top, bottom and side. (see, FIGS. 26-27); (6) Auto calibrate for reproducible illumination of light within and between experiments (see, FIG. 30); (7) Adjust the height of sample location (see, FIG. 30); (8) Rotate samples to ensure even illumination; (9) Energy and wavelength calibration meter; (10) Various detectors for measuring output signal (e.g., photo multiplier tube for detecting fluorescent or chemiluminescent signal); (11) Computer and instrument software; (12) Uniform illumination; (13) Heating and environmental control (e.g., for maintaining or stimulating cell culture); and, (14) Liquid handling for precision delivery of test compounds.

For example, one general class of embodiments provides an apparatus for performing an assay. The apparatus includes at least one reaction region that comprises at least one photoactivatable caged component of the assay (e.g., a photolabile caged component), a light source for directing light at the reaction region or a portion thereof, and a detector for detecting at least one signal produced by at least one labeled component of the assay. The light from the light source is capable of uncaging the photoactivatable caged component. The reaction region can comprise, e.g., a well of a multiwell microtiter plate, a sample tube, a channel of a microfluidic chip, a capillary, a spot on a two-dimensional array, or a spot on a three-dimensional array. Preferably, the apparatus also includes a fluid-handling element.

Instrument Description

The instrument typically has illumination sources for uncaging, stimulation and/or detection, an optical set-up to control the illumination power, and a waveguide to guide the light from illumination source to sample. A calibration light meter can be used to ensure reproducible exposure and automated power and location adjustments. Mechanical design can be used to manipulate samples and/or optics in an x, y or z direction depending on specific application and assay format. A liquid handling mechanism is preferably integrated into the reaction holder.

Figure 29:
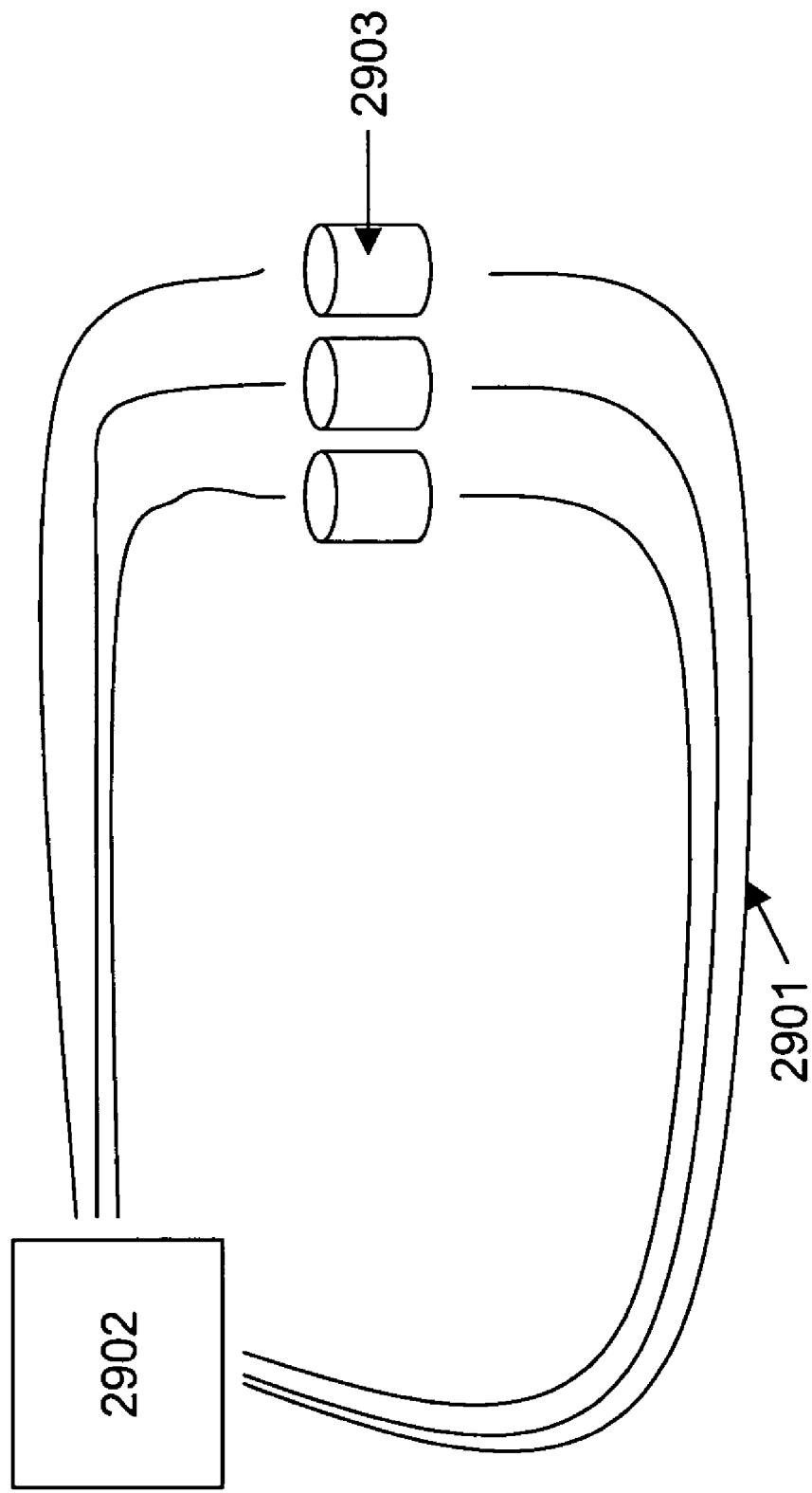
FIG. 29 schematically illustrates fiber-optic bundles used to guide uncaging light to the wells of a multiwell plate. As depicted, illumination can be provided to the top and/or bottom of the wells (singly or in any combination).

The illumination source can be, e.g., continuous or pulse lasers, flash lamps (e.g. Xenon or Mercury), continuous lamps and others. The light can be guided to the sample with one or more optical mirror, lens, fiber optic bundle, or the like. Illumination dimension (focus or broad beam) can be controlled using lenses or mirrors, for example. Uniform illumination can be achieved, e.g., by using a collimated lens. For a non-uniform light source, samples or the light source can be rotated to ensure even exposure of all samples. A diffuser can also be used to ensure even illumination. As an alternative example, fiber optic guided light can be directed to each well of a multiwell plate to uncage the entire well or only part of a well. FIG. 29 schematically illustrates fiber optic bundles 2901 used to guide uncaging light from light source 2902 (e.g., a laser or xenon, mercury or UV lamp) to wells 2903 of a multiwell plate. As depicted, illumination can be provided to the top and/or bottom of the wells (singly or in any combination). A light source with less energy can be used for uncaging a small part of a well in microtiter plate. The detection is then focused on the uncaged region of the well. Hence, uncaging a smaller part of a well can permit the use of a lower energy light source. FIG. 36 schematically depicts uncaging a smaller region within a well of a microtiter plate. Panel A depicts cells (white stars) grown on the bottom of the well. Panel B depicts light exposure of a portion of the well (boxed area), which uncages a caged molecule inside the cells. At the same time, detection of a signal from the same portion of the well (from the cells containing the uncaged molecule, represented by black stars) is performed.

After the samples (biochemical reactions or adherent or non-adherent cells) are photoactivated, the samples can be read on various detectors such as a microtiter plate reader (commercially available from many vendors), a flow cytometer (commercially available from, e.g., Beckman Coulter or BD Biosciences), a laser scanning cytometer (commercially available from, e.g., Acumen, Cellomics or Amersham), a fluorescent microscope (commercially available from, e.g., Nikon, Zeiss, Olympus and others), a confocal fluorescent microscope (commercially available from, e.g., Bio-Rad, Zeiss and others) or microfluidic chip systems (commercially available from, e.g., Caliper and others).

Figure 32:
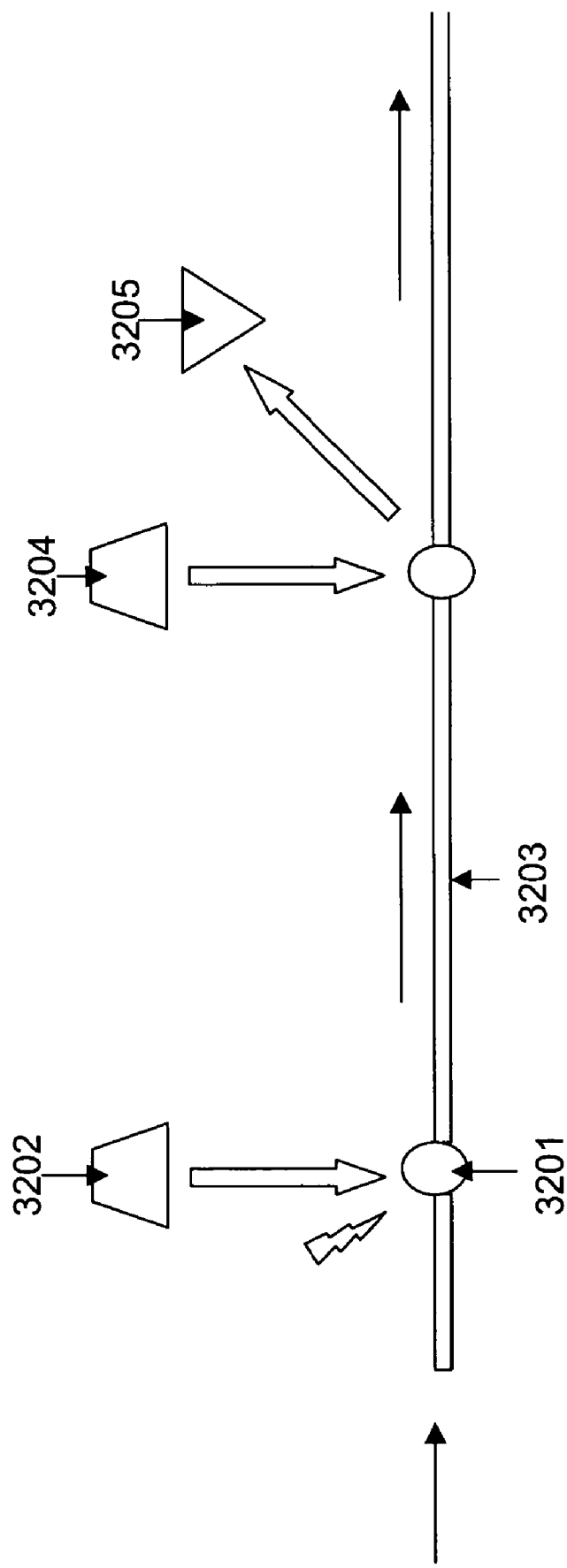
FIG. 32 schematically depicts uncaging in a flow cytometer.

An uncaging illumination source can be incorporated into any of the instruments listed above. For example, an uncaging illumination source can be incorporated into a microtiter plate reader so that photoactivation of samples can be immediately followed by detection, thus, permitting precise control of kinetic reading. For a flow cytometer, samples can be photoactivated by flowing the samples past an uncaging light source before they reach the detector location. For example, activation of non-adherent cells can be performed in high throughput mode using photoactivation flow cytometer devices (FIG. 32). As the cells flow pass the light source, they are activated one at a time before going to the detector. FIG. 32 schematically depicts uncaging in a flow cytometer. Cell 3201 comprising a caged component and flowing in channel 3203 in the direction of the solid arrows is exposed to uncaging light from uncaging light source 3202. Cell 3201, now comprising the uncaged, active component, is exposed to excitation light from excitation light source 3204, and a fluorescent signal emitted from the component is detected by detector 3205.

Non-fluorescent probes can also be employed with a photoactivation device. For example, a chemiluminescent reaction can be triggered using a light activated sensor/regulator.

Applications and Data

Figure 33:
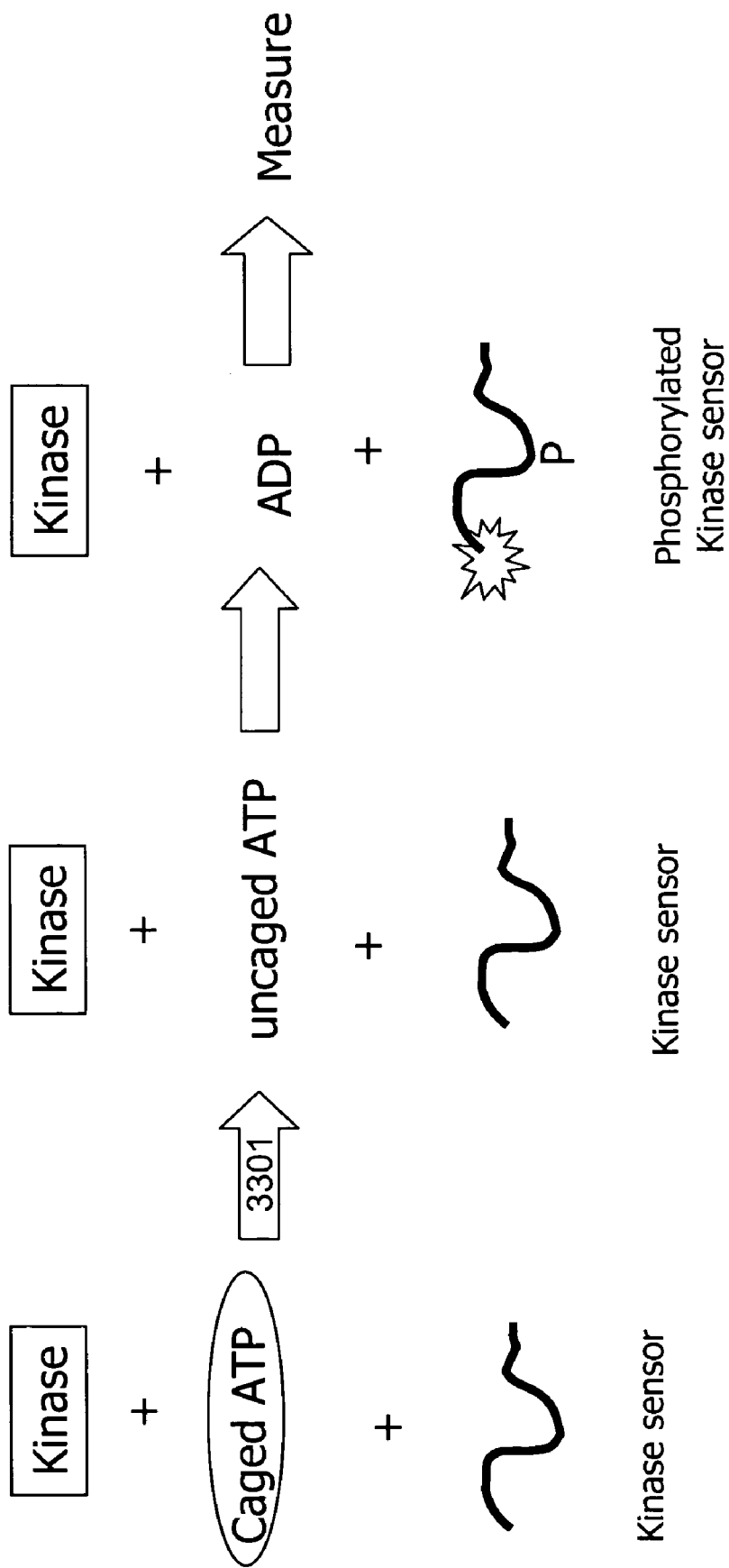
FIG. 33 schematically depicts a photoactivated protein kinase C (PKC) assay in which the reaction is initiated by uncaging ATP by exposure to light.
Figure 34:
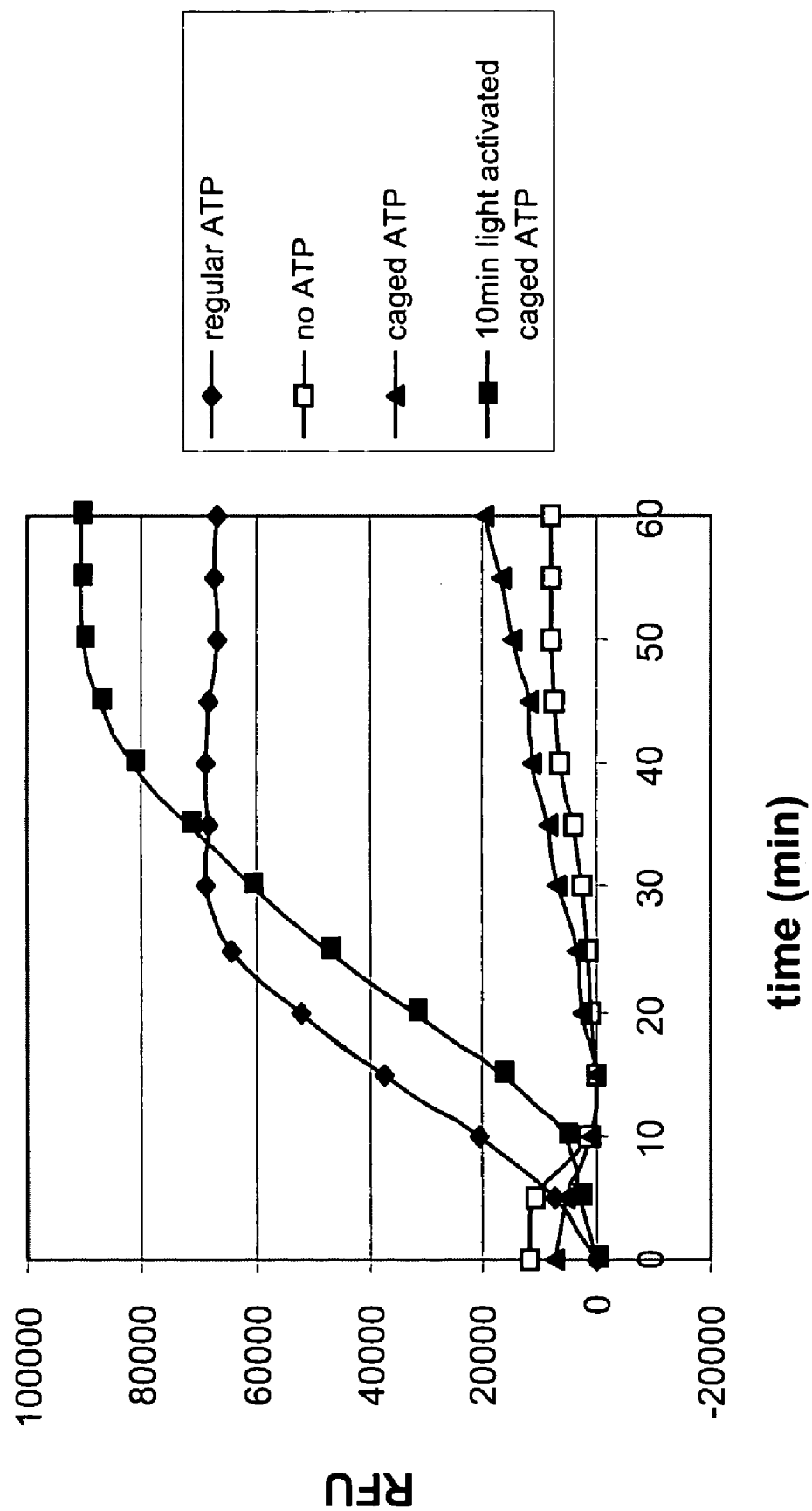
FIG. 34 is a line graph depicting the results of a photoactivated PKC assay using caged ATP and a PKC sensor. The graph shows relative fluorescence (RFU) versus time (min) for reactions with no ATP (open squares), caged ATP not exposed to uncaging light (filled triangles), uncaged regular ATP (filled diamonds), and caged ATP activated by exposure to uncaging light for 10 min (filled squares). Reactions were read on a fluorescent microtiter plate reader with excitation at 485 nm and emission at 535 nm.

FIG. 33 (see, also, FIG. 23) illustrates the activation of an in vitro PKC assay after exposure to 365 nm light. All components were mixed together in a 96-well microtiter plate. The plate was exposed to a 365 nm UV lamp for 10 min (step 3301) and immediately placed into a fluorescent microtiter plate reader for detection. The light-activated compound is DMNPE-caged ATP. FIG. 34 shows the result of the experiment. Only the reaction that was exposed to light exhibits signal response similar to the reaction with normal ATP. See, e.g., McCray and Trentham (1989) "Properties and Uses of Photoreactive Caged Compounds" *Annu Rev Biophys Biophys Chem* 18:239 for a description of the caged ATP. The PKC probes and reaction set-up are based on Yeh et al. (2002) "Real time visualization of protein kinase activity in living cells" *J Biol Chem* 277: 11527-11532, with the replacement of normal ATP by DMNPE-caged ATP.

Figure 26:
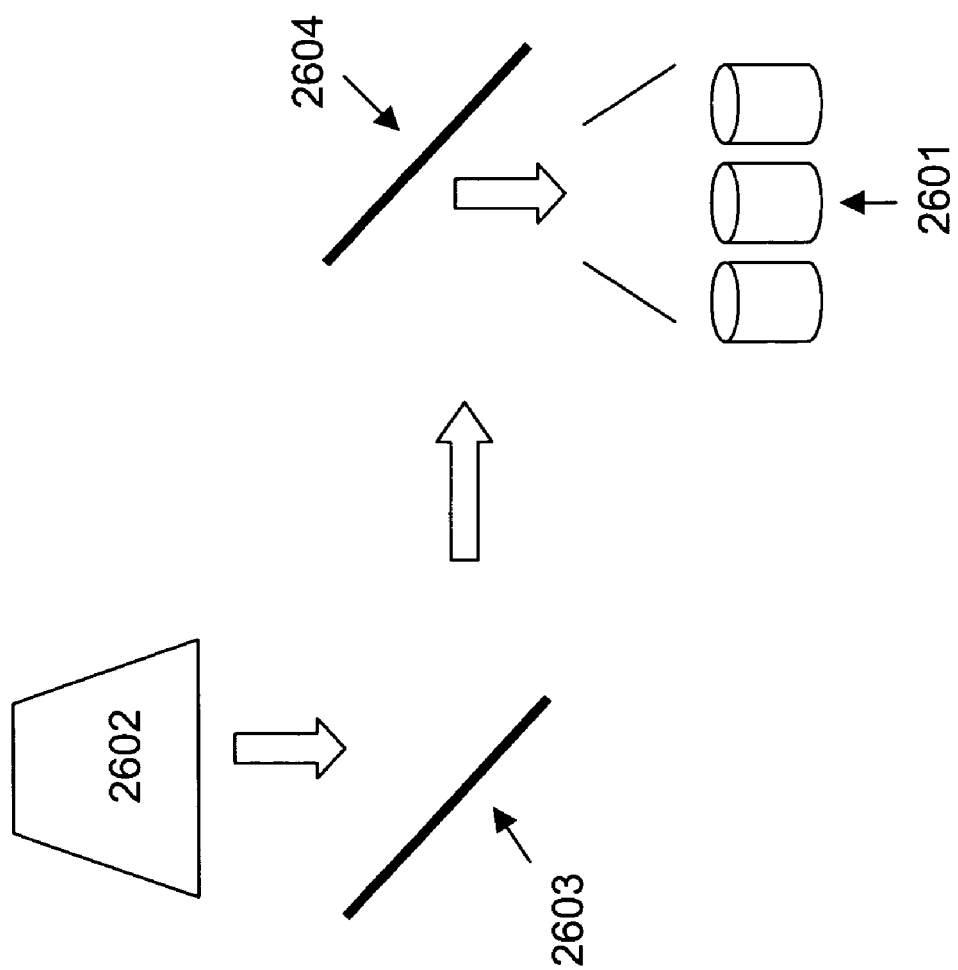
FIG. 26 schematically depicts uncaging using top illumination. In this example, illumination is provided from the top of the wells of a multiwell plate, e.g., for uncaging a sensor in solution to perform a biochemical assay.
Figure 27:
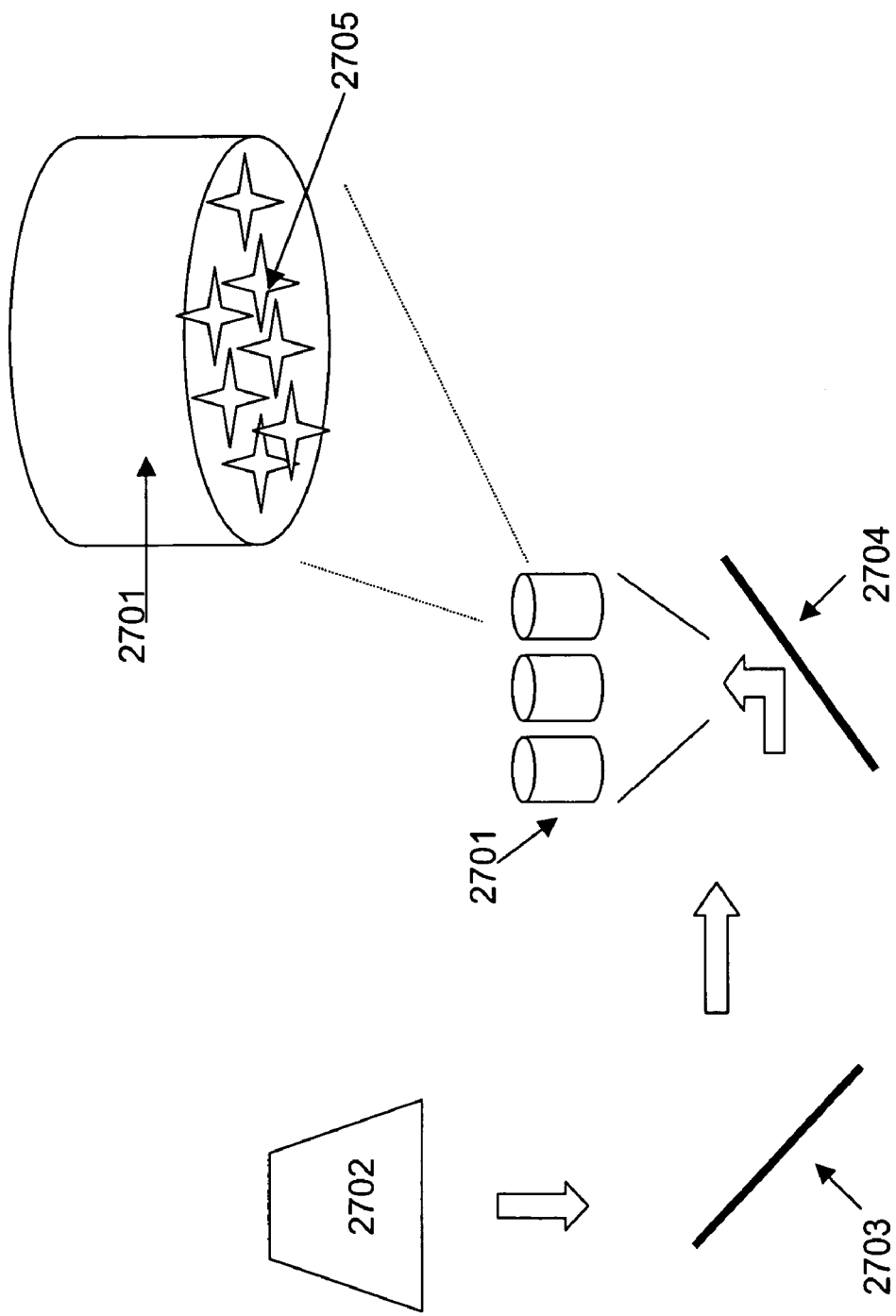
FIG. 27 schematically depicts uncaging using bottom illumination. In this example, illumination is provided from the bottom of the wells of a multiwell plate, e.g., for uncaging a sensor in adherent cells.
Figure 28:
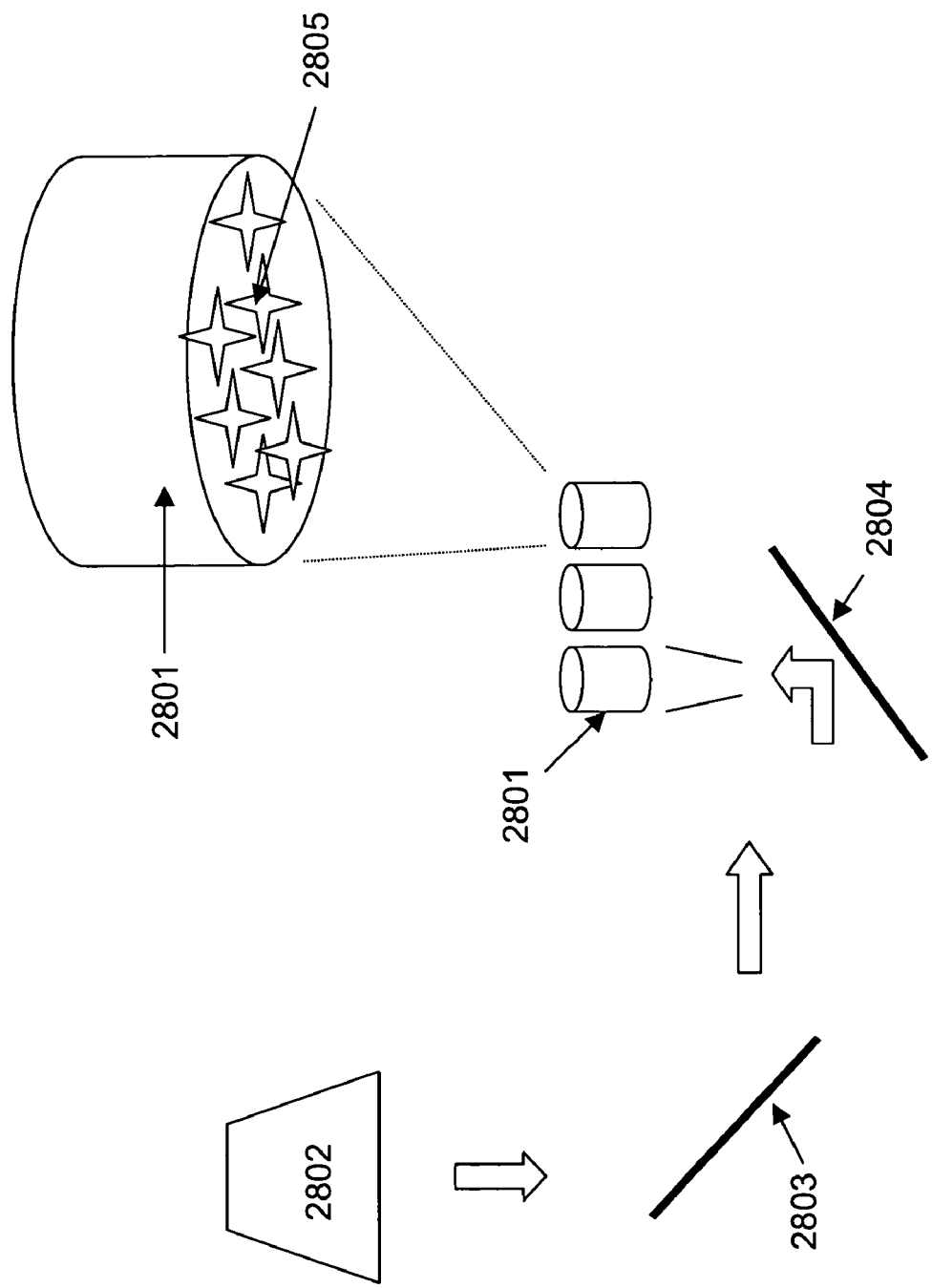
FIG. 28 schematically depicts uncaging using bottom illumination to each well. In this example, illumination is provided to a single well at a time, e.g., from the bottom of the wells, e.g., for uncaging a sensor in adherent cells.
Figure 30:
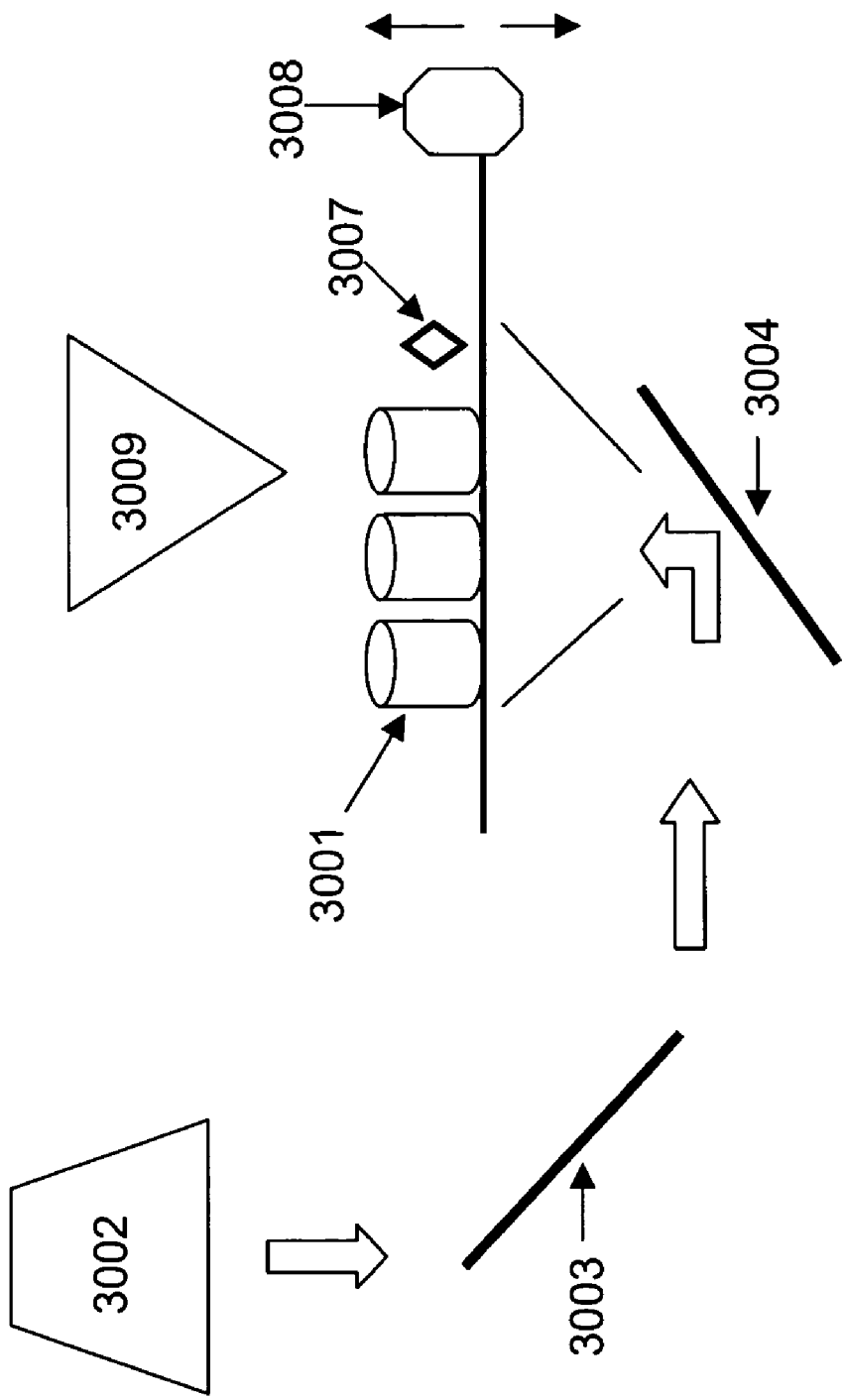
FIG. 30 schematically depicts automatic identification of optimal uncaging distance.
Figure 31A:
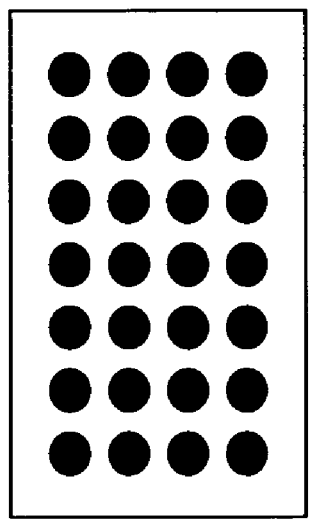
FIG. 31 schematically illustrates example formats suitable for uncaging: multiwell plate (e.g., 96, 384, 1536, or 3456 wells; Panel A), two-dimensional microarray of cells or biochemical assays (Panel B), three-dimensional microarray of cells or biochemical assays (Panel C), and capillary or flow channel (Panel D).
Figure 31B:
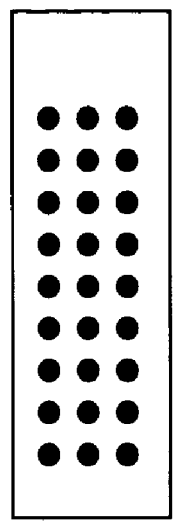
Figure 31C:
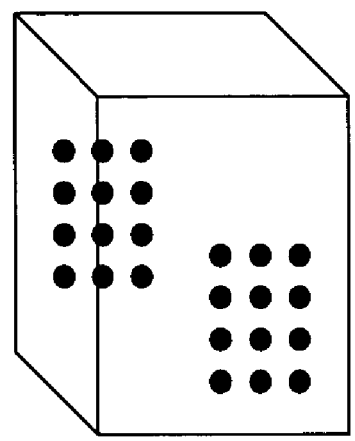
Figure 31D:
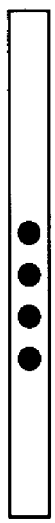

Illumination from the top of the wells (FIG. 26) is preferred for many applications, such as biochemical assays (illumination from the bottom or side of the wells may be preferred for other applications, such as uncaging in adherent cells). Small assay volume and smaller assay area are preferred in photoactivatable assays since less energy per area is required. For example, 1536 well assay format is more ideal than 96 and 384 well assay formats. In addition, a shallow assay reaction is preferred since light transmission through the assay buffer can be poor, especially for shorter wavelength light. FIG. 26 schematically depicts uncaging using illumination from the top of sample wells 2601 of a multiwell plate. Uncaging light provided by light source 2602 (e.g., a laser or xenon, mercury or UV lamp) is reflected by mirrors 2603 and 2604 as indicated by the open arrows. FIG. 27 schematically depicts uncaging using illumination from the bottom of wells 2701 of a multiwell plate. Uncaging light provided by light source 2702 (e.g., a laser or xenon, mercury or UV lamp) is reflected by mirrors 2703 and 2704 as indicated by the open arrows. The uncaging light impinges on the bottom of wells 2701, e.g., for uncaging a sensor in adherent cells 2705 comprising the sensor. FIG. 28 schematically depicts uncaging using illumination from the bottom of wells 2801, where illumination is provided to a single well at a time. Uncaging light provided by light source 2802 (e.g., a laser or xenon, mercury or UV lamp) is reflected by mirrors 2803 and 2804 as indicated by the open arrows. The uncaging light impinges on the bottom of well 2801, e.g., for uncaging a sensor in adherent cells 2805 comprising the sensor. FIG. 30 schematically depicts automatic identification of optimal distance from the light source for uncaging in sample wells. Uncaging light provided by light source 3002 (e.g., a laser or xenon, mercury or UV lamp) is reflected by mirrors 3003 and 3004 as indicated by the open arrows. The uncaging light impinges on the bottom of wells 3001. Light meter 3007, which is located in the same plane as sample wells 3001, monitors the uncaging light. Motor 3008 adjusts the position (e.g., the vertical and/or horizontal position) of sample wells 3001 and meter 3007 with respect to the beam of uncaging light, e.g., to position the wells in the most intense part of the beam. Optional detector 3009 detects a signal emitted from sample wells 3001 (e.g., from a sensor in the wells).

Figure 35:
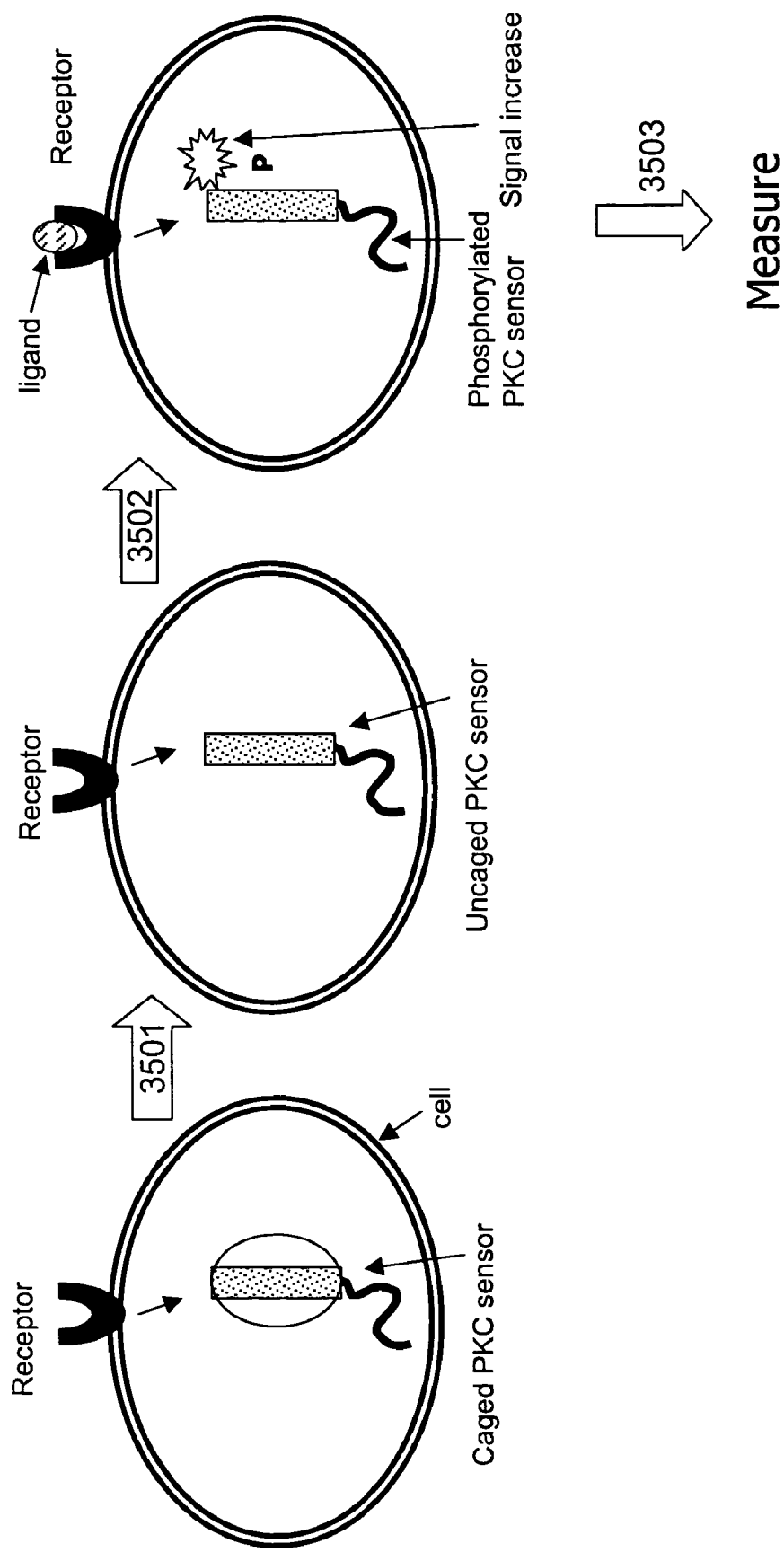
FIG. 35 schematically illustrates light triggering a cell-based assay for PKC.

FIG. 35 illustrates a cell-based assay for PKC. In this example, a photoactivatable caged PKC sensor (see, e.g., FIG. 6) is introduced into the cell, where it remains inactive and protected from degradation. The PKC sensor is then activated by exposure to light in step 3501. The addition of ligand (step 3502) and the binding of the ligand to its receptor trigger the phosphorylation of the PKC sensor, and a fluorescent signal from the phosphorylated sensor is read using a fluorescent microtiter plate reader in step 3503.

An example of a specific application for a cell based assay using such a PKC sensor is high throughput screening for compounds affecting a G-protein coupled receptor (GPCR). Activation of a GPCR triggers an increase in PKC activity in less than 3 sec (*J Biol Chem* (1999) 274:7565-7569). This rapid activation of PKC underscores the importance of being able to trigger and detect cell based (and biochemical) assays quickly for this and similar applications. Use of a caged PKC sensor permits such temporal control of the measurement period.

Photoactivatable Sensors and Screens

The PAC probes described herein (e.g., caged enzyme sensors, caged nucleic acid probes, caged labeled interfering RNAs, and the like) have a variety of applications. For example, the PAC probes can be used in a variety of assays, in dissection of gene regulatory networks and/or signaling pathways, and in screening for compounds involved in or affecting signaling pathways. As a specific example, as noted above, caged sensors can be used in screens (e.g., high throughput screens) for compounds affecting GPCR signaling pathways.

The G protein-coupled receptors (GPCRs) are a superfamily of proteins accounting for approximately 1% of the human genome. Based on the fact that all GPCRs display a seven transmembrane domain of alpha-helices and activate G proteins, these receptors are generally assumed to form a single super-family of receptors, perhaps the largest such super-family (Bockaert and Pin (1999) *EMBO J.* 18: 1723-1729). There are nearly 200 GPCRs whose natural ligands and function are known and approximately another 800 that are orphans. GPCRs are devoted to signal transduction in almost every living organism (e.g., viruses, diploblastic metazoa, yeasts, plants, invertebrates and vertebrates). During evolution, the structure of GPCRs has adapted to recognize a wide variety of environmental stimuli (e.g., light, Ca2+, odors, amino acids, peptides, lipids, nucleotides, and proteins) and to control the activity of a large variety of effectors (e.g., enzymes, ion channels and transport vesicles). Since GPCR dysfunctions generate various pathologies, these receptors are the targets of a large number of available therapeutic drugs. Understanding the structure and signaling of GPCRs is therefore an important prerequisite for successful development of new therapeutic targets.

Due to the overwhelming variety of physiologies regulated, GPCRs have been the richest targets in history for drug discovery. It is estimated that nearly 60% of all prescription drugs on the market owe their activity in whole or in part to GPCRs. While some of the natural ligands have important therapeutic value (e.g., epinephrine, dopamine and adenosine), most drugs are synthetic ligands or derivatives that bind and either activate or block the receptor, so-called agonists and antagonists, respectively. Many compounds have purely stimulatory or inhibitory properties, while others are a mixed breed, including partial agonists or antagonists, inverse agonists, and allosteric modulators. In addition to these drugs that act directly on GPCRs, other drugs act indirectly on GPCRs, e.g., by promoting or inhibiting the cellular synthesis, release or reuptake of the natural ligand.

Figure 55:
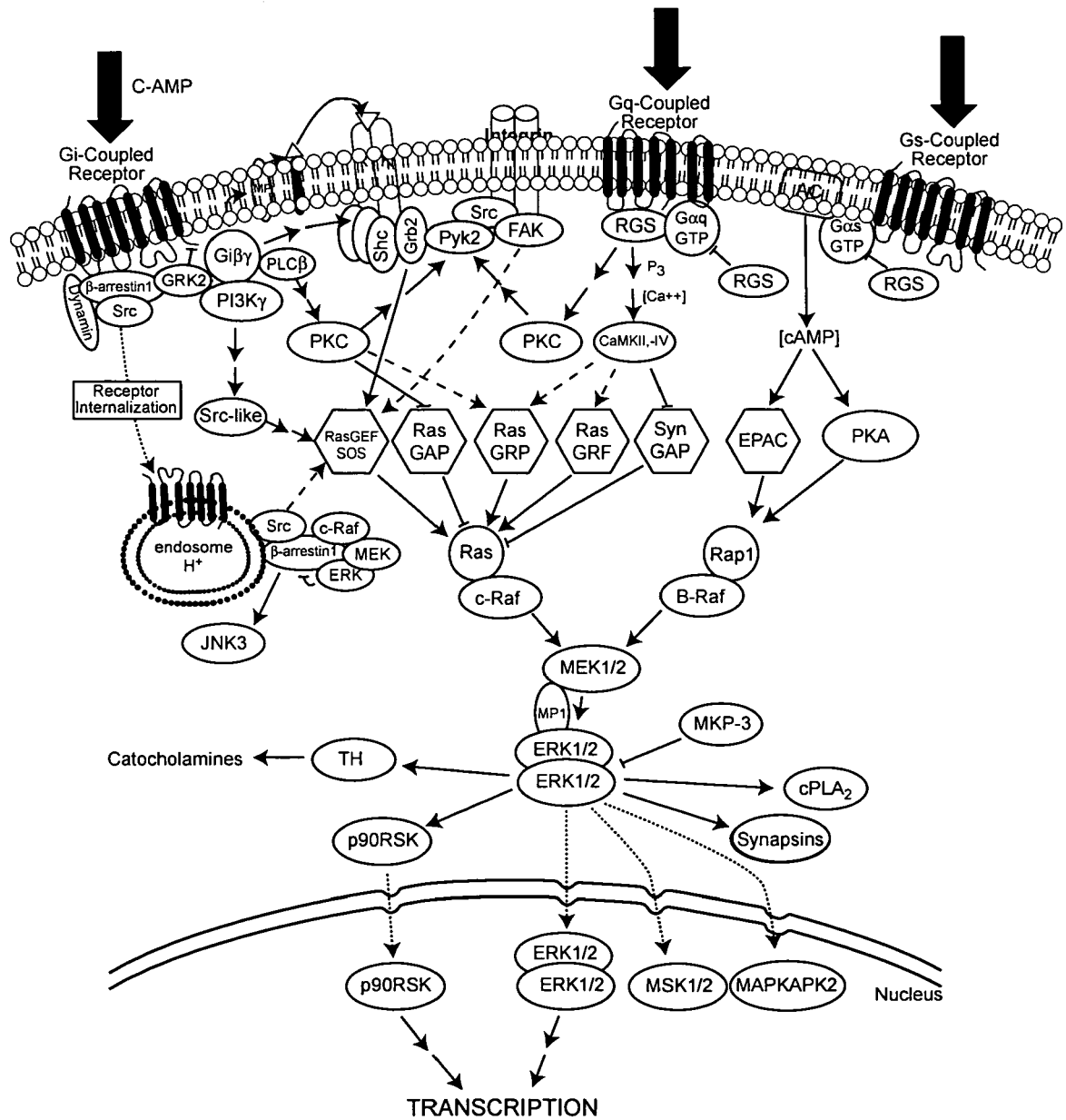
FIG. 55 schematically illustrates an example GPCR signaling pathway, to MAPK/ERK.

The G-protein coupled receptor family transduces extracellular signals across the plasma membrane, activating cellular responses through a variety of second messenger cascades, such as the protein kinase A (PKA) and protein kinase C (PKC) signaling pathways, for example. See, e.g., FIG. 55. These receptors provide rapid responses to a variety of stimuli, and are often rapidly attenuated in their signaling. Failure to attenuate GPCR signaling can have dramatic consequences and can, thus, have great therapeutic value. Attenuation of GPCR signaling is receptor desensitization, in which receptors are modified to no longer transduce a signal even if the stimulus is still present. Desensitization of GPCRs typically occurs through protein kinases that phosphorylate the GPCR to turn off signaling. For example, downstream protein kinases such as PKA (Gi & Gs coupled receptors) and PKC (Gq coupled receptors) turned on by GPCR signaling can phosphorylate the activated GPCR and other GPCRs to prevent further signaling. As another example, G-protein receptor kinases (GRKs) are a family of kinases (including GRK 1-7) that specifically phosphorylate only agonist-occupied GPCRs. GRKs attenuate GPCR signaling in concert with arrestins (proteins that bind GRK-phosphorylated GPCRs to disrupt interaction with G-protein and to terminate signaling), PKC and/or PKA. Reducing the number of receptors expressed on the cell surface can also attenuate receptor signaling. Many GPCRs are removed from the cell surface by receptor-mediated endocytosis when they are activated. Endocytosis of activated GPCRs appears to be stimulated by GRKs. Once internalized, receptors can either be degraded in lysosomes or they can be recycled back to the cell surface.

Figure 56:
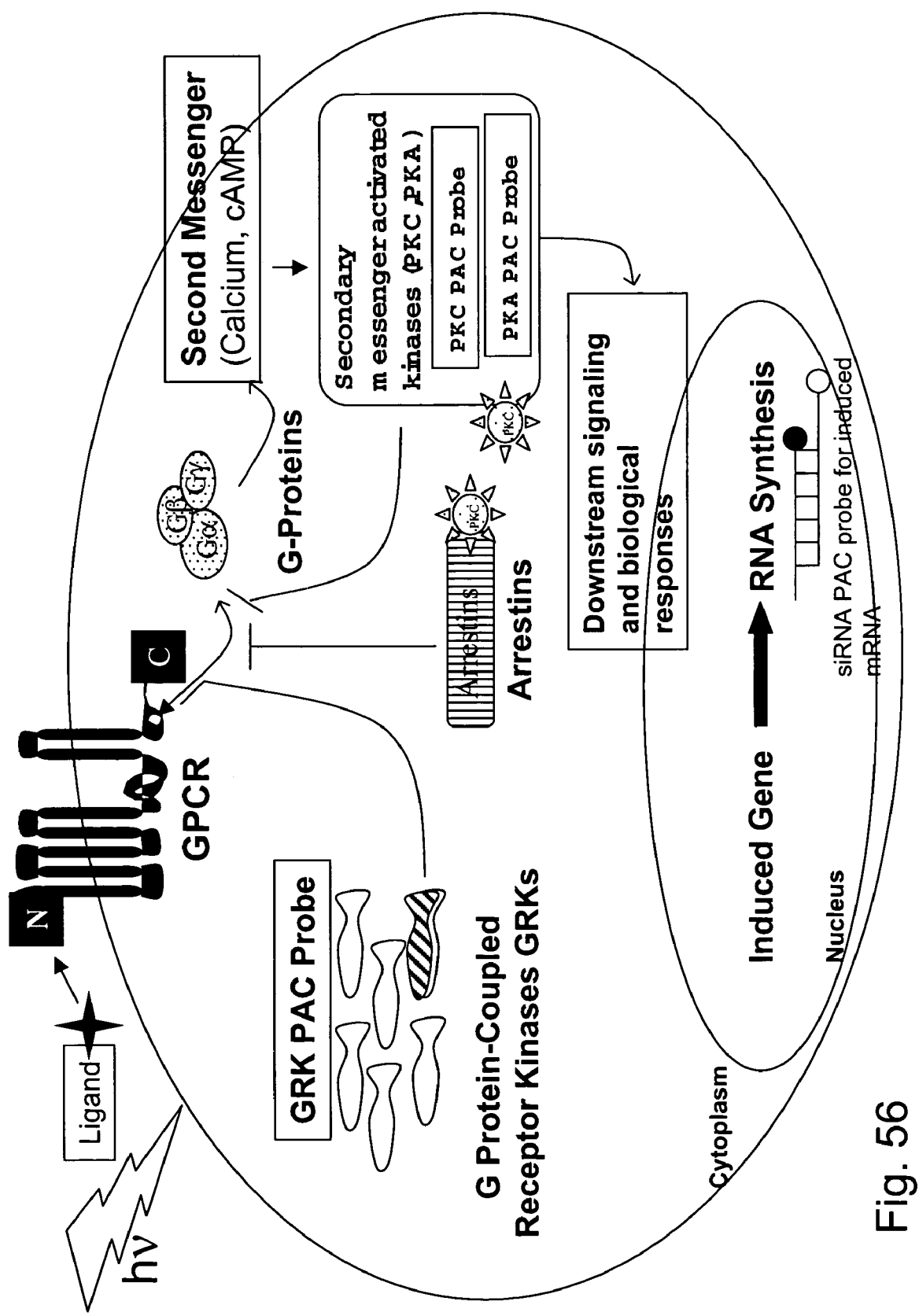
FIG. 56 schematically illustrates use of PAC probes to study GPCR signaling.

PAC probes can be used to study GPCR signaling and to screen for compounds affecting signaling. See, e.g., FIG. 56, which schematically illustrates an example GPCR signaling pathway. A signal is transmitted across the cell membrane by binding of the ligand to the GPCR. Signaling continues through the G-proteins, second messenger (e.g., calcium and cAMP) production or release, and activation of secondary messenger activated kinases (e.g., PKC and PKA), which leads to downstream signaling and biological responses (e.g., induction of mRNA synthesis). As one example of how caged sensors can be used to screen for compounds affecting GPCR signaling, GRK, PKC and/or PKA PAC probes can be used to identify compounds which inhibit desensitization of Gi, Gs and/or Gq GPCR coupled receptors. Caged siRNA PAC probes can similarly be used to monitor induction of MRNA synthesis.

For example, a caged sensor comprising a GRK, PKC or PKA substrate, a first label, and one or more caging groups can be introduced into a cell comprising a GPCR (e.g., by any of the delivery methods described herein). A GPCR agonist and a test compound can be contacted with the cell, and the cell can be exposed to uncaging energy to activate the sensor. A phosphorylation-dependent signal from the sensor can be measured and used to determine whether the test compound affects activity of the GRK, PKC or PKA (and, thus, whether the test compound affects GPCR desensitization). For example, treatment of a cell with a compound interfering with GPCR desensitization can result in increased GRK, PKC and/or PKA activity, in comparison with a control cell comprising the sensor and treated with the agonist but not with the test compound.

Another application of PAC probes is the identification of natural or synthetic agonists which activate an orphan GPCR and, thus, functionalize it. In the past, endogenous ligands were used to isolate GPCRs through demanding techniques such as protein purification and expression cloning. Cloning by sequence homology identified the major genes encoding GPCRs with known endogenous ligands. This shift from ligand-based to sequence-based receptor discovery facilitated the identification of many receptors and their subtypes. In addition, sequence-based discovery unveiled a host of novel receptors for which the endogenous ligands are not yet known. Of course, key to the value of any given orphan GPCR is an understanding of the physiology it regulates. Unfortunately, without its natural ligand, a synthetic ligand, or some other method of initiating receptor activation, it is difficult and time consuming to "functionalize" or "deorphanize" a GPCR. Since the GRKs, PKA, and PKC only signal in presence of a GPCR ligand, one or more GRK, PKA or PKC PAC probes can be used to identify a natural or synthetic ligand and thus deorphanize a GPCR.

Gene expression sensors can also be used in GPCR screens. For example, a labeled siRNA (e.g., a caged labeled siRNA such as those described herein or in U.S. Patent Application 60/484,785, filed Jul. 3, 2003), a caged nucleic acid probe (e.g., a caged molecular beacon) or the like, can be used to detect mRNA levels for a transcript that is induced or repressed following activation of a GPCR.

Thus, in one class of embodiments, the invention provides methods of determining whether a test compound affects an activity of a GPCR. The methods can be used, for example, to screen for compounds affecting (directly or indirectly) the activity of the GPCR. In the methods, a cell comprising the GPCR is provided, and at least one caged component is introduced into the cell. The caged component comprises a component and one or more caging groups associated with the component. The cell and the test compound are contacted, and the cell is exposed to uncaging energy, which exposure to frees the component from inhibition by the caging groups. A signal that provides an indication of the activity of the GPCR is detected from the component. Comparison with a signal from a like component in a cell comprising the GPCR and the component but not treated with the test compound, for example, can indicate whether the test compound increases, decreases, or does not affect activity of the GPCR.

The one or more caging groups associated with the component can be covalently or non-covalently attached to the component. In a preferred class of embodiments, the one or more caging groups are photoactivatable (e.g., photolabile).

The component can be essentially any component that can provide, directly or indirectly, an indication of the GPCR's activity. For example, the caged component can be a caged sensor for detecting an activity of an enzyme (e.g., an enzyme sensor such as those described herein, for example, a kinase sensor, e.g., a PKC, PKA, or GRK sensor), a caged binding sensor, a caged nucleic acid probe (e.g., a caged molecular beacon), or a caged interfering RNA sensor (e.g., a labeled siRNA or shRNA PAC probe such as those described herein, or a caged RNAi-based sensor as described in U.S. Patent Application 60/484,785, filed Jul. 3, 2003).

The test compound can be a putative ligand or agonist, or it can be a compound that may affect the activity of the GPCR directly or indirectly in another manner, e.g., a putative antagonist or a compound that may interfere with desensitization of the GPCR. Thus, in some embodiments, the methods include contacting the cell and an activating compound (e.g., an agonist), the activating compound increasing the activity of the GPCR. This class of methods can, for example, be used to screen for compounds affecting receptor desensitization.

Cellular Delivery and in Vivo Photoactivation of Photolabile Caged Kinase Sensor The following sets forth a series of examples that demonstrate use of a photolabile caged kinase sensor to detect protein kinase C (PKC) activity in vivo, in living HeLa cells. The experiments also demonstrate use of a cellular delivery module to introduce the PKC sensor into the cells.

Figure 59A:
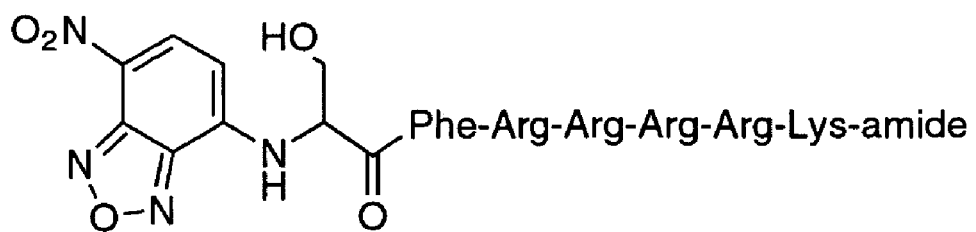
FIG. 59 Panel A depicts a PKC sensor. Panel B depicts a caged PKC sensor.
Figure 59B:
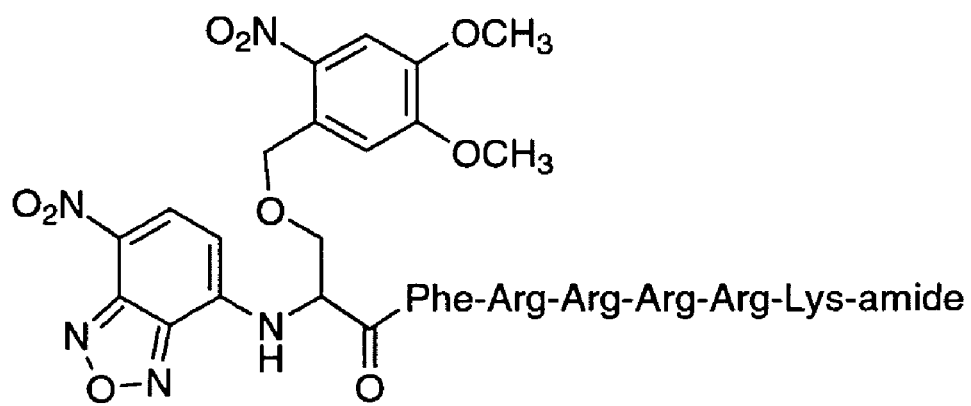

The caged PKC sensor is described in Veldhuyzen et al. (2003) "A light-activated probe of intracellular protein kinase activity" *J. Am. Chem. Soc.* 125:13358-13359 and is shown in FIG. 59 Panel B. Exposure to UV light (365 nm) releases the caging group and leaves the serine available for phosphorylation by PKC. The uncaged sensor is shown in FIG. 59 Panel A. The sensor comprises a substrate for PKC and an NBD fluorophore whose fluorescence changes upon phosphorylation of the adjacent serine. See, Yeh et al. (2002) *J. Biol. Chem.* 277:11527-11532).

The caged PKC sensor was transfected into HeLa cells using Profect P-2 (Targeting Systems, on the internet at targetingsystems.com), a non-lipid reagent that forms noncovalent complexes with polypeptides, enabling transport of the associated polypeptides into cells (and optionally nuclei). Profect P-2 also has endosomolytic properties that protect the internalized polypeptides from degradation in the lysosomes.

To demonstrate cellular delivery and in vivo activation of the caged PKC sensor, 10,000 HeLa cells were plated per well in 96 well plates in complete DMEM and incubated at 37° C. overnight. The caged PKC sensor was transfected into the cells at a concentration of 10 µM, as follows. To 37.5 µl serum-free DMEM, 2.5 µl Profect P-2 and then 10 µl of caged PKC sensor (diluted to 500 µM in PBS) were added. The reagents were mixed gently and incubated for 30 minutes at room temperature. The DMEM was removed from the well containing the HeLa cells, and the cells were washed once with PBS. After addition of 450 µl serum-free DMEM to the Profect P-2-caged sensor complex, 50 µl of the complex was added to each well. The HeLa cells were incubated with the complex at 37° C. for 2 h (or optionally longer, with the addition of fresh DMEM). To uncage the caged PKC sensor, cells were exposed from beneath the plate to 1 J/cm$^2$ 365 nm UV light. Uncaging light was produced by a BlueWave™ UV Spot Light System fitted with a Lightguide mount assembly, Cool Blue™ filter, and Lightguide rod lens assembly (Dymax Corp., on the internet at dymax.com, part numbers 38600, 38670, and 38699). Wells containing cells in which the sensor was not to be uncaged were masked with aluminum foil. Immediately after uncaging, PMA was added to 1 µM to induce PKC activity. Fluorescent signal from the PKC sensor was read on an Acumen Explorer™ microplate reader.

Figure 60:
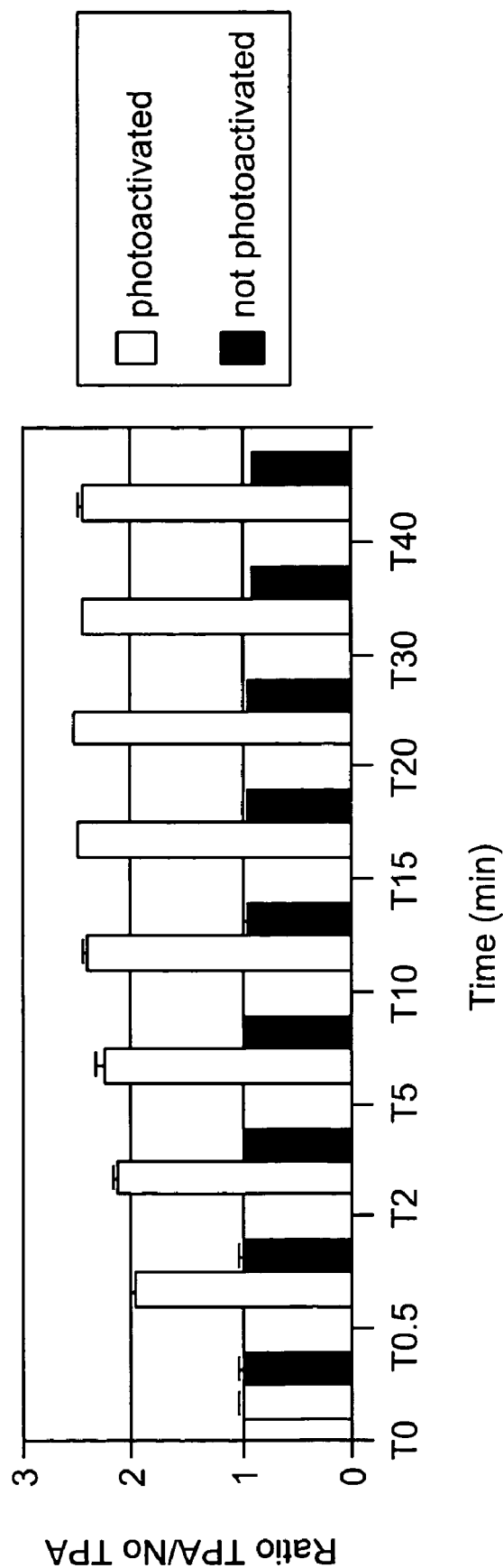
FIG. 60 presents a graph showing phosphorylation and increased fluorescence of the caged PKC sensor in cells exposed to uncaging light but not in cells protected from exposure to uncaging light.

Results are illustrated in FIG. 60, which graphs the ratio of relative fluorescent units (RFU) measured in TPA-treated to untreated cells at various time points after uncaging. Fluorescent signal from the sensor increases rapidly in cells exposed to the uncaging light, but remains constant and low in cells not exposed to the uncaging light.

Figures 61A, 61B:
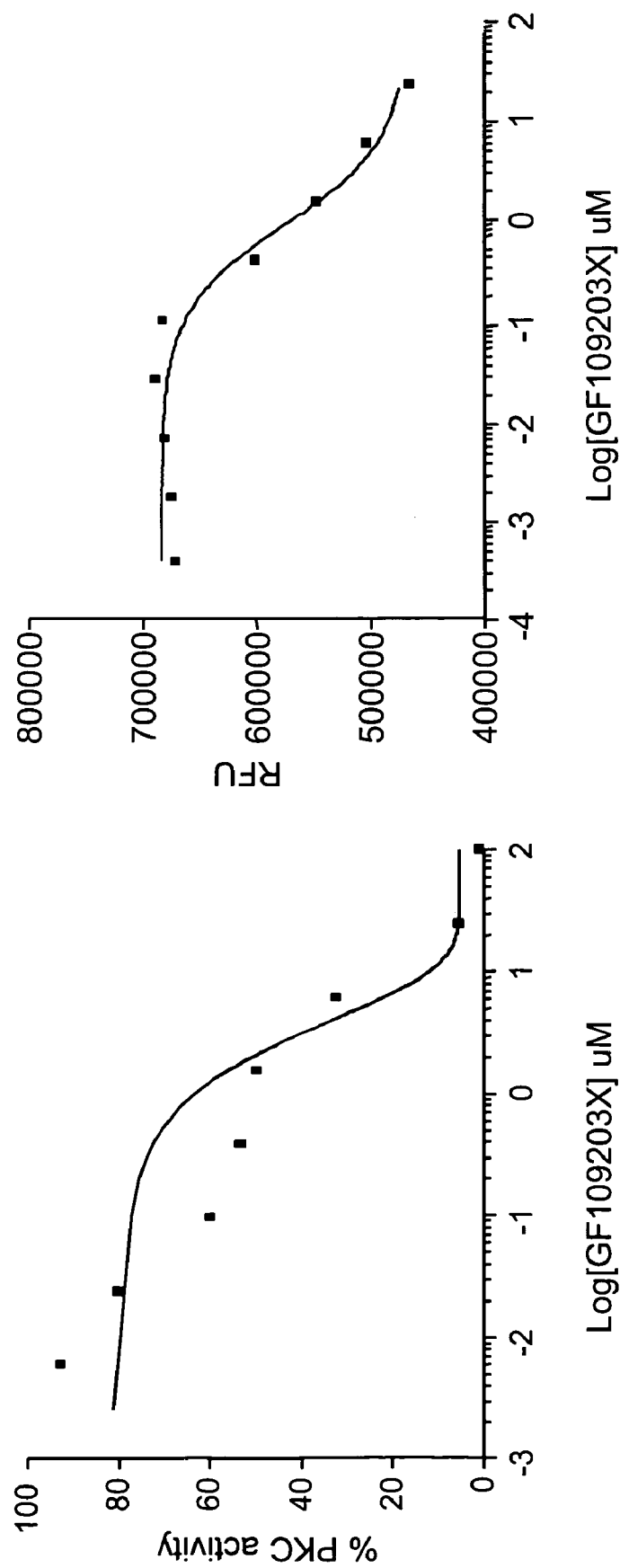
FIG. 61 Panel A presents an IC-50 curve determined in vivo using the photolabile caged PKC sensor. Panel B presents an IC-50 curve determined in vitro using the PKC sensor (not caged).

To demonstrate that cellular delivery of the caged PKC sensor can, for example, permit in vivo determination of the IC-50 of an inhibitor, 10,000 HeLa cells per well of 96 well plates were transfected with 10 µM caged PKC sensor as described above. Cells containing the caged sensor were incubated with 4-fold dilutions of GF109203X for 30 min before the cells were exposed to uncaging light (1 J/cm$^2$, 365 nm) and treated with 1 µM PMA. Fluorescent signal from the PKC sensor was read on an Acumen Explorer™ microplate reader. IC-50 determination was performed with GraphPad Prism 3.0 software (GraphPad Software, Inc.). Results are presented in FIG. 61 Panel A. The IC-50 determined in vivo, 1.6 µM, is comparable to the IC-50 of 1.1 uM determined in an in vitro biochemical assay (62.5 mM HEPES pH 7.4, 3 mM MgCl$_2$, 0.3 mM CaCl$_2$, 0.1 mM EGTA, 1 mM DTT, 0.5 µg/ml phosphatidylserine, 0.1 µg/ml diacylglycerol, 1 mM ATP, 1 µM PKC sensor (not caged), 22 nM PKC enzyme; fluorescent signal from the PKC sensor was read on an Envision fluorescent plate reader with excitation at 485 nm and emission at 535 nm; IC-50 determination was performed using Prism 3.0 software). These results demonstrate that the same sensor can be used in both in vitro and in vivo assays and that cellular delivery of the caged sensor facilitates in vivo assays of enzymatic activity (e.g., high throughput assays, including evaluation of effects of modulators, e.g., inhibitors, of the enzyme activity). As noted previously, a variety of other sensors (e.g., sensors such as those described in Chen et al. (2002) *J. Am. Chem. Soc.* 124:3840-3841) can be caged. As demonstrated in this example, cellular delivery of such caged sensors can be accomplished through the use of cellular delivery modules.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A composition, comprising:
a cell comprising an enzyme and a caged sensor for detecting an activity of the enzyme, which caged sensor comprises:
   a) one or more molecules collectively comprising:
      i) a substrate for the enzyme, wherein the substrate is in a first state on which the enzyme can act, thereby converting the substrate to a second state, and
      ii) a first label, wherein a first signal exhibited by the first label when the substrate is in its first state is distinguishable from a second signal exhibited by the first label when the substrate is in its second state;
   b) one or more first caging groups associated with the one or more molecules, the first caging groups inhibiting the enzyme from acting upon the substrate; and,
   c) optionally, one or more second caging groups associated with a phosphobinder;
wherein the enzyme is a protein kinase that phosphorylates tyrosine, serine and/or threonine;
wherein the one or more molecules comprise one polypeptide; wherein the one polypeptide comprises the substrate for the kinase and the first label and comprises a second label or a quencher; wherein the first label and the second label or the quencher interact to produce the first signal when the substrate is not phosphorylated; and wherein phosphorylation of the substrate prevents the interaction of the first label and the second label or the quencher, thereby resulting in production of the second signal;
wherein phosphorylation of the substrate triggers a conformational change in the polypeptide, the conformational change preventing the interaction of the first label and the second label or the quencher; or wherein phosphorylation of the substrate results in binding of the phosphobinder to the phosphorylated substrate, the binding of the phosphobinder preventing the interaction of the first label and the second label or the quencher; wherein the presence of the second caging groups prevents the phosphobinder from binding the phosphorylated substrate.

2. A composition, comprising:
an enzyme and a caged sensor for detecting an activity of the enzyme, which caged sensor comprises:
   a) one or more molecules collectively comprising:
      i) a substrate for the enzyme, wherein the substrate is in a first state on which the enzyme can act, thereby converting the substrate to a second state, wherein the first state is not converted to the second state by cleavage by the enzyme, and
      ii) a first label, wherein a first signal exhibited by the first label when the substrate is in its first state is distinguishable from a second signal exhibited by the first label when the substrate is in its second state;

b) one or more first caging groups associated with the one or more molecules, the first caging groups inhibiting the enzyme from acting upon the substrate; and, c) optionally, one or more second caging groups associated with a phosphobinder, wherein the presence of the second caging groups prevents the phosphobinder from binding the phosphorylated substrate;

the first caging groups inhibiting the enzyme from acting upon the substrate;

wherein the enzyme is a protein kinase that phosphorylates tyrosine, seine and/or threonine;

wherein the one or more molecules comprise one polypeptide; wherein the one polypeptide comprises the substrate for the kinase and the first label and comprises a second label or a quencher; wherein the first label and the second label or the quencher interact to produce the first signal when the substrate is not phosphorylated; and wherein phosphorylation of the substrate prevents the interaction of the first label and the second label or the quencher, thereby resulting in production of the second signal;

wherein phosphorylation of the substrate triggers a conformational change in the polypeptide, the conformational change preventing the interaction of the first label and the second label or the quencher; or wherein phosphorylation of the substrate results in binding of the phosphobinder to the phosphorylated substrate, the binding of the phosphobinder preventing the interaction of the first label and the second label or the quencher.

3. The composition of claim 1 or 2, wherein the second caging groups are removable under different conditions than the first caging groups preventing phosphorylation of the substrate.

4. A composition, comprising:
a cell comprising an enzyme and a caged sensor for detecting an activity of the enzyme, which caged sensor comprises:

a) one or more molecules collectively comprising:
i) a substrate for the enzyme, wherein the substrate is in a first state on which the enzyme can act, thereby converting the substrate to a second state, and
ii) a first label, wherein a first signal exhibited by the first label when the substrate is in its first state is distinguishable from a second signal exhibited by the first label when the substrate is in its second state;

b) one or more first caging groups associated with the one or more molecules, the first caging groups inhibiting the enzyme from acting upon the substrate; and, c) optionally, a phosphobinder comprising an antibody, an SH-2 domain, a PTB domain, a 14-3-3 domain, an FHA domain, a WD40 domain and/or a WW domain;

wherein the enzyme is a protein kinase that phosphorylates tyrosine, serine and/or threonine;

wherein the one or more molecules comprise one polypeptide; wherein the one polypeptide comprises the substrate for the kinase and the first label and comprises a second label or a quencher; wherein the first label and the second label or the quencher interact to produce the first signal when the substrate is not phosphorylated; and wherein phosphorylation of the substrate prevents the interaction of the first label and the second label or the quencher, thereby resulting in production of the second signal;

wherein phosphorylation of the substrate triggers a conformational change in the polypeptide, the conformational change preventing the interaction of the first label and the second label or the quencher; or wherein phosphorylation of the substrate results in binding of the phosphobinder to the phosphorylated substrate, the binding of the phosphobinder preventing the interaction of the first label and the second label or the quencher.

5. A composition, comprising:
a cell comprising an enzyme and a caged sensor for detecting an activity of the enzyme, which caged sensor comprises:

a) one or more molecules collectively comprising:
i) a substrate for the enzyme, wherein the substrate is in a first state on which the enzyme can act, thereby converting the substrate to a second state, and
ii) a first label, wherein a first signal exhibited by the first label when the substrate is in its first state is distinguishable from a second signal exhibited by the first label when the substrate is in its second state;

b) one or more first caging groups associated with the one or more molecules, the first caging groups inhibiting the enzyme from acting upon the substrate; and, c) one or more second caging groups associated with a phosphobinder, wherein the presence of the second caging groups prevents the phosphobinder from binding the phosphorylated substrate;

wherein the enzyme is a protein kinase that phosphorylates tyrosine, seine and/or threonine;

wherein the one or more molecules comprise one polypeptide; wherein the one polypeptide comprises the substrate for the kinase and the first label; wherein the polypeptide comprises the phosphobinder and a second label or a quencher; wherein the first label and the second label or the quencher do not interact when the substrate is not phosphorylated, thereby producing the first signal; and wherein phosphorylation of the substrate results in intramolecular binding of the phosphobinder to the phosphorylated substrate, the intramolecular binding resulting in the interaction of the first label and the second label or the quencher, thereby producing the second signal; or, wherein the one or more molecules comprise a first polypeptide and a second polypeptide; wherein the first polypeptide comprises the substrate for the kinase and the first label, wherein the second polypeptide comprises the phosphobinder and a second label or a quencher; wherein the first label and the second label or the quencher do not interact when the substrate is not phosphorylated, thereby producing the first signal; and wherein phosphorylation of the substrate results in intermolecular binding of the phosphobinder to the phosphorylated substrate, the intermolecular binding resulting in the interaction of the first label and the second label or the quencher, thereby producing the second signal.

6. A composition, comprising:
an enzyme and a caged sensor for detecting an activity of the enzyme, which caged sensor comprises:

a) one or more molecules collectively comprising:
i) a substrate for the enzyme, wherein the substrate is in a first state on which the enzyme can act, thereby converting the substrate to a second state, wherein the first state is not converted to the second state by cleavage by the enzyme, and
ii) a first label, wherein a first signal exhibited by the first label when the substrate is in its first state is distinguishable from a second signal exhibited by the first label when the substrate is in its second state;
b) one or more first caging groups associated with the one or more molecules, the first caging groups inhibiting the enzyme from acting upon the substrate; and,
c) one or more second caging groups associated with a phosphobinder, wherein the presence of the second caging groups prevents the phosphobinder from binding on the phosphorylated substrate;

wherein the enzyme is a protein kinase that phosphorylates tyrosine, serine and/or threonine;

wherein the one or more molecules comprise one polypeptide; wherein the one polypeptide comprises the substrate for the kinase and the first label; wherein the polypeptide comprises the phosphobinder and a second label or a quencher; wherein the first label and the second label or the quencher do not interact when the substrate is not phosphorylated, thereby producing the first signal; and wherein phosphorylation of the substrate results in intramolecular binding of the phosphobinder to the phosphorylated substrate, the intramolecular binding resulting in the interaction of the first label and the second label or the quencher, thereby producing the second signal; or, wherein the one or more molecules comprise a first polypeptide and a second polypeptide; wherein the first polypeptide comprises the substrate for the kinase and the first label; wherein the second polypeptide comprises the phosphobinder and a second label or a quencher; wherein the first label and the second label or the quencher do not interact when the substrate is not phosphorylated, thereby producing the first signal; and wherein phosphorylation of the substrate results in intermolecular binding of the phosphobinder to the phosphorylated substrate, the intermolecular binding resulting in the interaction of the first label and the second label or the quencher, thereby producing the second signal.

7. The composition of claim 5 or 6, wherein the second caging groups are removable under different conditions than the first caging groups preventing phosphorylation of the substrate.

8. A composition, comprising:
a cell comprising an enzyme and a caged sensor for detecting an activity of the enzyme, which caged sensor comprises:
a) one or more molecules collectively comprising:
i) a substrate for the enzyme, wherein the substrate is in a first state on which the enzyme can act, thereby converting the substrate to a second state, and
ii) a first label, wherein a first signal exhibited by the first label when the substrate is in its first state is distinguishable from a second signal exhibited by the first label when the substrate is in its second state;
b) one or more first caging groups associated with the one or more molecules, the first caging groups inhibiting the enzyme from acting upon the substrate; and,
c) a phosphobinder comprising: an antibody, an SH-2 domain, a PTB domain, a 14-3-3 domain, an FHA domain, a WD40 domain and/or a WW domain;

wherein the enzyme is a protein kinase that phosphorylates tyrosine, seine and/or threonine;

wherein the one or more molecules comprise one polypeptide; wherein the one polypeptide comprises the substrate for the kinase and the first label; wherein the polypeptide comprises the phosphobinder and a second label or a quencher; wherein the first label and the second label or the quencher do not interact when the substrate is not phosphoryiated, thereby producing the first signal; and wherein phosphorylation of the substrate results in intramolecular binding of the phosphobinder to the phosphorylated substrate, the intramolecular binding resulting in the interaction of the first label and the second label or the quencher, thereby producing the second signal; or, wherein the one or more molecules comprise a first polypeptide and a second polypeptide; wherein the first polypeptide comprises the substrate for the kinase and the first label; wherein the second polypeptide comprises the phosphobinder and a second label or a quencher; wherein the first label and the second label or the quencher do not interact when the substrate is not phosphorylated, thereby producing the first signal; and wherein phosphorylation of the substrate results in intermolecular binding of the phosphobinder to the phosphorylated substrate, the intermolecular binding resulting in the interaction of the first label and the second label or the quencher, thereby producing the second signal.

9. A composition, comprising:
a cell comprising an enzyme and a caged sensor for detecting an activity of the enzyme, which caged sensor comprises:
a) one or more molecules collectively comprising:
i) a substrate for the enzyme, wherein the substrate is in a first state on which the enzyme can act, thereby converting the substrate to a second state, and
ii) a first label, wherein a first signal exhibited by the first label when the substrate is in its first state is distinguishable from a second signal exhibited by the first label when the substrate is in its second state; and,
b) one or more first caging groups associated with the one or more molecules, the first caging groups inhibiting the enzyme from acting upon the substrate;

wherein the enzyme is a protein kinase that phosphorylates tyrosine, serine and/or threonine;

wherein the one or more molecules comprise one polypeptide; wherein the one polypeptide comprises the substrate for the kinase, a second substrate, the first label, a third label, a fourth label or a quencher, and a phosphobinder; the substrate comprising a seine, threonine, or tyrosine residue capable of being phosphorylated by the kinase; the second substrate being associated with one or more third caging groups, the presence of which prevents phosphorylation of the second substrate; wherein the first label is located at the seine, threonine, or tyrosine residue and exhibits the first signal when the residue is not phosphorylated and the second signal when the residue is phosphorylated; wherein the third label and the fourth label or the quencher do not interact when the second substrate is not phosphorylated, thereby producing a third signal; and wherein phosphorylation of the second substrate results in intramolecular binding of the phosphobinder to the phosphorylated second substrate, the intramolecular binding resulting in the interaction of the third label and the fourth label or the quencher, thereby producing a fourth signal, the fourth signal distinguishable from the first, second and third signals.

10. A composition, comprising:
an enzyme and a caged sensor for detecting an activity of the enzyme, which caged sensor comprises:

a) one or more molecules collectively comprising:
  i) a substrate for the enzyme, wherein the substrate is in a first state on which the enzyme can act, thereby converting the substrate to a second state, wherein the first state is not converted to the second state by cleavage by the enzyme, and
  ii) a first label, wherein a first signal exhibited by the first label when the substrate is in its first state is distinguishable from a second signal exhibited by the first label when the substrate is in its second state; and,
b) one or more first caging groups associated with the one or more molecules, the first caging groups inhibiting the enzyme from acting upon the substrate;
wherein the enzyme is a protein kinase that phosphorylates tyrosine, seine and/or threonine;
wherein the one or more molecules comprise one polypeptide; wherein the one polypeptide comprises the substrate for the kinase, a second substrate, the first label, a third label, a fourth label or a quencher, and a phosphobinder; the substrate comprising a seine, threonine, or tyrosine residue capable of being phosphorylated by the kinase; the second substrate being associated with one or more third caging groups, the presence of which prevents phosphorylation of the second substrate; wherein the first label is located at the seine, threonine, or tyrosine residue and exhibits the first signal when the residue is not phosphorylated and the second signal when the residue is phosphorylated; wherein the third label and the fourth label or the quencher do not interact when the second substrate is not phosphorylated, thereby producing a third signal; and wherein phosphorylation of the second substrate results in intramolecular binding of the phosphobinder to the phosphorylated second substrate, the intramolecular binding resulting in the interaction of the third label and the fourth label or the quencher, thereby producing a fourth signal, the fourth signal distinguishable from the first, second and third signals.

11. The composition of claim 9 or 10, wherein the second substrate is for the same kinase or for a different kinase.

12. The composition of claim 9 or 10, wherein the one or more third caging groups are located on a residue that can be phosphorylated by the kinase.

13. The composition of claim 12, wherein the third caging groups preventing phosphorylation of the second substrate are removable under different conditions than the first caging groups preventing phosphorylation of the substrate.

14. The composition of claim 9 or 10, wherein one of the third label and the fourth label or the quencher is located at the C-terminus of the polypeptide and the other of the third label and the fourth label or the quencher is within the polypeptide.

15. The composition of claim 9 or 10, wherein the third and fourth labels are fluorophores capable of exhibiting FRET.

16. The composition of claim 9 or 10, wherein the phosphobinder is associated with one or more second caging groups, the presence of which prevents the phosphobinder from binding the phosphorylated second substrate.

17. The composition of claim 16, wherein the second caging groups are removable under different conditions than the first caging groups preventing phosphorylation of the substrate and/or under different conditions than the third caging groups preventing phosphorylation of the second substrate.

18. The composition of claim 9 or 10, wherein the phosphobinder comprises an antibody, an SH-2 domain, a PTB domain, a 14-3-3 domain, an FHA domain, a WD40 domain and/or a WW domain.

19. A composition, comprising:
a cell comprising an enzyme and a caged sensor for detecting an activity of the enzyme, which caged sensor comprises:
a) one or more molecules collectively comprising:
  i) a substrate for the enzyme, wherein the substrate is in a first state on which the enzyme can act, thereby converting the substrate to a second state, and
  ii) a first label, wherein a first signal exhibited by the first label when the substrate is in its first state is distinguishable from a second signal exhibited by the first label when the substrate is in its second state, and,
b) one or more first caging groups associated with the one or more molecules, the first caging groups inhibiting the enzyme from acting upon the substrate;
wherein the one or more molecules comprise a fifth label, the fifth label exhibiting a unique fifth signal, the fifth signal being independent of the state of the substrate.

20. A composition, comprising:
an enzyme and a caged sensor for detecting an activity of the enzyme, which caged sensor comprises:
a) one or more molecules collectively comprising:
  i) a substrate for the enzyme, wherein the substrate is in a first state on which the enzyme can act, thereby converting the substrate to a second state, wherein the first state is not converted to the second state by cleavage by the enzyme, and
  ii) a first label, wherein a first signal exhibited by the first label when the substrate is in its first state is distinguishable from a second signal exhibited by the first label when the substrate is in its second state, and,
b) one or more first caging groups associated with the one or more molecules, the first caging groups inhibiting the enzyme from acting upon the substrate;
wherein the one or more molecules comprise a fifth label, the fifth label exhibiting a unique fifth signal, the fifth signal being independent of the state of the substrate.

21. The composition of claim 19 or 20, wherein the fifth label is a fluorophore or a quantum dot.

22. A composition, comprising:
an enzyme and a caged sensor for detecting an activity of the enzyme, which caged sensor comprises:
a) one or more molecules collectively comprising:
  i) a substrate for the enzyme, wherein the substrate is in a first state on which the enzyme can act, thereby converting the substrate to a second state, wherein the first state is not converted to the second state by cleavage by the enzyme, and
  ii) a first label, wherein a first signal exhibited by the first label when the substrate is in its first state is distinguishable from a second signal exhibited by the first label when the substrate is in its second state;
b) one or more first caging groups associated with the one or more molecules, the first caging groups inhibiting the enzyme from acting upon the substrate; and,
c) optionally, a phosphobinder comprising: an antibody, an SH-2 domain, a PTB domain, a 14-3-3 domain, an FHA domain, a WD40 domain and/or a WW domain;
wherein the enzyme is a protein kinase that phosphorylates tyrosine, seine and/or threonine;
wherein the one or more molecules comprise one polypeptide; wherein the one polypeptide comprises the substrate for the kinase and the first label and comprises a second label or a quencher; wherein the first label and the second label or the quencher interact to produce the first signal when the substrate is not phosphorylated; and wherein phosphorylation of the substrate prevents the interaction of the first label and the second label or the quencher, thereby resulting in production of the second signal;

wherein phosphorylation of the substrate triggers a conformational change in the polypeptide, the conformational change preventing the interaction of the first label and the second label or the quencher; or wherein phosphorylation of the substrate results in binding of the phosphobinder to the phosphorylated substrate, the binding of the phosphobinder preventing the interaction of the first label and the second label or the quencher.

23. A composition, comprising:

an enzyme and a caged sensor for detecting an activity of the enzyme, which caged sensor comprises:

a) one or more molecules collectively comprising:

i) a substrate for the enzyme, wherein the substrate is in a first state on which the enzyme can act, thereby converting the substrate to a second state, wherein the first state is not converted to the second state by cleavage by the enzyme, and ii) a first label, wherein a first signal exhibited by the first label when the substrate is in its first state is distinguishable from a second signal exhibited by the first label when the substrate is in its second state; and, b) one or more first caging groups associated with the one or more molecules, the first caging groups inhibiting the enzyme from acting upon the substrate;

wherein the enzyme is a protein kinase that phosphorylates tyrosine, seine and/or threonine;

wherein the one or more molecules comprise one polypeptide; wherein the one polypeptide comprises the substrate for the kinase and the first label; wherein the polypeptide comprises a phosphobinder and a second label or a quencher; wherein the first label and the second label or the quencher do not interact when the substrate is not phosphorylated, thereby producing the first signal; and wherein phosphorylation of the substrate results in intramolecular binding of the phosphobinder to the phosphorylated substrate, the intramolecular binding resulting in the interaction of the first label and the second label or the quencher, thereby producing the second signal; or, wherein the one or more molecules comprise a first polypeptide and a second polypeptide; wherein the first polypeptide comprises the substrate for the kinase and the first label; wherein the second polypeptide comprises a phosphobinder and a second label or a quencher; wherein the first label and the second label or the quencher do not interact when the substrate is not phosphorylated, thereby producing the first signal; and wherein phosphorylation of the substrate results in intermolecular binding of the phosphobinder to the phosphorylated substrate, the intermolecular binding resulting in the interaction of the first label and the second label or the quencher, thereby producing the second signal;

wherein the phosphobinder comprises an antibody, an SH-2 domain, a PTB domain, a 14-3-3 domain, an FHA domain, a WD40 domain and/or a WW domain.

\* \* \* \* \*